(12) United States Patent
Guo et al.

(10) Patent No.: US 11,976,092 B2
(45) Date of Patent: May 7, 2024

(54) RNA NANOSTRUCTURES, METHODS OF MAKING, AND USES THEREOF

(71) Applicants: Ohio State Innovation Foundation, Columbus, OH (US); UNIVERSITY OF KENTUCKY RESEARCH FOUNDATION, Lexington, KY (US)

(72) Inventors: Peixuan Guo, Dublin, OH (US); Mario Vieweger, Columbus, OH (US); Xin Li, Dublin, OH (US); Sijin Guo, Dublin, OH (US); Hongran Yin, Dublin, OH (US); Xijun Piao, San Diego, CA (US); Yi Shu, Columbus, OH (US); Dan Shu, Columbus, OH (US); Mehdi Rajabi, Columbus, OH (US)

(73) Assignees: Ohio State Innovation Foundation, Columbus, OH (US); University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/635,312

(22) PCT Filed: Nov. 12, 2018

(86) PCT No.: PCT/US2018/060567
§ 371 (c)(1),
(2) Date: Jan. 30, 2020

(87) PCT Pub. No.: WO2019/156726
PCT Pub. Date: Aug. 15, 2019

(65) Prior Publication Data
US 2020/0369710 A1 Nov. 26, 2020

Related U.S. Application Data

(60) Provisional application No. 62/628,591, filed on Feb. 9, 2018, provisional application No. 62/755,696, filed on Nov. 5, 2018.

(51) Int. Cl.
| | |
|---|---|
| C07H 21/02 | (2006.01) |
| A61K 45/06 | (2006.01) |
| A61K 47/54 | (2017.01) |
| A61K 47/55 | (2017.01) |
| A61K 51/06 | (2006.01) |
| C12N 15/115 | (2010.01) |

(52) U.S. Cl.
CPC .......... *C07H 21/02* (2013.01); *A61K 47/549* (2017.08); *A61K 47/55* (2017.08); *C12N 15/115* (2013.01); *A61K 45/06* (2013.01); *A61K 51/06* (2013.01); *C12N 2310/35* (2013.01); *C12N 2310/351* (2013.01); *C12N 2310/3519* (2013.01); *C12N 2330/30* (2013.01)

(58) Field of Classification Search
None
See application file for complete search history.

(56) References Cited

U.S. PATENT DOCUMENTS

| | | | | |
|---|---|---|---|---|
| 2005/0191625 | A1* | 9/2005 | Kobler | G16B 30/10 435/6.18 |
| 2013/0236967 | A1* | 9/2013 | Behlke | C12N 15/113 435/375 |
| 2015/0018540 | A1* | 1/2015 | Prakash | C07H 21/00 536/24.5 |
| 2016/0289675 | A1 | 10/2016 | Ryan et al. | |

FOREIGN PATENT DOCUMENTS

| | | |
|---|---|---|
| WO | 2016145003 A1 | 9/2016 |
| WO | 2016145005 A1 | 9/2016 |
| WO | 2016168784 A2 | 10/2016 |
| WO | WO 2016/168784 A2 * | 10/2016 |
| WO | 2017147557 A1 | 8/2017 |
| WO | 2017197009 A1 | 11/2017 |

OTHER PUBLICATIONS

International Search Report issued for PCT/US2018/060567, dated Mar. 21, 2019.
Paulmurugan et al., Folate Receptor-Targeted Polymeric Micellar Nanocarriers for Delivery of Orlistat as a Repurposed Drug against Triple-Negative Breast Cancer. Mol Cancer Ther. 15, 221-231, 2016.
Lee et al., Self-assembled RNA interference microsponges for efficient siRNA delivery. Nat.Mater. 11, 316-322, 2012.
Li, Controllable Self-Assembly of RNA Tetrahedrons with Precise Shape and Size for Cancer Targeting. Adv.Mater. 28, 7501-7507, 2016.
Douglas et al., Self-assembly of DNA into nanoscale three-dimensional shapes. Nature 459, 414-418, 2009.
International Search Reported issued by the European Patent Office for application No. 18905354.9, dated Dec. 10, 2020.
Li et al., RNA as a stable polymer to build controllable and defined nanostructures for material and biomedical applications, Nano Today, 10, p. 631-655, 2015.
Afonin et al., In Silico Design and Enzymatic Synthesis of Functional RNA Nanoparticles, Acc. Chem. Res 47, p. 1731-1741, 2014.

(Continued)

*Primary Examiner* — Tracy Vivlemore
(74) *Attorney, Agent, or Firm* — Thomas | Horstemeyer, LLP

(57) ABSTRACT

Disclosed herein are high Tm RNA nanostructures that can be composed of one or more modules or motifs to build RNA nanostructures with or without layers. The RNA nanostructures can have a core domain and three or more double-stranded arms and formulations thereof to conjugate high copy numbers of therapeutics, pH responsive or enzyme cleavable drug cargo. Also described herein is a design strategy for generation of synthetic RNA oligonucleotides that can self assemble into highly thermostable RNA structures. Also described herein are uses of the RNA nanostructures described herein.

19 Claims, 134 Drawing Sheets
Specification includes a Sequence Listing.

(56) References Cited

OTHER PUBLICATIONS

Shu et al., Fabrication of pRNA nanoparticles to deliver therapeutic RNAs and bioactive compounds into tumor cells, Nature Protocols, vol. 8, No. 9, p. 1635-1659, 2013.

* cited by examiner

| Content | Theoretical Value (m/z) | Experiment Value (m/z) | Error (Da) |
|---|---|---|---|
| $a_{3WJ}$ | 5784.4 | 5784.9 | -0.5 |
| $a_{3WJ}$-Alkyne | 5784.4+160.0=5944.4 | 5945.6 | -1.2 |
| $a_{3WJ}$-PTX | 5944.4+992.4=6936.8 | 6939.2 | -2.4 |

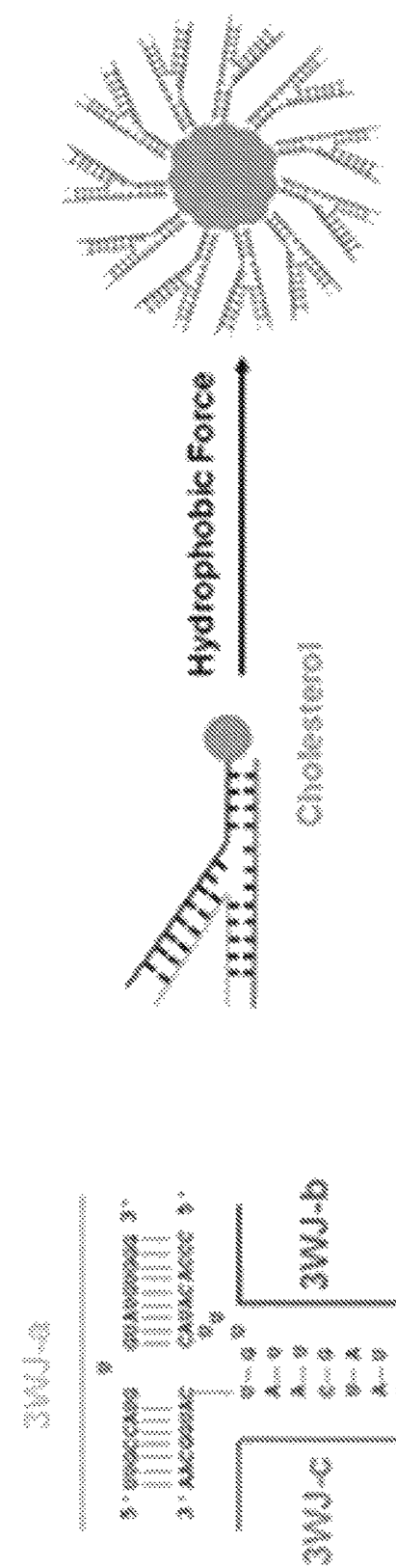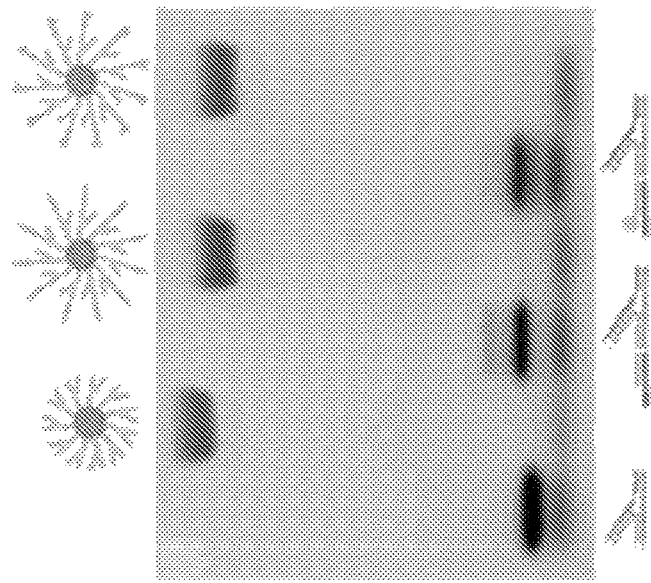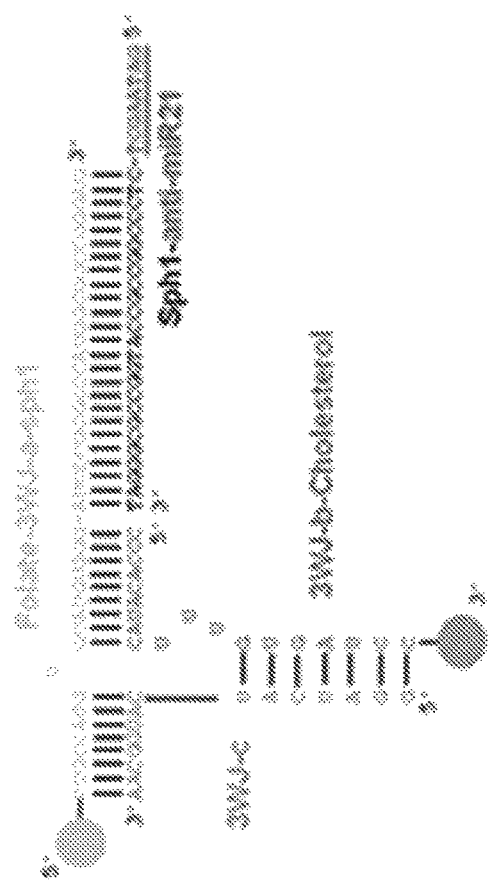
FIG. 6A
FIG. 6B 1. 11ext SF5-3WJ a-6 Taxol
2. 11ext SF5-3WJ a+b-12 Taxol
3. 11ext SF5-3WJ a+b+c-18 Taxol
4. 11ext SF5-3WJ a+b+c-18 alkyne
5. 11ext SF5-4WJ a-6 Taxol
6. 11ext SF5-4WJ a+b-12 Taxol
7. 11ext SF5-4WJ a+b+c-18 Taxol
8. 11ext SF5-4WJ a+b+c+d-24 Taxol
9. 11ext SF5-4WJ a+b+c+d-24 alkyne Three 3WJ cores: Phi29, SF5, M2
Four sets of helixes: WT, Mod, 30, 32

| Design 3WJ | C (μM) | Tm (°C) (TGGE) | C (μM) | Tm (°C) (qPCR) |
|---|---|---|---|---|
| Phi29-WT | 2.5 | 56 | 2 | 60.00 |
| Phi29-Mod | 2.5 | 62 | 2 | 63.69 |
| Phi29-30 | 2.5 | 70 | 2 | 72.45 |
| SF5-30 | 2.5 | 80 | 2 | 76.23 |
| M2-30 | 2.5 | 68 | 2 | 73.91 |
| Phi29-32 | N/A | N/A | 2 | 75.13 |
| SF5-32 | N/A | N/A | 2 | 79.06 |
| M2-32 | N/A | N/A | 2 | 82.03 |

FIG. 30C

| 3WJ | C (μM) | $t_{1/2}$ (h) |
|---|---|---|
| Phi29 WT | 2.5 | 8 |
| Phi29-Mod | 2.5 | 24 |
| Phi29-30 | 2.5 | >72 |
| SF5-30 | 2.5 | >72 |
| M2-30 | 2.5 | >72 |
| Phi29-32 | 2.5 | >72 |
| SF5-32 | 2.5 | >72 |
| M2-32 | 2.5 | N/A |

FIG. 31B

| | Conc. (µM) | Tm (°C) | Conc. (µM) | Tm (°C) |
|---|---|---|---|---|
| 3WJ-WT | 2.5 | 56 | 5 | 63.5 |
| 3WJ-Mod | 2.5 | 62 | 5 | 67.2 |
| 3WJ-30 | 2.5 | 70 | 5 | 74.4 |
| MW-2L | 1 | 52 | 5 | 72.3 |
| 30M-2L | 1 | 58 | 5 | 79.4 |
| 30MW-3L | 1 | 54 | 3 | 76.5 |
| Ext 30MW-3L | 1 | 54 | 3 | 92* |

FIG. 33C

| | | |
|---|---|---|
| 12rev | GAGUAUAUGUUAGGCCUGGGUGAGUCCUUGCGUCUCUACCG | SEQ ID NO: 1 |
| 23rev | CGGUAGAAGAGCAAGGACUUGCUAGUGUGGUACUGUUCCC | SEQ ID NO: 2 |
| 34rev | GGGAACAGUACCACAACUAGUGUCCCGGAUAGGACAUACA | SEQ ID NO: 4 |
| 45rev | UGUAUGUCCCUAUCCCGGGAUGCUCCCAUGAUGAAUACAGC | SEQ ID NO: 6 |
| 56rev | GCUGUAUUCAUCAUGGGAGUGGCCAUUGGAUCGUAUGAGC | SEQ ID NO: 8 |
| 67rev | GCUCAUACGAUCCCAAUGCCUGAAACAAACAGAGCAAGCCUCC | SEQ ID NO: 10 |
| 78rev | GGAGGCUUGCUCUGUUUUGUUUGCGAUUCCGCGUUACACA | SEQ ID NO: 11 |
| 89rev | UGUGUAACGCGGAAAUCGCGUGCCUUGCGUACGUCUUAC | SEQ ID NO: 14 |
| 31rev | GGGAACAGUACCACAACUAGUGCCCAGGCCUAACAUAUACUC | SEQ ID NO: 3 |
| 41rev | UGUAUGUCCCUAUCCCGGGAUGCCCAGGCCUAACAUAUACUC | SEQ ID NO: 5 |
| 51rev | GCUGUAUUCAUCAUGCGGAGUGCCCAGGCCUAACAUAUACUC | SEQ ID NO: 7 |
| 61rev | GCUCAUACGAUCCAAUGCCUGCCCAGGCCUAACAUAUACUC | SEQ ID NO: 9 |
| 71rev | GGAGGCUUGCUCUGUUUGUUUGCCCAGGCCUAACAUAUACUC | SEQ ID NO: 10 |
| 81rev | UGUGUAACGCGGAAAUCGCGUGCCCAGGCCUAACAUAUACUC | SEQ ID NO: 12 |
| 91rev | GUAAGACGUACGCGAGCAGGUGCCCAGGCCUAACAUAUACUC | SEQ ID NO: 15 |

FIG. 37B

| | Conc. (μM) | Tm (°C) (TGGE) | Conc. (μM) | Tm (°C) (qPCR) |
|---|---|---|---|---|
| Phi29-WT 3WJ | 2 | 56 | 2.5 | 62.0 |
| 4WJ | 2.5 | >80 | 2.5 | 86.0 |
| 5WJ | 2.5 | >80 | 2.5 | 87.8 |
| 6WJ | 2.5 | >80 | 2.5 | 88.3 |

★ cargo compound or functional group

★ First cargo compound or Functional group
● Second cargo compound Functional group Ext 30MW-3layer
With 18 Taxol 3D represntations:
https://commons.wikimedia.org/w/index.php?curid=16096179

Gd(III) chelation

■ = DOTA

▨ = DOTA-Gd

◕ = Folic acid

SF5 3WJ-DOTA, multiple

SF5 3WJ-NH₂

1. SF5 3WJ-DOTA, multiple
2. SF5 3WJ-DOTA/(Gd), multiple; desalted in PBS
3. SF5 3WJ-DOTA/(Gd), multiple; desalted in H2O
4. SF5 3WJ-DOTA, Three
5. SF5 3WJ-DOTA/(Gd), Three; desalted in PBS
6. SF5 3WJ-DOTA/(Gd), Three; desalted in H2O 1. SF5 3WJa-NOTA
2. SF5 3WJa-NOTA + 3WJb-NOTA
3. SF5 3WJa-NOTA + 3WJb-NOTA + 3WJc-NOTA

- Hydrophobic core: Tocopherol
- Conjugate : Erlotinib
- Ligand: Folic acid

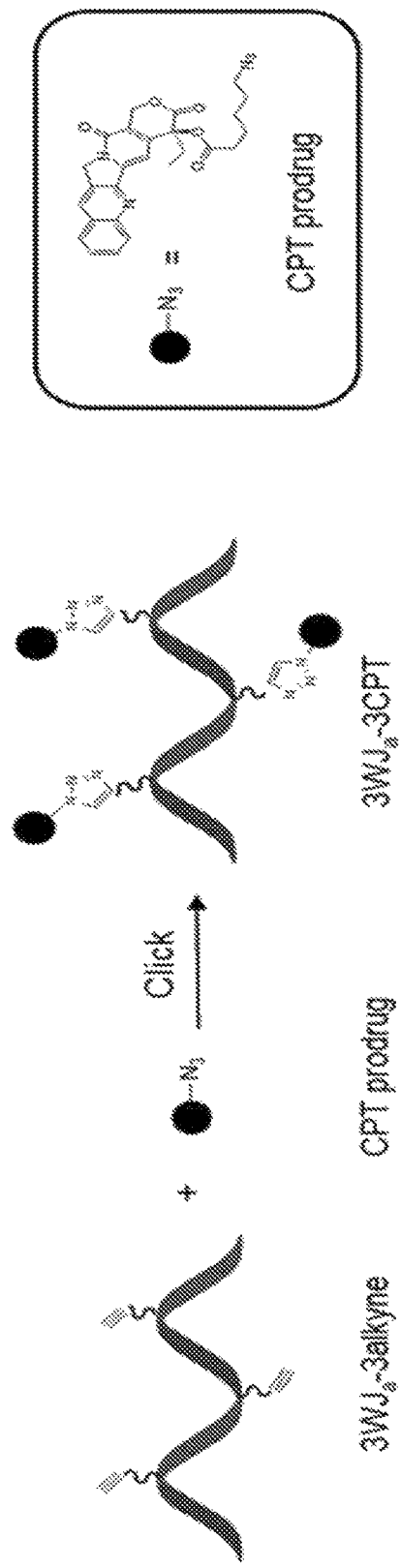
FIG. 54A
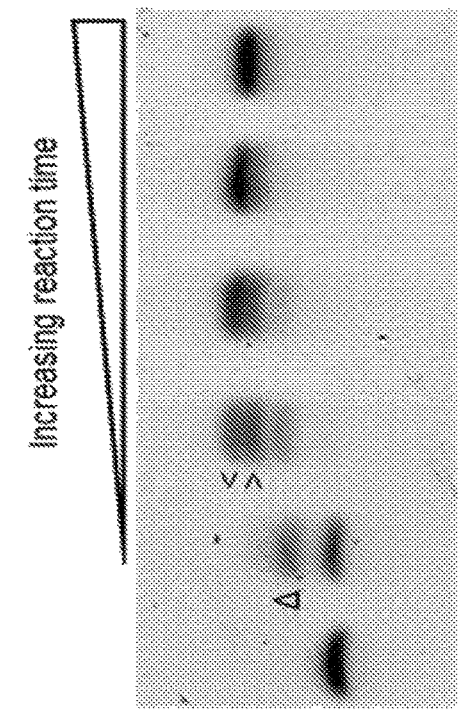
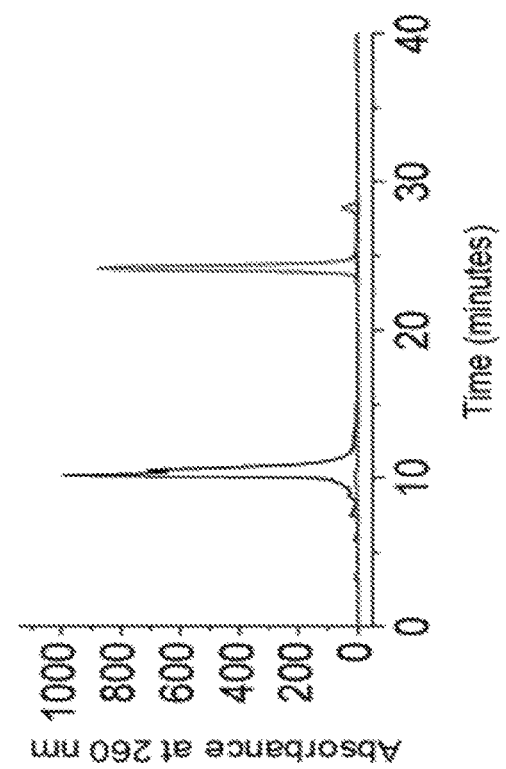
FIG. 54C
FIG. 54B

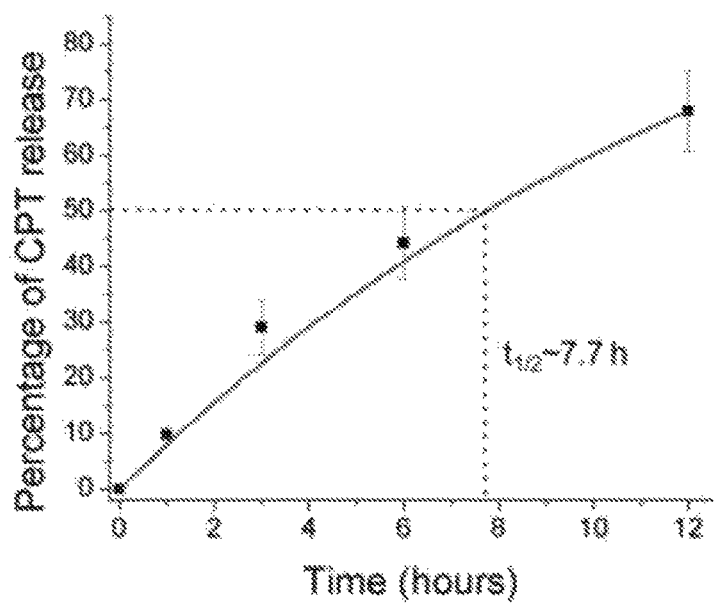
FIG. 54I
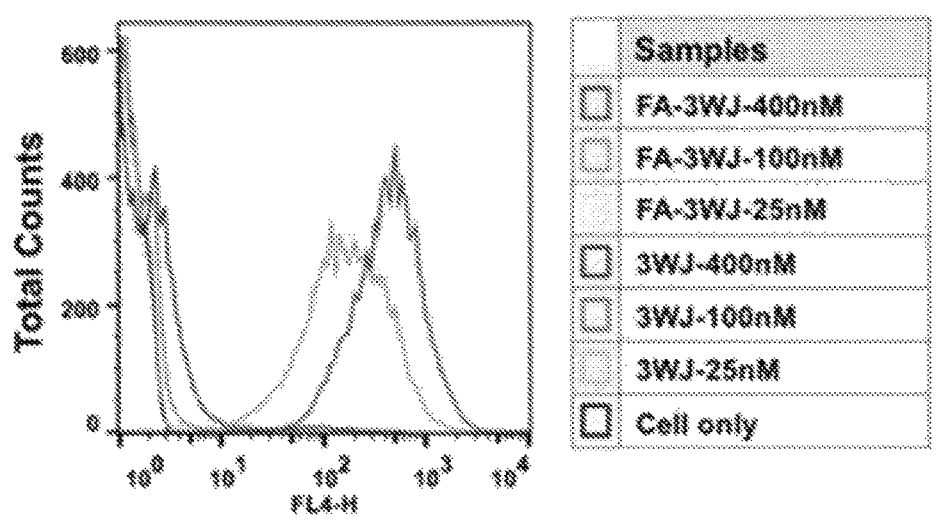
FIG. 54J
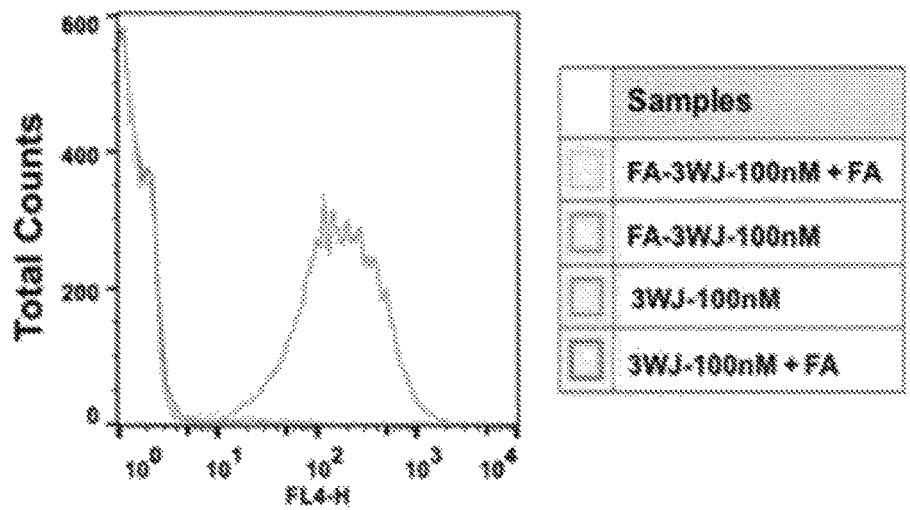

SEQUENCE LISTING

<160> NUMBER OF SEQ ID NOS: 69

<210> SEQ ID NO 1
<211> LENGTH: 42
<212> TYPE: DNA
<213> ORGANISM: Artificial Sequence
<220> FEATURE:
<223> OTHER INFORMATION: Synthetic RNA Oligonucleotide 12rev

<400> SEQUENCE: 1
gacuauaugu uaggccuggg ugaguccuug cgucuucuac cg                           42

<210> SEQ ID NO 2
<211> LENGTH: 42
<212> TYPE: DNA
<213> ORGANISM: Artificial Sequence
<220> FEATURE:
<223> OTHER INFORMATION: synthetic RNA oligonucleotide 23rev

<400> SEQUENCE: 2
cgguagaaga cgcaaggacu ugcuaguugu gguacuguuc cc                           42

<210> SEQ ID NO 3
<211> LENGTH: 42
<212> TYPE: DNA
<213> ORGANISM: Artificial Sequence
<220> FEATURE:
<223> OTHER INFORMATION: synthetic RNA oligonucleotide 31rev

<400> SEQUENCE: 3
gggaacagua ccacaacuag ugcccaggcc uaacauauac uc                           42

<210> SEQ ID NO 4
<211> LENGTH: 42
<212> TYPE: DNA
<213> ORGANISM: Artificial Sequence
<220> FEATURE:
<223> OTHER INFORMATION: synthetic RNA oligonucleotide 34rev

<400> SEQUENCE: 4
gggaacagua ccacaacuag ugucccggga uagggacaua ca                           42

<210> SEQ ID NO 5
<211> LENGTH: 42
<212> TYPE: DNA
<213> ORGANISM: Artificial Sequence
<220> FEATURE:
<223> OTHER INFORMATION: synthetic RNA oligonucleotide 41rev

<400> SEQUENCE: 5
uguauguccc uaucccggga ugcccaggcc uaacauauac uc                           42

<210> SEQ ID NO 6
<211> LENGTH: 42
<212> TYPE: DNA
<213> ORGANISM: Artificial Sequence
<220> FEATURE:
<223> OTHER INFORMATION: synthetic RNA oligonucleotide 45rev

<400> SEQUENCE: 6
uguauguccc uaucccggga ugcuccgcau gaugaauaca gc                           42

<210> SEQ ID NO 7
<211> LENGTH: 42
<212> TYPE: DNA
<213> ORGANISM: Artificial Sequence

```
<220> FEATURE:
<223> OTHER INFORMATION: synthetic RNA oligonucleotide 51rev

<400> SEQUENCE: 7
gcuguauuca ucaugcggag ugcccaggcc uaacauauac uc                           42

<210> SEQ ID NO 8
<211> LENGTH: 42
<212> TYPE: DNA
<213> ORGANISM: Artificial Sequence
<220> FEATURE:
<223> OTHER INFORMATION: synthetic RNA oligonucleotide 56rev

<400> SEQUENCE: 8
gcuguauuca ucaugcggag ugggcauugg gaucguauga gc                           42

<210> SEQ ID NO 9
<211> LENGTH: 42
<212> TYPE: DNA
<213> ORGANISM: Artificial Sequence
<220> FEATURE:
<223> OTHER INFORMATION: synthetic RNA oligonucleotide 61rev

<400> SEQUENCE: 9
gcucauacga ucccaaugcc ugcccaggcc uaacauauac uc                           42

<210> SEQ ID NO 10
<211> LENGTH: 42
<212> TYPE: DNA
<213> ORGANISM: Artificial Sequence
<220> FEATURE:
<223> OTHER INFORMATION: synthetic RNA oligonucleotide 67rev

<400> SEQUENCE: 10
gcucauacga ucccaaugcc ugaacaaaca gagcaagccu cc                           42

<210> SEQ ID NO 11
<211> LENGTH: 42
<212> TYPE: DNA
<213> ORGANISM: Artificial Sequence
<220> FEATURE:
<223> OTHER INFORMATION: synthetic RNA oligonucleotide 71rev

<400> SEQUENCE: 11
ggaggcuugc ucuguuuguu ugcccaggcc uaacauauac uc                           42

<210> SEQ ID NO 12
<211> LENGTH: 42
<212> TYPE: DNA
<213> ORGANISM: Artificial Sequence
<220> FEATURE:
<223> OTHER INFORMATION: synthetic RNA oligonucleotide 78rev

<400> SEQUENCE: 12
ggaggcuugc ucuguuuguu ugcgcgauuu ccgcguuaca ca                           42

<210> SEQ ID NO 13
<211> LENGTH: 42
<212> TYPE: DNA
<213> ORGANISM: Artificial Sequence
<220> FEATURE:
<223> OTHER INFORMATION: synthetic RNA oligonucleotide 81rev

<400> SEQUENCE: 13
uguguaacgc ggaaaucgcg ugcccaggcc uaacauauac uc                           42
```

<210> SEQ ID NO 14
<211> LENGTH: 42
<212> TYPE: DNA
<213> ORGANISM: Artificial Sequence
<220> FEATURE:
<223> OTHER INFORMATION: synthetic RNA oligonucleotide 89rev

<400> SEQUENCE: 14
uguguaacgc ggaaaucgcg ugccugcucg cguacgucuu ac                42

<210> SEQ ID NO 15
<211> LENGTH: 42
<212> TYPE: DNA
<213> ORGANISM: Artificial Sequence
<220> FEATURE:
<223> OTHER INFORMATION: synthetic RNA oligonucleotide 91rev

<400> SEQUENCE: 15
guaagacgua cgcgacgagg ugcccaggcc uaacauauac uc                42

<210> SEQ ID NO 16
<211> LENGTH: 18
<212> TYPE: DNA
<213> ORGANISM: Artificial Sequence
<220> FEATURE:
<223> OTHER INFORMATION: synthetic RNA oligonucleotide a3WJ

<400> SEQUENCE: 16
uugccaugug uauguggg                                           18

<210> SEQ ID NO 17
<211> LENGTH: 20
<212> TYPE: DNA
<213> ORGANISM: Artificial Sequence
<220> FEATURE:
<223> OTHER INFORMATION: synthetic RNA oligonucleotide b3WJ

<400> SEQUENCE: 17
cccacauacu uguugaucc                                          20

<210> SEQ ID NO 18
<211> LENGTH: 16
<212> TYPE: DNA
<213> ORGANISM: Artificial Sequence
<220> FEATURE:
<223> OTHER INFORMATION: synthetic RNA oligonucleotide c3WJ

<400> SEQUENCE: 18
ggaucaauca uggcaa                                             16

<210> SEQ ID NO 19
<211> LENGTH: 18
<212> TYPE: DNA
<213> ORGANISM: Artificial Sequence
<220> FEATURE:
<223> OTHER INFORMATION: synthetic RNA oligonucleotide aPhi29-Mod

<400> SEQUENCE: 19
auucgcugug ugguagug                                           18

<210> SEQ ID NO 20
<211> LENGTH: 20
<212> TYPE: DNA
<213> ORGANISM: Artificial Sequence
<220> FEATURE:
<223> OTHER INFORMATION: synthetic RNA oligonucleotide bPhi29-Mod

```
<400> SEQUENCE: 20
cacuaccacu uguccuacg                                            20

<210> SEQ ID NO 21
<211> LENGTH: 16
<212> TYPE: DNA
<213> ORGANISM: Artificial Sequence
<220> FEATURE:
<223> OTHER INFORMATION: synthetic RNA oligonucleotide cPhi29-Mod

<400> SEQUENCE: 21
cguaggacca gcgaau                                               16

<210> SEQ ID NO 22
<211> LENGTH: 18
<212> TYPE: DNA
<213> ORGANISM: Artificial Sequence
<220> FEATURE:
<223> OTHER INFORMATION: synthetic RNA oligonucleotide aPhi29-30

<400> SEQUENCE: 22
gcgugcugug ugcuaccg                                             18

<210> SEQ ID NO 23
<211> LENGTH: 20
<212> TYPE: DNA
<213> ORGANISM: Artificial Sequence
<220> FEATURE:
<223> OTHER INFORMATION: synthetic RNA oligonucleotide bPhi29-30

<400> SEQUENCE: 23
cgguagcacu uugcugugcg                                           20

<210> SEQ ID NO 24
<211> LENGTH: 20
<212> TYPE: DNA
<213> ORGANISM: Artificial Sequence
<220> FEATURE:
<223> OTHER INFORMATION: synthetic RNA oligonucleotide cPhi29-30

<400> SEQUENCE: 24
cgguagcacu uugcugugcg                                           20

<210> SEQ ID NO 25
<211> LENGTH: 17
<212> TYPE: DNA
<213> ORGANISM: Artificial Sequence
<220> FEATURE:
<223> OTHER INFORMATION: synthetic RNA oligonucleotide aSF5-30

<400> SEQUENCE: 25
gcgugcuggu gcuaccg                                              17

<210> SEQ ID NO 26
<211> LENGTH: 19
<212> TYPE: DNA
<213> ORGANISM: Artificial Sequence
<220> FEATURE:
<223> OTHER INFORMATION: synthetic RNA oligonucleotide bSF5-30

<400> SEQUENCE: 26
cgguagcacg ggcugugcg                                            19

<210> SEQ ID NO 27
```

```
<210> SEQ ID NO 27
<211> LENGTH: 16
<212> TYPE: DNA
<213> ORGANISM: Artificial Sequence
<220> FEATURE:
<223> OTHER INFORMATION: synthetic RNA oligonucleotide cSF5-30

<400> SEQUENCE: 27
cgcacagcca gcacgc                                                     16

<210> SEQ ID NO 28
<211> LENGTH: 17
<212> TYPE: DNA
<213> ORGANISM: Artificial Sequence
<220> FEATURE:
<223> OTHER INFORMATION: Synthetic RNA oligonucleotide aM2-30

<400> SEQUENCE: 28
gcgugcuggu gcuaccg                                                    17

<210> SEQ ID NO 29
<211> LENGTH: 18
<212> TYPE: DNA
<213> ORGANISM: Artificial Sequence
<220> FEATURE:
<223> OTHER INFORMATION: Synthetic RNA oligonucleotide bM2-30

<400> SEQUENCE: 29
cgguagcacc gcugugcg                                                   18

<210> SEQ ID NO 30
<211> LENGTH: 18
<212> TYPE: DNA
<213> ORGANISM: Artificial Sequence
<220> FEATURE:
<223> OTHER INFORMATION: Synthetic RNA oligonucleotide cM2-30

<400> SEQUENCE: 30
cgcacagccu cagcacgc                                                   18

<210> SEQ ID NO 31
<211> LENGTH: 18
<212> TYPE: DNA
<213> ORGANISM: Artificial Sequence
<220> FEATURE:
<223> OTHER INFORMATION: Synthetic RNA oligonucleotide aPhi29-32

<400> SEQUENCE: 31
acgcgacgug ugcaugcc                                                   18

<210> SEQ ID NO 32
<211> LENGTH: 20
<212> TYPE: DNA
<213> ORGANISM: Artificial Sequence
<220> FEATURE:
<223> OTHER INFORMATION: Synthetic RNA oligonucleotide bPhi29-32

<400> SEQUENCE: 32
ggcaugcacu uugcguugcg                                                 20

<210> SEQ ID NO 33
<211> LENGTH: 16
<212> TYPE: DNA
<213> ORGANISM: Artificial Sequence
<220> FEATURE:
<223> OTHER INFORMATION: Synthetic RNA oligonucleotide cPhi29-32

<400> SEQUENCE: 33
```
cgcaacgccg ucgcgu    16

<210> SEQ ID NO 34
<211> LENGTH: 17
<212> TYPE: DNA
<213> ORGANISM: Artificial Sequence
<220> FEATURE:
<223> OTHER INFORMATION: Synthetic RNA oligonucleotide aSF5-32

<400> SEQUENCE: 34
acgcgacggu gcaugcc    17

<210> SEQ ID NO 35
<211> LENGTH: 19
<212> TYPE: DNA
<213> ORGANISM: Artificial Sequence
<220> FEATURE:
<223> OTHER INFORMATION: Synthetic RNA oligonucleotide bSF5-32

<400> SEQUENCE: 35
ggcaugcacg ggcguugcg    19

<210> SEQ ID NO 36
<211> LENGTH: 16
<212> TYPE: DNA
<213> ORGANISM: Artificial Sequence
<220> FEATURE:
<223> OTHER INFORMATION: Synthetic RNA oligonucleotide cSF5-32

<400> SEQUENCE: 36
cgcaacgccg ucgcgu    16

<210> SEQ ID NO 37
<211> LENGTH: 17
<212> TYPE: DNA
<213> ORGANISM: Artificial Sequence
<220> FEATURE:
<223> OTHER INFORMATION: Synthetic RNA oligonucleotide aM2-32

<400> SEQUENCE: 37
acgcgacggu gcaugcc    17

<210> SEQ ID NO 38
<211> LENGTH: 18
<212> TYPE: DNA
<213> ORGANISM: Artificial Sequence
<220> FEATURE:
<223> OTHER INFORMATION: Synthetic RNA oligonucleotide bM2-32

<400> SEQUENCE: 38
ggcaugcacc gcguugcg    18

<210> SEQ ID NO 39
<211> LENGTH: 18
<212> TYPE: DNA
<213> ORGANISM: Artificial Sequence
<220> FEATURE:
<223> OTHER INFORMATION: Synthetic RNA oligonucleotide cM2-32

<400> SEQUENCE: 39
cgcaacgccu cgucgcgu    18

<210> SEQ ID NO 40
<211> LENGTH: 38
<212> TYPE: DNA

```
<213> ORGANISM: Artificial Sequence
<220> FEATURE:
<223> OTHER INFORMATION: Synthetic RNA oligonucleotide Mod-a/WT-b

<400> SEQUENCE: 40
auucgcugug ugguagugcc cacauacuuu guugaucc                                    38

<210> SEQ ID NO 41
<211> LENGTH: 40
<212> TYPE: DNA
<213> ORGANISM: Artificial Sequence
<220> FEATURE:
<223> OTHER INFORMATION: Synthetic RNA oligonucleotide Mod-b/WT-b

<400> SEQUENCE: 41
cacuaccacu uuguccuacg cccacauacu uuguugaucc                                  40

<210> SEQ ID NO 42
<211> LENGTH: 36
<212> TYPE: DNA
<213> ORGANISM: Artificial Sequence
<220> FEATURE:
<223> OTHER INFORMATION: Synthetic RNA oligonucleotide Mod-c/WT-b

<400> SEQUENCE: 42
cguaggacca gcgaauccca cauacuuugu ugaucc                                      36

<210> SEQ ID NO 43
<211> LENGTH: 38
<212> TYPE: DNA
<213> ORGANISM: Artificial Sequence
<220> FEATURE:
<223> OTHER INFORMATION: Synthetic RNA oligonucleotide 30a/Mod-b

<400> SEQUENCE: 43
gcgugcugug ugcuaccgca cuaccacuuu guccuacg                                    38

<210> SEQ ID NO 44
<211> LENGTH: 40
<212> TYPE: DNA
<213> ORGANISM: Artificial Sequence
<220> FEATURE:
<223> OTHER INFORMATION: Synthetic RNA oligonucleotide 30b/Mod-b

<400> SEQUENCE: 44
cgguagcacu uugcugugcg cacuaccacu uuguccuacg                                  40

<210> SEQ ID NO 45
<211> LENGTH: 36
<212> TYPE: DNA
<213> ORGANISM: Artificial Sequence
<220> FEATURE:
<223> OTHER INFORMATION: Synthetic RNA oligonucleotide 30c/Mod-b

<400> SEQUENCE: 45
cgcacagcca gcacgccacu accacuuugu ccuacg                                      36

<210> SEQ ID NO 46
<211> LENGTH: 60
<212> TYPE: DNA
<213> ORGANISM: Artificial Sequence
<220> FEATURE:
<223> OTHER INFORMATION: Synthetic RNA oligonucleotide Ext30-a/Mod-b

<400> SEQUENCE: 46
ccuauucagg ugcgugcugu gugcuaccga uguaauucaa cacuaccacu uuguccuacg            60
```

<210> SEQ ID NO 47
<211> LENGTH: 62
<212> TYPE: DNA
<213> ORGANISM: Artificial Sequence
<220> FEATURE:
<223> OTHER INFORMATION: Synthetic RNA oligonucleotide Ext30-b/Mod-b

<400> SEQUENCE: 47
uugaauuaca ucgguagcac uuugcugugc gaggcugaac agcacuacca cuuuguccua    60
cg                                                                  62

<210> SEQ ID NO 48
<211> LENGTH: 58
<212> TYPE: DNA
<213> ORGANISM: Artificial Sequence
<220> FEATURE:
<223> OTHER INFORMATION: Synthetic RNA oligonucleotide Ext30-c/Mod-b

<400> SEQUENCE: 48
cuguucagcc ucgcacagcc agcacgcacc ugaauaggca cuaccacuuu guccuacg      58

<210> SEQ ID NO 49
<211> LENGTH: 38
<212> TYPE: DNA
<213> ORGANISM: Artificial Sequence
<220> FEATURE:
<223> OTHER INFORMATION: Synthetic RNA oligonucleotide WT-b/Mod-a

<400> SEQUENCE: 49
cccacauacu uguugaucc auucgcugug ugguagug                             38

<210> SEQ ID NO 50
<211> LENGTH: 36
<212> TYPE: DNA
<213> ORGANISM: Artificial Sequence
<220> FEATURE:
<223> OTHER INFORMATION: Synthetic RNA oligonucleotide WT-b/Mod-c

<400> SEQUENCE: 50
cccacauacu uguugaucc cguaggacca gcgaau                               36

<210> SEQ ID NO 51
<211> LENGTH: 40
<212> TYPE: DNA
<213> ORGANISM: Artificial Sequence
<220> FEATURE:
<223> OTHER INFORMATION: Synthetic RNA oligonucleotide SF5-4WJ-a

<400> SEQUENCE: 51
uuagguaaag ccaccugcag gugcuaccga uguaauucaa                          40

<210> SEQ ID NO 52
<211> LENGTH: 41
<212> TYPE: DNA
<213> ORGANISM: Artificial Sequence
<220> FEATURE:
<223> OTHER INFORMATION: Synthetic RNA oligonucleotide SF5-4WJ-b

<400> SEQUENCE: 52
uugaauuaca ucgguagcac gggcugugcg aggcugaaca g                        41

<210> SEQ ID NO 53
<211> LENGTH: 38
<212> TYPE: DNA

```
<213> ORGANISM: Artificial Sequence
<220> FEATURE:
<223> OTHER INFORMATION: Synthetic RNA oligonucleotide SF5-4WJ-c

<400> SEQUENCE: 53 cguucagcc ucgcacagcc agcacgcacc ugaauagg                              38

<210> SEQ ID NO 54
<211> LENGTH: 41
<212> TYPE: DNA
<213> ORGANISM: Artificial Sequence
<220> FEATURE:
<223> OTHER INFORMATION: Synthetic RNA oligonucleotide SF5-4WJ-d

<400> SEQUENCE: 54
ccuauucagg ugcgugcugg gcugcaggug gcuuuaccua a                         41

<210> SEQ ID NO 55
<211> LENGTH: 43
<212> TYPE: RNA
<213> ORGANISM: Artificial Sequence
<220> FEATURE:
<223> OTHER INFORMATION: Synthetic Construct

<400> SEQUENCE: 55
uugccaugug uauguggggau cccgcggcca uggcggccgg gag                      43

<210> SEQ ID NO 56
<211> LENGTH: 33
<212> TYPE: DNA
<213> ORGANISM: Artificial Sequence
<220> FEATURE:
<223> OTHER INFORMATION: Synthetic Construct

<400> SEQUENCE: 56
gataagctct cccggccgcc atggccgcgg gat                                  33

<210> SEQ ID NO 57
<211> LENGTH: 18
<212> TYPE: RNA
<213> ORGANISM: Artificial Sequence
<220> FEATURE:
<223> OTHER INFORMATION: Synthetic Construct

<400> SEQUENCE: 57
auucgcugug ugguagug                                                   18

<210> SEQ ID NO 58
<211> LENGTH: 21
<212> TYPE: RNA
<213> ORGANISM: Artificial Sequence
<220> FEATURE:
<223> OTHER INFORMATION: Synthetic Construct

<400> SEQUENCE: 58
cacuaccacu uuguggguagu g                                              21

<210> SEQ ID NO 59
<211> LENGTH: 17
<212> TYPE: RNA
<213> ORGANISM: Artificial Sequence
<220> FEATURE:
<223> OTHER INFORMATION: Synthetic Construct

<400> SEQUENCE: 59
cacuaccacc agcgaau                                                    17
```

<210> SEQ ID NO 60
<211> LENGTH: 18
<212> TYPE: RNA
<213> ORGANISM: Artificial Sequence
<220> FEATURE:
<223> OTHER INFORMATION: Synthetic Construct

<400> SEQUENCE: 60
gcgugcugug ugcuaccg                                          18

<210> SEQ ID NO 61
<211> LENGTH: 20
<212> TYPE: RNA
<213> ORGANISM: Artificial Sequence
<220> FEATURE:
<223> OTHER INFORMATION: Synthetic Construct

<400> SEQUENCE: 61
cgguagcacu uugcugugcg                                        20

<210> SEQ ID NO 62
<211> LENGTH: 16
<212> TYPE: RNA
<213> ORGANISM: Artificial Sequence
<220> FEATURE:
<223> OTHER INFORMATION: Synthetic Construct

<400> SEQUENCE: 62
cgcacagcca gcacgc                                            16

<210> SEQ ID NO 63
<211> LENGTH: 39
<212> TYPE: RNA
<213> ORGANISM: Artificial Sequence
<220> FEATURE:
<223> OTHER INFORMATION: Synthetic Construct

<400> SEQUENCE: 63
ccuauucagg ugcgugcugg ugcuaccgau guaauucaa                   39

<210> SEQ ID NO 64
<211> LENGTH: 41
<212> TYPE: RNA
<213> ORGANISM: Artificial Sequence
<220> FEATURE:
<223> OTHER INFORMATION: Synthetic Construct

<400> SEQUENCE: 64
uugaauuaca ucgguagcac gggcugugcg aggcugaaca g                41

<210> SEQ ID NO 65
<211> LENGTH: 38
<212> TYPE: RNA
<213> ORGANISM: Artificial Sequence
<220> FEATURE:
<223> OTHER INFORMATION: Synthetic Construct

<400> SEQUENCE: 65 cguucagcc ucgcacagcc agcacgcacc ugaauagg                     38

<210> SEQ ID NO 66
<211> LENGTH: 40
<212> TYPE: RNA
<213> ORGANISM: Artificial Sequence
<220> FEATURE:

```
<223> OTHER INFORMATION: Synthetic Construct

<400> SEQUENCE: 66
uuagguaaag ccaccugcag gugcuaccga uguaauucaa                    40

<210> SEQ ID NO 67
<211> LENGTH: 41
<212> TYPE: RNA
<213> ORGANISM: Artificial Sequence
<220> FEATURE:
<223> OTHER INFORMATION: Synthetic Construct

<400> SEQUENCE: 67
uugaauuaca ucgguagcac gggcugugcg aggcugaaca g                  41

<210> SEQ ID NO 68
<211> LENGTH: 38
<212> TYPE: RNA
<213> ORGANISM: Artificial Sequence
<220> FEATURE:
<223> OTHER INFORMATION: Synthetic Construct

<400> SEQUENCE: 68
cuguucagcc ucgcacagcc agcacgcacc ugaauagg                      38

<210> SEQ ID NO 69
<211> LENGTH: 41
<212> TYPE: RNA
<213> ORGANISM: Artificial Sequence
<220> FEATURE:
<223> OTHER INFORMATION: Synthetic Construct

<400> SEQUENCE: 69
ccuauucagg ugcgugcugg gcugcaggug gcuuuaccua a                  41
```

RNA NANOSTRUCTURES, METHODS OF MAKING, AND USES THEREOF

CROSS-REFERENCE TO RELATED APPLICATIONS

This application is a National Stage of International Application No. PCT/US2018/060567, filed Nov. 12, 2018, which claims benefit of U.S. Provisional Application No. 62/628,591, filed Feb. 9, 2018, and U.S. Provisional Application No. 62/755,696, filed Nov. 5, 2018, which are hereby incorporated herein by reference in their entireties.

STATEMENT REGARDING FEDERALLY SPONSORED RESEARCH OR DEVELOPMENT

This invention was made with Government Support under Grant Nos. CA207946 and CA186100 awarded by the National Institutes of Health, and Grant No. W81XWH-15-1-0052 awarded by the United States Army Medical Research and Materiel Command. The Government has certain rights in the invention.

SEQUENCE LISTING

This application contains a sequence listing filed in electronic form as an ASCII.txt file entitled "321501-2160_ST25" created on Oct. 15, 2021 having 14,612 bytes. The content of the sequence listing is incorporated herein in its entirety.

BACKGROUND

Chemotherapy still plays a key role in cancer therapy. However, most frequently used anti-cancer drugs are hydrophobic small molecules, including paclitaxel which is one of the most active chemotherapeutic agents for a variety of cancer treatments. The poor water-solubility of these small molecules frequently leads to severe side effects, non-specific toxicity, and low drug efficacy. An efficient and controlled drug delivery and release platform is in demand.

SUMMARY

In aspects, described herein are RNA motifs that can be composed of at least three synthetic RNA oligonucleotides, wherein the at least three synthetic RNA oligonucleotides can be coupled to each other, wherein the at least three synthetic RNA oligonucleotides can form a central core domain and at least three double-stranded arms arranged around the core domain and extending away from the central core domain, wherein the melting temperature of the RNA motif can be greater than 65 degrees Celcius. The modular RNA motif can include 3-9 strands of synthetic RNA oligonucleotides. One or more of the at least three synthetic RNA oligonucleotides can include one or more modified nucleotides. One or more modified nucleotides can be a terminal nucleotide or a non-terminal nucleotide. The modification can be an alkyne attached to the one or more modified nucleotides. The modification can be a linker attached to the one more modified nucleotides. The modular RNA motif can further include a cargo compound molecule attached to a synthetic RNA oligonucleotide of the at least three synthetic RNA oligonucleotides. At least 3 to 100 cargo compound molecules can be attached to the synthetic RNA oligonucleotide. The modular RNA motif can further include a functional group attached to a nucleotide of one or more of the at least three synthetic RNA oligonucleotides. The functional group can be attached to a terminal nucleotide. The functional group can be attached to a non-terminal nucleotide. The modular RNA motif can further include a cargo compound attached to functional group. Each of the at least three synthetic RNA oligonucleotides can include a oligonucleotide sequence having a sequence that is about 80-100% identical to any one of SEQ ID NOS: 1-54. The at least three synthetic RNA oligonucleotides can be configured to self-assemble to form the modular RNA motif. The Tm of the modular RNA motif can be greater than about 70 degrees Celcius. The Tm of the modular RNA motif can range from about 70 degrees Celcius to about 100 degrees Celcius. The Tm of the modular RNA motif can range from about 65 degrees Celcius to about 100 degrees Celcius.

In aspects, also described herein are modular RNA motifs that can be composed of at least four synthetic RNA oligonucleotides, wherein the at least three synthetic RNA oligonucleotides can be coupled to each other, wherein the at least three synthetic RNA oligonucleotides can form a central core domain and at least three double-stranded arms can be arranged around the core domain and can extend away from the central core domain. The modular RNA motif can include 4-9 strands of synthetic RNA oligonucleotides. One or more of the at least three synthetic RNA oligonucleotides can include one or more modified nucleotides. One or more modified nucleotides can be a terminal nucleotide or a non-terminal nucleotide. The modification can be an alkyne attached to the one or more modified nucleotides. The modification can be a linker attached to the one more modified nucleotides. The modular RNA motif can further include a cargo compound molecule attached to a synthetic RNA oligonucleotide of the at least three synthetic RNA oligonucleotides. In aspects, at least 3 to 100 cargo compound molecules can be attached to the synthetic RNA oligonucleotide. The modular RNA motif can further include a functional group attached to a nucleotide of one or more of the at least three synthetic RNA oligonucleotides. The functional group can be attached to a terminal nucleotide. The functional group is attached to a non-terminal nucleotide. The modular RNA motif can further include a cargo compound attached to functional group. Each of the at least three synthetic RNA oligonucleotides can be composed of an oligonucleotide sequence having a sequence that is about 70-100% identical to any one of SEQ ID NOS: 1-54. The at least three synthetic RNA oligonucleotides can be configured to self-assemble to form the modular RNA motif.

In aspects, also described herein are RNA nanostructure that can include at least two modular RNA motifs as described herein, wherein the at least two modular RNA motifs can be attached to each other. The RNA nanostructure can include a central core, wherein the central core can include a first modular RNA motif; a first layer, wherein the first layer can include at least three modular RNA motifs, wherein each of modular RNA motifs in the at least three modular RNA motifs of the first layer can be attached to the first modular RNA motif; and a second layer, wherein the second layer comprises at least three modular RNA motifs, wherein each of the at least three modular RNA motifs of the second layer can be attached to a modular RNA motif of the at least three modular motifs of the first layer. In aspects, all of the modular RNA motifs in the nanostructure can have the same number of double-stranded arms. In aspects, the number of double-stranded arms on the modular RNA motifs of the first layer can be different than the number of double-stranded arms on the first modular RNA motif, on the modular RNA motifs of the second layer, or on both the first modular RNA motif and the modular RNA motifs of the second layer. In aspects, the number of double-stranded arms on the modular RNA motifs of the second layer can be different than the number of double-stranded arms on the first modular RNA motif, on the modular RNA motifs of the first layer, or on both the first modular RNA motif and the modular RNA motifs of the first layer. The number of double-stranded arms on the first modular RNA motif can be different than the number of double-stranded arms on the modular RNA motifs of the first layer, on the modular RNA motifs of the second layer, or on both the modular RNA motifs of the first layer and the second layer. The melting temperature (Tm) of the RNA nanostructure can be greater than 70 degrees Celcius. The Tm of the RNA nanostructure can range from 70 degrees Celcius to about 100 degrees Celcius. The first modular RNA motif can have a greater Tm then the modular RNA motifs of the first layer and the modular RNA motifs of the second layer. The modular RNA motifs of the first layer can have a greater Tm than the modular RNA motifs of the second layer. One or more of the RNA motifs can be coupled to one or more cargo compounds. One or more of the RNA motifs can be coupled to one or more functional groups. The cargo compound can be an anti-cancer compound, a chelator, radioactive isotope, a fluorophore, a miRNA, a anti-miRNA, a siRNA, a pH responsive prodrug, an enzyme cleavable prodrug, or any combination thereof. One or more of the RNA motifs is coupled to two or more cargo compounds and wherein at least two of the two or more cargo compounds are different types of cargo compounds.

In aspects, also described herein are methods that can include the step administering a modular RNA motif as described herein or a RNA nanostructure as described herein to a subject. The subject can have or be suspected of having a cancer.

In aspects, also described herein are methods of treating a cancer or a disease in subject that can include the step of administering a modular RNA motif as described herein or a RNA nanostructure as described herein to the subject.

In aspects, also described herein is a RNA nanostructure as described herein for use in the preparation of a medicament for treatment of a disease or a cancer.

In aspects, also described herein are systems that can include a computing device; and an application executable on the computing device, wherein when executed, the application can cause the computing device to at least: generate theoretical double-stranded arm (DA) sequences that can be based at least in part on the GC content of the theoretical DA sequence, melting temperature (Tm) of the theoretical DA sequence, and ability to self-dimerize; select one or more DA(s) for a set of oligomers that can be based at least in part on a computed cross complementarity of a saved set of DAs, wherein DAs having the lowest overall complementarity are selected; can compute oligomer sequences, which can include computing the reverse complement of DA sequences, computing extension oligomer sequences, and computing termination oligomer sequences; and can select oligomers based at least in part on the ability of the oligomers to self-dimerize or form dimers, wherein those oligomers that do not self-dimerize and do not form dimers are selected.

In aspects, also described herein are methods that can at least include the steps of generating theoretical double-stranded arm (DA) sequences based at least in part on the GC content of the theoretical DA sequence, melting temperature (Tm) of the theoretical DA sequence, and ability to self-dimerize; selecting one or more DA(s) for a set of oligomers based at least in part on a computed cross complementarity of a saved set of DAs, wherein DAs having the lowest overall complementarity are selected; computing oligomer sequences, which can include computing the reverse complement of DA sequences, computing extension oligomer sequences, and computing termination oligomer sequences; and selecting oligomers based at least in part on the ability of the oligomers to self-dimerize or form dimers, wherein those oligomers that do not self-dimerize and do not form dimers are selected.

In aspects, also described herein is the use of nucleotides, RNA or RNA structures described herein to make hydrophobic or low soluble drugs become soluble, thus reducing the dosage of drugs for reducing drug toxicity or side-effects or avoiding the use of oil or organic solvent to dissolve drugs in cancer chemotherapy.

In aspects, also described herein is the use of hydrophobic materials to produce RNA micelle structure to carry anti-cancer compound, therapeutics, miRNA, anti-miRNA, siRNA, chelator, radioactive isotope, fluorophore, the pH responsive or enzyme cleavable prodrugs.

The details of one or more aspects of the invention are set forth in the accompanying drawings and the description below. Other features, objects, and advantages of the invention will be apparent from the description and drawings, and from the claims.

BRIEF DESCRIPTION OF DRAWINGS

FIG. 1A. pRNA-3WJ motif from bacteriophage phi29 packaging RNA, containing $3WJ_a$ (SEQ ID NO:16); $3WJ_b$ (SEQ ID NO:17); and $3WJ_c$ (SEQ ID NO:18). FIG. 1B. The angled branch structure of pRNA-3WJ again containing a3WJ (SEQ ID NO:16); b3WJ (SEQ ID NO:17); and c3WJ (SEQ ID NO:18). FIG. 1C. Conjugating pRNA-3WJ with a lipophilic module (cholesterol), a therapeutic module (PTX), and a reporter module (Alexa dye). FIG. 1D. Illustration of the formation of pRNA-3WJ micelles via hydrophobic interaction of conjugated lipophilic module in aqueous solutions. FIG. 1E. Assay the assembly of pRNA-3WJ micelles by 1% TAE agarose gel electrophoresis. Upper gel: EtBr channel; lower gel: Alexa647 channel (M: 1 kb plus DNA ladder).

FIG. 2A. AFM image. Scale bar: 200 nm. FIG. 2B. The apparent hydrodynamic diameters measurement by DLS. Upper panel: 3WJ in TMS buffer; Lower panel: pRNA-3WJ-PTX micelles in TMS buffer. FIG. 2C. The Zeta potential measurement by DLS. FIG. 2D. Validate the assembly of pRNA-3WJ micelles via Nile Red binding assay.

FIG. 3A. The design rational of RNA-PTX conjugates. PTX-N3 can react with end Alkyne labeled RNA via Click chemistry and PTX can be later released from RNA strand by hydrolysis. FIG. 3B. Assay of successful RNA-PTX conjugation by 20% 8M Urea PAGE in TBE buffer. FIG. 3C. The experimental mass prediction of a3WJ-PTX conjugates by Mass Spectrometry. FIG. 3D. In vitro PTX release profile along time.

FIG. 5A. Assay for cytotoxicity effects of pRNA-3WJ-PTX micelles by MTT assay. FIG. 5B. Assay for apoptotic effects of pRNA-3WJ-PTX micelles by PI/Annexin V-FITC dual staining and FACS analysis. FIG. 5C. Caspase-3 assay. FIG. 5D shows in vivo tumor targeting of pRNA-3WJ-PTX micelles in mouse xenografts. Left. Whole body image obtained 4 hr post injection. Right. Organ image obtained 24 hr post injection.

FIGS. 6A-6R RNA micelles for micro RNA delivery. FIGS. 6A-6D. 3WJ motif, illustration of 3WJ RNA micelle formation, 2D structure of 3WJ/FA/anti-miR21 micelles, assembly of RNA micelles assayed by 2% Agarose gel. (Lanes from left to right: 3WJ, 3WJ micelles, 3WJ/anti-miR21, 3WJ/anti-miR21 micelles, 3WJ/FA/anti-miR21, 3WJ/FA/anti-miR21 micelles), size distribution, and zeta potential of 3WJ/FA/anti-miR21 micelles. FIG. 6A shows sequences for $3WJ_a$ (SEQ ID NO:16); $3WJ_b$ (SEQ ID NO:17); $3WJ_c$ (SEQ ID NO:18); 3WJ-a-sph1 (SEQ ID NO:55); and sph1-anti-miR21 (SEQ ID NO:56). FIGS. 6O-6R shows in vivo therapeutic effect of RNA micelles in mice with xenograft. Tumor regression curve over the course of 5 injections (arrow shows day of injection). Mice weight curve during treatment period. qRT-PCR and Western Blot showing the upregulation of PTEN after in vivo delivery of anti-miR21.

FIG. 7A. In vitro evaluation of the TNF-α, IL6, and IFN-α production after incubating pRNA-3WJ micelles with mouse macrophage-like RAW 264.7 cells by ELISA assay. FIG. 7C. In vivo chemokines induction profiling for pRNA-3WJ micelle formulation.

FIG. 10A. The stepwise assembly of pRNA-3WJ with non-modified a3WJ strand, 5'-Alkyne modified a3WJ strand, and 5'-PTX modified a3WJ strand. (M: UltraLow DNA ladder). FIG. 10B. The solubility of 1 mM free PTX and RNA-PTX in DEPC $H_2O$.

FIGS. 11A and 11B show micelle formation concentration by Nile Red binding assay. FIG. 11C shows 1% TAE agarose gel electrophoresis (ladder: 1 kb plus DNA ladder).

FIG. 15A. 3WJs with different sequence and thermostability. Shown are SEQ ID NOs:16-18 and 57-62. FIG. 15B. Tm assay by TGGE (Thermal Gradient Gel Electrophoresis). FIG. 15C. Tm determination by qPCR. FIG. 15D. Exemplary RNA designs varying in shape and cholesterol labeling strategies for optimization of membranes anchoring efficiency.

FIG. 16A. 3WJ modular RNA motif modified with 18 alkyne groups. Shown are SEQ ID NOs: 63-65. FIG. 16B. 4WJ modular RNA motif modified with 24 alkyne groups. Shown are SEQ ID NOs: 66-69.

FIG. 20A. Sequence design of extended 3WJ and 4WJ RNA vector with Paclitaxel (PTX) conjugation. Conjugation of 6 PTX to one 4WJ synthetic RNA oligonucleotide. Shown are SEQ ID NOs:63-69. FIG. 20B. HPLC chromatogram of purified 4WJ synthetic RNA oligonucleotide with and without 6-PTX conjugation.

FIG. 21A. Step-wise self-assembly of 3WJ with 18 PTX and 4WJ with 24 PTX (M, D, T mean monomer, dimer, and trimer, respectively). FIG. 21B. Size distribution of 4WJ-24 PTX measured by DLS. FIG. 21C. Improved solubility of PTX by conjugation to RNA.

FIG. 22A. TGGE of bare 4WJ vector and 4WJ-24 PTX. FIG. 22B. qPCR of bare 4WJ vector and 4WJ-24 PTX.

FIG. 24A. Daily record of tumor volume and weight of mice. FIG. 24B. Comparison of weight of tumor before and after sacrifice. 4WJ-FA-Taxol showed slower tumor growth as compared with negative control groups. No significant reduction in mouse weight was observed after treatment, which can be indicative of no significant toxicity.

FIG. 25A. Scheme of click reaction of modified oligonucleotide and Camptothecin (CPT) prodrug. FIG. 25B. Denaturing PAGE to monitor conjugation (* indicates 2'-F 4alkyne; < indicates 2'-F 4CPT). FIG. 25C. HPLC chromatogram of purified 3WJ strand with and without 4CPT conjugation (Black: 2'-Fb 4alkyne; Gray: 2'-Fb 4CPT).

FIG. 26A. Illustration of 3WJ-FA-7CPT. FIG. 26B. Native PAGE of stepwise assembly of FA-7CPT-3WJ with control 3WJs (Lane 1, 2'-Fa 3CPT; Lane 2, 2'-Fa 3CPT+2'-Fc Folate; Lane 3, FA-7CPT-3WJ; Lane 4, 7CPT-3WJ; Lane 5, FA-3CPT-3WJ; Lane 6, FA-4CPT-3WJ; Lane 7, FA-3WJ; Lane 8, 3WJ). FIG. 26C. Temperature-gradient gel electrophoresis of FA-7CPT-3WJ.

FIG. 29A. Design schematic showing different combinations of cores and helixes. Shown are SEQ ID NOs:16-18. FIG. 29B. Sequence design of seven 3WJ modular RNA motifs (Phi29-Mod (SEQ ID NOs:19-21), Phi29-30 (SEQ ID NOs:22-24), SF5-30 (SEQ ID NOs:25-27), M2-30 (SEQ ID NOs:28-30), Phi29-32 (SEQ ID NOs: 31-33), SF5-32 (SEQ ID NOs:34-36), M2-32 (SEQ ID NOs:37-39)). FIG. 29C. Comparison of branched 3WJ modular RNA motifs with same set of helices (DAs) but differend bulges separating the DAs in the core for Phi29-30 (SEQ ID NOs:22-24), SF5-30 (SEQ ID NOs:25-27), and M2-30 (SEQ ID NOs:28-30).

FIGS. 30A to 30C show thermal stability of branched 3WJs modular RNA motifs in TES buffer. FIG. 30A. qPCR showing annealing profile. FIG. 30B. TGGE showing melting profile. FIG. 30C. Comparison of Tm measured for annealing and melting of branched 3WJ modular RNA motifs.

FIGS. 31A and 31B show enzymatic stability of branched 3WJs modular RNA motifs. FIG. 31A. Serum degradation curve. FIG. 31B. Half life of 3WJs in 50% serum.

FIG. 32A. Three 3WJ modular RNA motifs with different thermal stability used as the building block of branched 3WJs RNA nanostructures. FIG. 32B. 2D schematic of branched 3WJ RNA nanostructures with different layers. FIG. 32C. 3D schematic of branched 3WJ RNA nanostructures with different layers. FIG. 32D. Composition and coupling of individual branched 3WJ modular RNA motifs to form 3 layer branched nanostructure.

FIGS. 33A to 33D show thermal stability of branched 3WJ RNA nanostructures. FIG. 33A. qPCR showing annealing profile. FIG. 33B. TGGE showing melting profile. FIG. 33C. Comparison of Tm of annealing and melting. FIG. 33D. TGGE showing release profile of thermodynamically stacked layers of branched 3WJ RNA modules.

FIG. 34A. Size comparison gel showing the assembly of 2-layer and 3-layer 3WJ RNA nanostructures. FIG. 34B. Size distribution of 2-layer and 3-layer 3WJ RNA nanostructures measured by dynamic light scattering (DLS).

FIG. 35A. Serum stability gel. FIG. 35B. Serum degradation curve. FIG. 35C. Half life of 3WJ RNA nanostructures in 50% serum.

FIGS. 37A-37C show design and construction of branched 3WJ-based modular RNA motifs and variants having different arm numbers. FIG. 37A. Different higher order junctions (cores) used as the building block of modular RNA motifs. FIG. 37B. Nucleotide sequences for synthetic modular RNA motifs. FIG. 37C. 3D structure of one of modular RNA motif using 6WJ as core and 4WJ as an arm (or branch).

Sequences Also Shown in FIG. 37B.

Figure 39A:
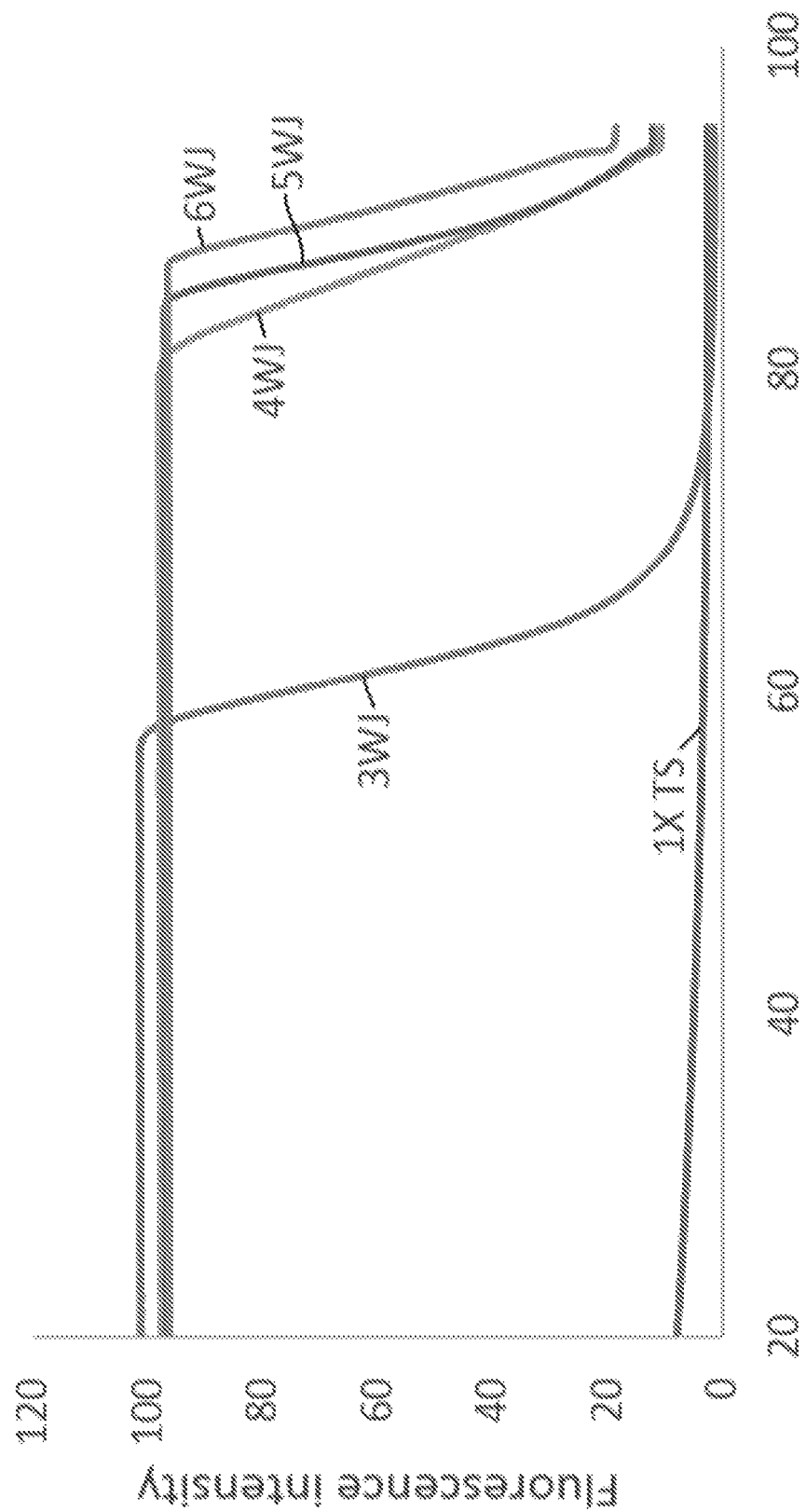
Figure 39B:
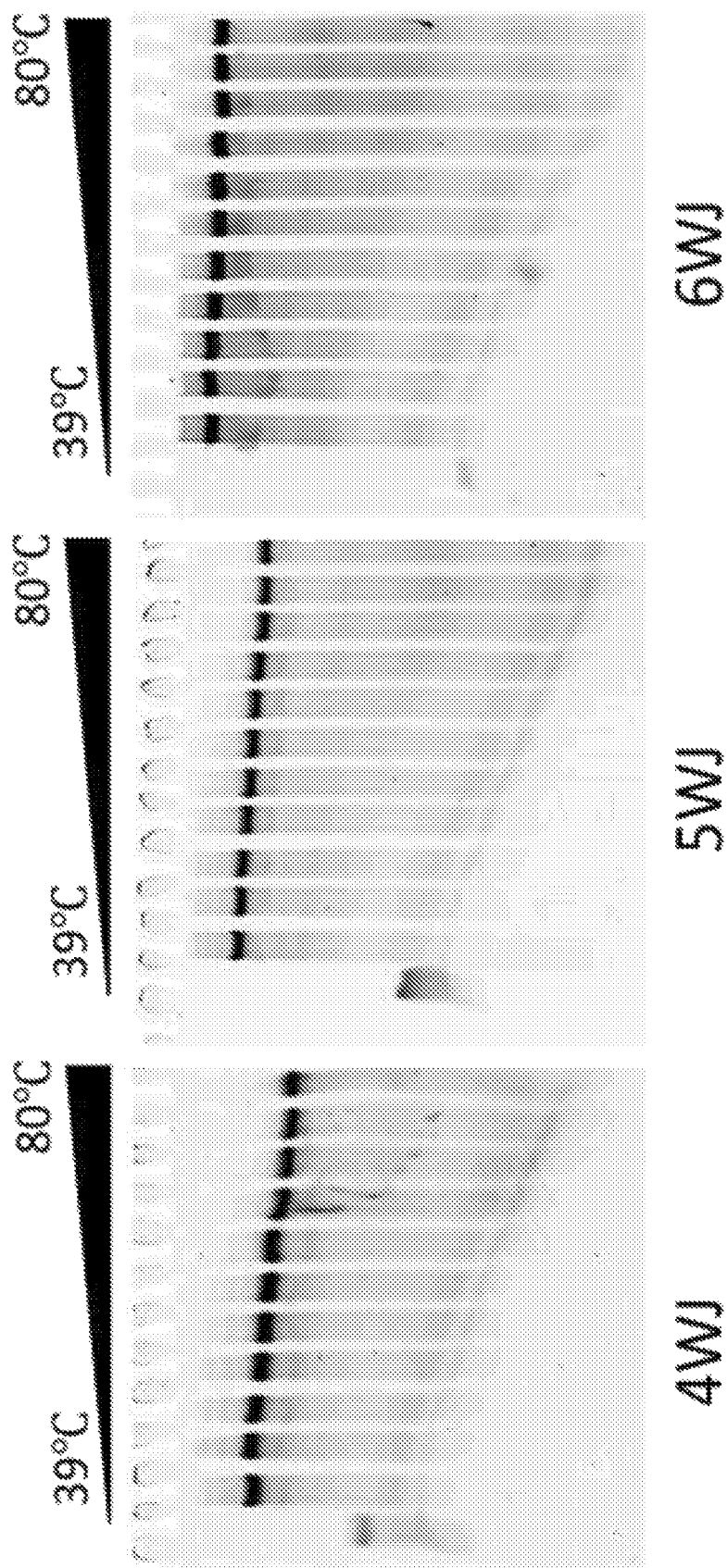
Figures 39C, 40A:
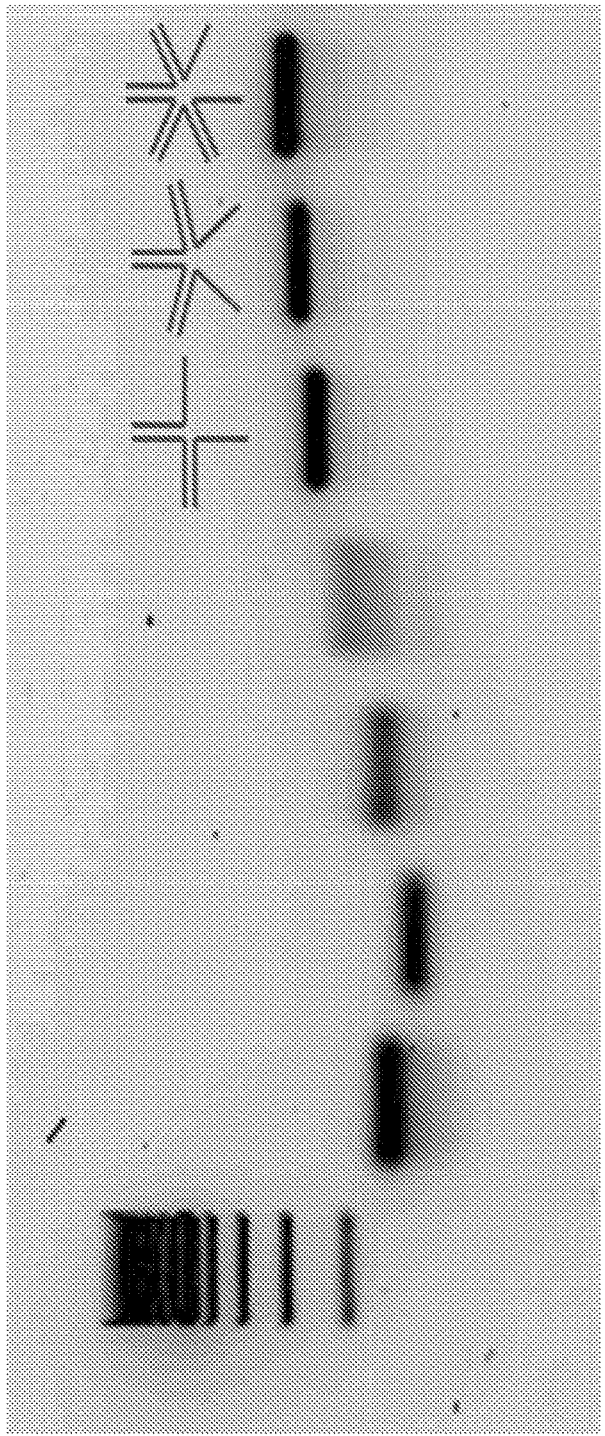

FIGS. 39A to 39C show thermal stability of various modular RNA motifs. FIG. 39A. qPCR showing annealing profile. FIG. 39B. TGGE showing melting profile. FIG. 39C. Comparison of Tm for modular RNA motif annealing and melting.

Figure 40B:
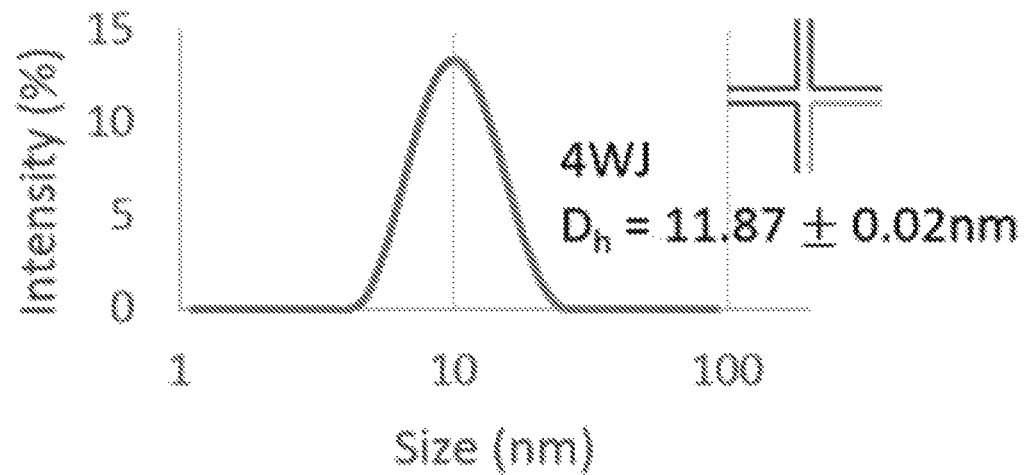
Figure 40B:
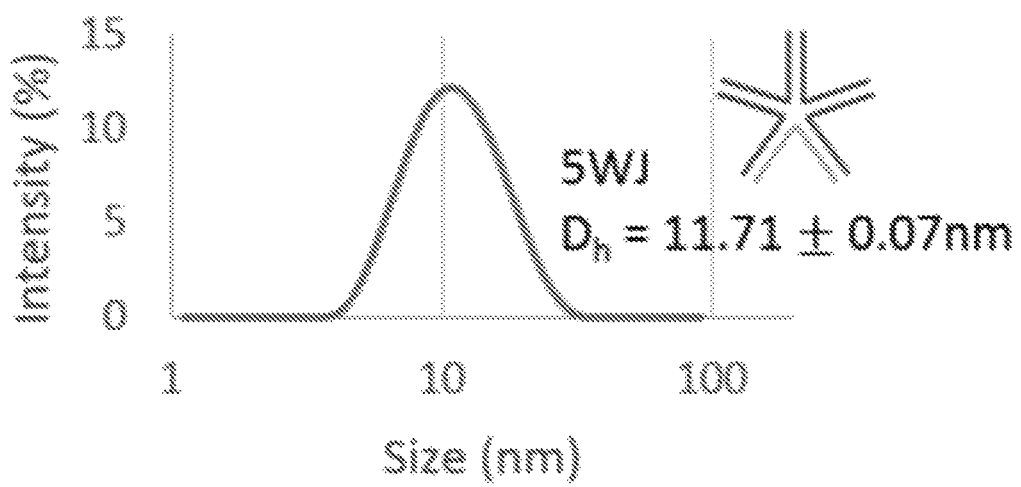
Figure 40B:
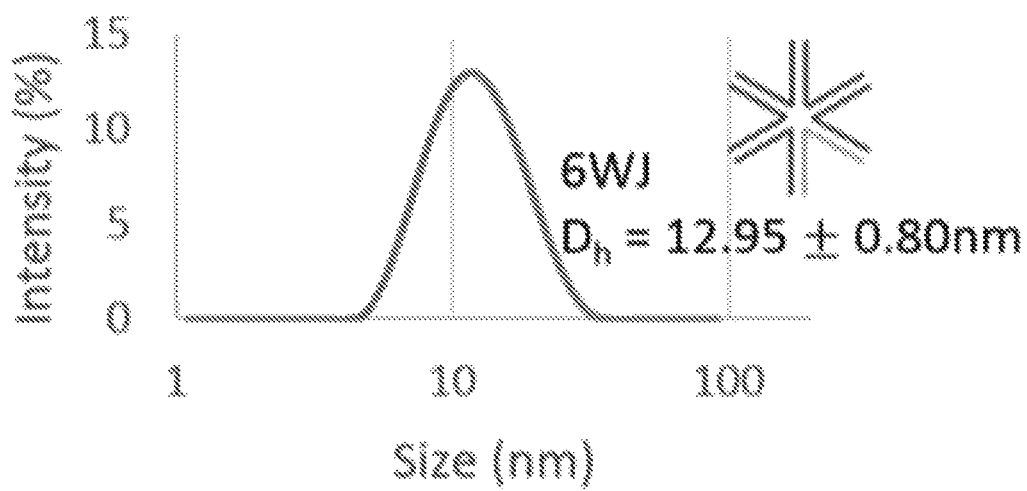
Figure 41A:
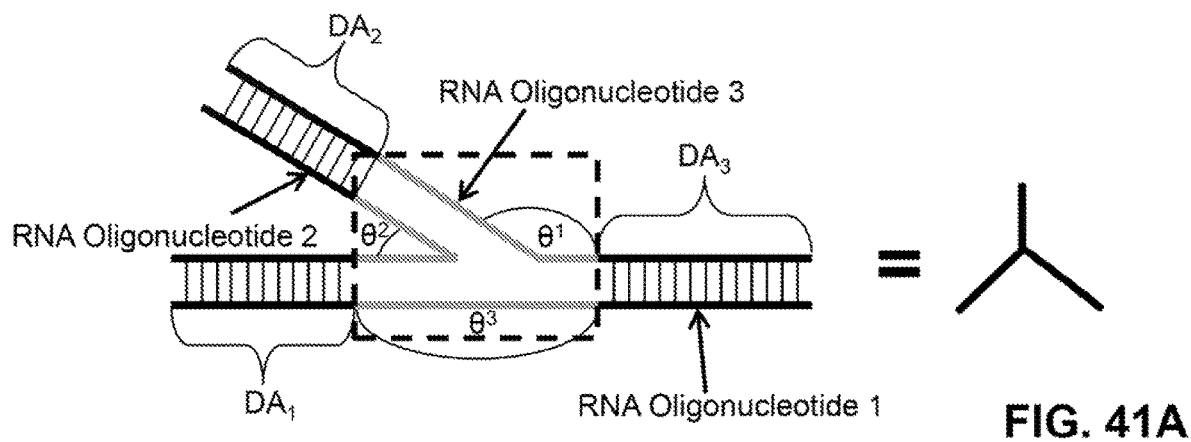
Figure 41B:
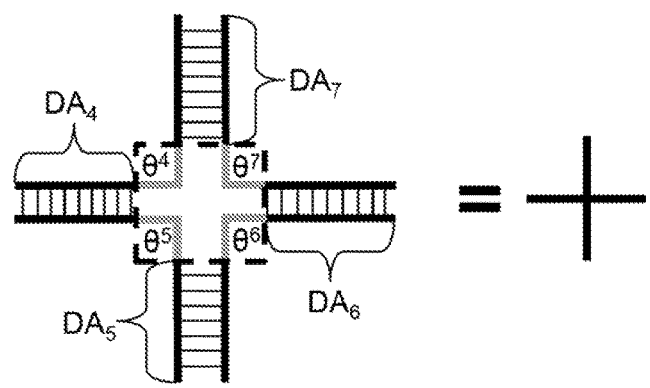
Figure 41C:
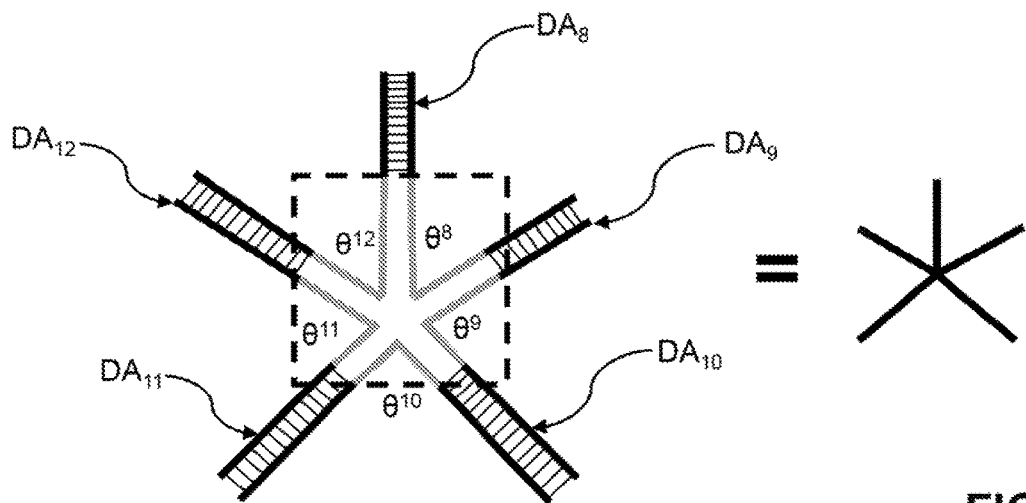
Figure 41D:
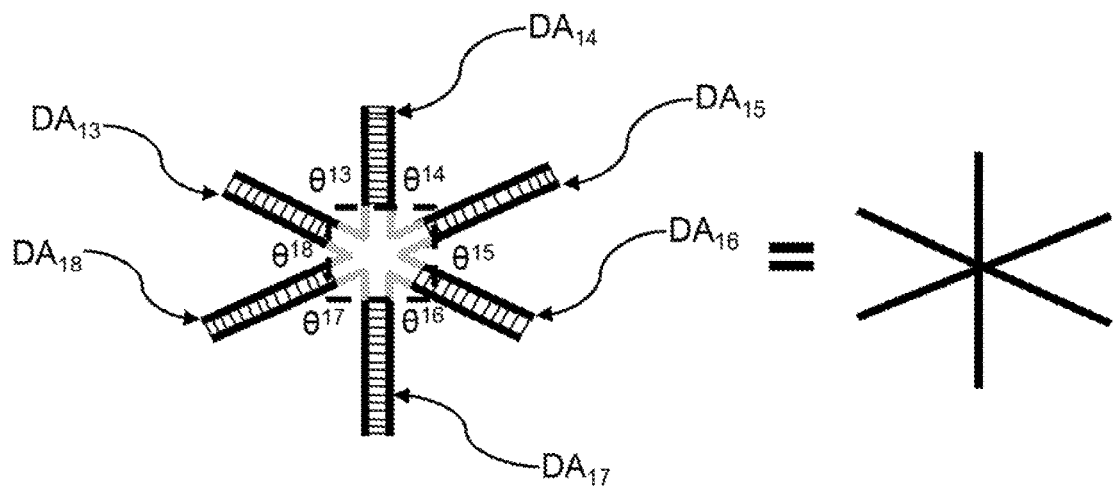
Figure 41E:
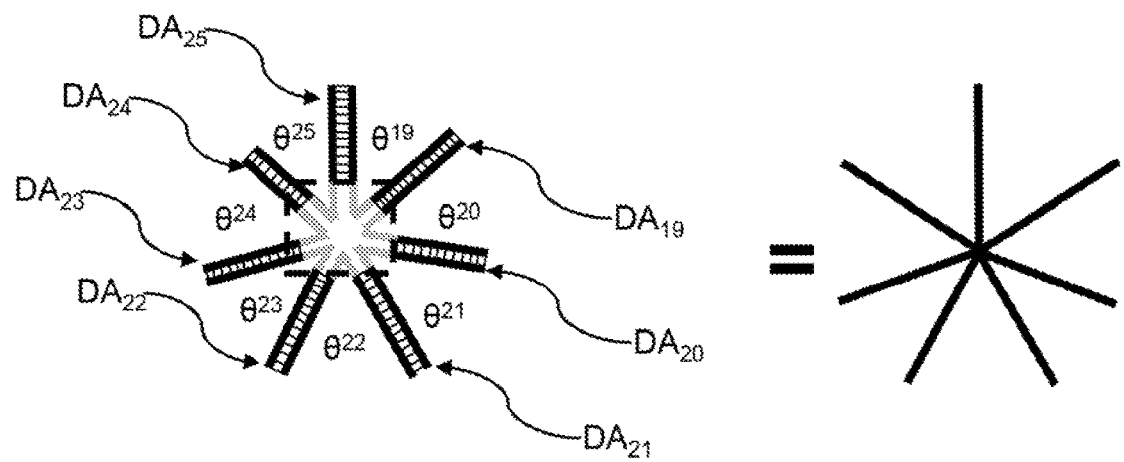
Figure 41F:
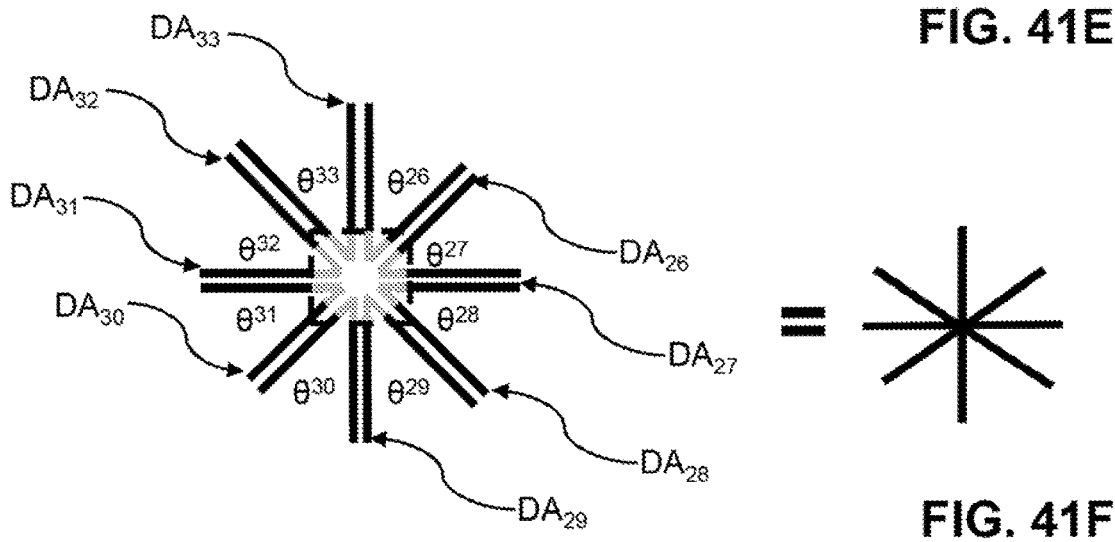
Figure 41G:
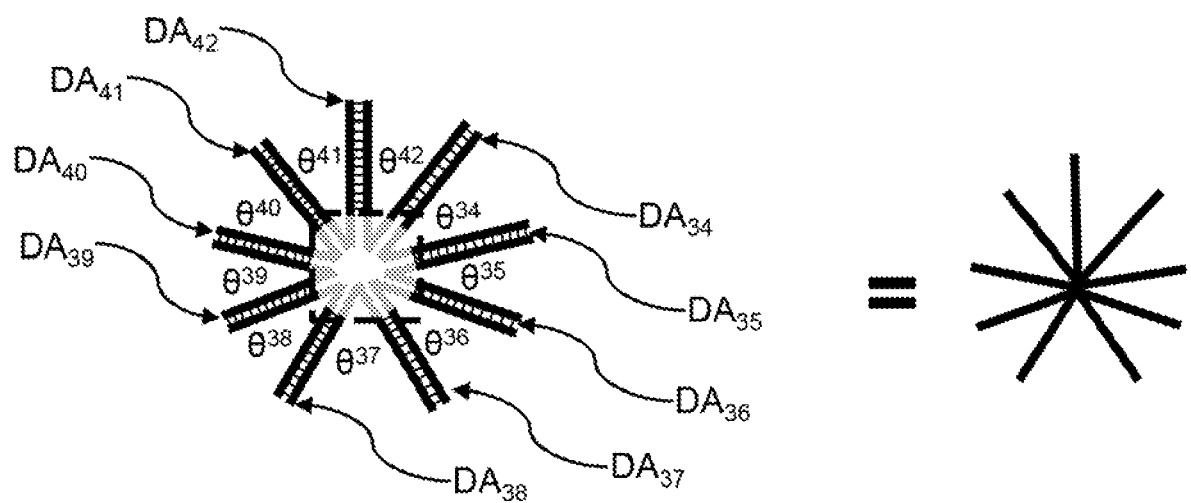
Figure 42A:
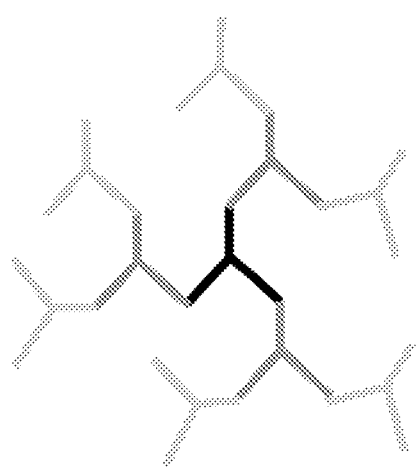
Figure 42B:
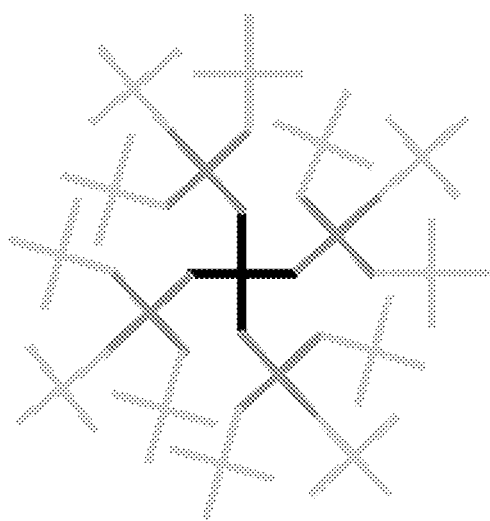
Figure 42C:
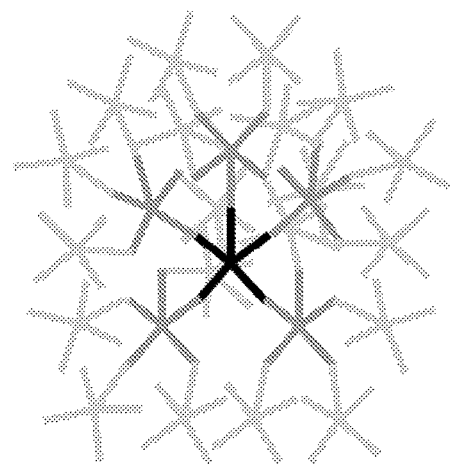
Figure 42D:
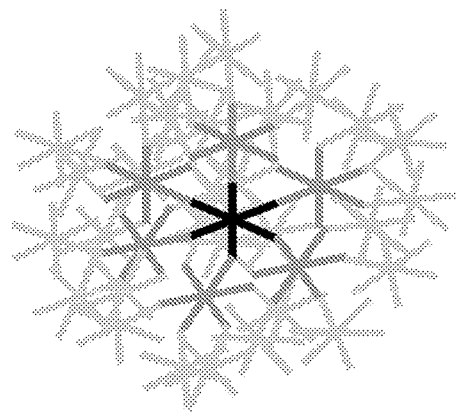
Figure 42E:
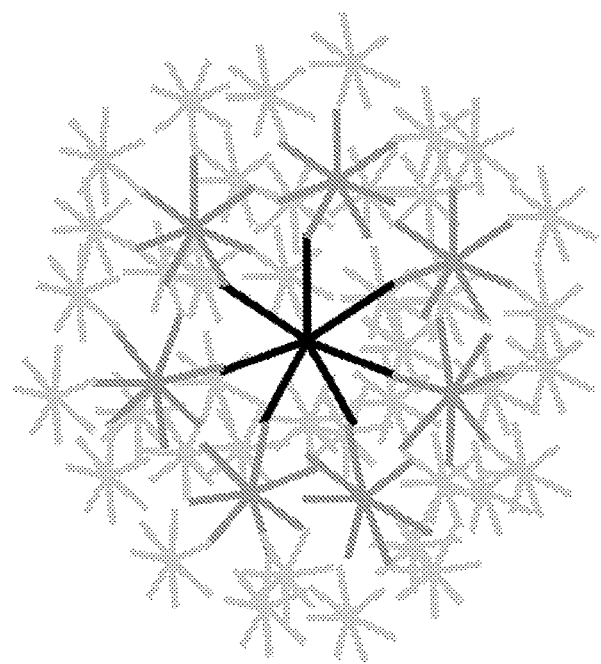
Figure 42F:
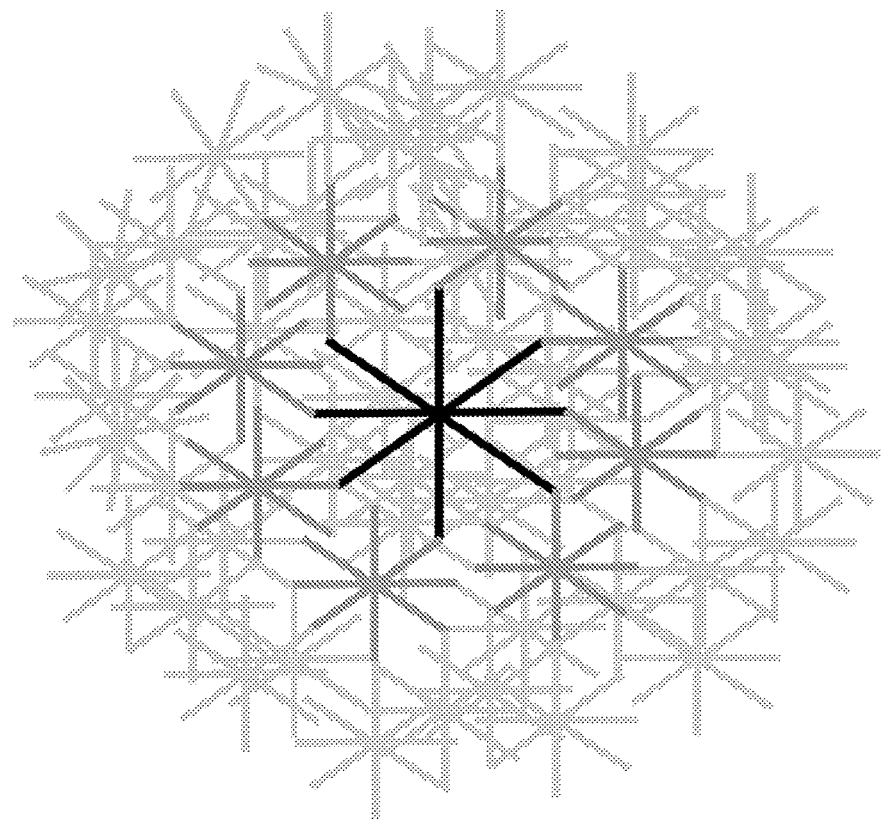
Figure 42G:
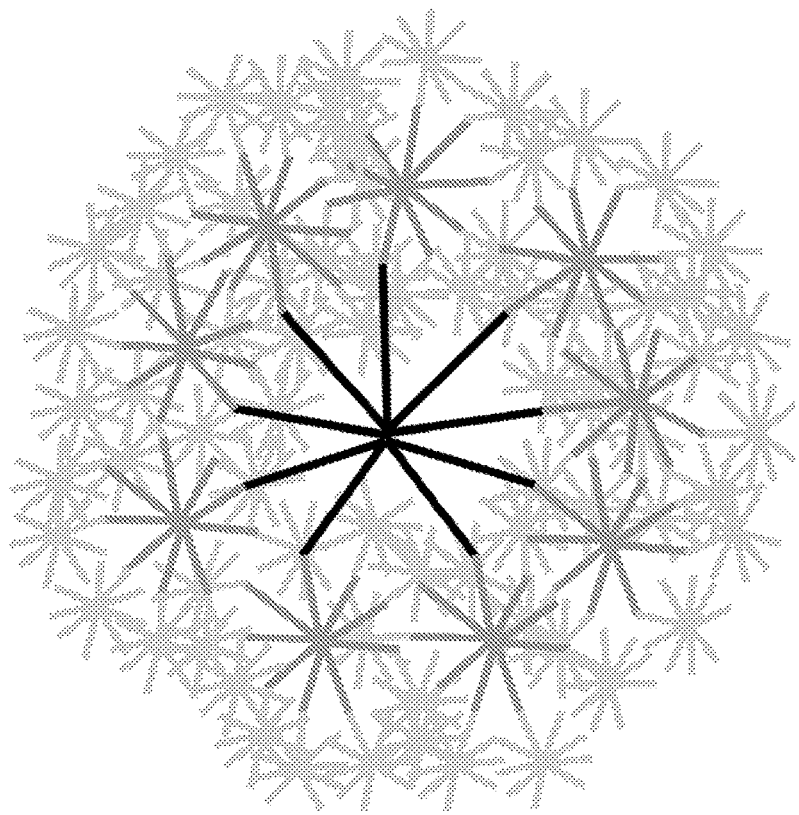

FIGS. 40A and 40B show in vitro characterization of branched 3WJ based modular RNA motifs. FIG. 40A. Size comparison gel: 2% agarose gel showing the assembly of 4-6WJ (from left to right: ladder, phi29-3WJ, monomer, dimer, trimer, 4WJ, 5WJ, 6WJ). FIG. 40B. Size distribution of 4-6WJ measured by dynamic light scattering (DLS).

FIGS. 41A-41G show aspects of modular RNA motifs. The black regions identify double stranded arms (DAs) and the gray regions indicate the core domain of the modular RNA motifs. The core domain is also designated as the region of the modular RNA motif contained inside the dashed box.

FIGS. 42A-42G show aspects of RNA nanostructures each containing a single type of modular RNA motif. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

Figure 43:
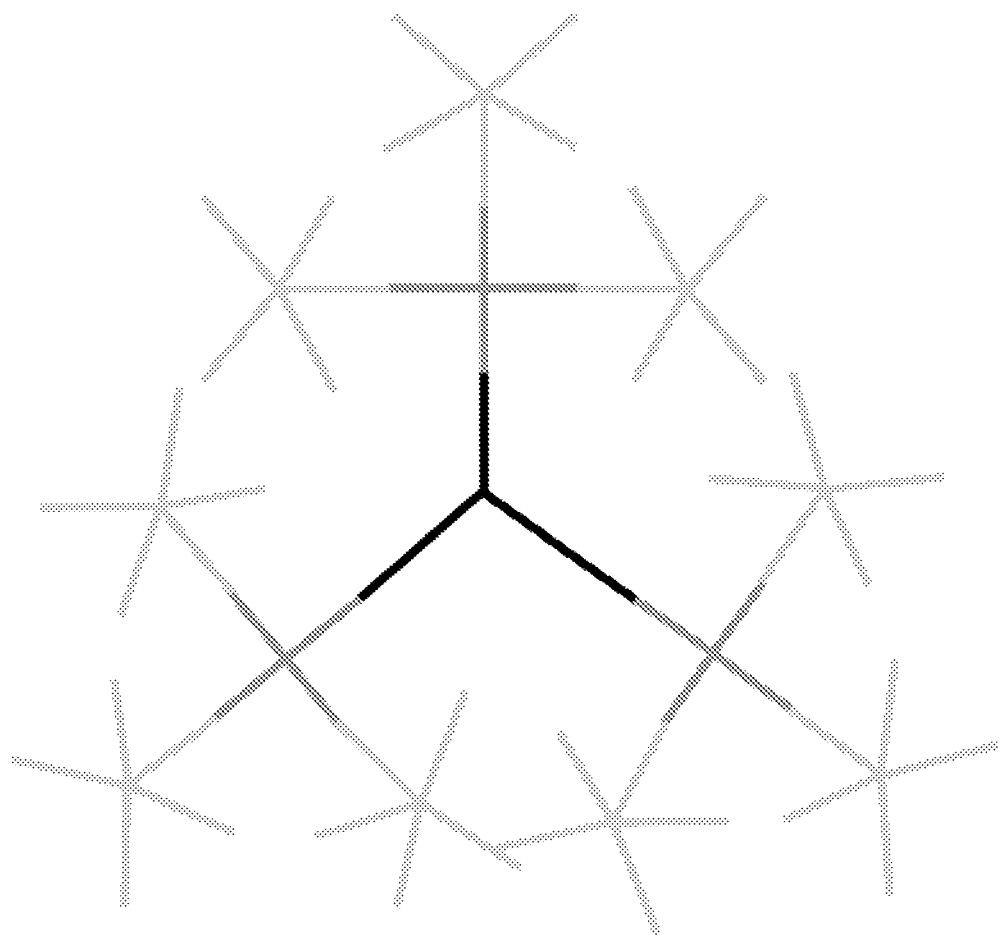

FIG. 43 shows an aspect of an RNA nanostructure containing different types of modular RNA motifs. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

Figure 44A:
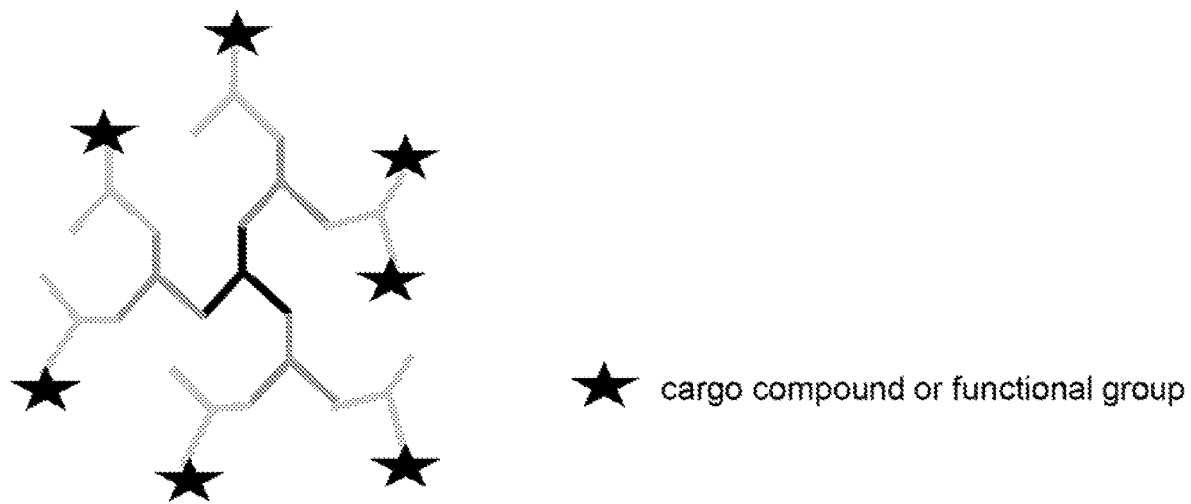
Figure 44B:
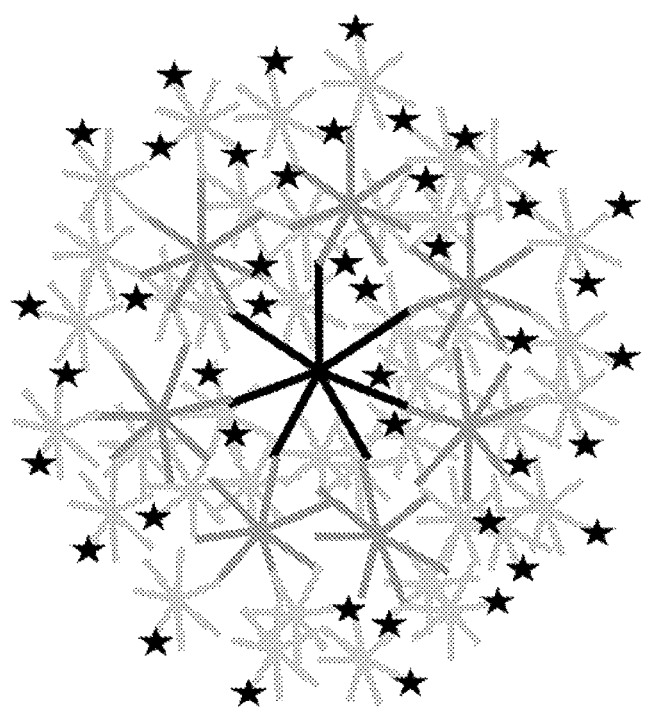

FIGS. 44A-44B shows aspects of RNA nanostructures loaded with a single type of cargo compound or functional group. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

Figure 45A:
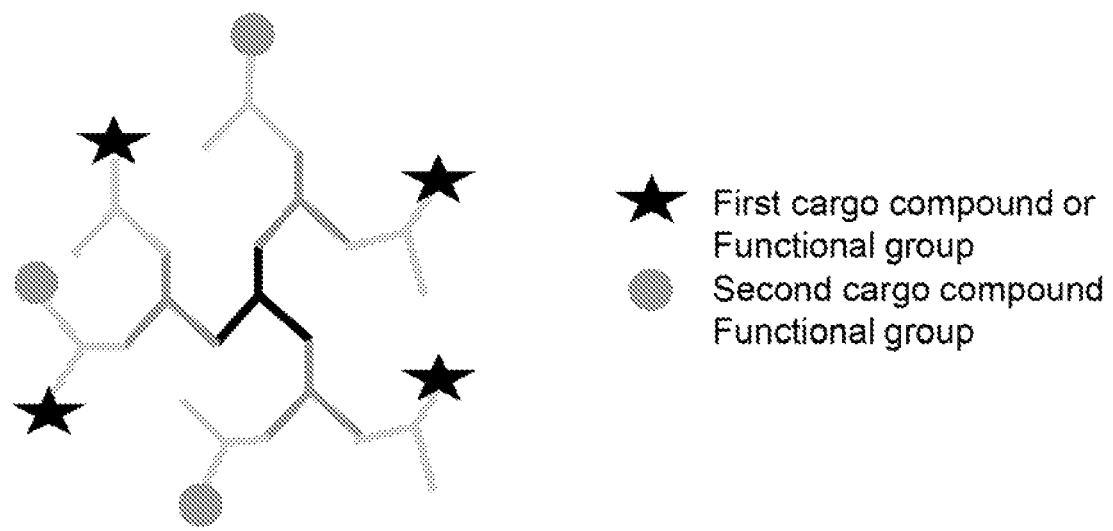
Figure 45B:
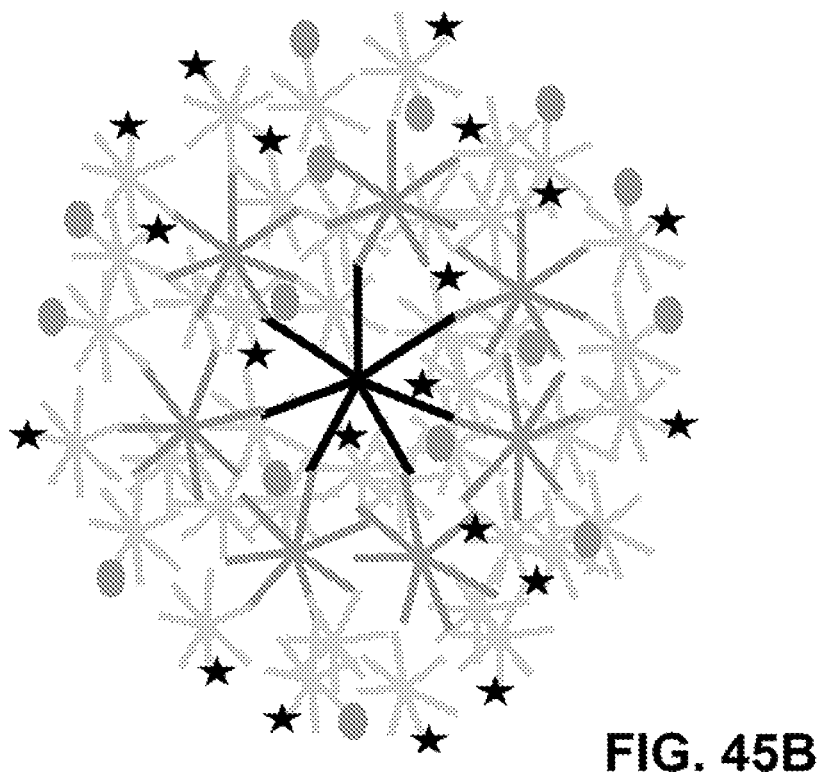

FIGS. 45A-45B shows aspects of RNA nanostructures loaded with multiple types of cargo compounds and/or functional groups, including but not limited to active agents. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

Figure 46A:
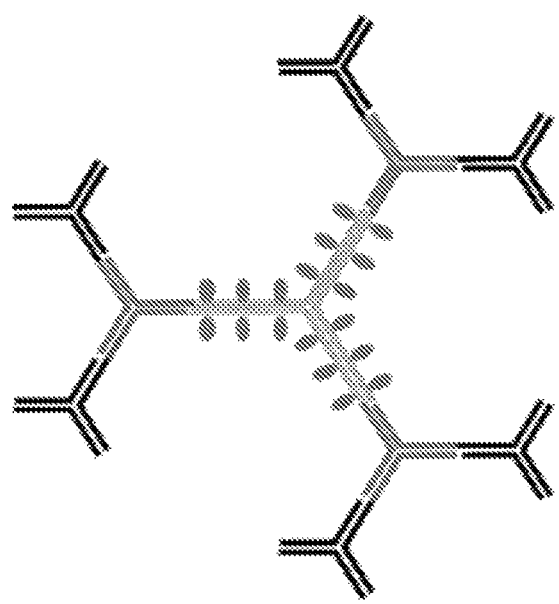
Figure 46B:

FIGS. 46A-46B show aspects of RNA nanostructures loaded with multiple types of cargo compounds and/or functional groups, including but not limited to Paclitaxel. FIG. 46A. A nanostructure with a modular RNA motif containing an elongated core with internal modifications that allow specific attachment of active agents to the core of the nanostructure. FIG. 46B. A nanostructure with different functional groups attached to the 5' or 3' termini of oligonucleotides in each layer.

Figure 47A:
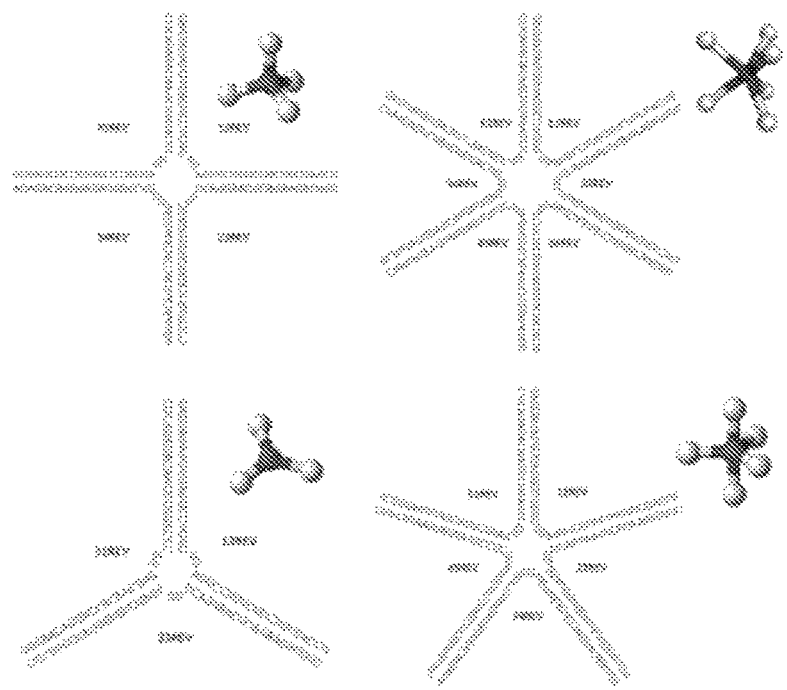
Figure 47B:
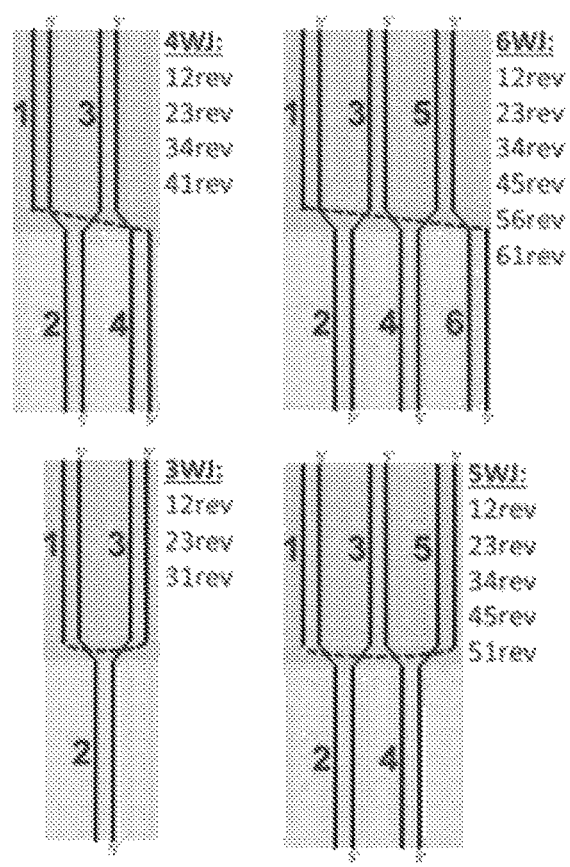
Figure 47C:

FIGS. 47A-47C show design concepts of in silico derived RNA nanostructures. FIG. 47A shows 2D and 3D representations of 3-6 branched RNA nanostructures. FIG. 47B shows the design of oligomer sequences and interlocking domains for 3-6 branched RNA nanostructures. FIG. 47C shows the makeup of individual RNA nanostructure oligomers.

Figure 48:
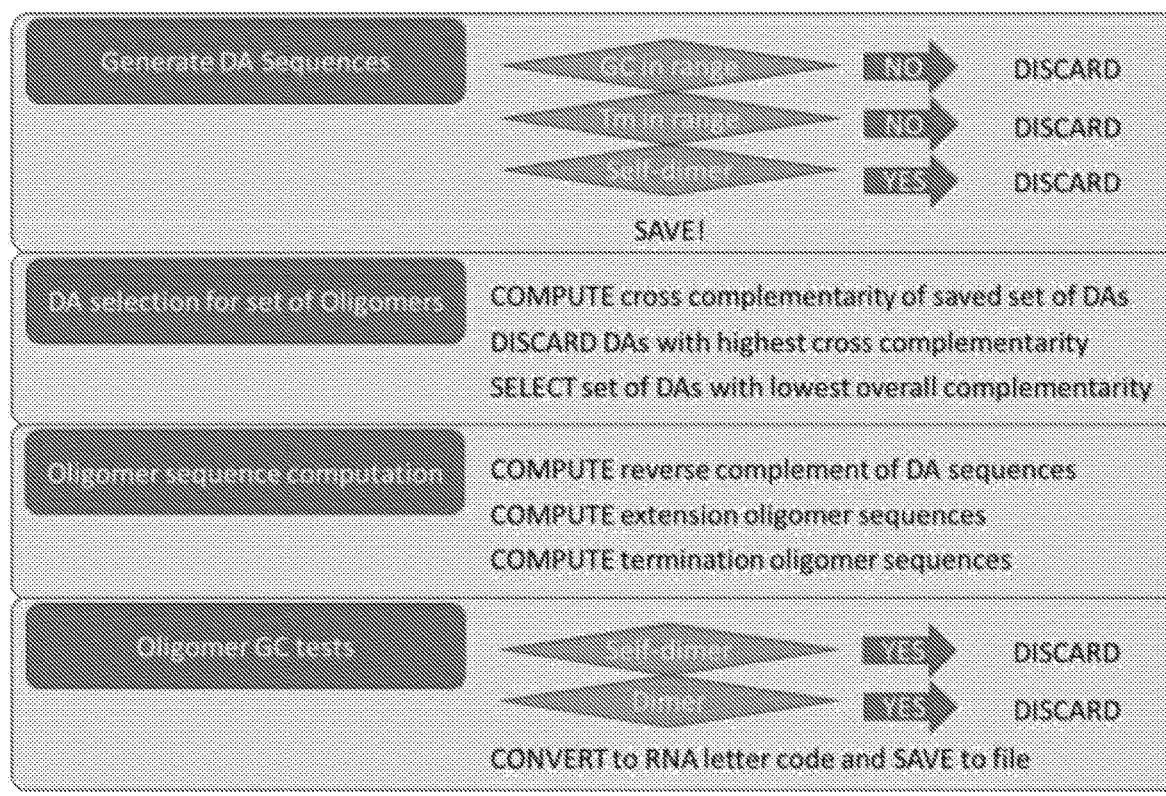

FIG. 48 shows a flowchart of the computation algorithm for in silico design of RNA nanostructure oligomer sequences.

Figure 49A:
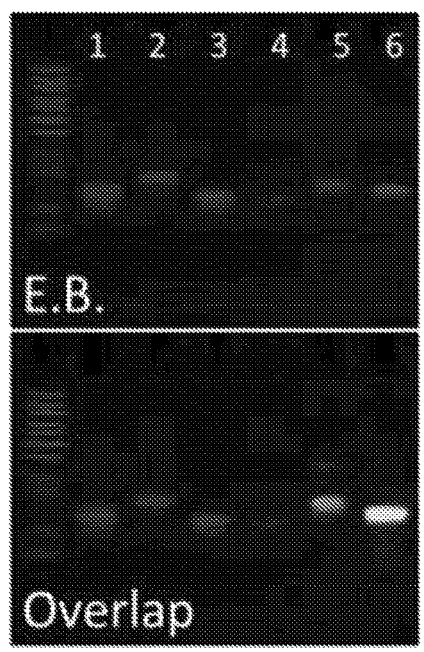
Figure 49B:
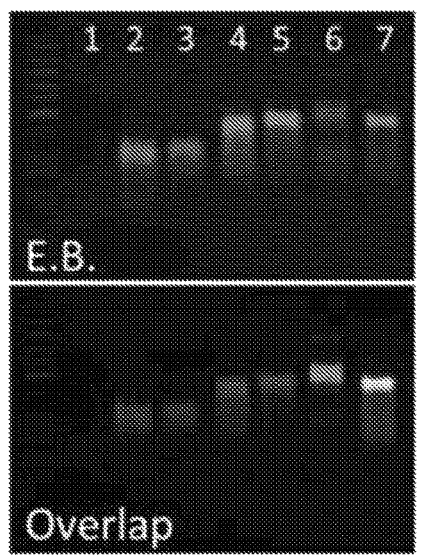
Figure 49C:
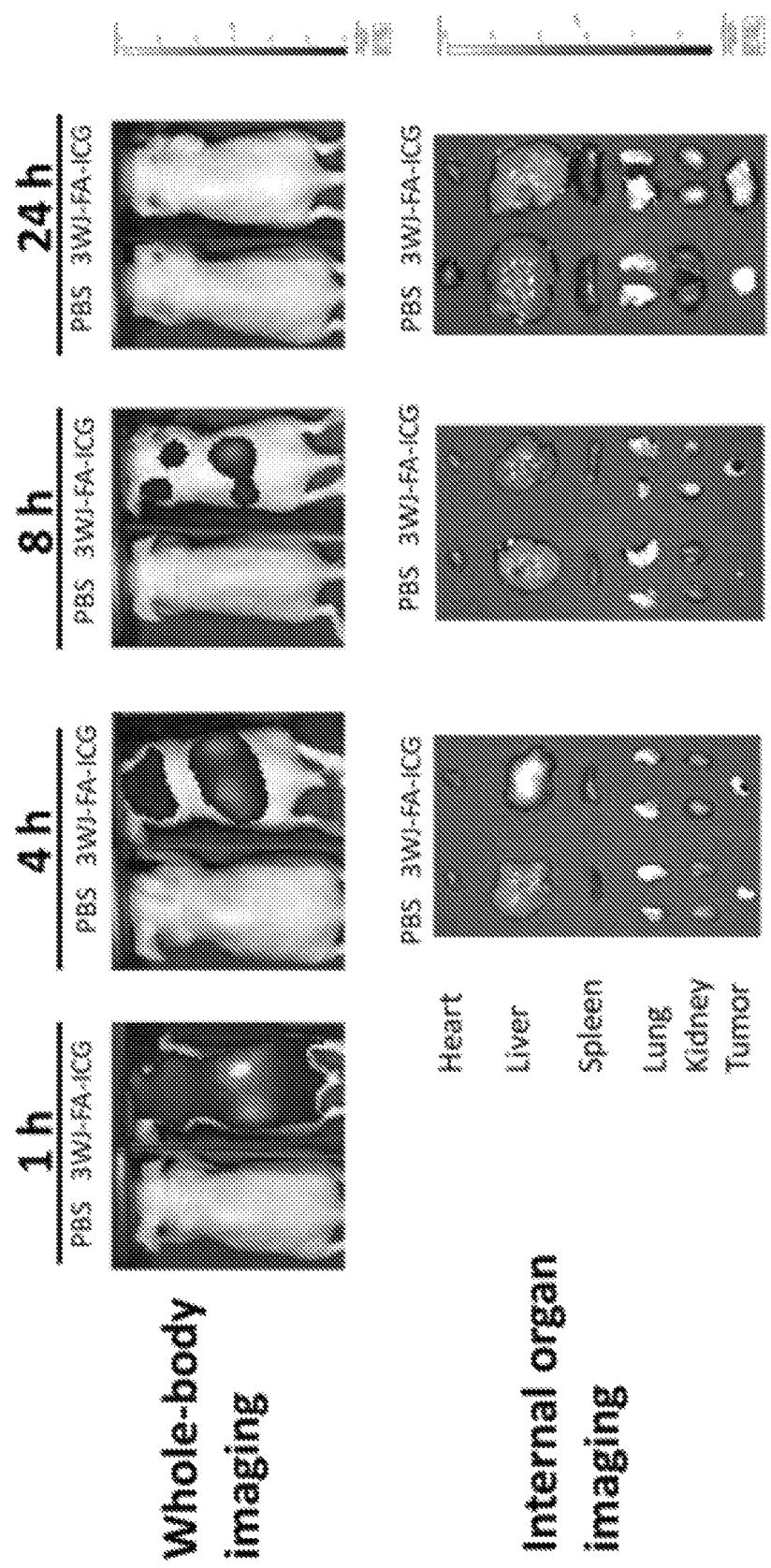

FIGS. 49A-49C. Conjugation of fluorophores to nucleic acid nanoparticles for use in in vivo cancer imaging. FIG. 49A. PAGE analysis demonstrating RNA oligomers and nanoparticles can carry multi-color fluorescent materials. FIG. 49B. Assembly gel demonstrating that oligomers can efficiently assemble after modification with fluorophores. FIG. 49C. Biodistribution of Phi29 3WJ nanoparticles coupled with ICG fluorophores.

Figure 50A:
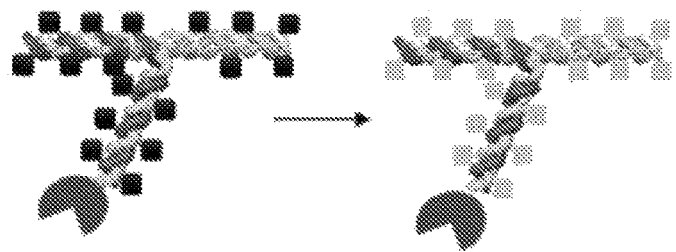
Figure 50A:
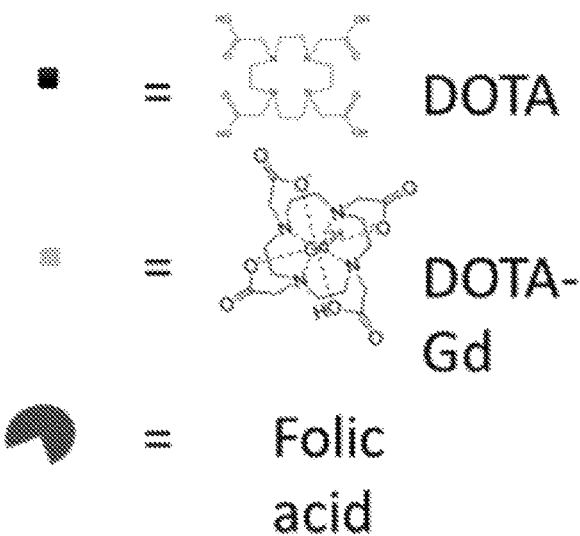
Figure 50A:
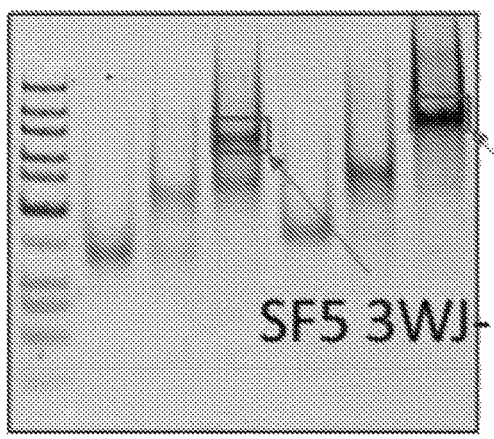
Figure 50C:
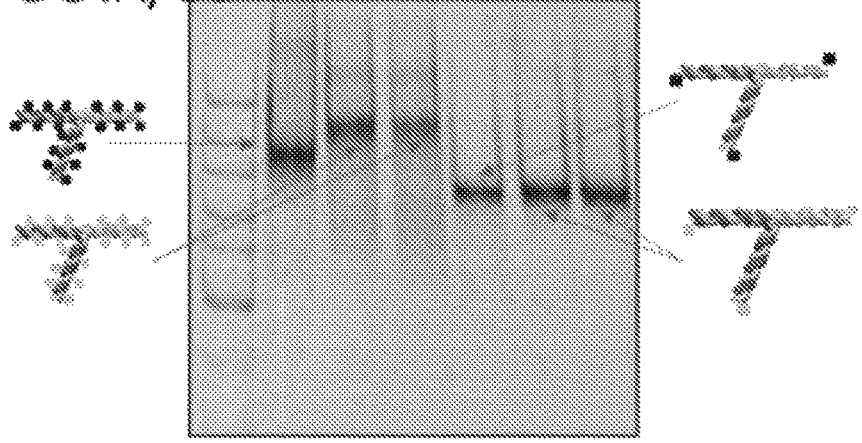

FIGS. 50A-50C. High density conjugation of DOTA chelator to RNA oligomers and nanoparticles. FIGS. 50A-50B. Assembly of amine modified and DOTA conjugated oligomers into RNA nanoparticles. FIGS. 50B-50C. Comparison of RNA nanoparticles with varying densities of DOTA conjugates with and without chelated $Gd^{3+}$.

Figure 51A:
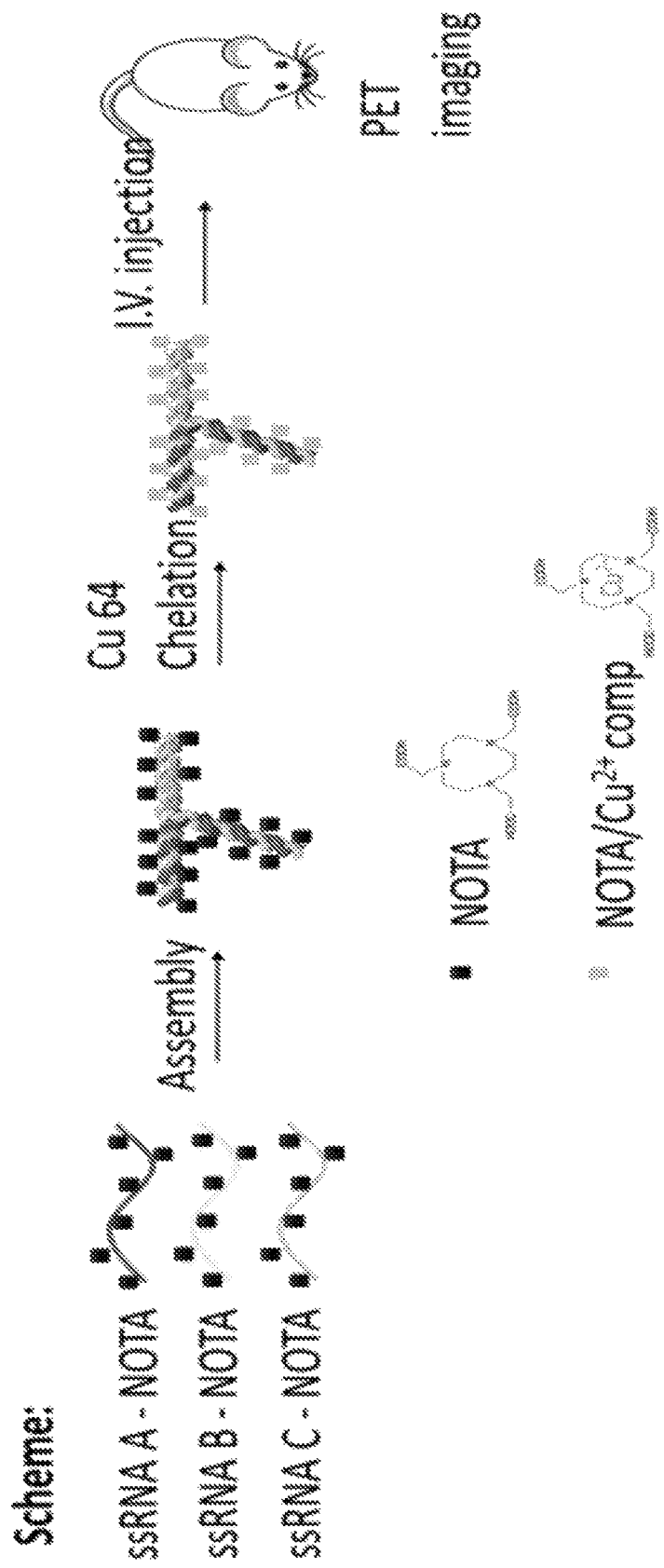
Figure 51B:
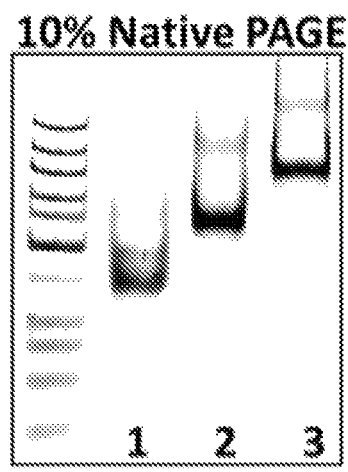
Figure 51C:
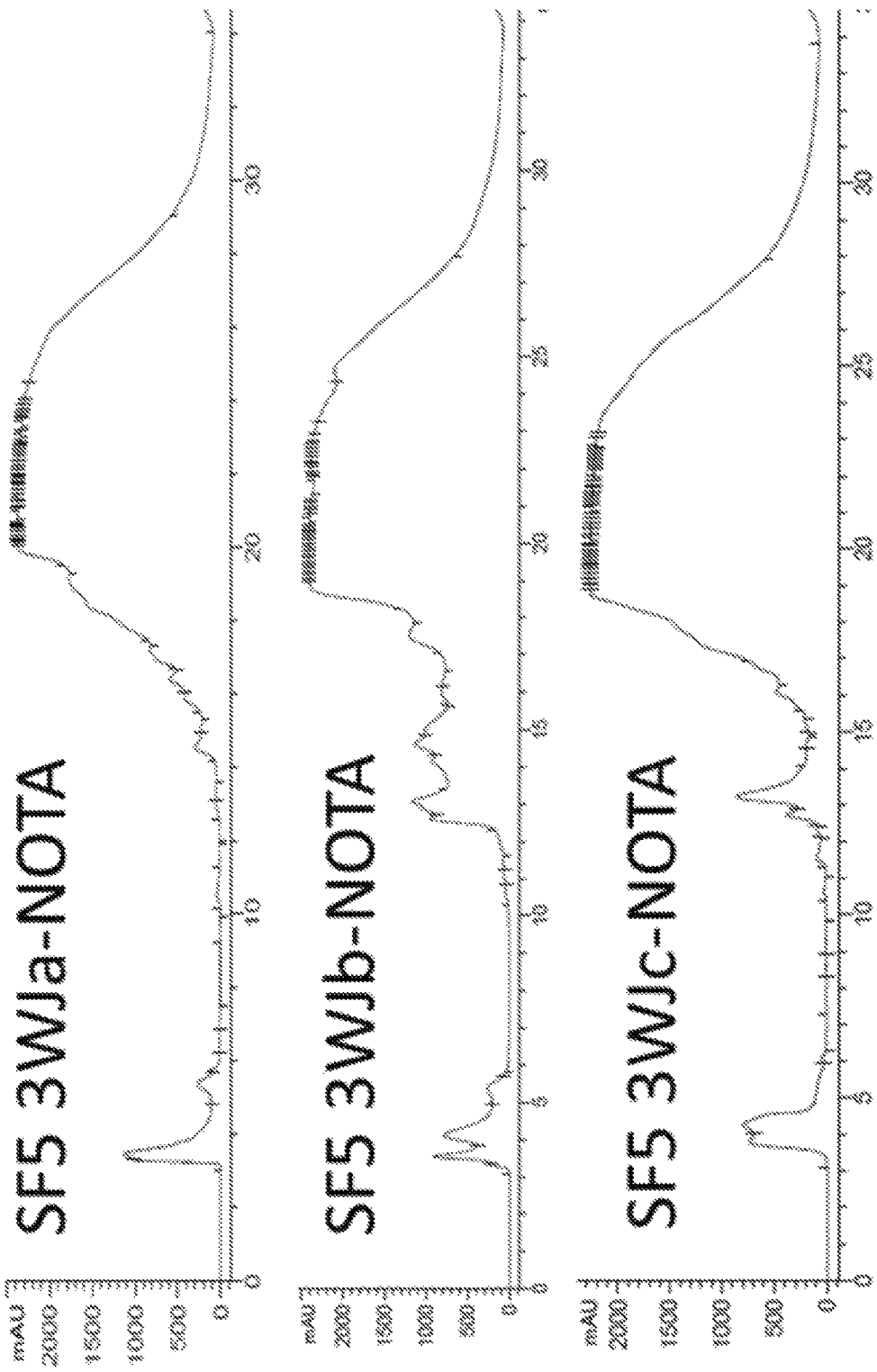

FIGS. 51A-51C. High density conjugation of NOTA chelator to oligomers and nanoparticles. FIG. 51A. Schematic of NOTA chelation of Cu64 to RNA nanoparticle for PET imaging. FIGS. 51B-51C. Assembly gel of NOTA conjugated RNA nanoparticles and reverse phase HPLC purification.

Figure 52A:
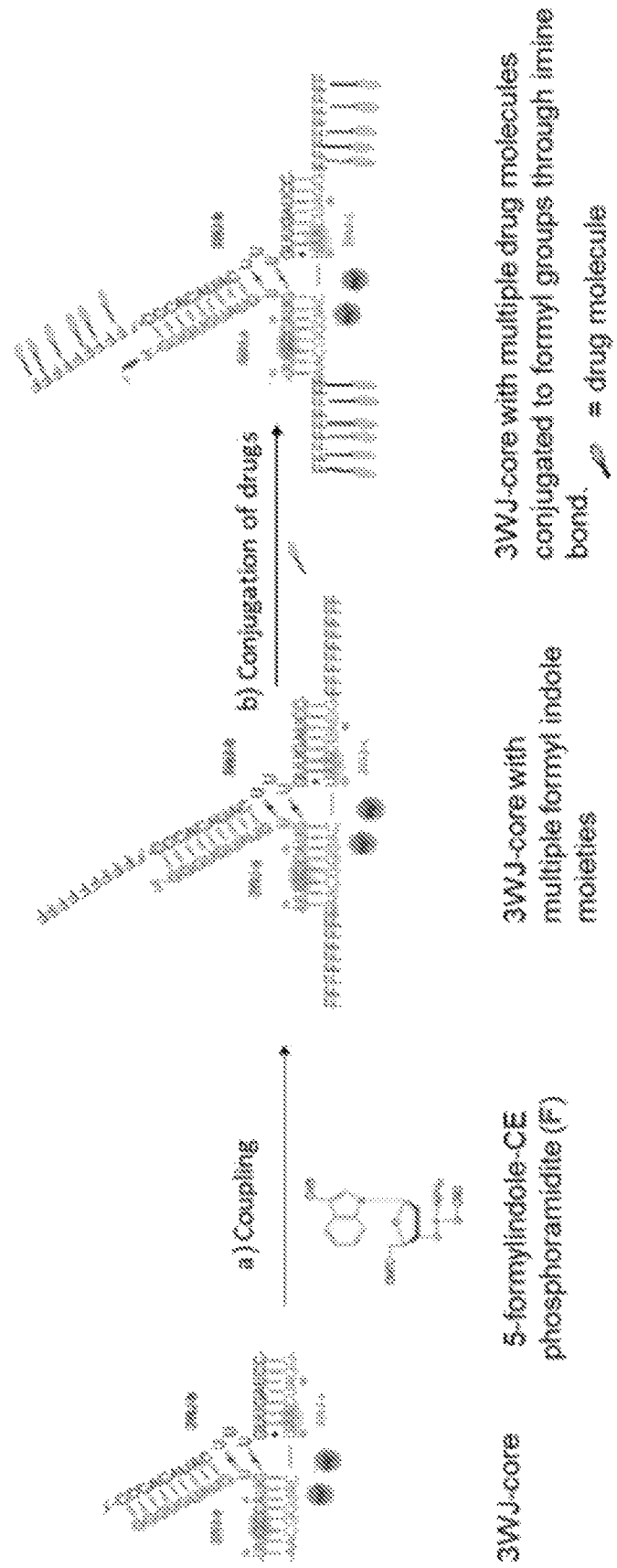
Figure 52B:
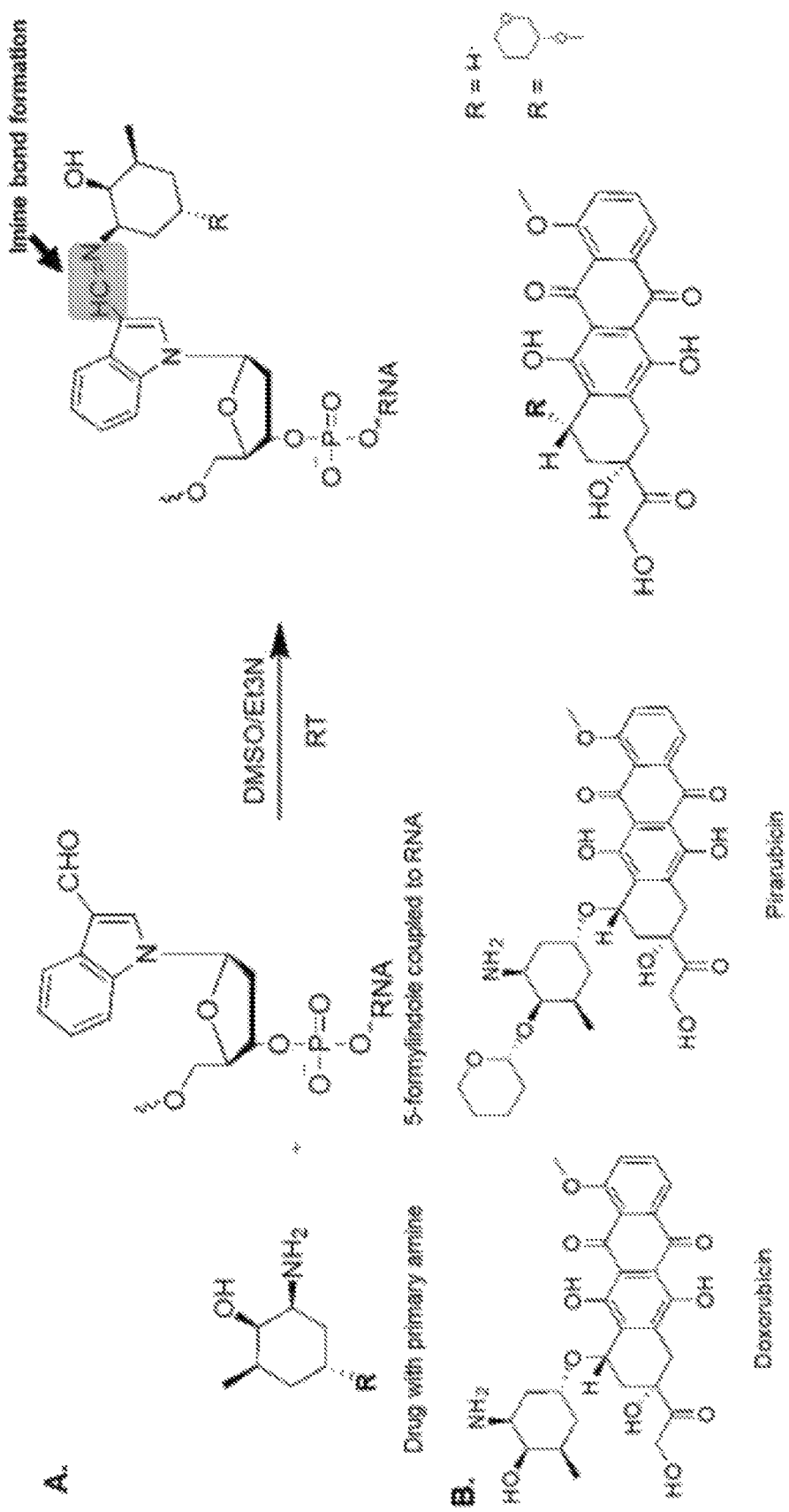
Figure 52C:
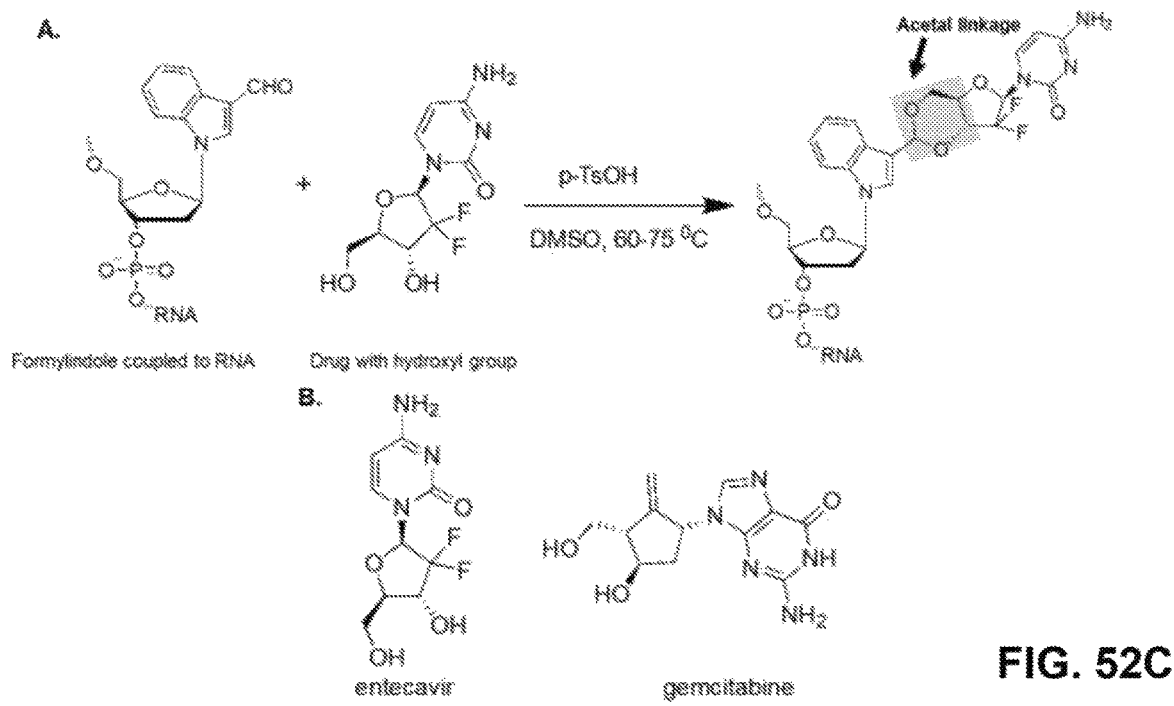
Figure 52D:
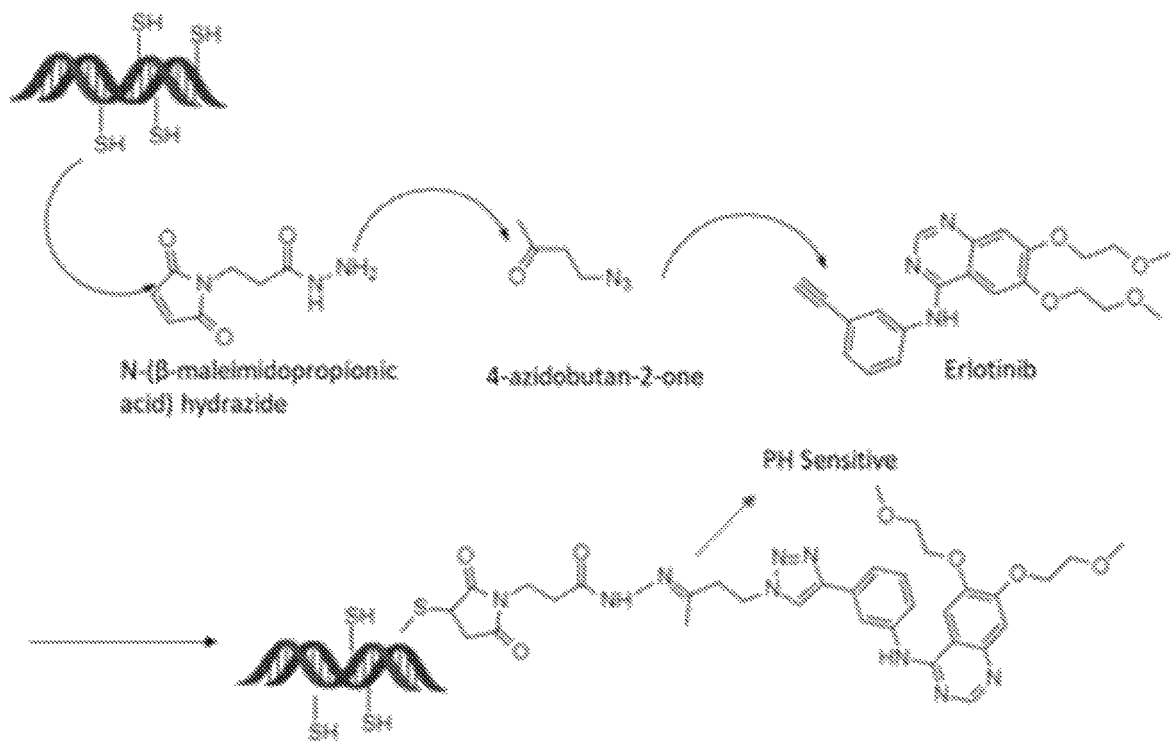
Figure 52E:
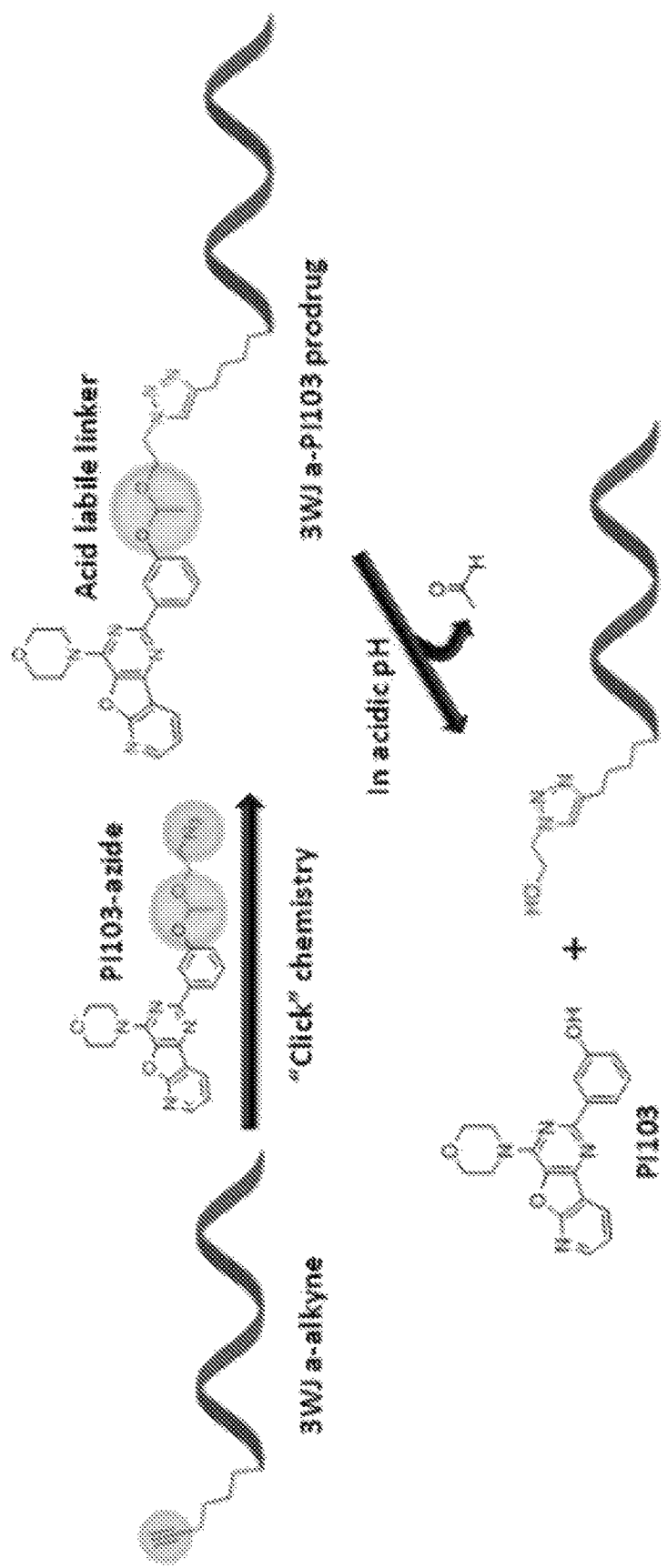

FIGS. 52A-52E shows design and synthesis of pRNA strands with multiple aldehyde groups to conjugate drugs for pH responsive drug release. FIG. 52A. Schematic illustration of conjugation of multiple drugs on 3WJ core. Shown are SEQ ID NOs:16-18. FIG. 52B Example of drugs bearing free amine groups for imine bond linkage. FIG. 52C. Example of drugs bearing hydroxyl groups for acetal linkage. FIG. 52D. Example of pH sensitive linker design using hydrazine bonds. FIG. 52E. Example of acil labile linker to conjugate P1103 prodrug to nucleic acid oligomers.

Figure 53A:
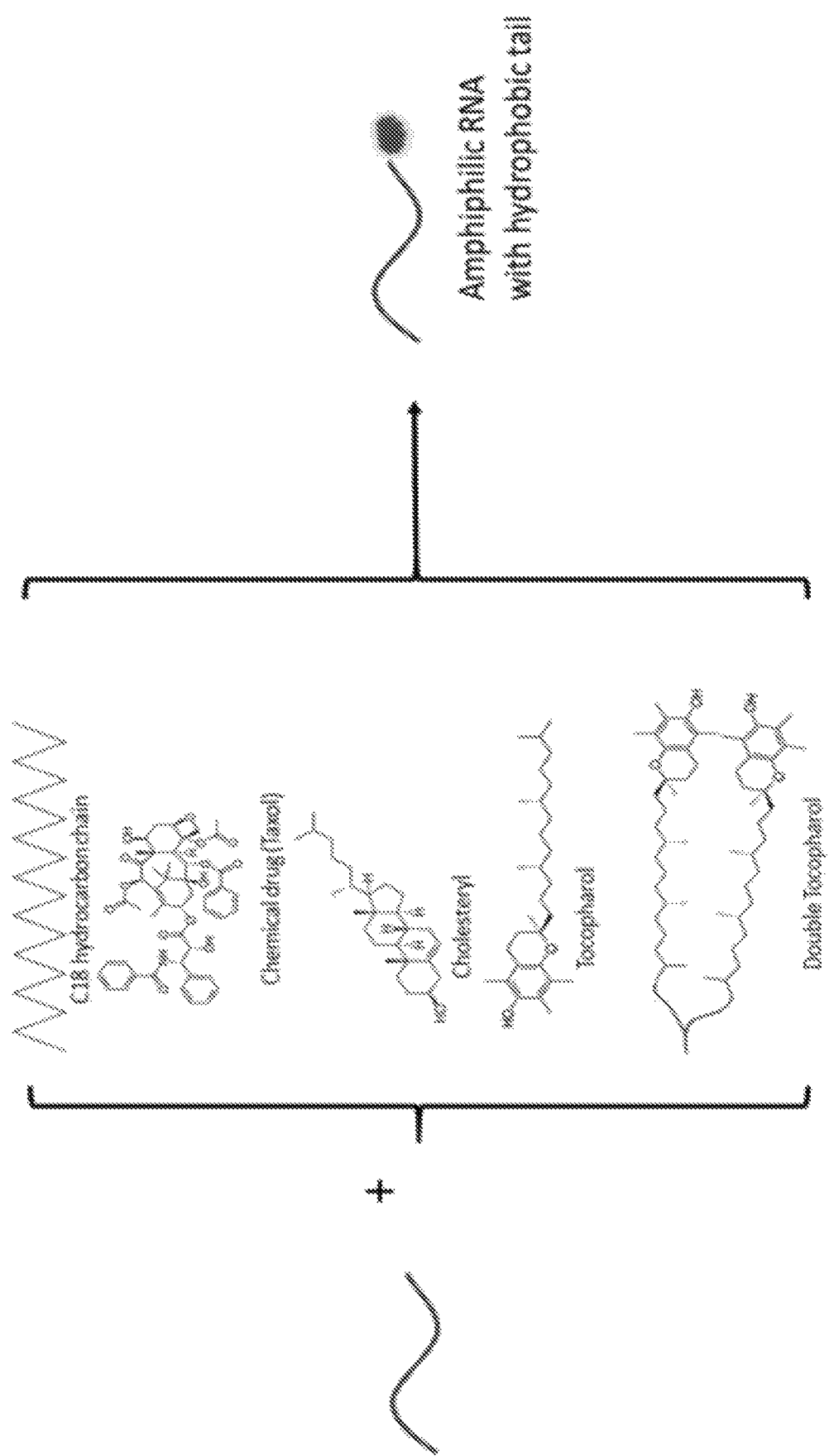
Figure 53B:
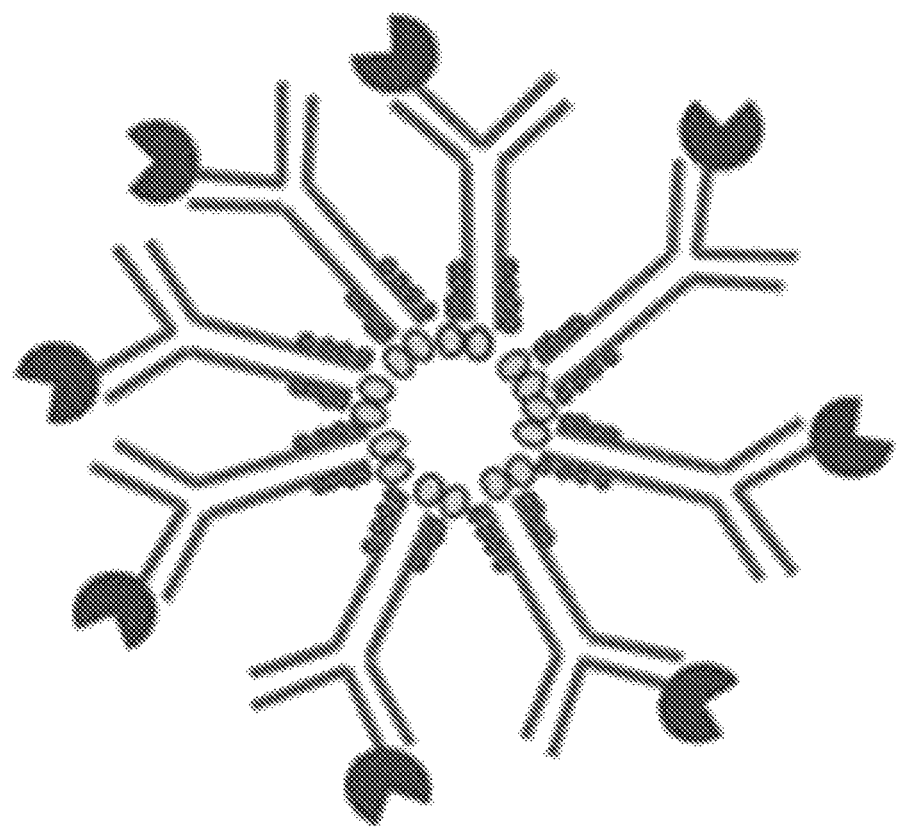
Figure 53B:
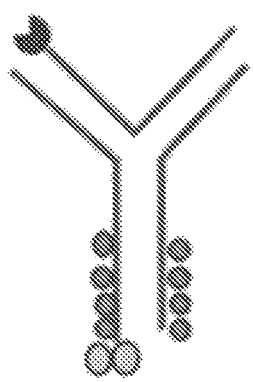
Figure 53C:
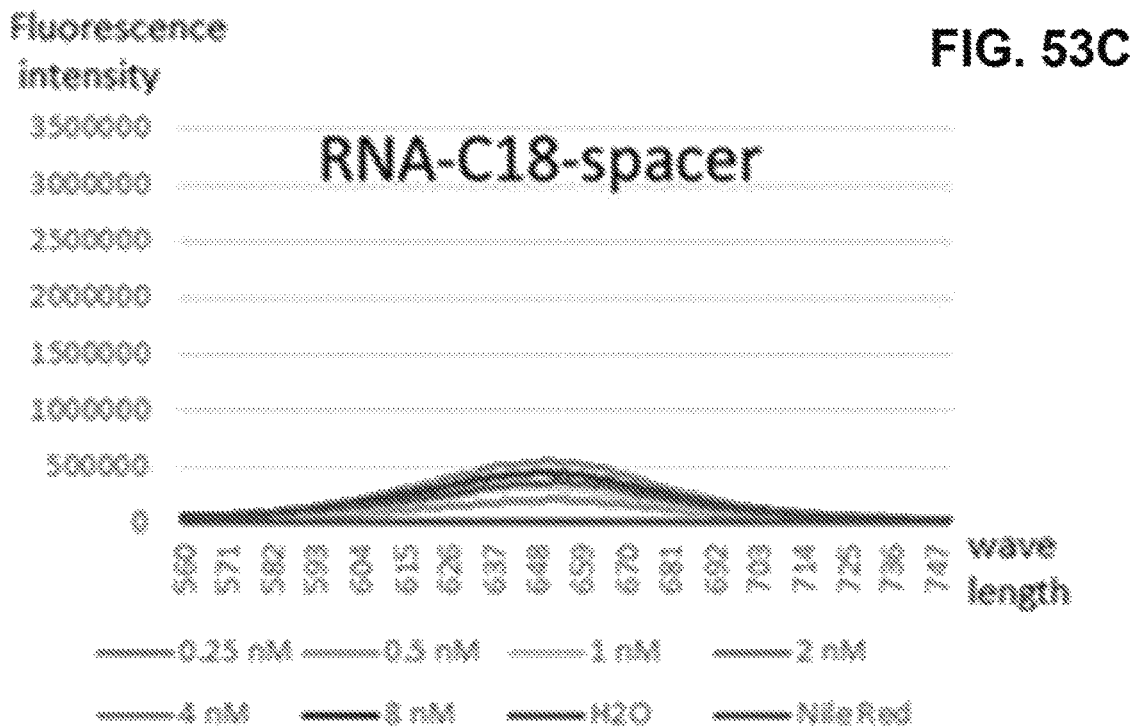
Figure 53D:
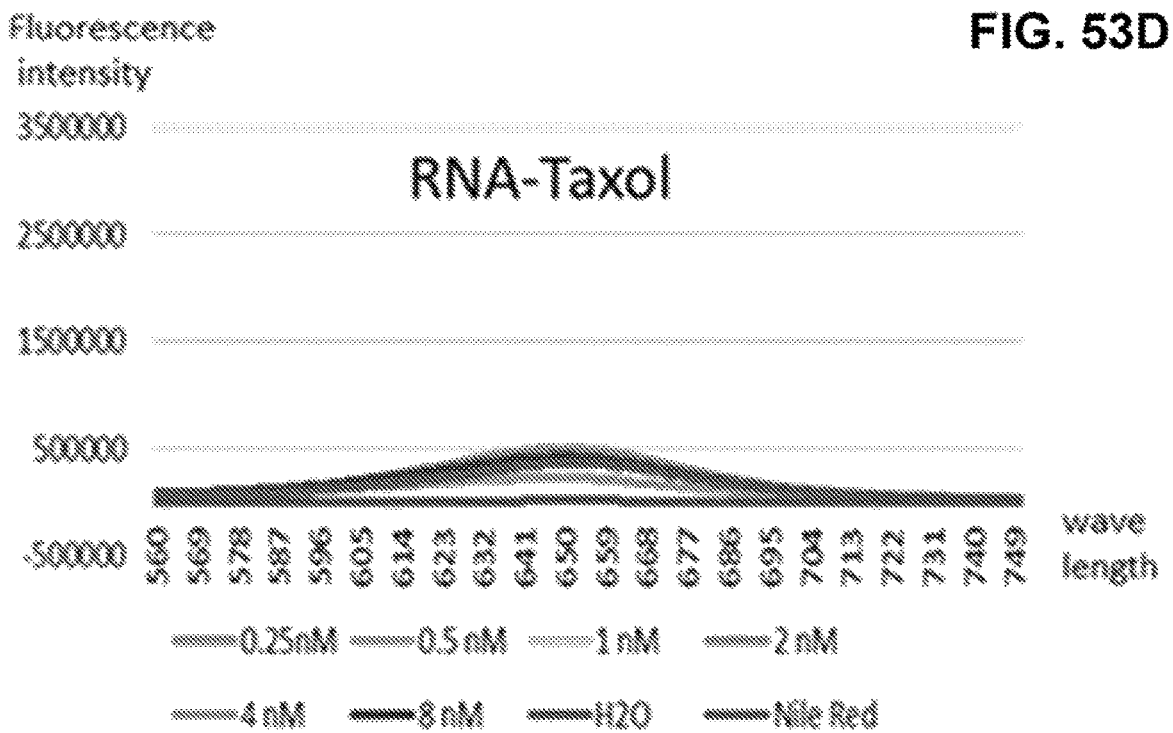
Figure 53E:
Figure 53F:
Figures 53G, 53H:
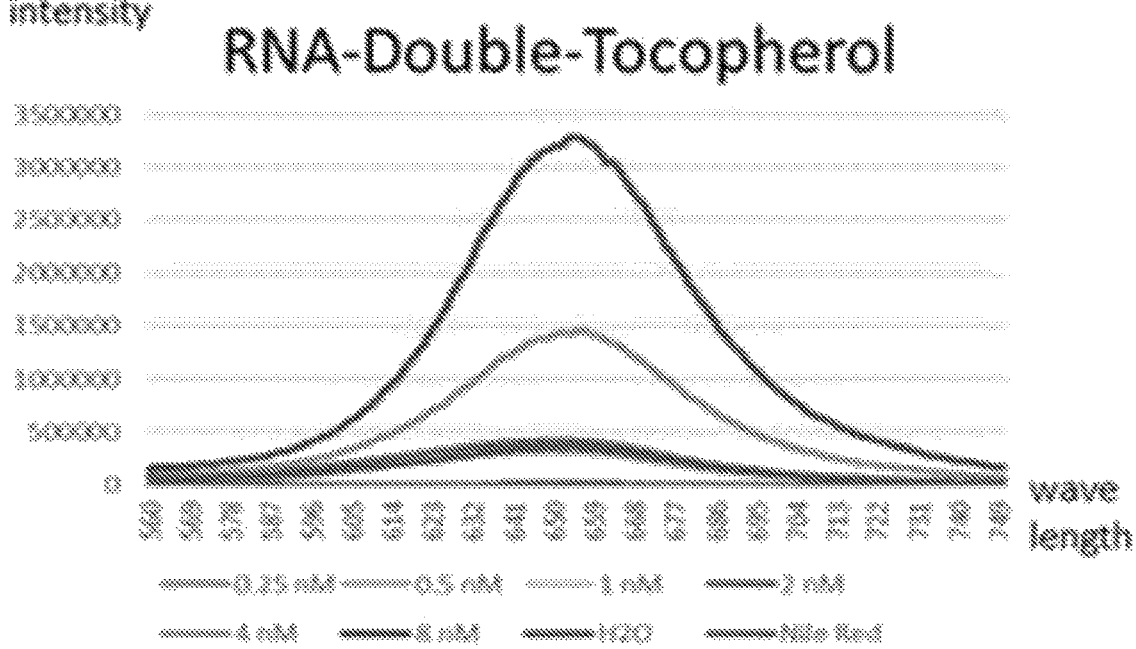

FIGS. 53A-53H shows design and preparation of RNA-based thermostable micelles for delivery of erlotinib for cancer therapy. FIG. 53A. Amphiphilic RNA strands with tunable hydrophobic modifications for formation of RNA micelles. FIG. 53B. Illustration of RNA-tocopherol micelles conjugated with functional moieties. FIGS. 53C-53H. Critical micelle concentration determination of 5 amphiphilic RNA strands with tunable hydrophobic modifications.

Figure 54D:
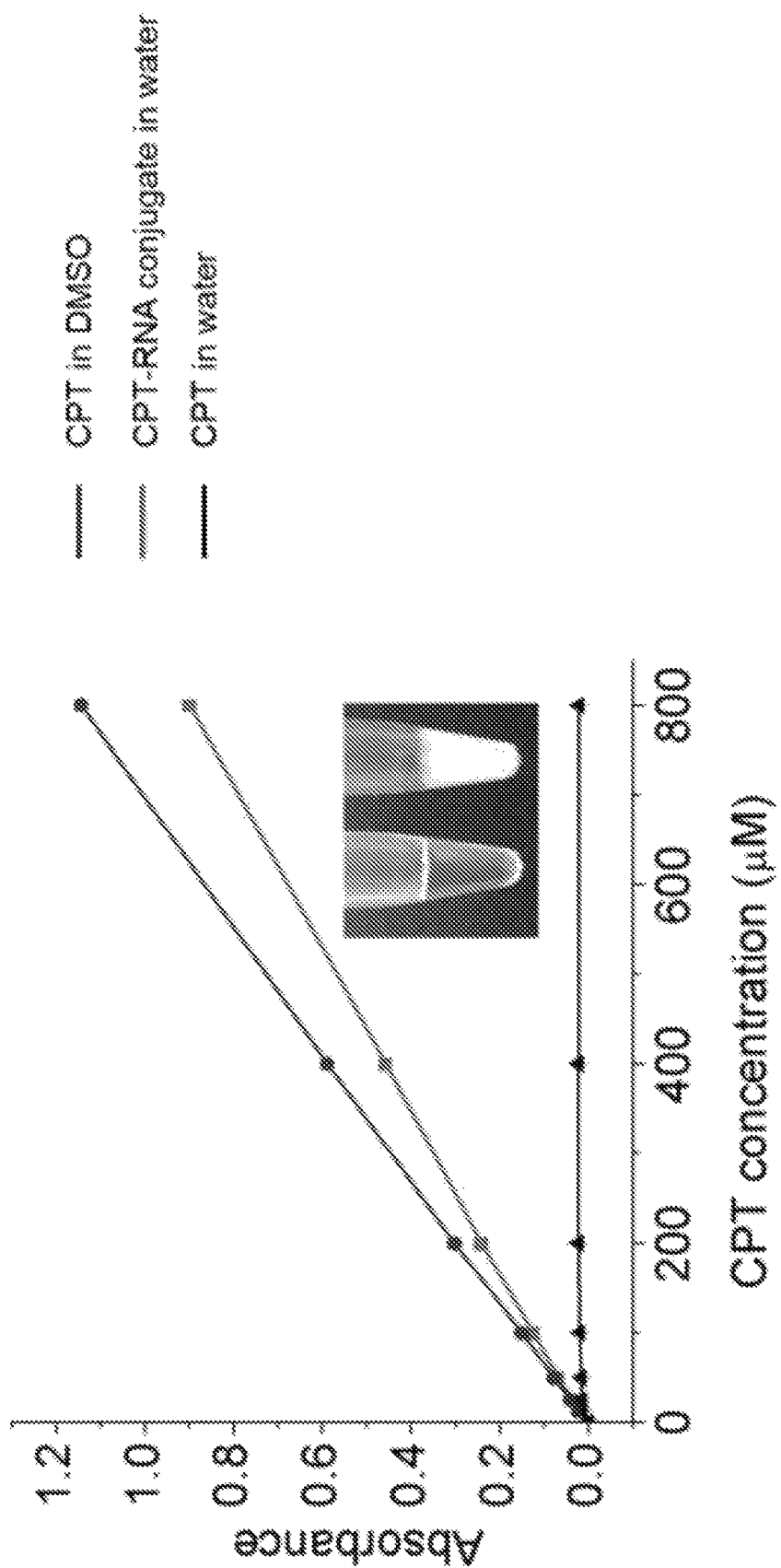
Figure 54E:
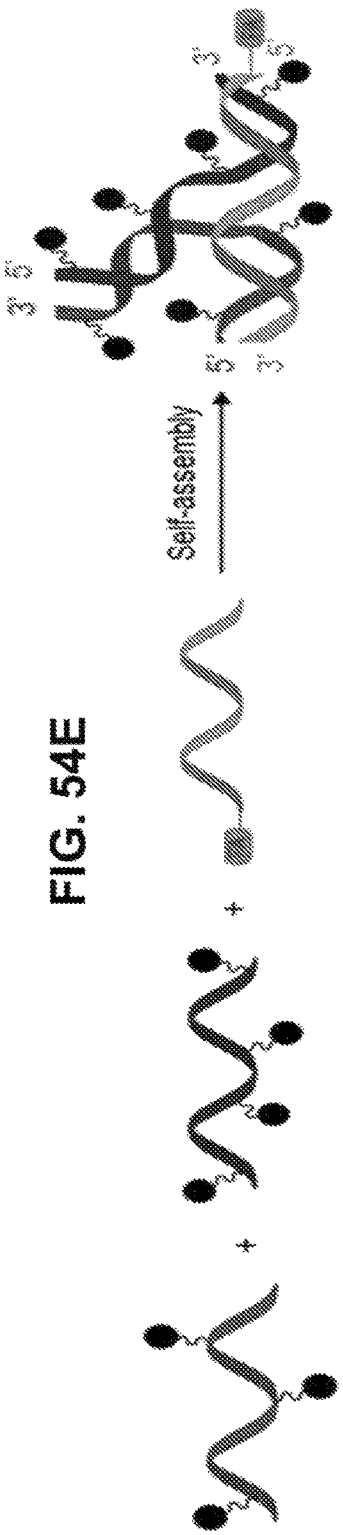
Figure 54H:
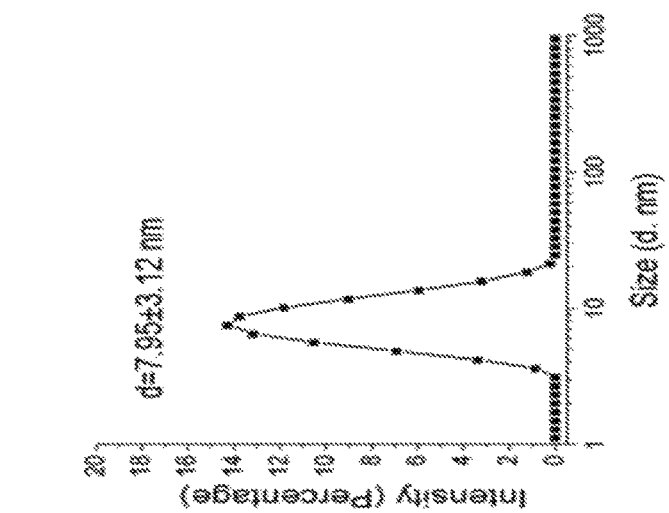
Figure 54G:
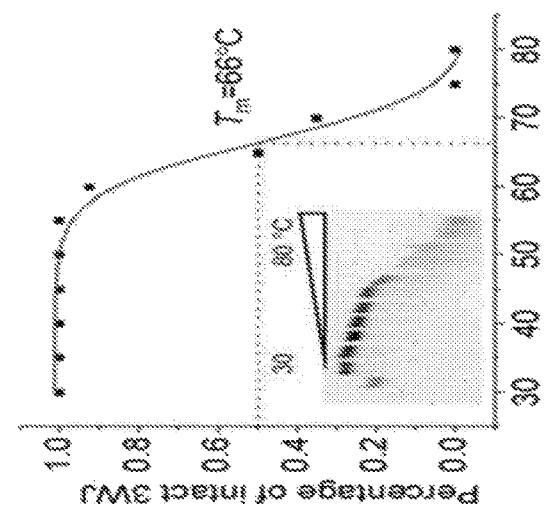
Figure 54F:
Figure 54K:
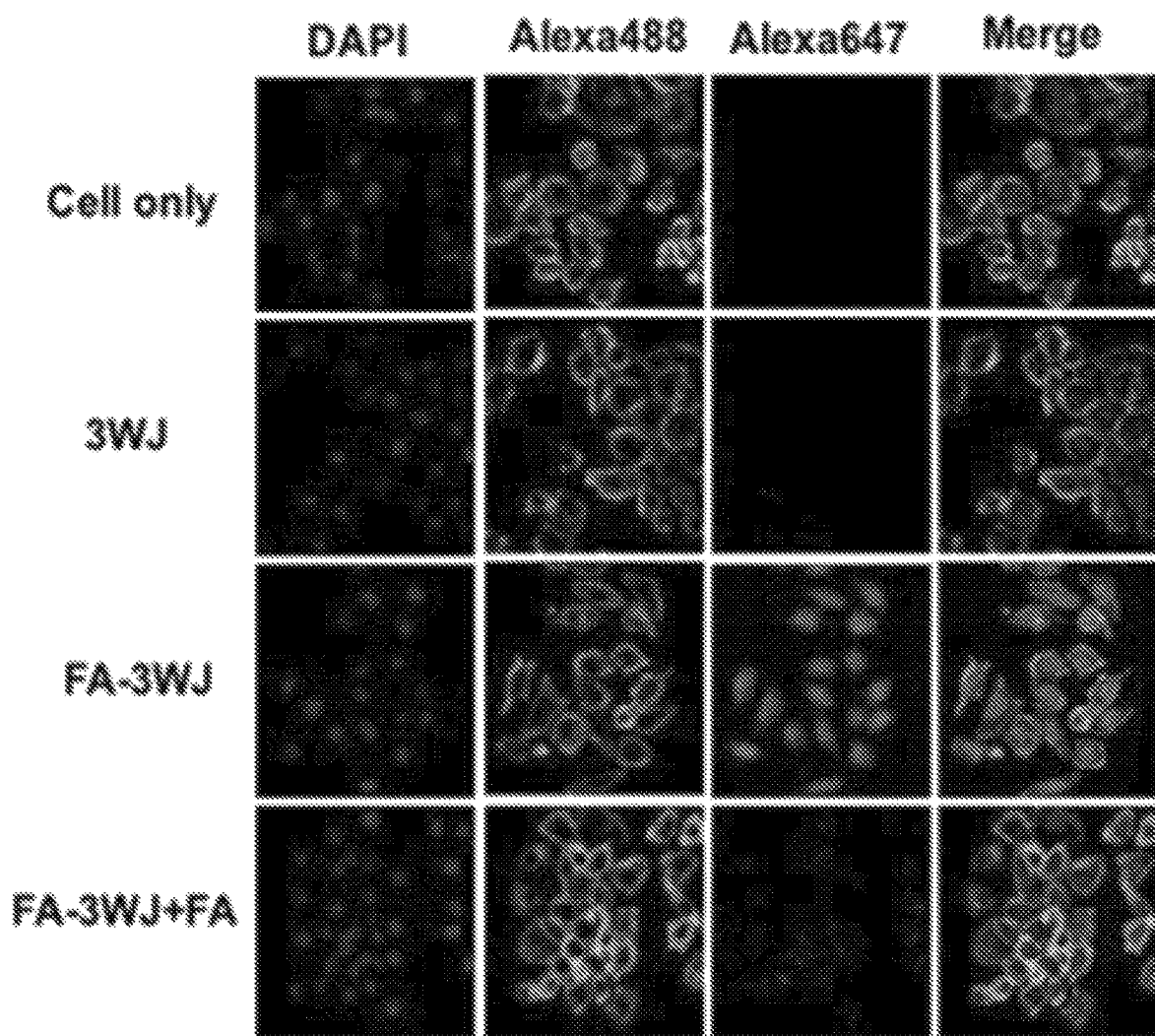
Figure 54L:
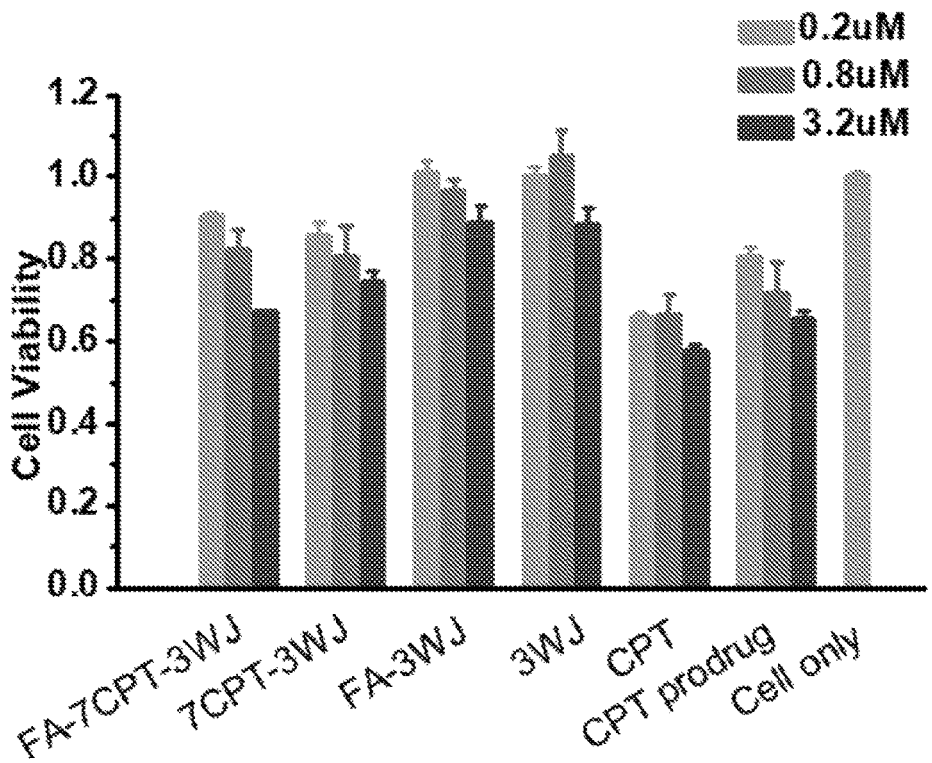
Figure 54M:
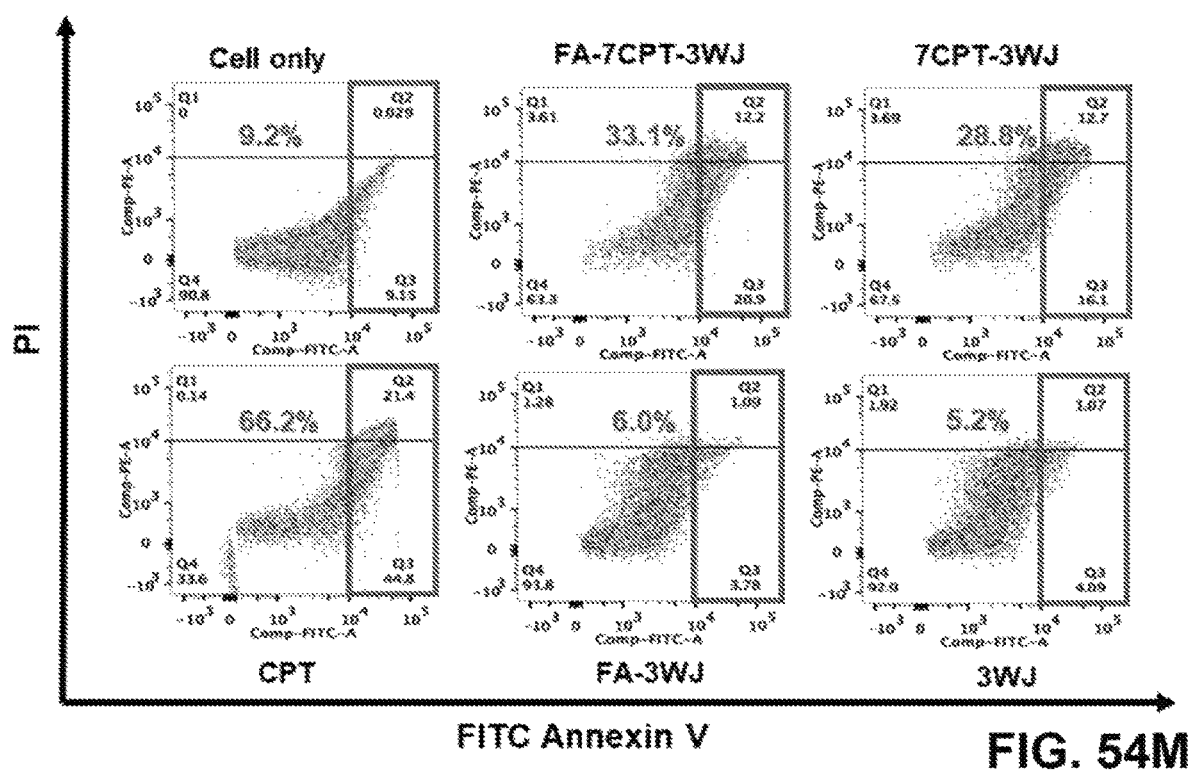
Figure 54N:
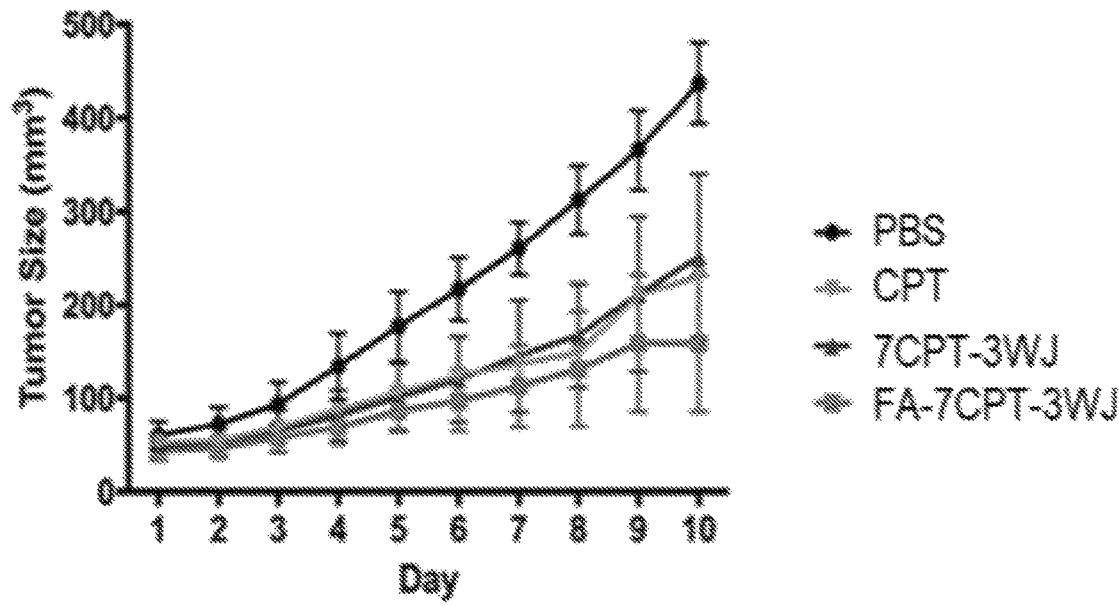
Figure 54O:
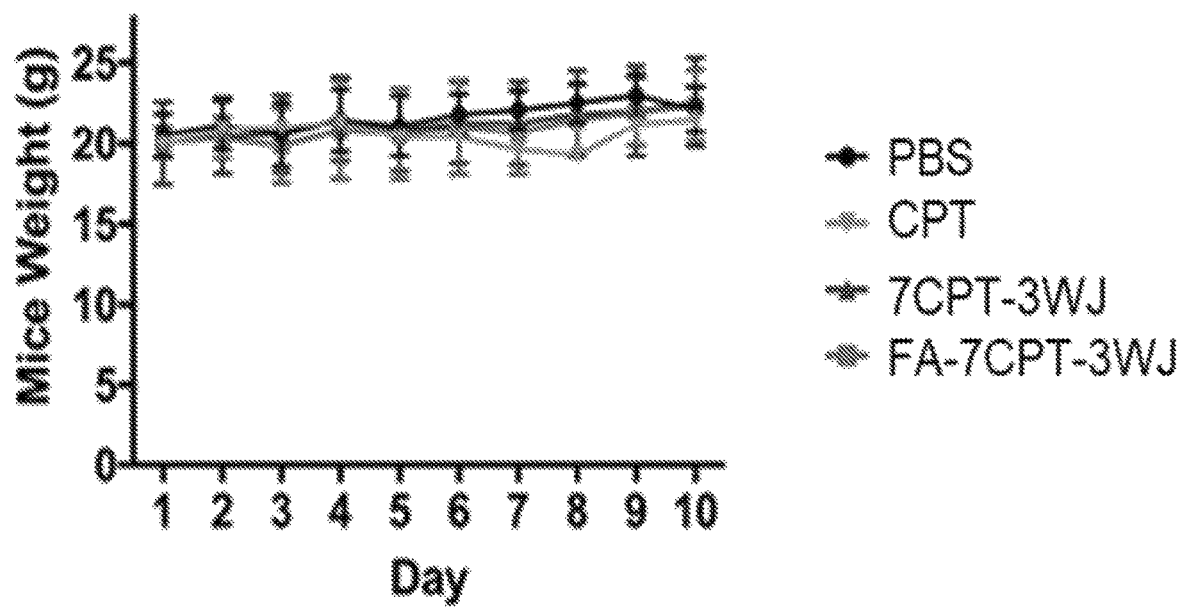
Figure 54P:
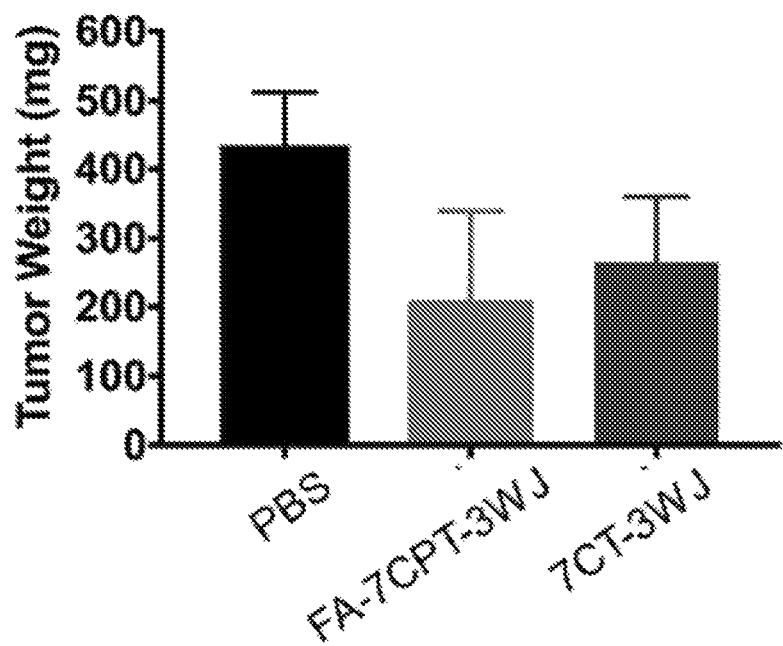

FIGS. 54A-54P shows design and preparation of CPT-RNA conjugates for suppression of KB tumor xenograft growth. FIGS. 54A-54C. CPT-RNA conjugation. FIGS. 54B-54D. Drug solubilization by conjugation to RNA. FIGS. 54C-54H. Assembly, thermodynamic stability and size distribution of CPT carrying RNA nanoparticles. FIGS. 54D-54I. CPT release profile from RNA nanoparticles. FIGS. 54J-54K. Cell binding and internalization of CPT-RNA nanoparticles. FIGS. 54L-54M. Cytotoxicity and Apoptosis effect of CPT RNA nanoparticles. FIGS. 54N-54P. Tumor suppression of CPT RNA NPs in KB tumor xenograft mouse model.

DETAILED DESCRIPTION

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Aspects of the present disclosure will employ, unless otherwise indicated, techniques of molecular biology, microbiology, organic chemistry, biochemistry, physiology, cell biology, cancer biology, physics, and the like, which are within the skill of the art. Such techniques are explained fully in the literature.

Before the aspects of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular aspects only, and is not intended to be limiting. It is also possible in the present disclosure that steps can be executed in different sequence where this is logically possible unless the context clearly dictates otherwise.

Definitions

As used herein, "active agent" or "active ingredient" refers to a component or components of a composition to which the whole or part of the effect of the composition is attributed. Active agents can be pharmaceutically active compounds, molecules (including but not limited to chemical and biological molecules), or other substance that, when in contact with an RNA nanostructure and/or when not in contact with an RNA nanostructure can elicit an effect (e.g. a pharmaceutical and/or biological effect) in a subject to which it is administered.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein "anti-infectives" can include, but are not limited to, antibiotics, antibacterials, antifungals, antivirals, and antiproatozoals.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, "control" is an alternative subject or sample used in an experiment for comparison purposes and included to minimize or distinguish the effect of variables other than an independent variable. A "control" can be positive or negative.

As used herein, "coupled" or "coupled to" refers to the direct or indirect attachment or linkage or other joining of two or more components of a larger structure or system.

As used herein, "conjugated" has the same meaning as "attached". As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

As used herein, "identity," "identical to", and the like can refer to the relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, the term "motif" in reference to a nanoparticle age is meant to refer to a double-stranded or single-stranded ribonucleic acid or analog thereof. Individual motifs are joined together into larger particles by attachment to each other. Attachment can occur by non-covalent linking.

As used herein, the term "nanoparticle" is meant to refer to a particle between 1 nm up to 1,000 nm in diameter. The nanoparticle can be between 5 nm and 30, 10 nm and 50 nm, between 10 nm and 40 nm, between 10 nm and 30 nm, between 10 nm and 20 nm, and 10 nm and 15 nm. The RNA can be obtained from any source, for example bacteriophages phi 29, HIV, *Drosophila*, the ribosome, or be a synthetic RNA.

As used herein, the term "nanostructure" is meant to refer to a structure between 1 nm up to 1,000 nm when measured along its largest dimension in any direction. The nanostructure can be between 5 nm and 30, 10 nm and 50 nm, between 10 nm and 40 nm, between 10 nm and 30 nm, between 10 nm, and 20 nm, and 10 nm and 15 nm as measured along its largest dimension in any direction.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. In particular, "Polynucleotide" and "nucleic acids" also includes 2 Fluoro, 2'O-methyl, LNA (locked nucleic acids), and A other variants of 2' modifications of the ribose (sugar) moiety of native nucleic acids. Natural nucleic acids have a proton or hydroxyl group at the 2'ribose position (DNA and RNA, respectively), artificial nucleic acids may contain other types of 2' modification to increase thermodynamic and enzymatic stability. Thus, DNAs or RNAs with the 2' ribose position modified for stability or for other reasons are "nucleic acids" or "polynucleotide" as that term is intended herein. As used herein, "nucleic acid sequence" and "oligonucleotide" also encompasses a nucleic acid and polynucleotide as defined above.

The term "pharmaceutically acceptable" describes a material that is not biologically or otherwise undesirable, i.e., without causing an unacceptable level of undesirable biological effects or interacting in a deleterious manner.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. In some aspects, at least 95% by weight of the particles of the active ingredient have an effective particle size in the range of 0.01 to 10 micrometers.

As used herein, the term "prevent" or "preventing" refers to precluding, averting, obviating, forestalling, stopping, or hindering something, e.g. a disease or symptom thereof, from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells. The term "prevent" or "preventing" includes maintaining or limiting a disease in a subclinical state.

As used herein, "self-assembly" refers to the ability of nucleic acids (and, in some instances, preformed nucleic acid nanostructures (e.g., crystals)) to anneal to each other, in a sequence-specific manner, in a predicted manner and without external control. In some aspects, nucleic acid nanostructure self-assembly methods include combining nucleic acids (e.g., single-stranded nucleic acids, or oligonucleotides) in a single vessel and allowing the nucleic acids to anneal to each other, based on sequence complementarity. In some aspects, this annealing process involves placing the nucleic acids at an elevated temperature and then reducing the temperature gradually in order to favor sequence-specific binding. Various nucleic acid nanostructures or self-assembly methods are known and described herein.

As used herein, the term "subject" refers to the target of administration, e.g., an animal, human, cell, or population of cells. Thus, the subject of the herein disclosed methods can be a vertebrate, such as a mammal, a fish, a bird, a reptile, or an amphibian. The subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

Discussion

RNA nanotechnology provides great promise for the treatment of diseases, including, but not limited to cancer. RNA nanoparticles can be used as a carrier for various active agents. However, current RNA nanoparticles fall short of delivering on the promise of RNA nanotechnology. For example, current RNA nanoparticles are limited in that they can only be conjugated to one active agent per RNA strand of the RNA nanoparticle. Due to the large size of the RNA nanoparticle as compared to the conjugated active agent, the molar concentration of the active agent carried by the RNA nanoparticles is low. In other words, the loading efficiency of the RNA nanoparticles is low. This results in a low and ineffective amount of active agent being delivered to the subject via these RNA nanoparticles rendering current RNA nanoparticles an unsuitable carrier for active agent delivery for treatment and/or prevention of a disease.

While a straightforward approach to address this problem is to conjugate more molecules of active agent to each RNA nanoparticle, attempts to address the issue of loading inefficiency in this manner have failed. This failure can be due at least in part to the folding energy and melting temperature (Tm) of RNA. Conjugation of more than one molecule of active agent per RNA nanoparticle via covalent linkages results in dissociation of the RNA nanoparticle.

In addition to the low loading efficiency of current RNA nanoparticles, current RNA nanoparticles also suffer from dissociation after systemic injection. This can be due to the physical hinderance, low Tm, and/or low thermostability of current RNA nanoparticles.

With the deficiencies of current RNA nanoparticles in mind, described herein are RNA nanostructures that can be composed of one or more modular RNA motifs. The RNA nanostructures can be loaded with one or more active agents and can have ultra-high thermostability, ultra-high melting temperature, and other physical properties that contribute to an increased loading efficiency and/or capacity. The RNA nanostructures described herein with or without an active agent can be administered to a subject. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

RNA Nanostructures

Described herein are RNA nanostructures that can be composed of one or more modular RNA motifs. The modular RNA motifs can each be composed of 3-9 individual synthetic RNA oligonucleotides that are designed (or configured) to self-assemble into the highly ordered modular RNA motif. When assembled, the modular RNA motifs can be composed of multiple double-stranded arms (DAs) that can be arranged around a core domain. Multiple modular RNA motifs can be attached to each other to form the RNA nanostructures. FIGS. 41A-45B show various aspects of the modular RNA motifs and RNA nanostructures. With a general understanding of the RNA nanostructures in mind, various aspects of the modular RNA motifs and the RNA nanostructures are now described in greater detail.

Modular RNA Motifs

As described above, the RNA nanostructures can include one or more modular RNA motifs. FIGS. 41A-41G show various aspects of modular RNA motifs. As shown in FIGS. 41A-41G, the modular RNA motif can be composed of 3, 4, 5, 6, 7, 8, or 9 synthetic single-stranded RNA oligonucleotides that can self-assemble into the modular RNA motifs via hybridization. Each synthetic single-stranded RNA oligonucleotide can be about 16 to about 120 bases in length. The exact sequence of each synthetic single-stranded RNA oligonucleotide in each modular RNA motif can be designed such that they achieve specific physical characteristics when assembled with 2 or more other synthetic single-stranded RNA oligonucleotides. The RNA motifs can be composed of 3, 4, 5, 6, 7, 8, or 9 synthetic RNA oligonucleotides. The synthetic RNA oligonucleotides can be designed such that they form highly ordered 2-D and/or 3-D structures upon self-assembly. When self-assembled, the synthetic RNA oligonucleotides form highly ordered structures that are referred to herein as modular RNA motifs. As shown, for example, in FIGS. 41A-41G, the 2-D structure can depend, at least in part, on the number of synthetic RNA oligonucleotides. The RNA nanostructures can have 3, 4, 5, 6, 7, 8, or 9 double-stranded arms (DAs) that stem off of a core domain. The DAs can be symmetrically or asymmetrically arranged around the core domain.

Figure 1A:
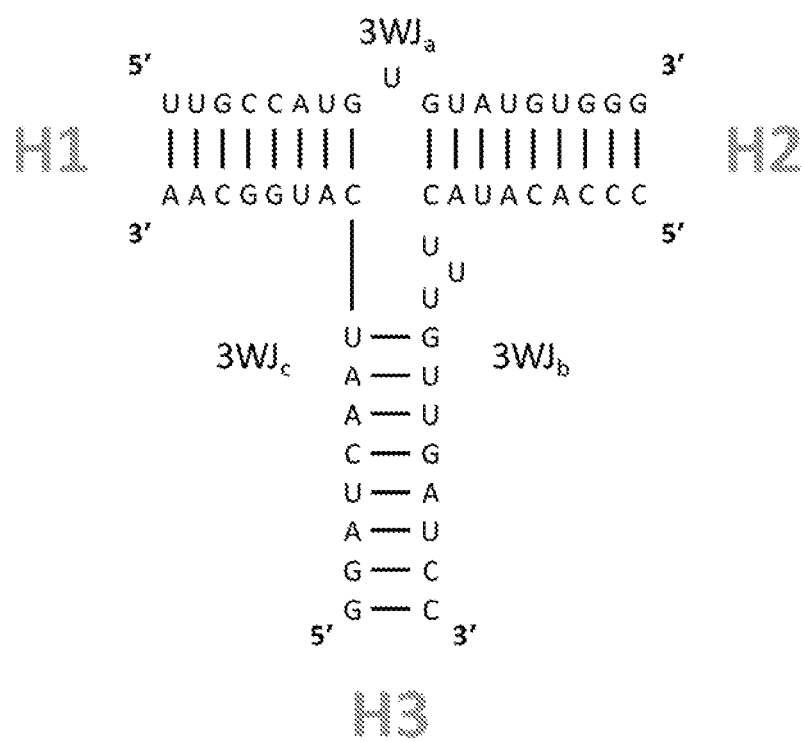
FIGS. 1A to 1E show structure base and assembly principle of pRNA-3WJ-PTX micelles.
Figure 1B:
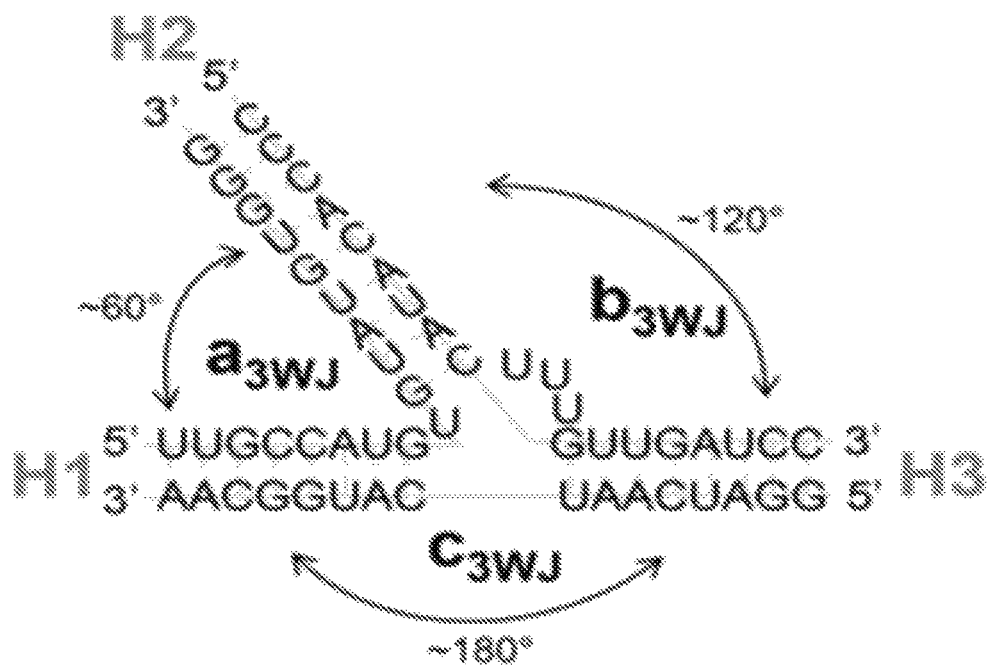
Figure 29A:
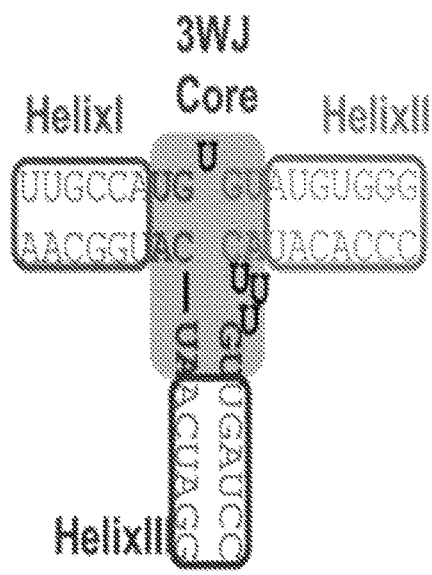
FIGS. 29A to 29C show design and sequences of branched 3WJ modular RNA motifs with three different cores (Phi29, SF5, M2) and four sets of helixes (WT, Mod, 30, 32).
Figure 29B:
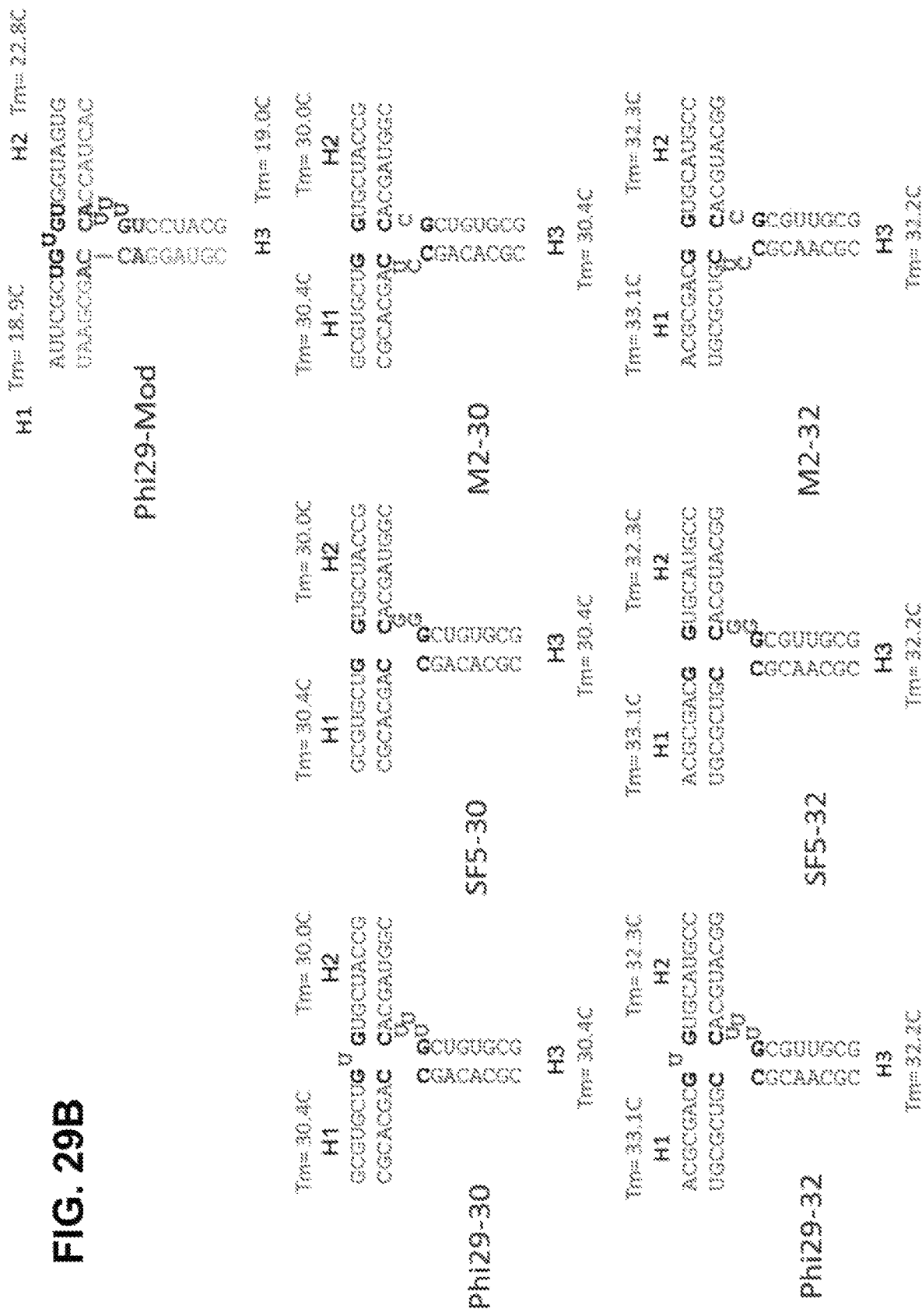
Figure 29C:
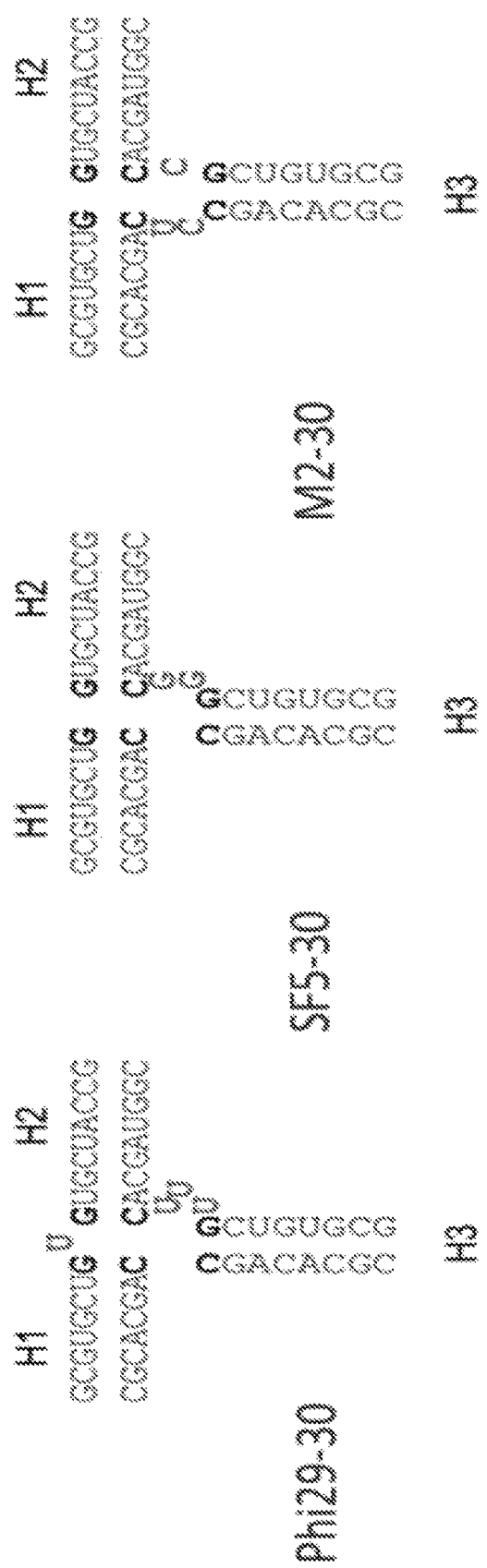
Figure 30A:
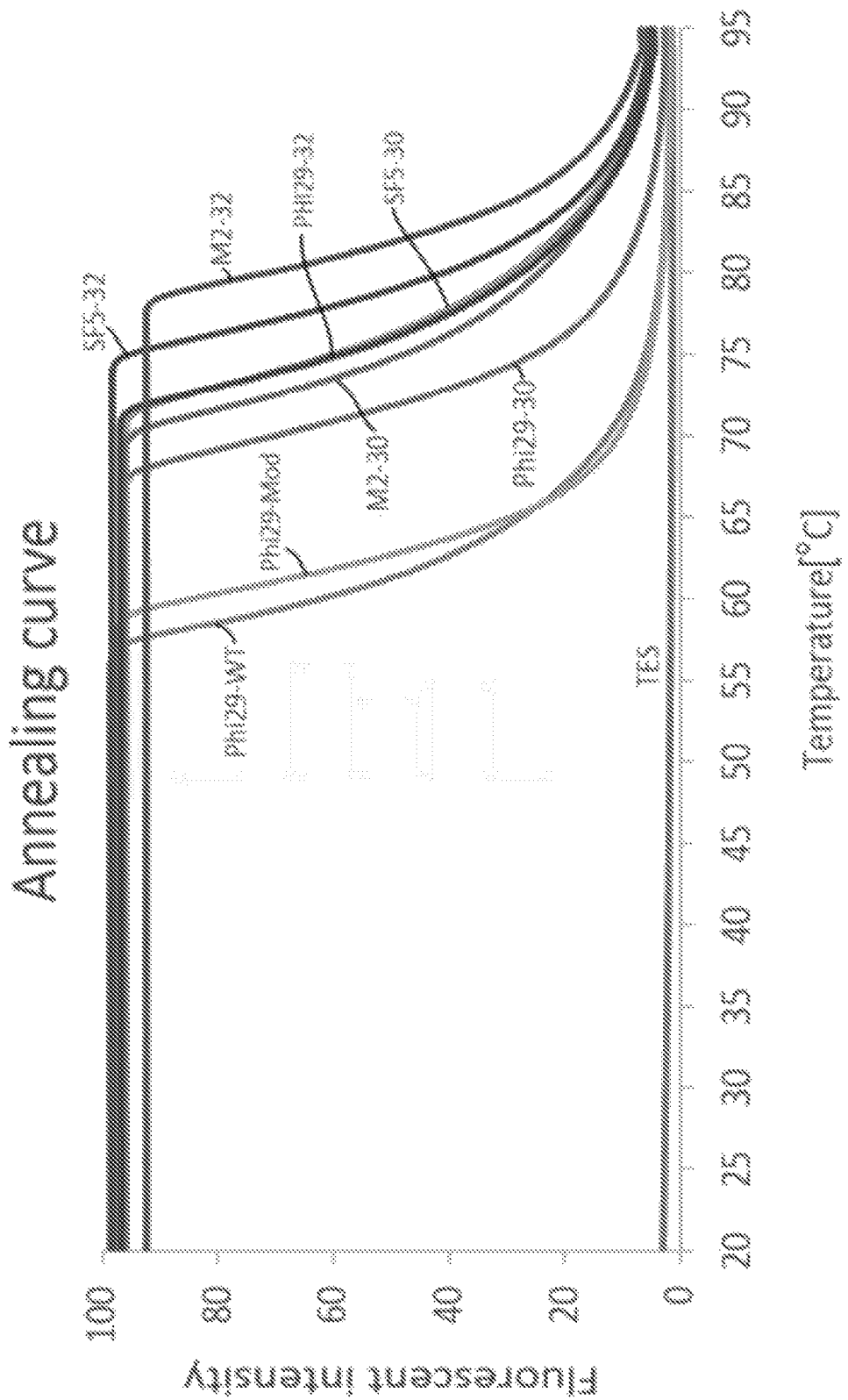
Figure 30B:
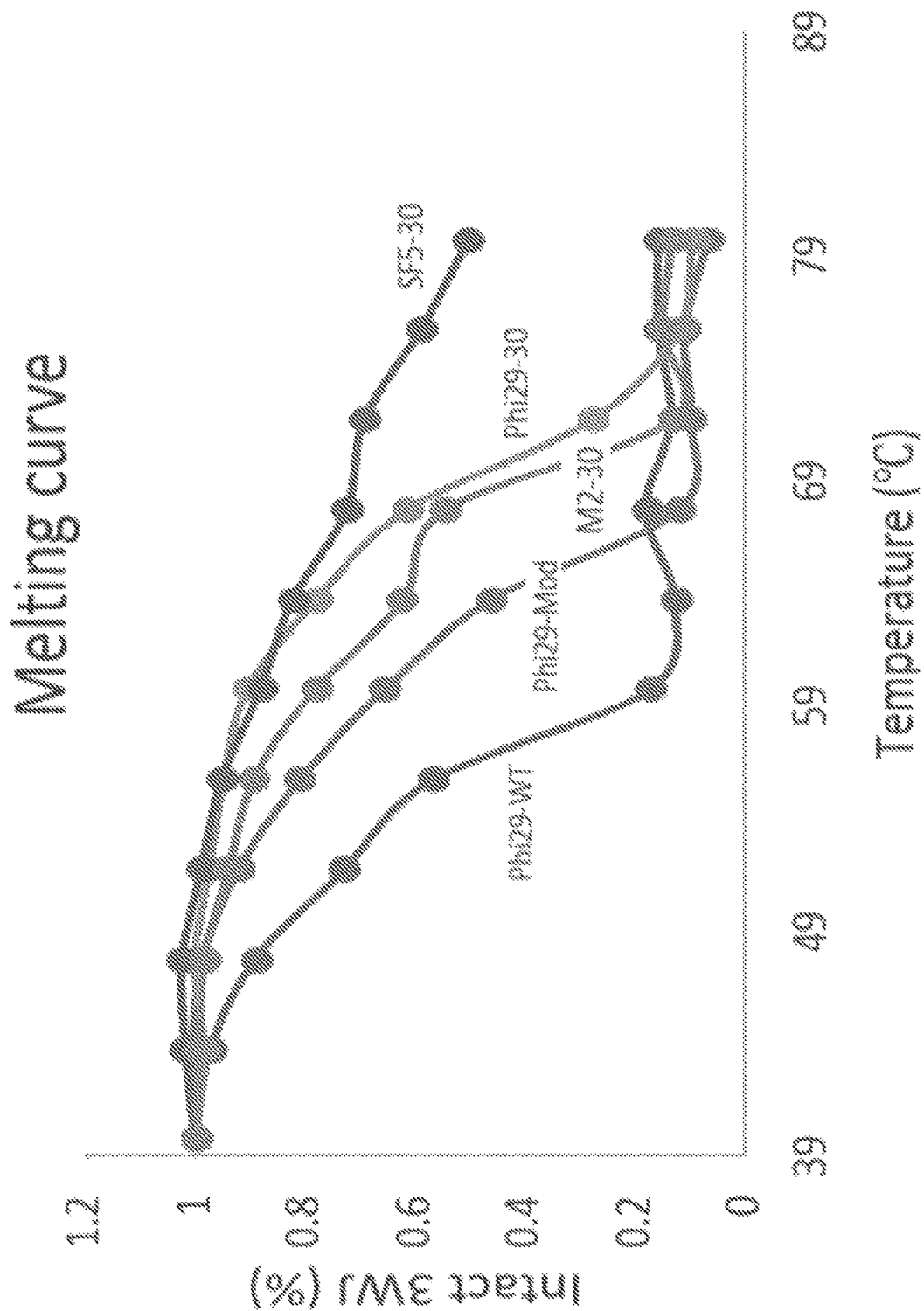
Figure 31A:
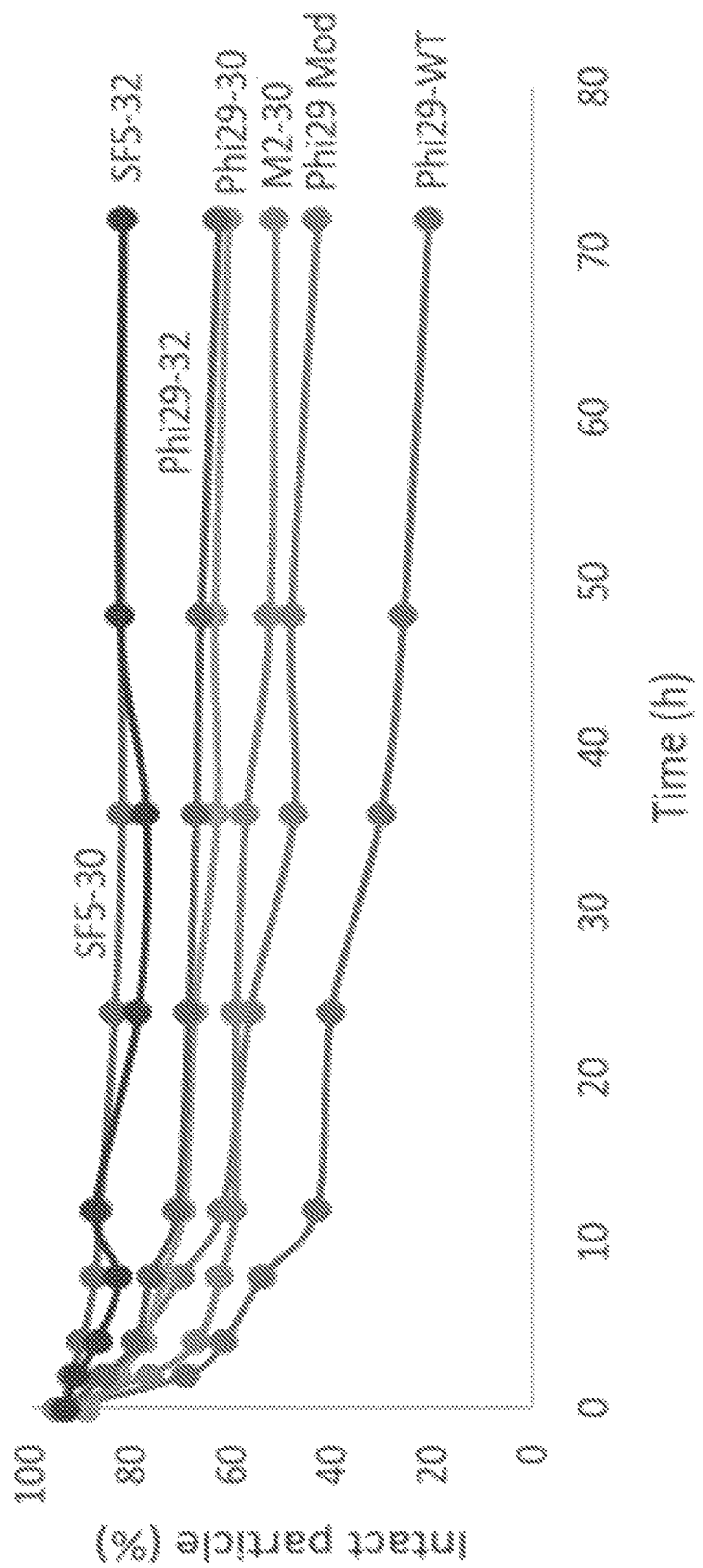

The core domain can have 0-4 symmetric or asymmetric bulge nucleotides separating individual DAs, which can allow for optimization of thermodynamic stability, steric constraints, and/or structural arrangements of individual loops. Changes in duplex sequence (the DAs) and number unpaired core nucleotides can both affect thermodynamic stability of the modular RNA motif and/or RNA nanostructure. Thus the physical properties and functional characteristics can be optimized by altering the sequence of the synthetic RNA oligonucleotides that form the modular RNA motifs. As an example, FIG. 1B shows a modular RNA motif having 3 DAs and an asymmetric bulge of (5' UUU 3') between the H2 and H3 DAs and (5' U 3') between the H1 and H2 DAs. In another example, FIG. 29C shows modular RNA motifs with three DAs having different asymmetric bulges but identical DAs, (U|UUU|-, -|GG|-, and -|C|CU between their H1|H2|H3 DAs, respectively) resulting in differing Tm values for annealing (FIG. 30A). Also, FIGS. 38A-38G show modular RNA motifs with 3-9 DAs having symmetric bulges of (5' UG 3') between each DA.

As shown in FIGS. 41A-41G, the RNA oligonucleotides self-assemble such that the modular RNA motif contains a core domain (light gray region inside dashed box in FIGS. 41A-41G) with 3, 4, 5, 6, 7, 8, or 9 DAs (black portions shown in FIGS. 41A-41G). The DAs can be arranged around the core region such that there is an angle (theta) between any two adjacent DAs. For example, in FIG. 41A, the modular RNA motif contains 3 synthetic RNA oligonucleotides that self assemble to form a modular RNA motif having 3 DAs. The angle formed between $DA_1$ and $DA_2$ is noted as $\theta^2$, the angle formed between $DA_2$ and $DA_3$ is noted as $\theta^3$, and the angle formed between $DA_3$ and $DA_2$ is noted as $\theta^1$. FIGS. 41B-41G have similar notations with respect to the modular RNA motif shown in each FIG. The DAs can be positioned substantially symmetrically around the core domain. In other aspects, the DAs are not positioned symmetrically around the core domain. Table 1 shows the angle ranges for each modular RNA motif as referenced in FIGS. 41A-41G.

TABLE 1

Angles for modular RNA motifs.

| θ | Degree Range |
|---|---|
| 1 | About 30° to about 180° |
| 2 | About 30° to about 180° |
| 3 | About 30° to about 180° |
| 4 | About 30° to about 180° |
| 5 | About 30° to about 180° |
| 6 | About 30° to about 180° |
| 7 | About 30° to about 180° |
| 8 | About 30° to about 180° |
| 9 | About 30° to about 180° |
| 11 | About 30° to about 180° |
| 12 | About 30° to about 180° |
| 13 | About 30° to about 180° |
| 14 | About 30° to about 180° |
| 15 | About 30° to about 180° |
| 16 | About 30° to about 180° |
| 17 | About 30° to about 180° |
| 18 | About 30° to about 180° |
| 19 | About 30° to about 180° |
| 20 | About 30° to about 180° |
| 21 | About 30° to about 180° |
| 22 | About 30° to about 180° |
| 23 | About 30° to about 180° |
| 24 | About 30° to about 180° |
| 25 | About 30° to about 180° |
| 26 | About 30° to about 180° |
| 27 | About 30° to about 180° |
| 28 | About 30° to about 180° |
| 29 | About 30° to about 180° |
| 30 | About 30° to about 180° |
| 31 | About 30° to about 180° |
| 32 | About 30° to about 180° |
| 33 | About 30° to about 180° |
| 34 | About 30° to about 180° |
| 35 | About 30° to about 180° |
| 36 | About 30° to about 180° |
| 37 | About 30° to about 180° |
| 38 | About 30° to about 180° |
| 39 | About 30° to about 180° |
| 40 | About 30° to about 180° |
| 41 | About 30° to about 180° |
| 42 | About 30° to about 180° |

The melting temperature (Tm) of the modular RNA motif can be about 65° C. or more. In some aspects, the melting temperature of the modular RNA motif can be greater than 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the Tm of the modular RNA motif can be 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 65° C. to 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 66 to 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of modular RNA motif can range from 67 to 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 68 to 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 69 to 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 70 to 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 71 to 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 72 to 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 73 to 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 74 to 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 75 to 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 76 to 77, 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 77 to 78, 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 78 to 79, 80, 81, 82, 83, 84, 85, 86, 87, 88, 89, 90, 91, 92, 93, 94, 95, 96, 97, 98, 99, or 100° C. In some aspects, the melting temperature of the modular RNA motif can range from 79 to 80, 81, 82, 83, 84, 85, 86, 87, 88, 89, 90, 91, 92, 93, 94, 95, 96, 97, 98, 99, or 100° C. In some aspects, the melting temperature of modular RNA motif can range from 80 to 81, 82, 83, 84, 85, 86, 87, 88, 89, 90, 91, 92, 93, 94, 95, 96, 97, 98, 99, or 100° C. In some aspects, the melting temperature of the modular RNA motif can range from 81 to 82, 83, 84, 85, 86, 87, 88, 89, 90, 91, 92, 93, 94, 95, 96, 97, 98, 99, or 100° C. In some aspects, the melting temperature of the modular RNA motif can range from 82 to 83, 84, 85, 86, 87, 88, 89, 90, 91, 92, 93, 94, 95, 96, 97, 98, 99, or 100° C. In some aspects, the melting temperature of the modular RNA motif can range from 83 to 84, 85, 86, 87, 88, 89, 90, 91, 92, 93, 94, 95, 96, 97, 98, 99, or 100° C. In some aspects, the melting temperature of the modular RNA motif can range from 84 to 85, 86, 87, 88, 89, 90, 91, 92, 93, 94, 95, 96, 97, 98, 99, or 100° C. In some aspects, the melting temperature of the modular RNA motif can range from 85 to 86, 87, 88, 89, 90, 91, 92, 93, 94, 95, 96, 97, 98, 99, or 100° C. In some aspects, the melting temperature of the modular RNA motif can range from 86 to 87, 88, 89, 90, 91, 92, 93, 94, 95, 96, 97, 98, 99, or 100° C. In some aspects, the melting temperature of modular RNA motif can range from 87 to 88, 89, 90, 91, 92, 93, 94, 95, 96, 97, 98, 99, or 100° C. In some aspects, the melting temperature of the modular RNA motif can range from 88 to 89, 90, 91, 92, 93, 94, 95, 96, 97, 98, 99, or 100° C. In some aspects, the melting temperature of the modular RNA motif can range from 89 to 90, 91, 92, 93, 94, 95, 96, 97, 98, 99, or 100° C. In some aspects, the melting temperature of the modular RNA motif can range from 90 to 91, 92, 93, 94, 95, 96, 97, 98, 99, or 100° C. In some aspects, the melting temperature of the modular RNA motif can range from 91 to 92, 93, 94, 95, 96, 97, 98, 99, or 100° C. In some aspects, the melting temperature of modular RNA motif can range from 92 to 93, 94, 95, 96, 97, 98, 99, or 100° C. In some aspects, the melting temperature of the modular RNA motif can range from 93 to 94, 95, 96, 97, 98, 99, or 100° C. In some aspects, the melting temperature of the modular RNA motif can range from 94 to 95, 96, 97, 98, 99, or 100° C. In some aspects, the melting temperature of the modular RNA motif can range from 95 to 96, 97, 98, 99, or 100° C. In some aspects, the melting temperature of the modular RNA motif can range from 96 to 97, 98, 99, or 100° C. In some aspects, the melting temperature of the modular RNA motif can range from 97 to 98, 99, or 100° C. In some aspects, the melting temperature of the modular RNA motif can range from 98 to 99, or 100° C. In some aspects, the melting temperature of the modular RNA motif can range from 99 to 100° C.

Synthetic RNA Oligonucleotides

As previously discussed, the modular RNA motifs can be composed of 3-9 individual synthetic RNA oligonucleotides that can self-assemble to form the modular RNA motifs. The synthetic RNA oligonucleotides can be single-stranded. Each individual synthetic RNA oligonucleotide can be composed of 16-120 nucleotides. The nucleotides can be native ribonucleotide or can be modified. In some aspects, the synthetic RNA oligonucleotide(s) can be 2' modified. The 2' or other modification can be a 2'Fluoro-, 2'O-methyl-, LNA- or any other backbone, sugar, or base modified ribonucleotide or any combination of native, backbone, sugar, and base modified ribonucleotides. Modifications are further discussed elsewhere herein. Each synthetic RNA oligonucleotide can be composed of 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides or any range therein. Each synthetic RNA oligonucleotide can be designed and configured such that it can self assemble with 2, 3, 4, 5, 6, 7, or 8 other synthetic RNA oligonucleotides into a modular RNA motif as described elsewhere herein. Rationale design of synthetic RNA oligonucleotides is described elsewhere herein.

The nucleotides can be unmodified or modified nucleotides. The modifications can be 5'-terminal modifications and/or 3'-terminal modifications and/or 2'-internal sugar modifications and/or base-internal modifications. Typical 5' terminal modifications include amino, carboxy, phosphate, thiol, maleimide, alkyne, cholesterol, aldehyde, carbon spacers, Peg-spacer, doubler, trebler, photocleavable amino, photocleavable spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 5' modifications known to an experienced user of the art. Typical 3' terminal modifications include amino, carboxy, phosphate, thiol, alkyne, cholesterol, carbon spacers, Peg-spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 3' modifications known to an experienced user of the art. Typical internal modifications include amino-dA, amino-dC, amino-dT, carboxy-dT, 2'O-propargyl, 2'amino, 2'fluoro, 2'methoxy, 5-ethynyl-dU, C8-alkyne-dC, C8-alkyne-dT, carbon spacers, Peg-spacer, fluorophores (e.g. Cyanine 3, 3.5, 5, 5.5, 7, Fluorescein, etc.), biotin, desthiobiotin, digoxigenin, quenchers (dabcyl, dabsyl, BlackHole, BBQ650, etc.) or other 5' modifications known to an experienced user of the art. The modification can be an alkyne group attached to a nucleotide. The modification can be a functional group attached to a nucleotide. Suitable functional groups are described elsewhere herein. The alkyne group(s) or functional group(s) present in each synthetic RNA oligonucleotide can facilitate conjugation of a cargo compound at the site(s) containing the alkyne group via, for example, click chemistry. See e.g. FIG. 3A. One or more of the terminal (e.g. the 5' and/or 3' end) nucleotides can be modified in a synthetic RNA oligonucleotide. One or both termini of the synthetic RNA oligonucleotide can be modified. In some aspects, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides can be modified. In some aspects, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides can be unmodified. If considering each nucleotide in a synthetic RNA oligonucleotide sequentially from the 5' terminal to the 3' terminal ends, the modified nucleotide(s) can be nucleotide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 or any combination thereof. Where more than one modified nucleotide is present, the modified nucleotides can be next to each other or can be spaced apart by one or more unmodified nucleotides. In some aspects, 1, 2, 3, 4, 5, 6, 7, 8, 9, 10 or more unmodified nucleotides can be between two modified nucleotides.

In some aspects, a synthetic RNA oligonucleotide can have a sequence according to any one of SEQ ID NOs: 1-54. In some aspects, a synthetic RNA oligonucleotide can have a sequence that is 80, 85, 90, 91, 92, 93, 94, 95, 96, 97, 98, or about 99 percent identical to any one of SEQ ID NOs: 1-54.

Methods of Making the Synthetic RNA Oligonucleotides

The synthetic RNA oligonucleotides, polynucleotide functional groups, and polynucleotide cargo compounds can be synthesized using standard molecular biologic and biochemical techniques. In other words, the various nucleic acids that can form the RNA nanoparticles can be de novo synthesized as desired or be generated from various nucleic acid expression vectors or transcribed in vitro. Such synthesis techniques will be known to the skilled artisan.

RNA Nanostructures

In some aspects, a single modular RNA motif can be an RNA nanostructure. Also described herein are RNA nanostructures that can include two or more modular RNA motifs. As shown, for example, in FIGS. 42A-42G, the RNA nanostructures can be ordered. A primary modular RNA motif (black modular RNA motif in e.g. FIGS. 42A-42G) can be attached or otherwise coupled to 3-9 additional modular RNA motifs to form an intermediate layer (dark grey modular RNA motifs in e.g. FIGS. 42A-42G). Each modular RNA motif in the intermediate layer can be attached or otherwise coupled to 3-9 additional modular RNA motifs. In some aspects, the modular RNA motifs attached or otherwise coupled to the intermediate layer of the RNA nanostructure can form a terminal or outer layer of the RNA nanostructure (light gray modular RNA motifs in e.g. FIGS. 42A-42G). In other embodiments, the modular RNA motifs attached or otherwise coupled to an intermediate layer of the RNA nanostructure can form another intermediate layer. In some aspects, the RNA nanostructure can have 1 intermediate layers of modular RNA motifs. It will be appreciated that the total number of modular RNA motifs that can be attached or otherwise coupled to it is limited only by the number of DAs in the modular RNA motif. Attachment or coupling can occur at the 3' and/or 5' ends of a synthetic oligonucleotide that composes a modular RNA motif.

In some aspects, the RNA nanostructures can be homogeneous (e.g. all the modular RNA motifs contained in the RNA nanostructure can be the same). In some aspects, the RNA nanostructures can be heterogenous (e.g. at least two modular RNA motifs contained in the RNA nanostructure are different from each other differ in one or more of the following characteristics: number of DAs, length of oligonucleotide sequence, and/or oligonucleotide sequence. A layer of the RNA nanostructure can be homogeneous (e.g. each modular RNA motif in a given layer can be the same). A layer of the RNA nanostructure can be heterogeneous (e.g. at least two modular RNA motifs contained in the layer are different from each other in at least one of the following characteristics: number of DAs, length of oligonucleotide sequence, and/or oligonucleotide sequence. In some aspects, one or more layers of the RNA nanostructure can each be homogenous but the RNA nanostructure can be heterogenous because of two or more modular RNA motifs in the RNA nanostructure differ from each other with respect to one or more of the following characteristics: number of DAs, length of oligonucleotide sequence, and/or oligonucleotide sequence. FIGS. 42A-42G show aspects of homogeneous RNA nanostructures that contain homogenous layers. FIG. 43 shows an aspect of a heterogeneous RNA nanostructure that can contain homogenous layers. As shown in FIG. 43, in some aspects, each layer can be composed of a modular RNA motif with a different number of DAs. In some aspects, a heterogeneous RNA nanostructure can contain homogeneous and at least one heterogenous layer. In some aspects, a RNA nanostructure can be considered heterogenous if loaded with one or more different cargo compound within a motif, layer, or across one or more layers.

The RNA nanostructures described herein can have a high or ultra-high thermostability as defined herein via Tm measurements of particle annealing in qPCR or particle dissociation in Thermal Gradient Gel Analysis (TGGE). The RNA nanostructures described herein can have a high or ultra-high melting temperature (Tm). RNA oligonucleotides typically exhibit a length dependent melting temperature that plateaus at 70-75° C. for long hybridized duplexes. Modification of said duplexes and conjugation of hydrophobic molecules lowers the stability of RNA duplexes and thus results in lower melting temperatures and dissociation into individual strands leading to enzymatic digestion in vivo. RNA nanostructures suitable to carry a high density of functional groups have a Tm of about 70 or ° C. or more. In some aspects, the melting temperature of the RNA nanostructure can be greater than 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspect the Tm of the RNA nanostructure can be 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects the melting temperature of the RNA nanostructure can range from 65° C. to 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 66 to 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 67 to 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 68 to 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 69 to 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 70 to 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 71 to 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 72 to 73, 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 73 to 74, 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 74 to 75, 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 75 to 76, 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 76 to 77, 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 77 to 78, 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 78 to 79, 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 79 to 80, 81, 82, 83, 84, 85, 86, 87, 88, 89, 90, 91, 92, 93, 94, 95, 96, 97, 98, 99, or 100° C. In some aspects, the melting temperature of the RNA nanostructure can range from 80 to 81, 82, 83, 84, 85, 86, 87, 88, 89, 90, 91, 92, 93, 94, 95, 96, 97, 98, 99, or 100° C. In some aspects, the melting temperature of the RNA nanostructure can range from 81 to 82, 83, 84, 85, 86, 87, 88, 89, 90, 91, 92, 93, 94, 95, 96, 97, 98, 99, or 100° C. In some aspects, the melting temperature of the RNA nanostructure can range from 82 to 83, 84, 85, 86, 87, 88, 89, 90, 91, 92, 93, 94, 95, 96, 97, 98, 99, or 100° C. In some aspects, the melting temperature of the RNA nanostructure can range from 83 to 84, 85, 86, 87, 88, 89, 90, 91, 92, 93, 94, 95, 96, 97, 98, 99, or 100° C. In some aspects, the melting temperature of the RNA nanostructure can range from 84 to 85, 86, 87, 88, 89, 90, 91, 92, 93, 94, 95, 96, 97, 98, 99, or 100° C. In some aspects, the melting temperature of the RNA nanostructure can range from 85 to 86, 87, 88, 89, 90, 91, 92, 93, 94, 95, 96, 97, 98, 99, or 100° C. In some aspects, the melting temperature of the RNA nanostructure can range from 86 to 87, 88, 89, 90, 91, 92, 93, 94, 95, 96, 97, 98, 99, or 100° C. In some aspects, the melting temperature of the RNA nanostructure can range from 87 to 88, 89, 90, 91, 92, 93, 94, 95, 96, 97, 98, 99, or 100° C. In some aspects, the melting temperature of the RNA nanostructure can range from 88 to 89, 90, 91, 92, 93, 94, 95, 96, 97, 98, 99, or 100° C. In some aspects, the melting temperature of the RNA nanostructure can range from 89 to 90, 91, 92, 93, 94, 95, 96, 97, 98, 99, or 100° C. In some aspects, the melting temperature of the RNA nanostructure can range from 90 to 91, 92, 93, 94, 95, 96, 97, 98, 99, or 100° C. In some aspects, the melting temperature of the RNA nanostructure can range from 91 to 92, 93, 94, 95, 96, 97, 98, 99, or 100° C. In some aspects, the melting temperature of the RNA nanostructure can range from 92 to 93, 94, 95, 96, 97, 98, 99, or 100° C. In some aspects, the melting temperature of the RNA nanostructure can range from 93 to 94, 95, 96, 97, 98, 99, or 100° C. In some aspects, the melting temperature of the RNA nanostructure can range from 94 to 95, 96, 97, 98, 99, or 100° C. In some aspects, the melting temperature of the RNA nanostructure can range from 95 to 96, 97, 98, 99, or 100° C. In some aspects, the melting temperature of the RNA nanostructure can range from 96 to 97, 98, 99, or 100° C. In some aspects, the melting temperature of the RNA nanostructure can range from 97 to 98, 99, or 100° C. In some aspects, the melting temperature of the RNA nanostructure can range from 98 to 99, or 100° C. In some aspects, the melting temperature of the RNA nanostructure can range from 99 to 100° C.

Figure 33A:
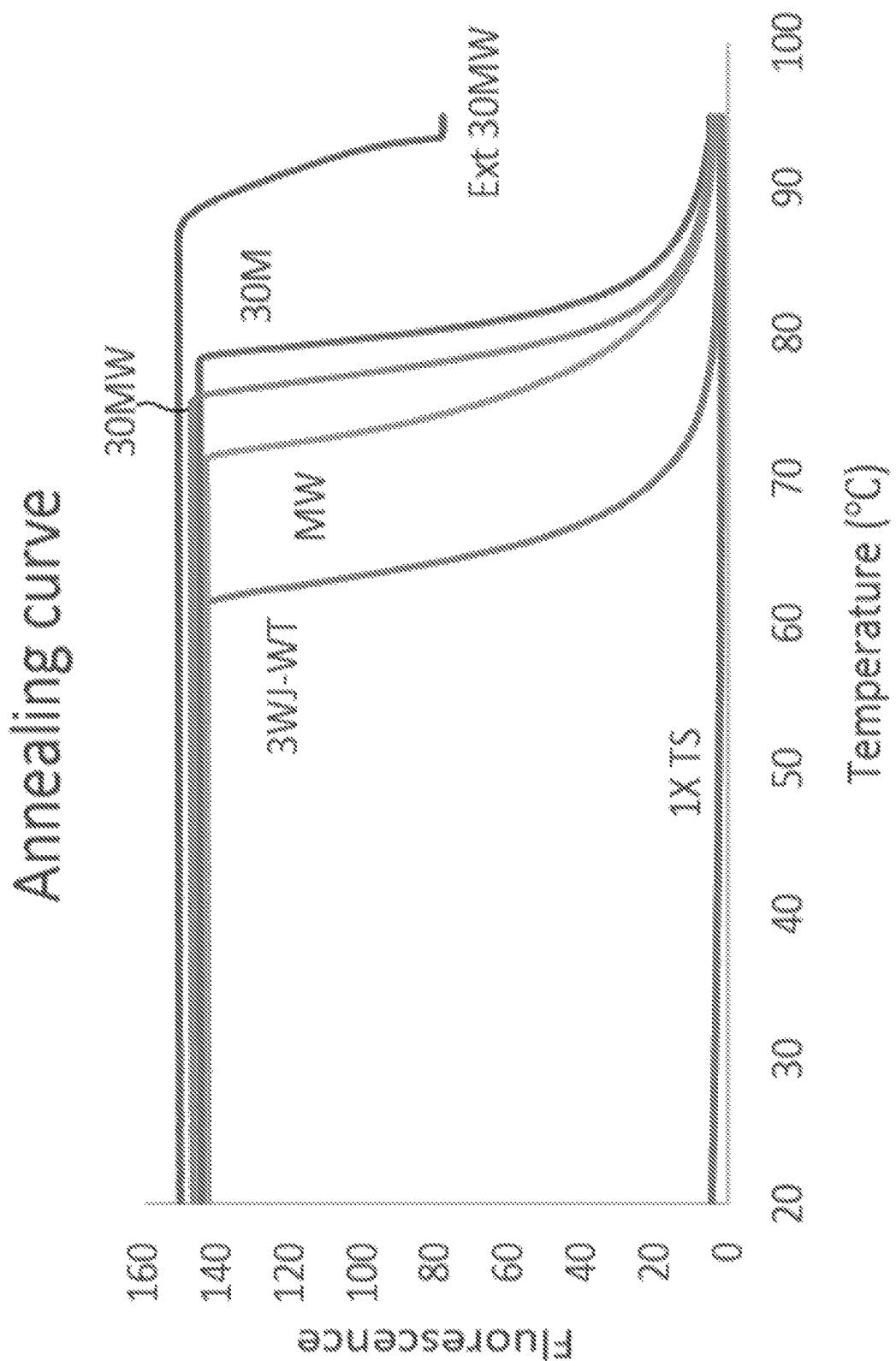
Figure 33B:
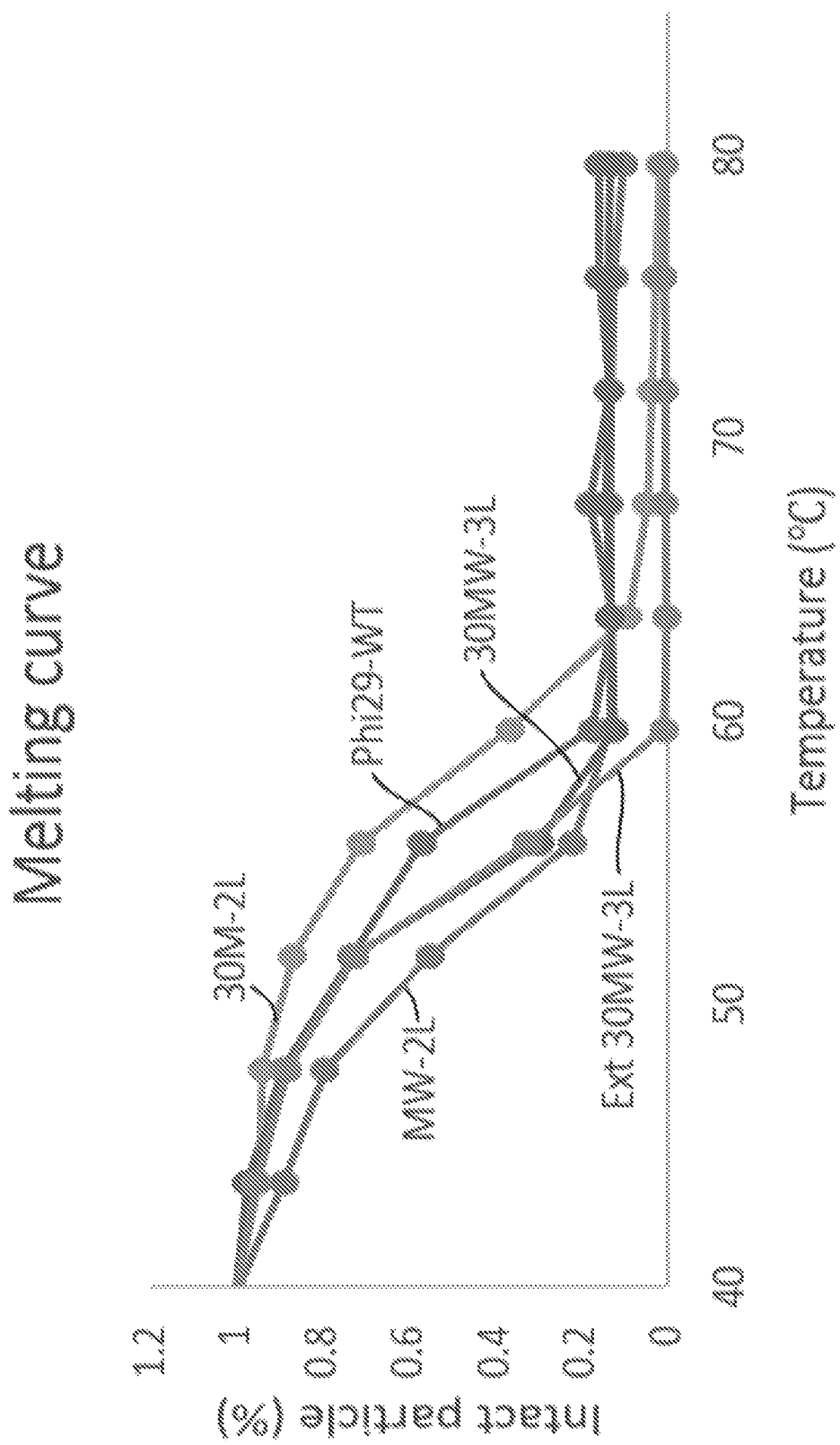
Figure 33D:
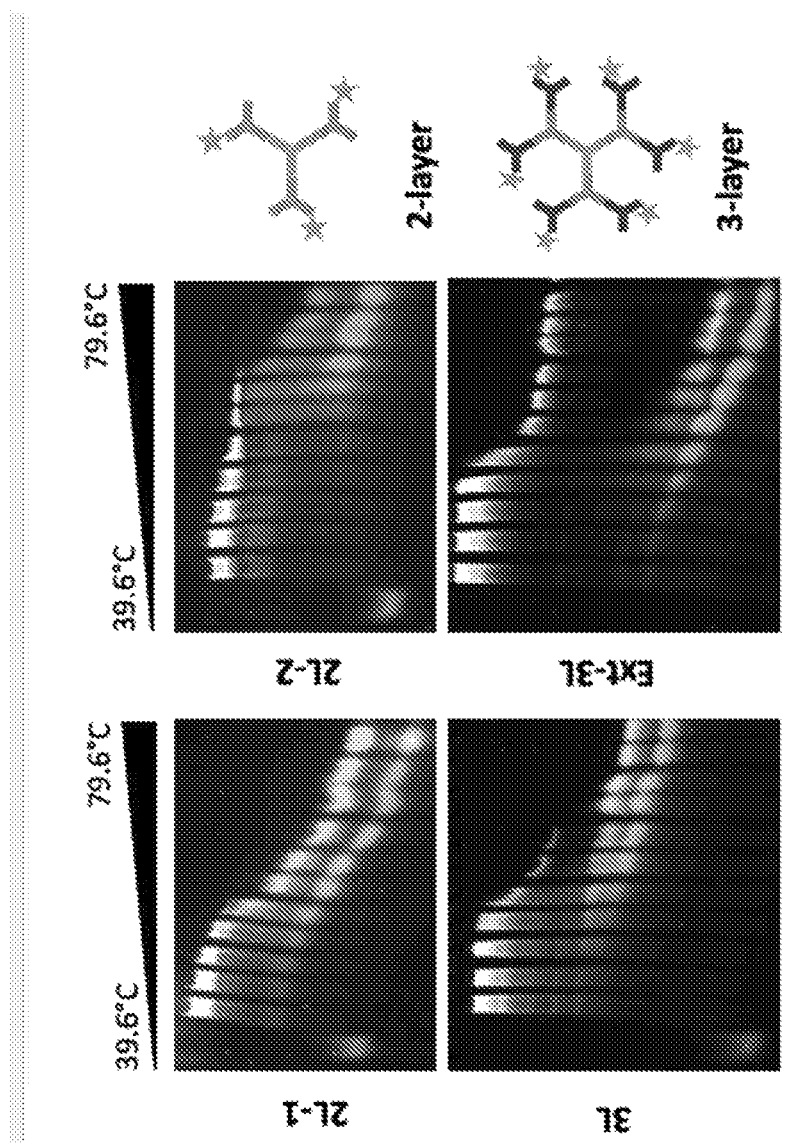
Figure 34A:
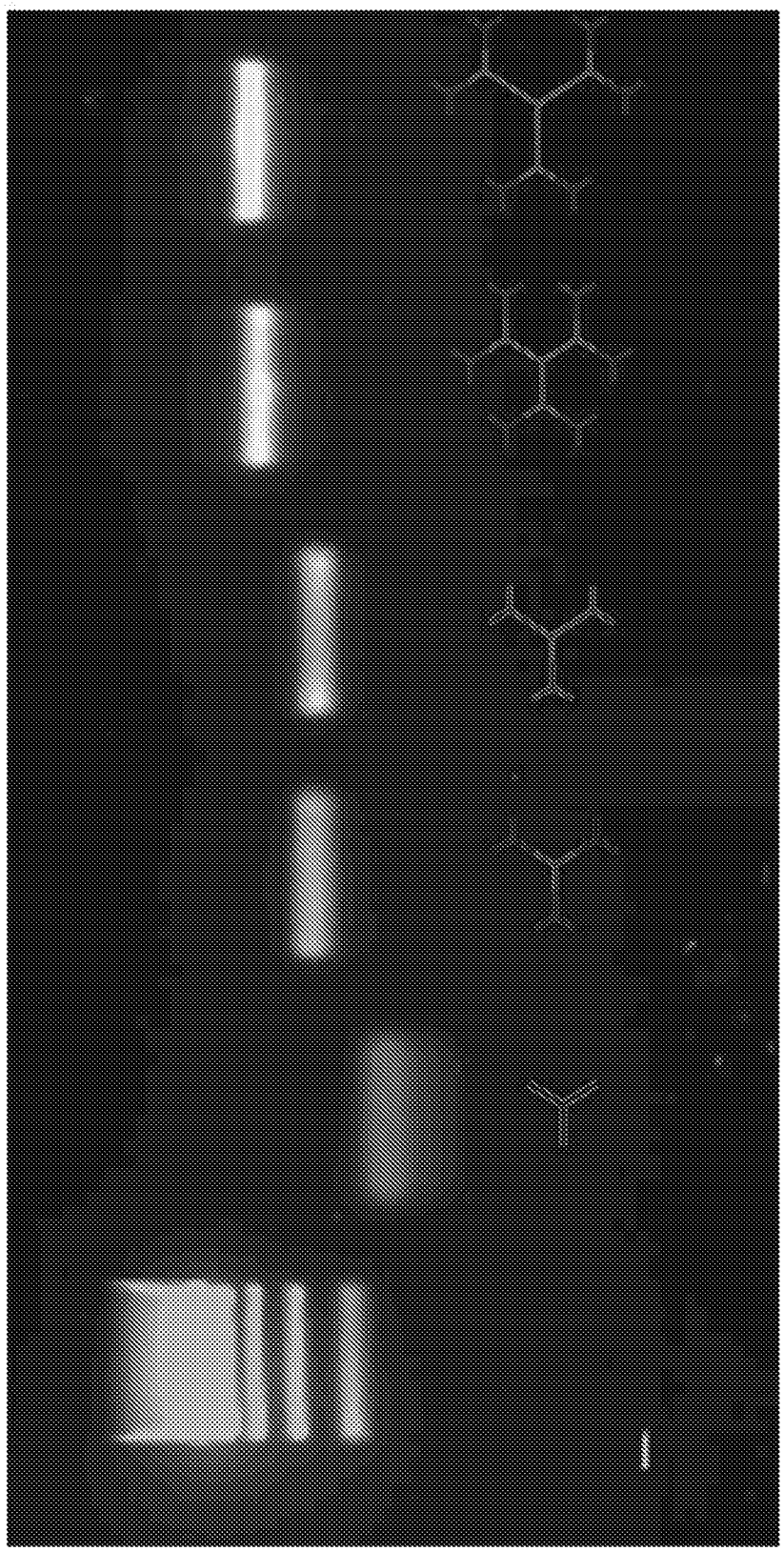
FIGS. 34A and 34B show in vitro characterization of branched 3WJ RNA nanostructures.
Figure 34B:
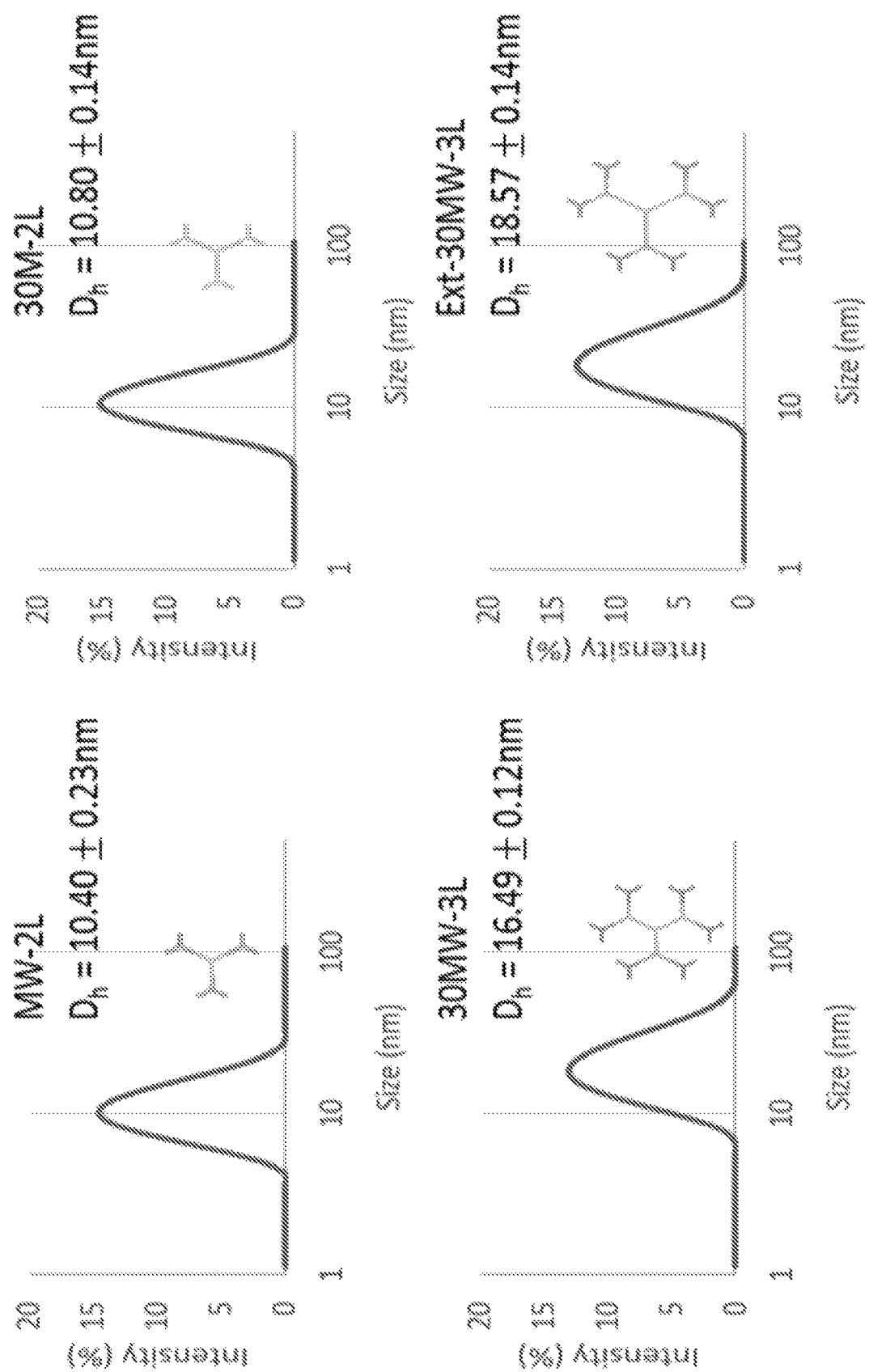
Figure 35A:
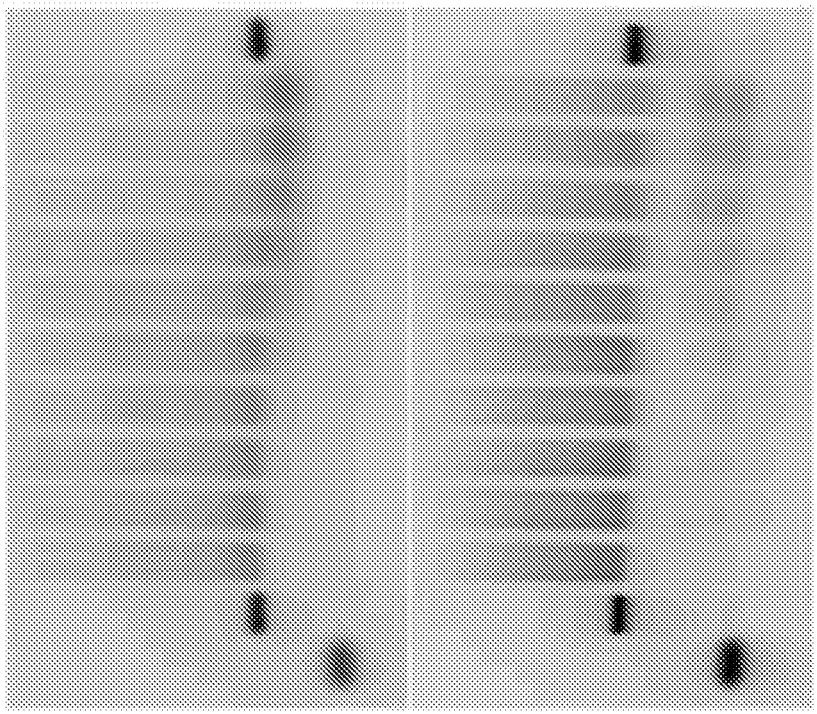
FIGS. 35A to 35C show enzymatic stability of branched 3WJ RNA nanostructures.
Figure 35A:
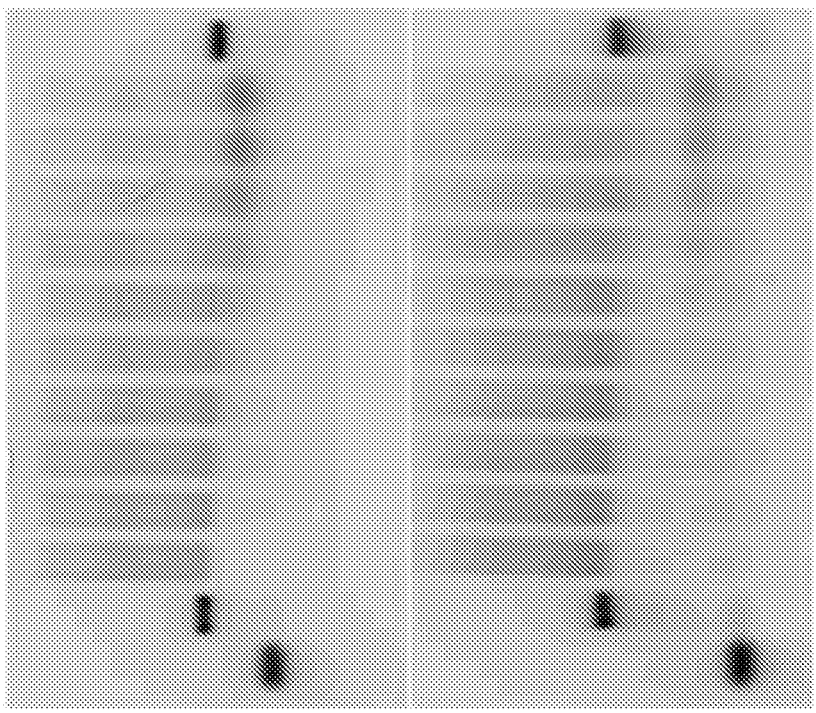
Figures 35B, 35C:
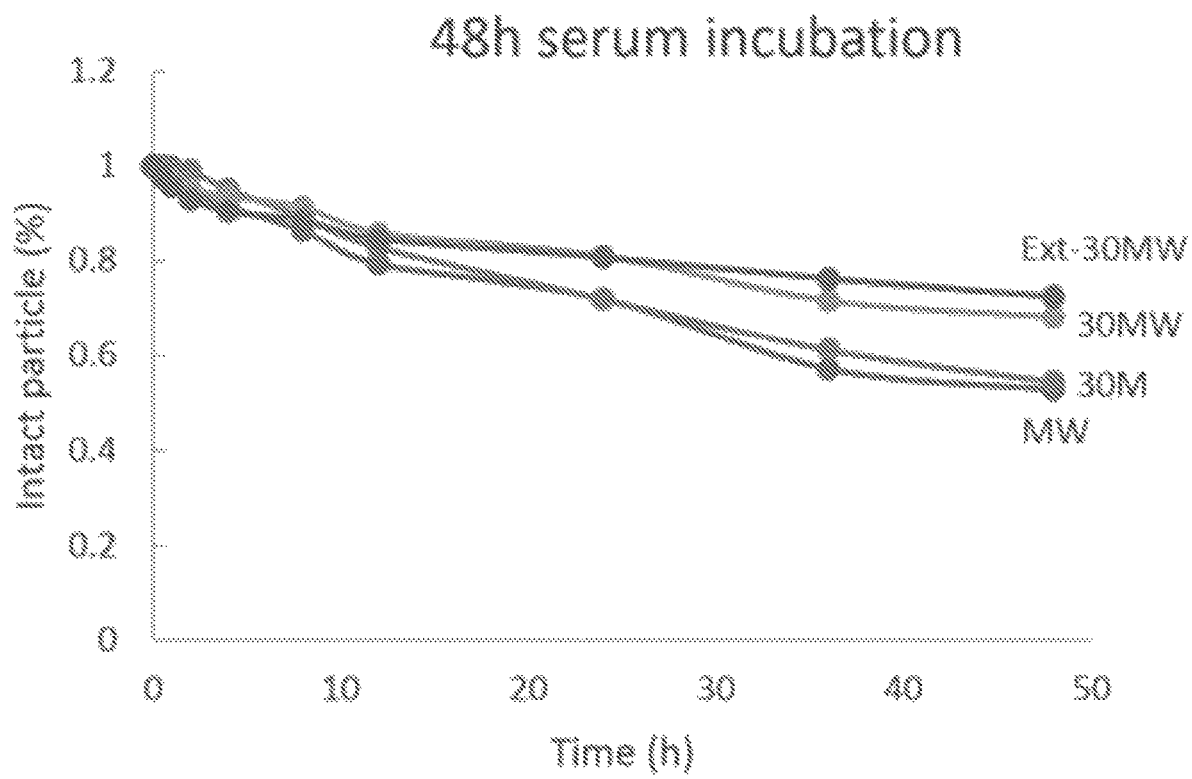
Figure 36A:
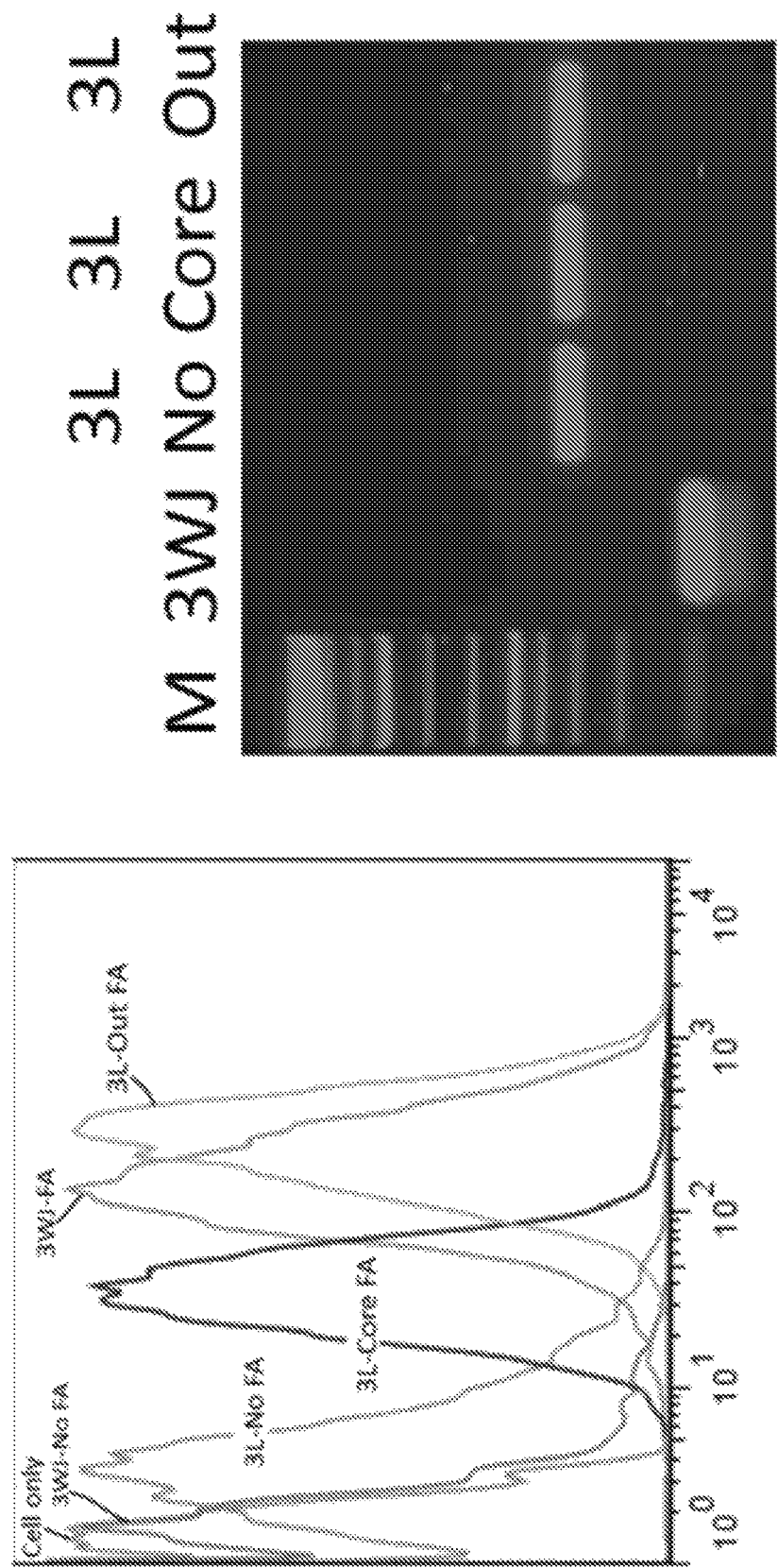
FIGS. 36A and 36B show cell binding comparison of 3L-no FA, 3L-core FA and 3L-out FA in vitro by flow cytometry (FIG. 36A) and confocal microscopy (FIG. 36B).
Figure 36B:
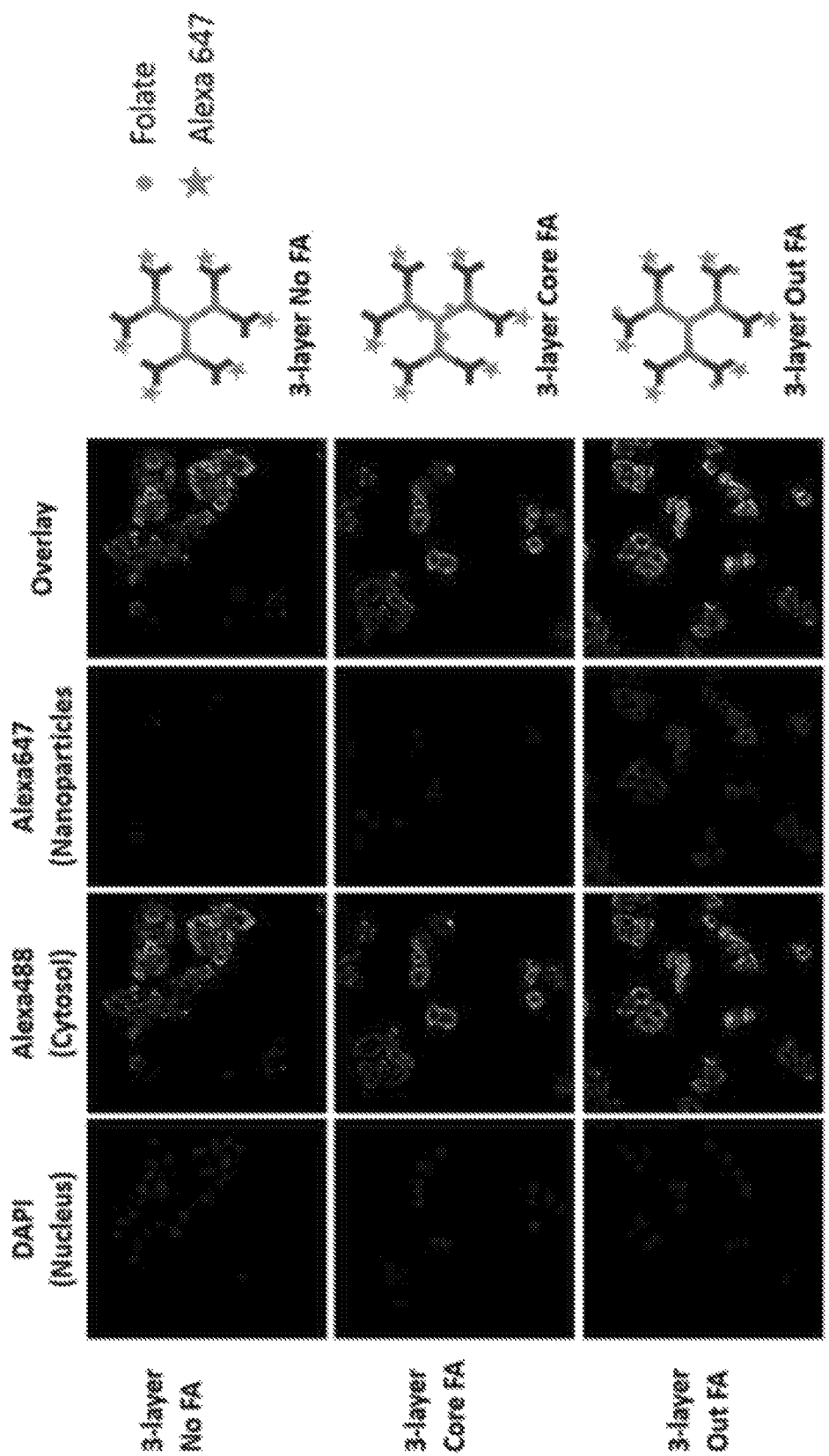

In some aspects, the Tm of the core modular RNA motif can be greater than the Tm of the modular RNA motifs forming the intermediate layer(s), which can be greater than the Tm of the modular RNA motifs forming terminal or outer most layer. It will be appreciated that where there is multiple intermediate layers that the Tm of the modular RNA motifs forming the innermost intermediate layer can be greater than the Tm of the modular RNA motifs forming the outermost intermediate layer. Any intermediate layers that lie between the innermost intermediate layer and the outer most intermediate layer can have modular RNA motifs with Tms that are less than the Tms of modular RNA motifs forming the innermost intermediate layer, greater than the Tms of the modular RNA motifs forming the outer most intermediate layer, and can decrease as distance from the innermost intermediate layer increases. This feature can result in a thermodynamically driven nanostructure assembly that can occur at temperatures above measured Tm values of the modular RNA motifs (FIG. 33A). This further can allow for a thermodynamic mechanism for payload release by shedding each layer at a rate proportional to the Tm of the individual modular RNA motifs (FIG. 33D).

The RNA nanostructure, when measured along its longest or largest dimension, can have a size of up to a micrometer. The size of the RNA nanostructure, when measured along its longest or largest dimension, can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 600, 700, 800 or about 900 nm. In some aspects, the size of the RNA nanostructure, when measured along its longest or largest dimension, can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nm or any range of values therein. In some aspects, the size of the RNA nanostructure, when measured along its longest or largest dimension, can be about 1-30, 1-40, 1-50, 10-50, 10-40, 10-30, 30-50, 30-40, or 40-50 nm. In some aspects, the RNA nanostructure can be substantially spherical. In other aspects, the RNA nanostructure can be trigonal planar, trigonal pyramidal, T-shaped, tetrahedral, square planar, seesaw, trigonal bipyramidal, square pyramidal, pentagonal planar, octahedral, trigonal prismatic, pentagonal pyramidal, pentagonal bipyramidal, square antiprismatic, tricapped trigonal prismatic, capped square antiprismatic, arrow head shaped, arrow tail shaped, X-shaped, or a distorted version of any of these shapes.

Loaded and/or Functionalized RNA Nanostructures

The modular RNA motifs that make up the RNA nanostructures described herein can provide various sites at which a cargo compound(s) and/or functional group(s) can be attached or otherwise coupled to the modular RNA motifs. By attaching or otherwise coupling cargo compounds and/or functional groups to the modular RNA motifs, the RNA nanostructures can be loaded with one or more cargo compound(s) and/or functionalized with one or more functional group(s). The cargo compound(s) and/or the functional group(s) can be attached or otherwise coupled to the modular RNA motifs before or after the RNA nanostructure is assembled.

Figure 16B:
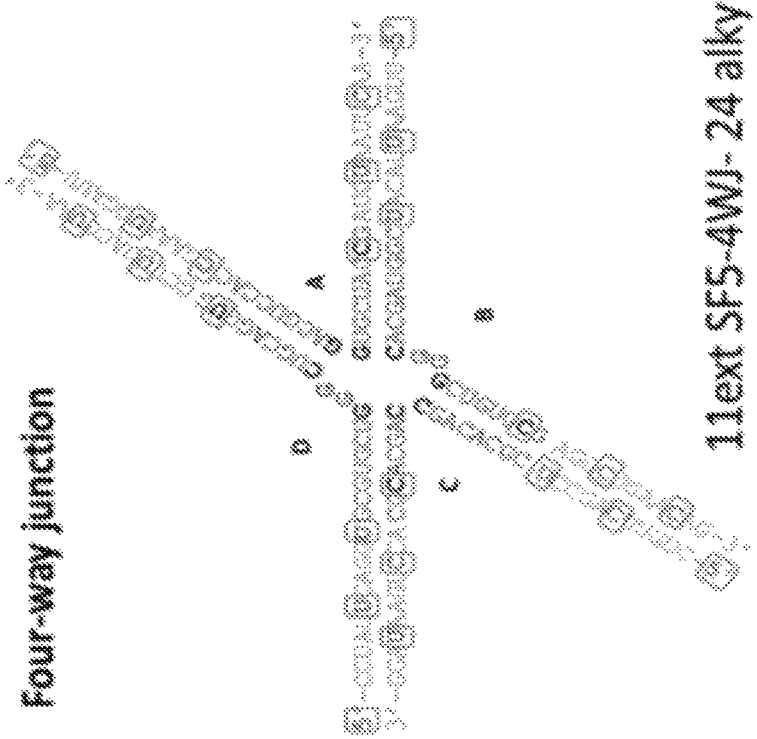
FIGS. 16A and 16B show secondary structures of multi-branch or multi-arm modular RNA motifs modified with multiple alkyne groups.
Figure 16A:
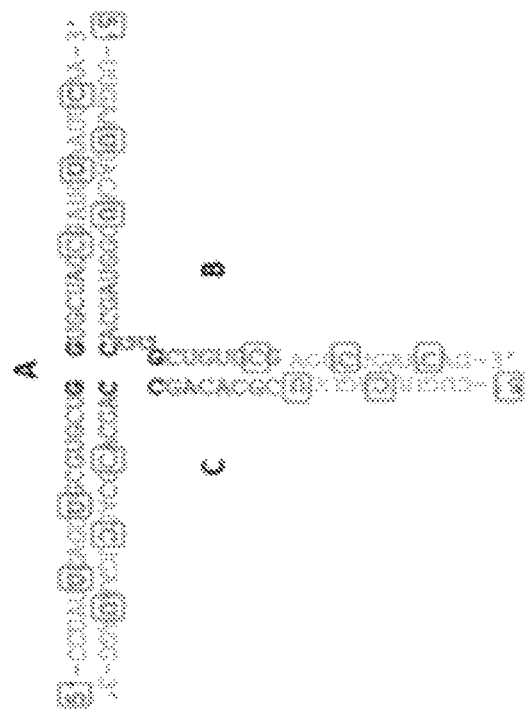
Figure 17:
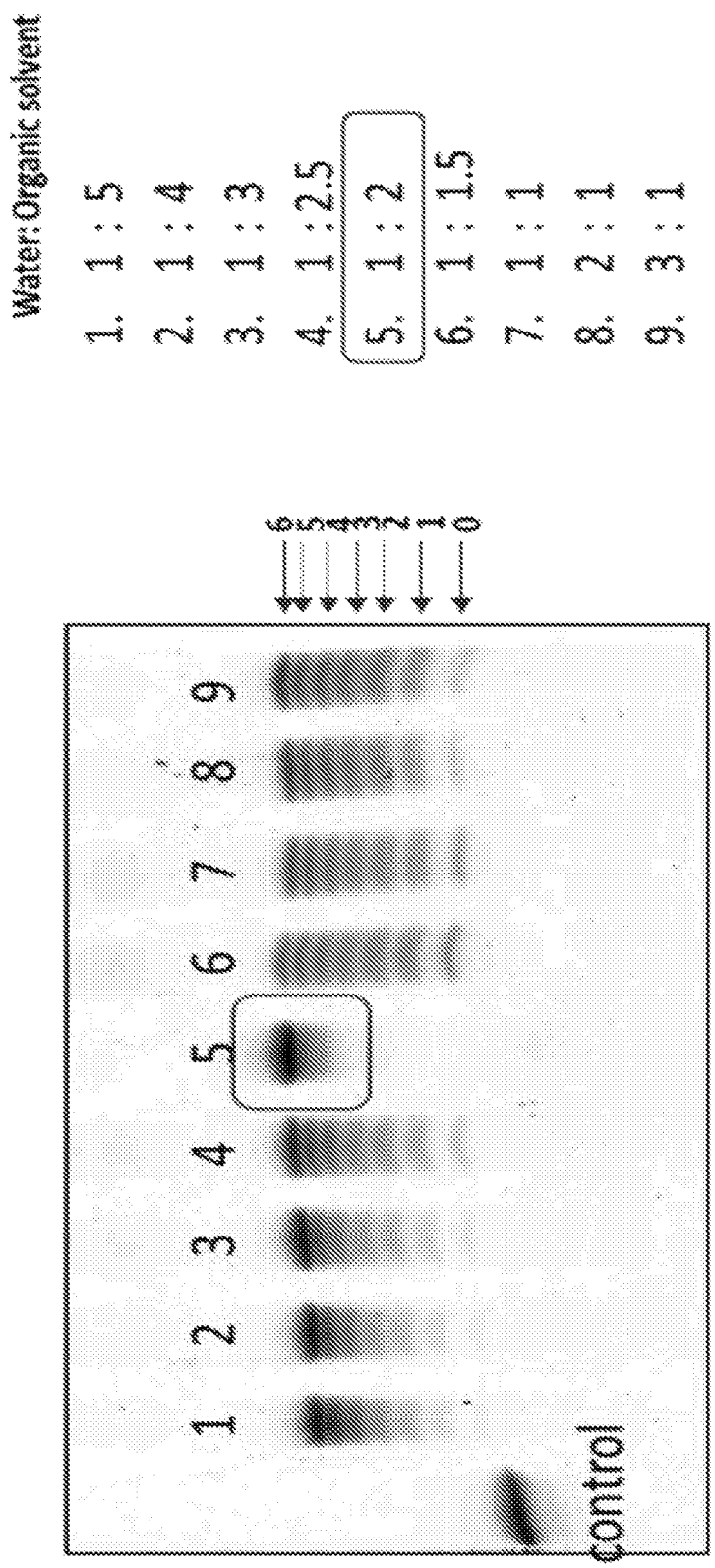
FIG. 17 shows optimal ratio of water/organic media for efficient multiple paclitaxel conjugation to RNA strands.
Figure 18:
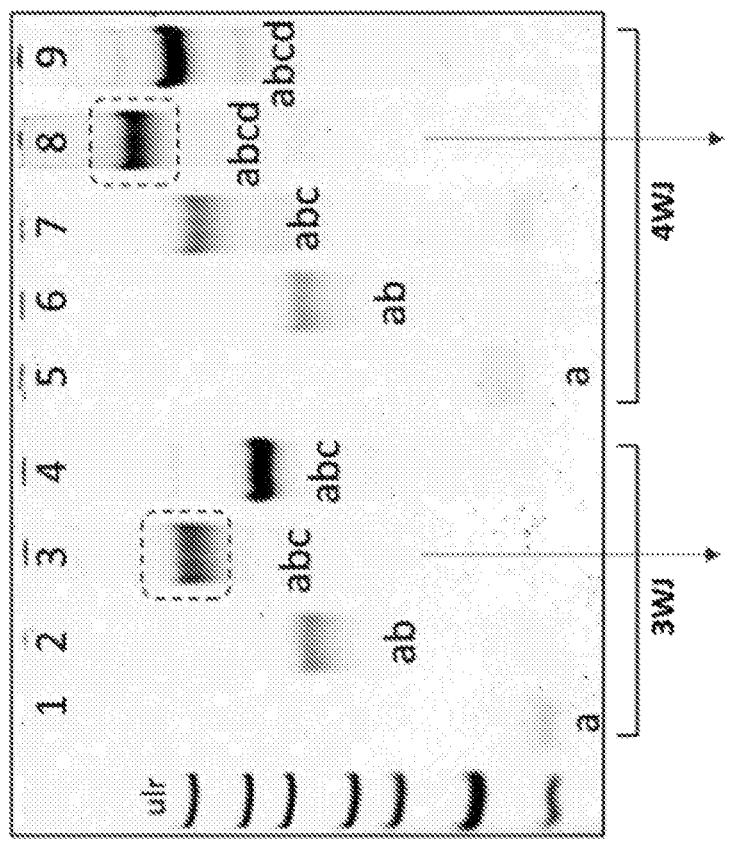
FIG. 18 shows step-wise self-assembly of 3WJ and 4WJ RNA nanostructures conjugated with 18 paclitaxel and 24 paclitaxel, respectively, by native PAGE (ladder: ultra-low range DNA marker). Shown are SEQ ID NOs:63-69.
Figure 18:
Figure 19:
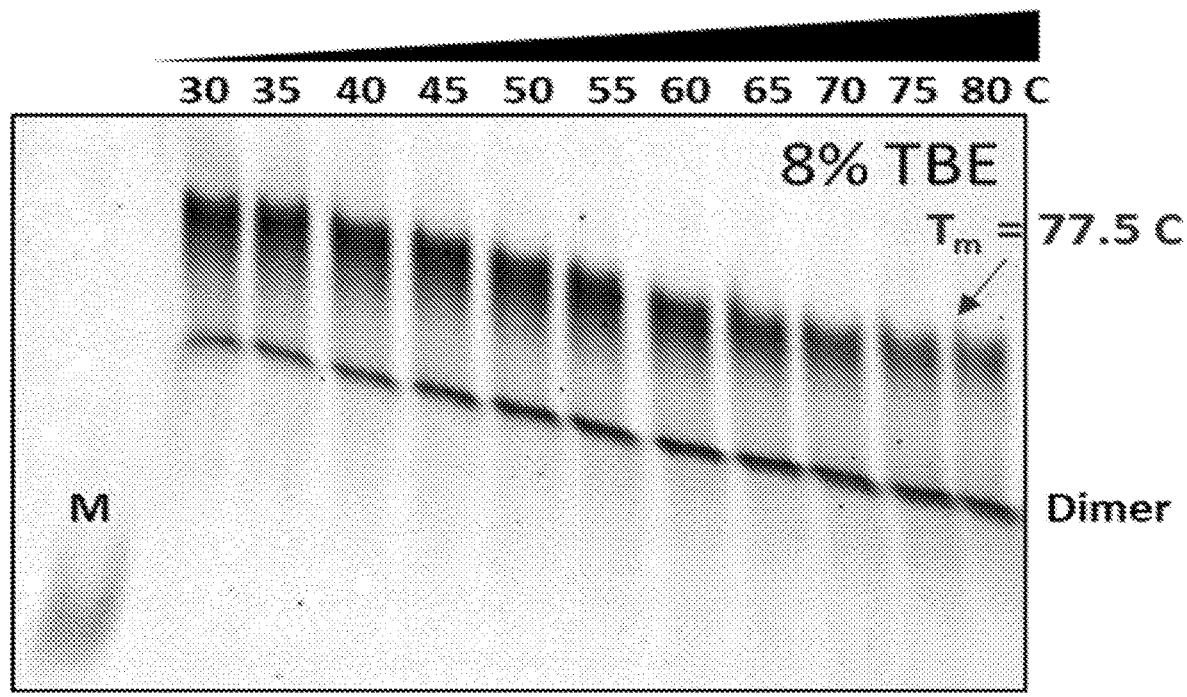
FIG. 19 shows Tm of 3WJ nanostructures conjugated with 18 paclitaxel by TGGE (M: monomer).
Figure 20A:
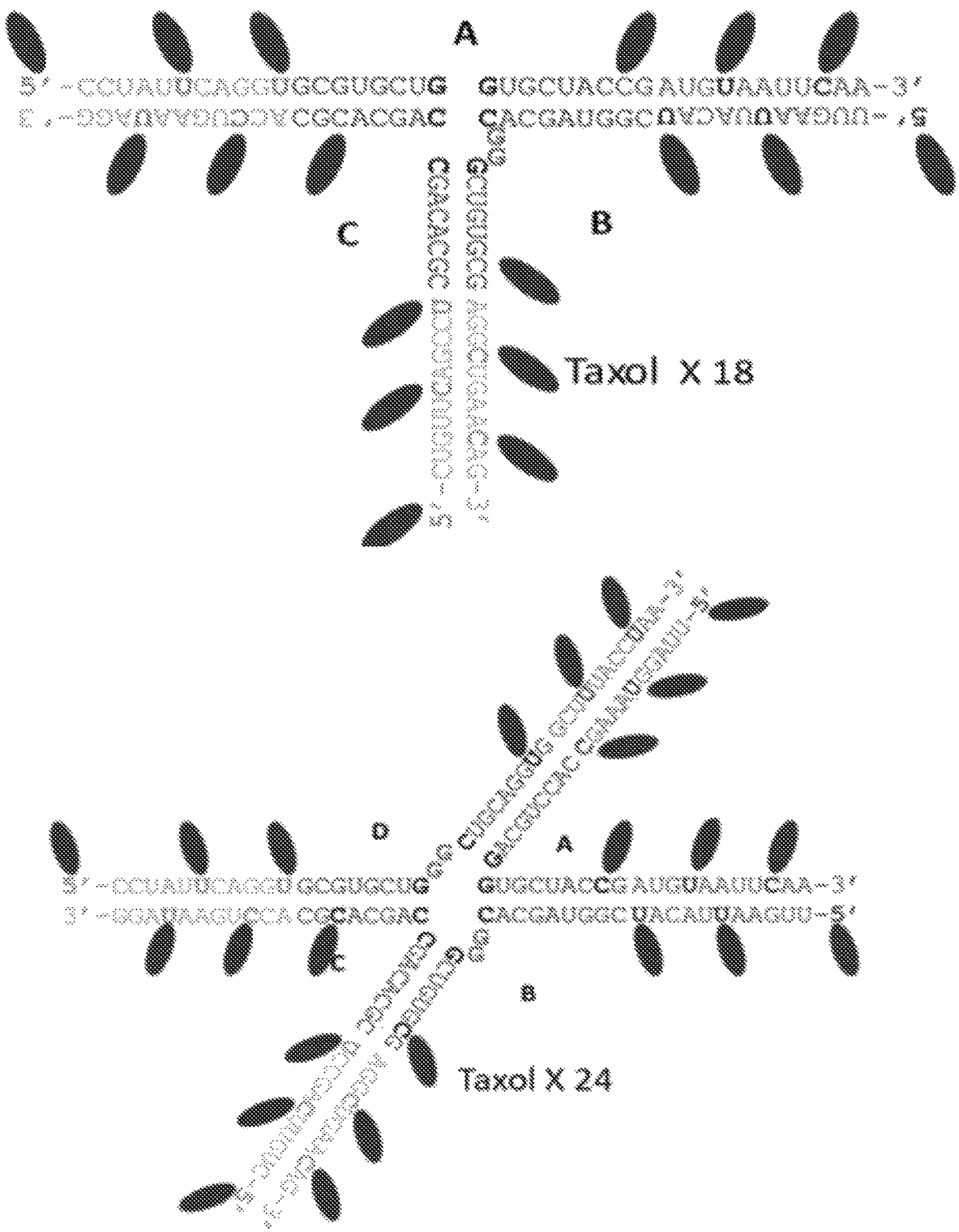
FIGS. 20A and 20B show sequence design and drug conjugation to a synthetic RNA oligonucleotide.
Figure 20B:
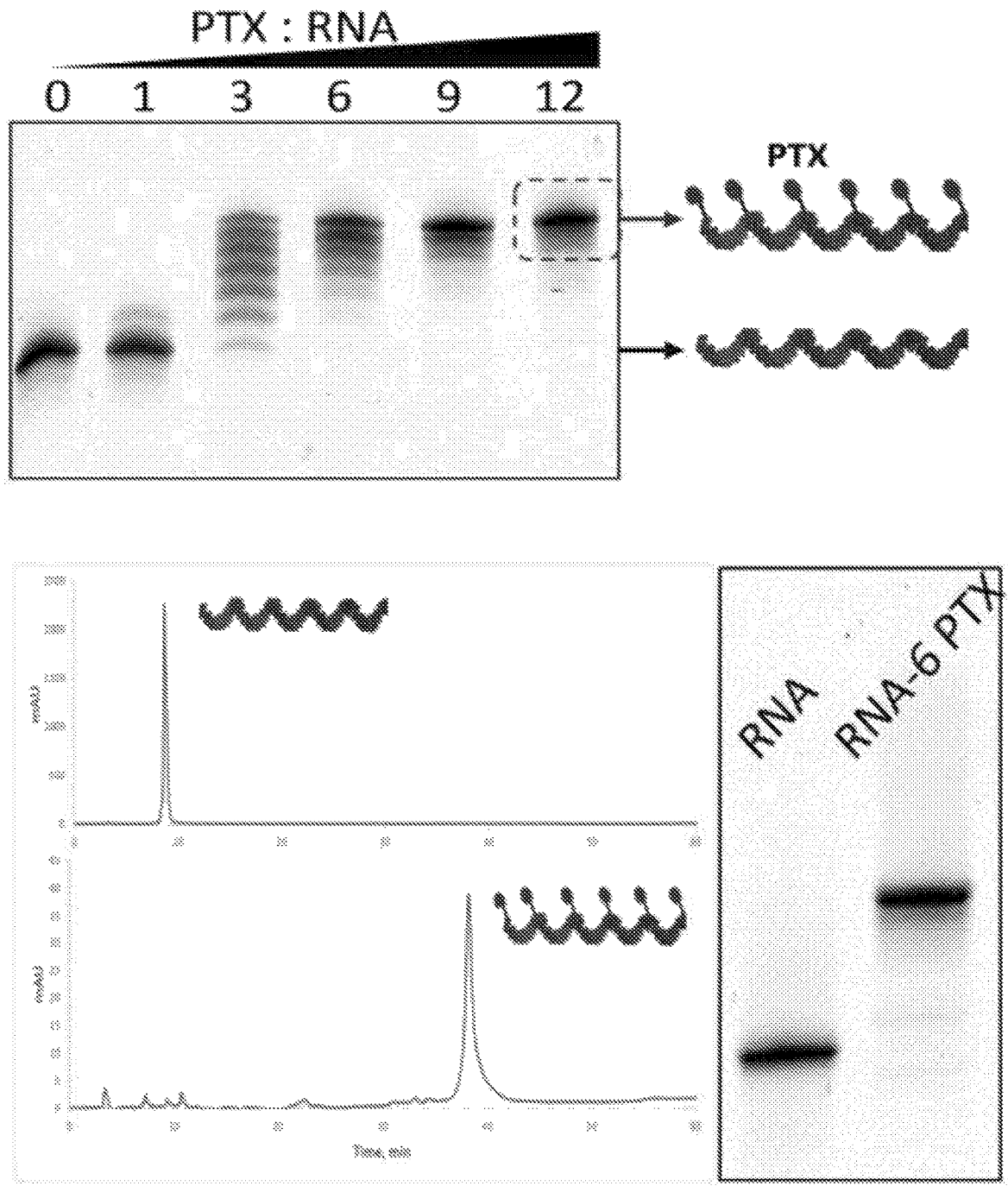
Figure 21A:
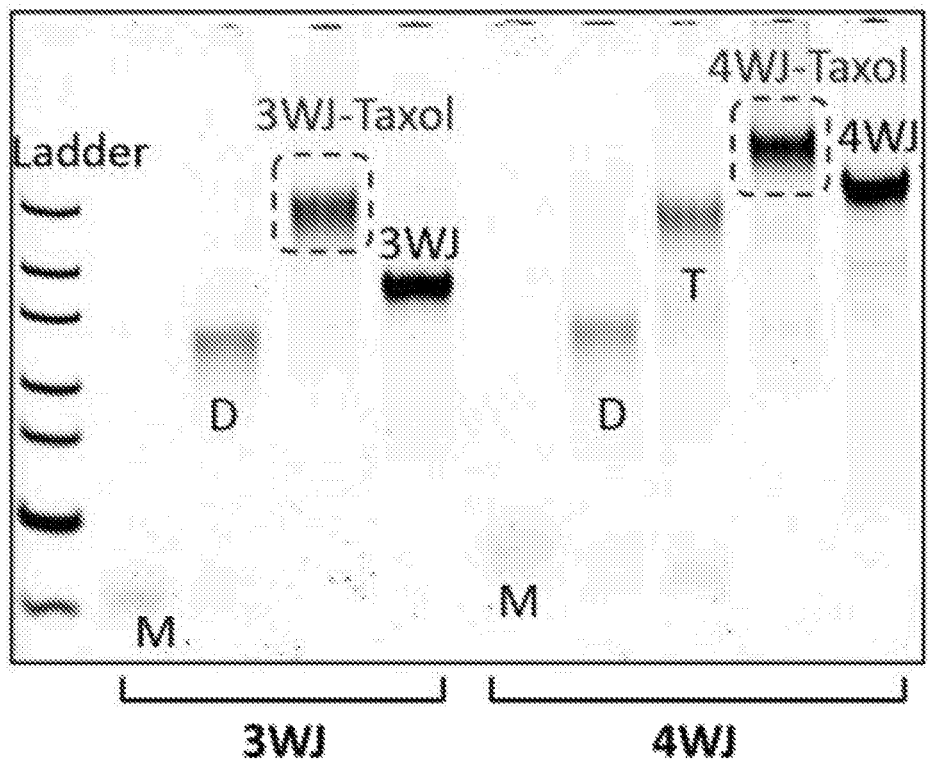
FIGS. 21A to 21C show in vitro characterization.
Figure 21B:
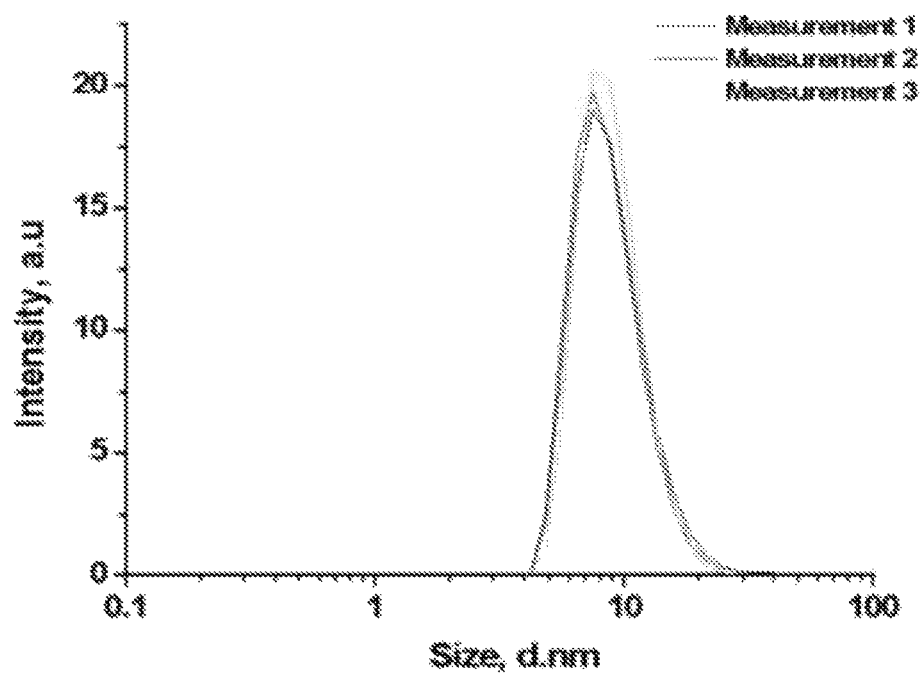
Figure 21C:
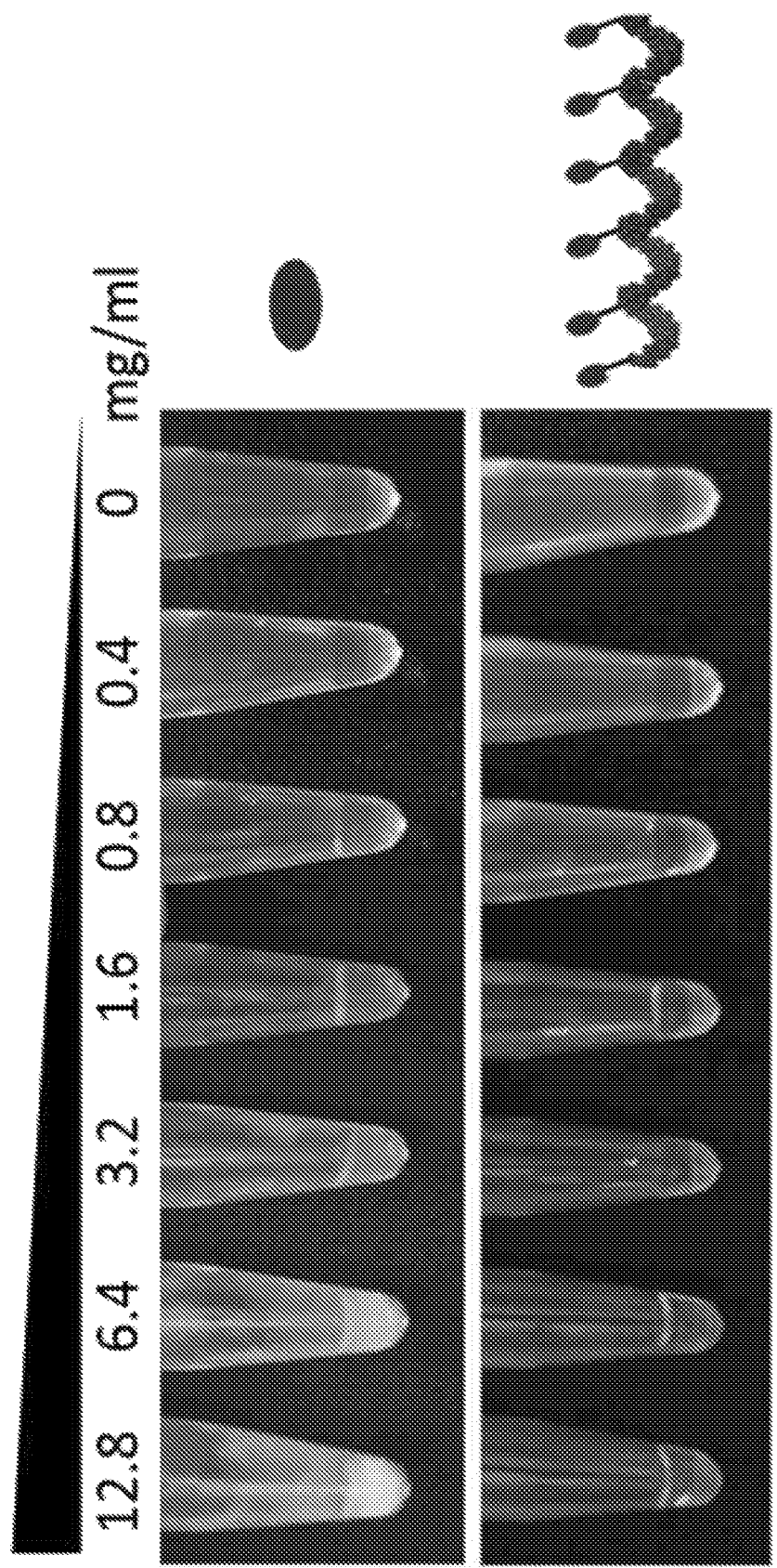
Figure 22A:
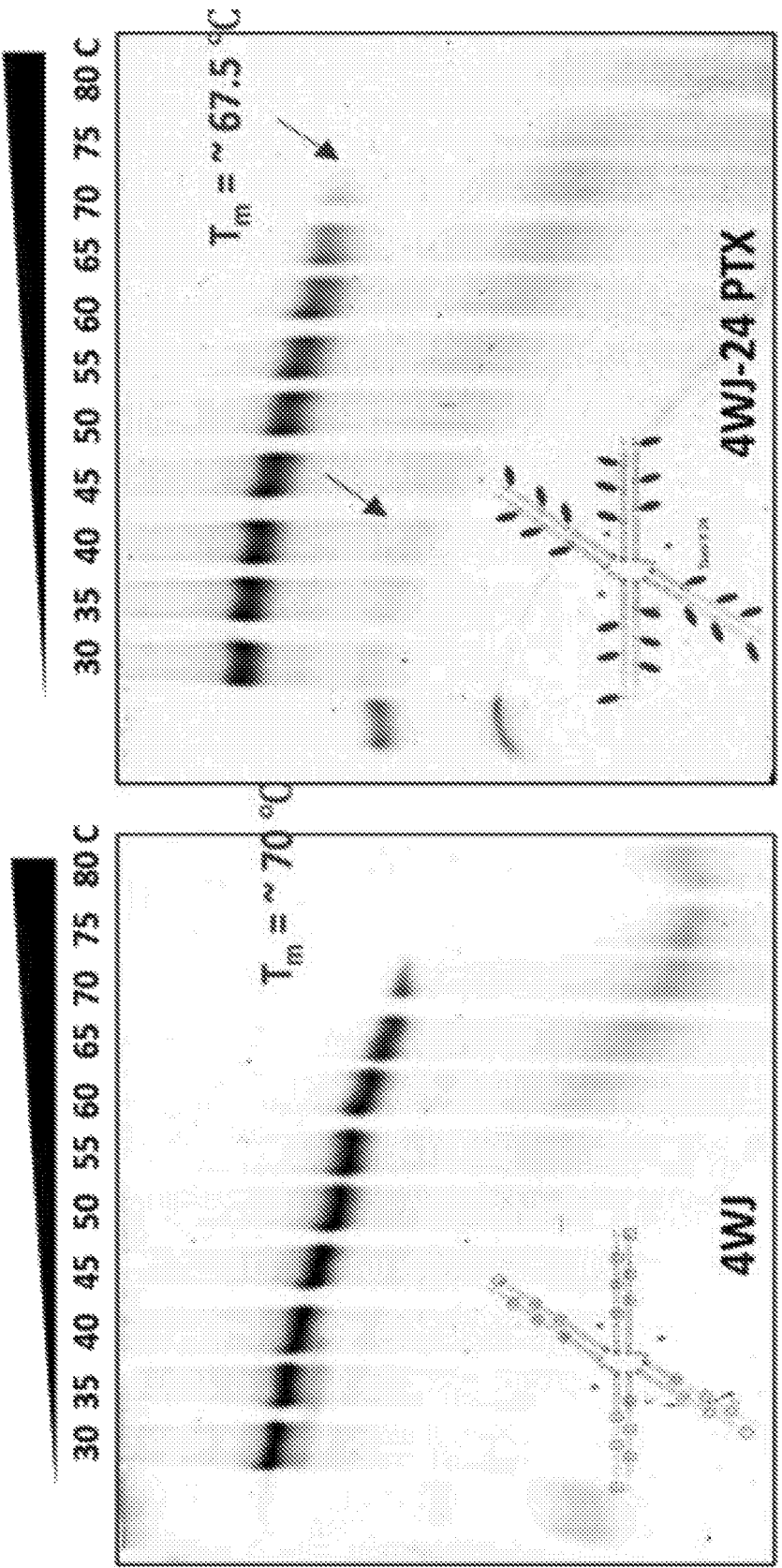
FIGS. 22A and 22B show thermal stability.
Figure 22B:
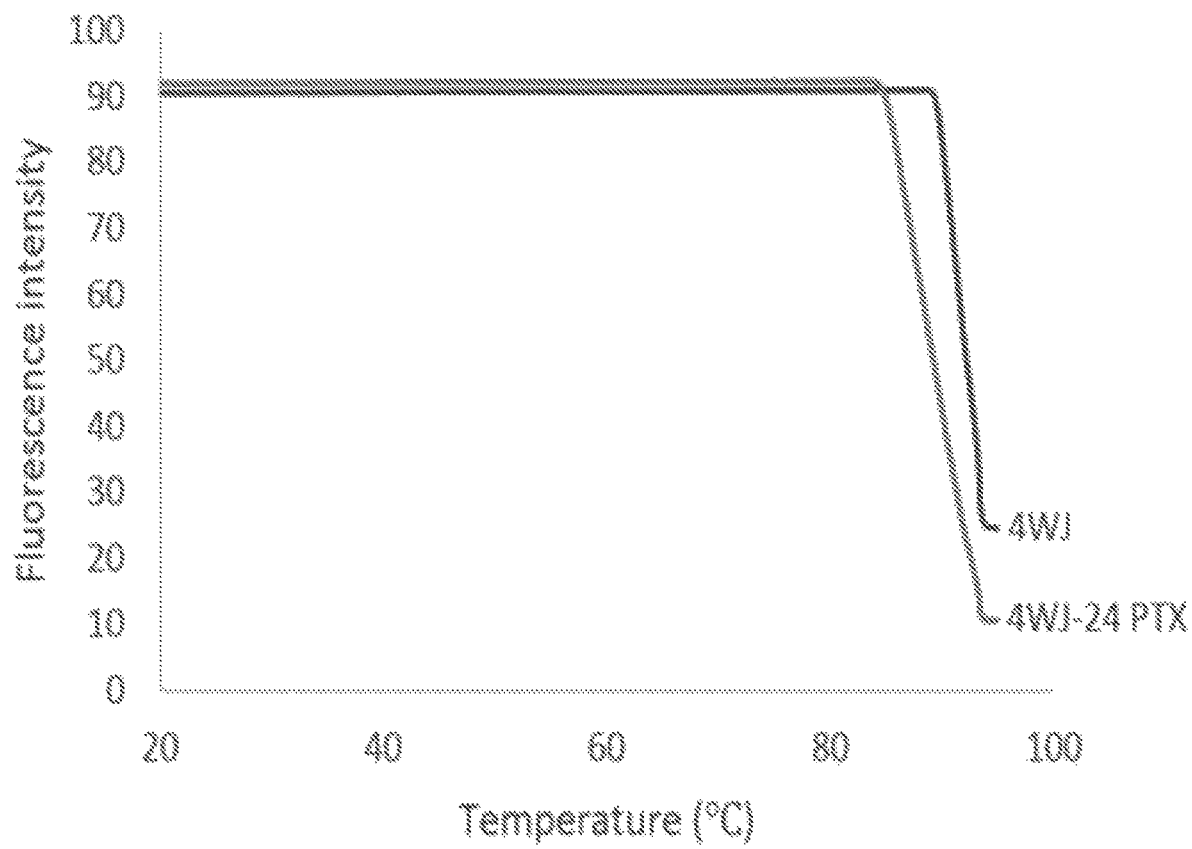
Figure 23:
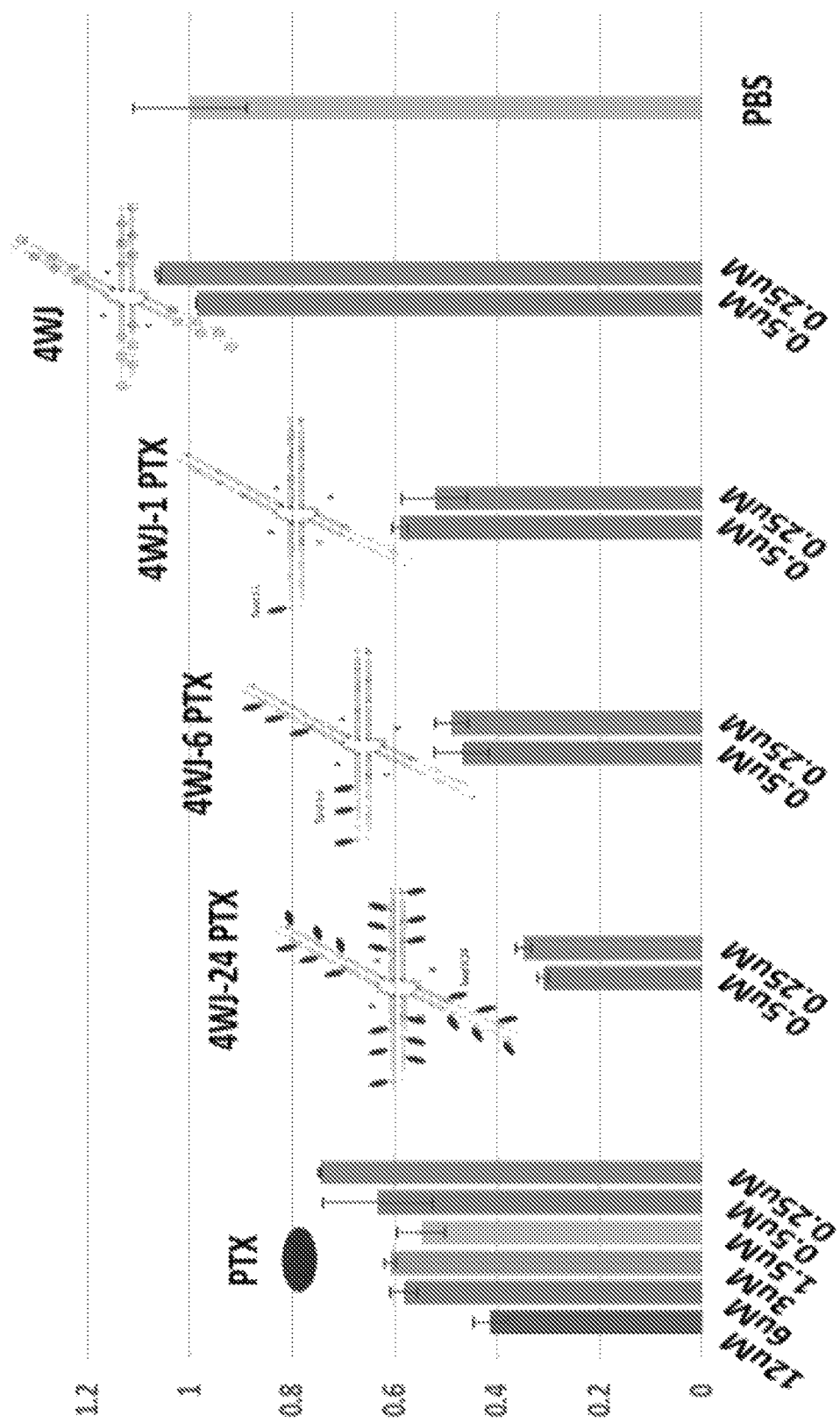
FIG. 23 shows in vitro cytotoxicity using an MTT assay of 4WJ with multi-Taxol. 4WJ with 24 PTX shows higher cytotoxicity compared to PTX only at the same PTX concentration.

The cargo compound(s) and/or functional groups can be attached or otherwise coupled to the 5' terminus and/or 3' terminus of one or more DAs of the modular RNA motif(s) in the RNA nanostructure (see e.g. FIG. 10). As previously discussed, one or more of the nucleotides of the synthetic RNA oligonucleotides that make up a modular RNA motif can be modified such that attachment or coupling of a functional group or cargo compound can occur at that nucleotide. In some aspects, the modified nucleotide(s) can be present at positions in the RNA oligonucleotide such that when assembled into a modular RNA motif, the modified nucleotides are present in the DAs (see e.g. FIGS. 16A-16B and 18). Thus, the modular RNA motifs can be loaded with a cargo compound(s) and/or functional group(s) at one or more nucleotides in the DAs of the modular RNA motifs. The modular RNA motif(s) present in the RNA nanostructure can be loaded at the 5' terminus and/or the 3' terminus of each DA and/or one or more internal nucleotides (e.g. a modified nucleotide) in each DA.

In some aspects, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 130, 140, 150, 160, 170, 180, 190, 200, 250, 300, 350, 400, 450, 500, 550, to 600 or more termini of modular RNA motifs in the RNA nanostructure can be available for attachment or coupling to a cargo compound or functional group. In some aspects, 0, 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 250, 300, 350, 400, 450, 500, 550, 600, 650, 700, 750, 800, 850, 900, 950, to 1000 or more nucleotides in an RNA nanostructure can be available for modification and/or attachment or coupling to a cargo compound or functional group. Thus, the number of cargo compounds and/or functional groups that can be attached to or otherwise coupled to the RNA nanostructure can be the same as those sites available for loading so long as the RNA nanostructure is stable when loaded and loading does not violate chemical or physical constraints (e.g. steric hindrance).

The RNA nanostructures can be loaded with a single type of cargo compound. The RNA nanostructures can be loaded with a single type of functional group. The RNA nanostructures can be loaded with 2, 3, 4, 5, 6, 7, 8, 9, 10, 11, 12, 13, 14, 15, 16, 17, 18, 19, 20 or more types of cargo compounds. The RNA nanostructures can be loaded with 2, 3, 4, 5, 6, 7, 8, 9, 10, 11, 12, 13, 14, 15, 16, 17, 18, 19, 20 or more types of functional groups.

Figure 32A:
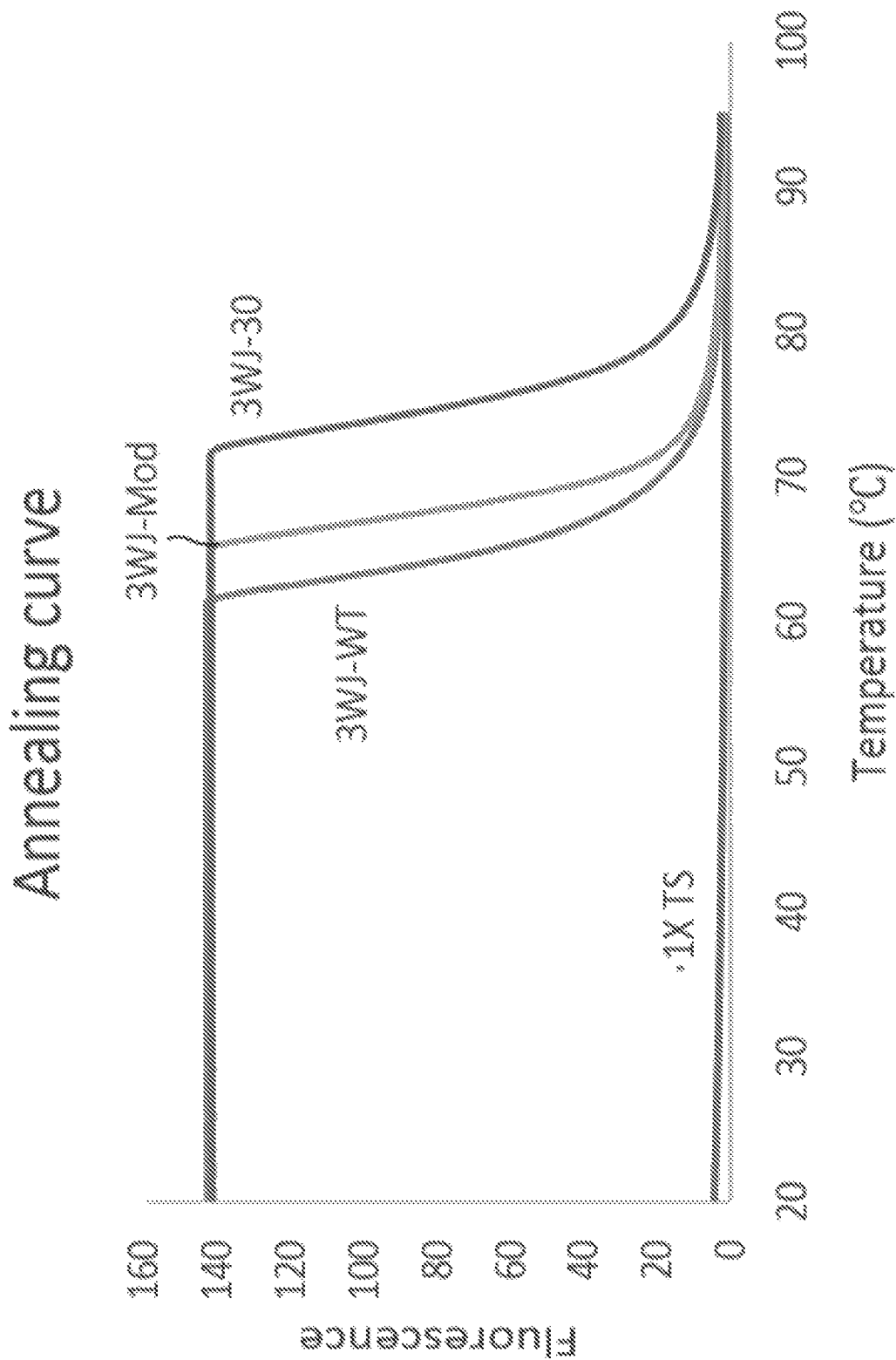
FIGS. 32A to 32D show design and construction of branched 3WJ RNA nanostructures made from branched 3WJ modular RNA motifs.
Figure 32B:
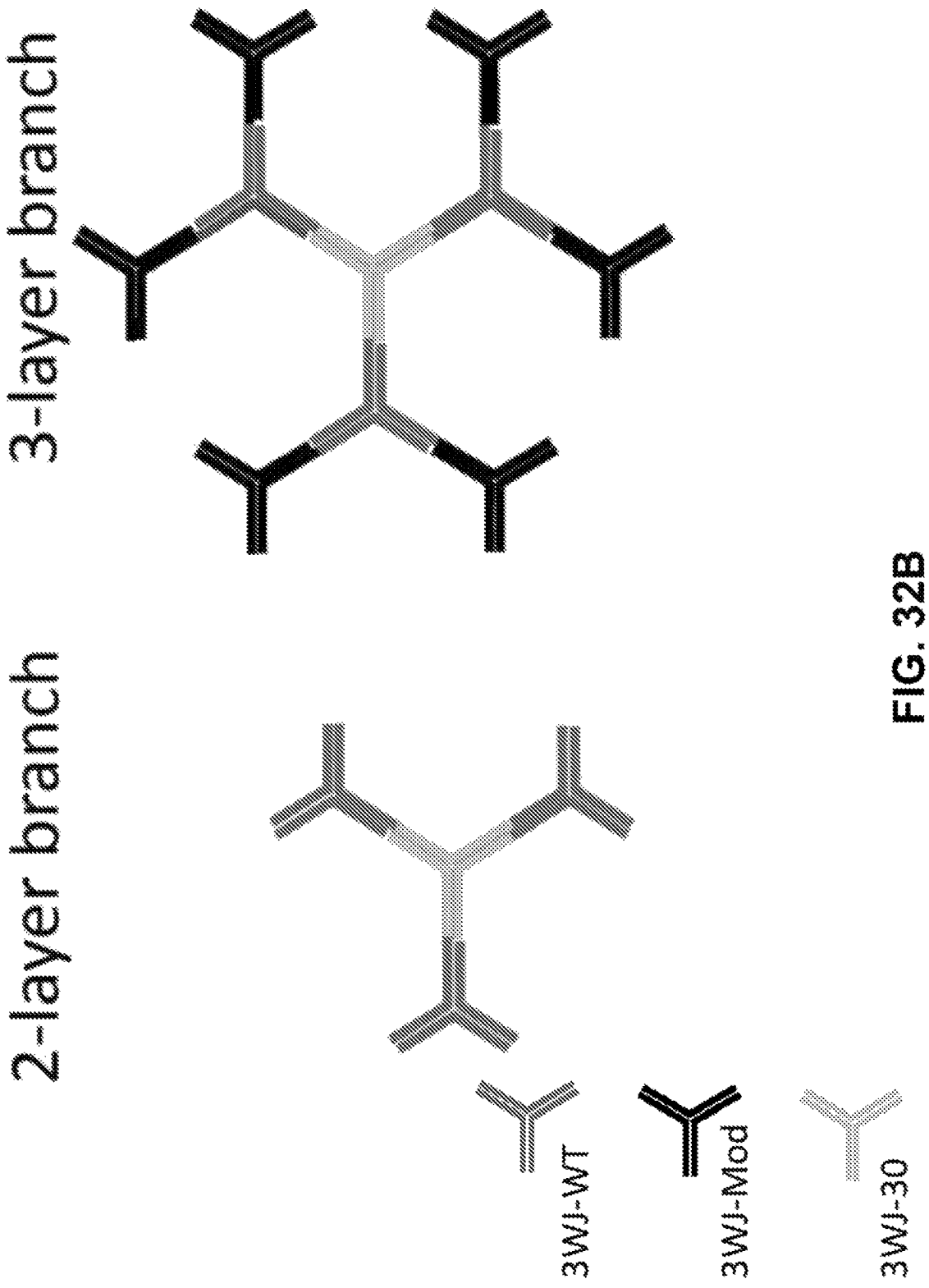
Figure 32C:
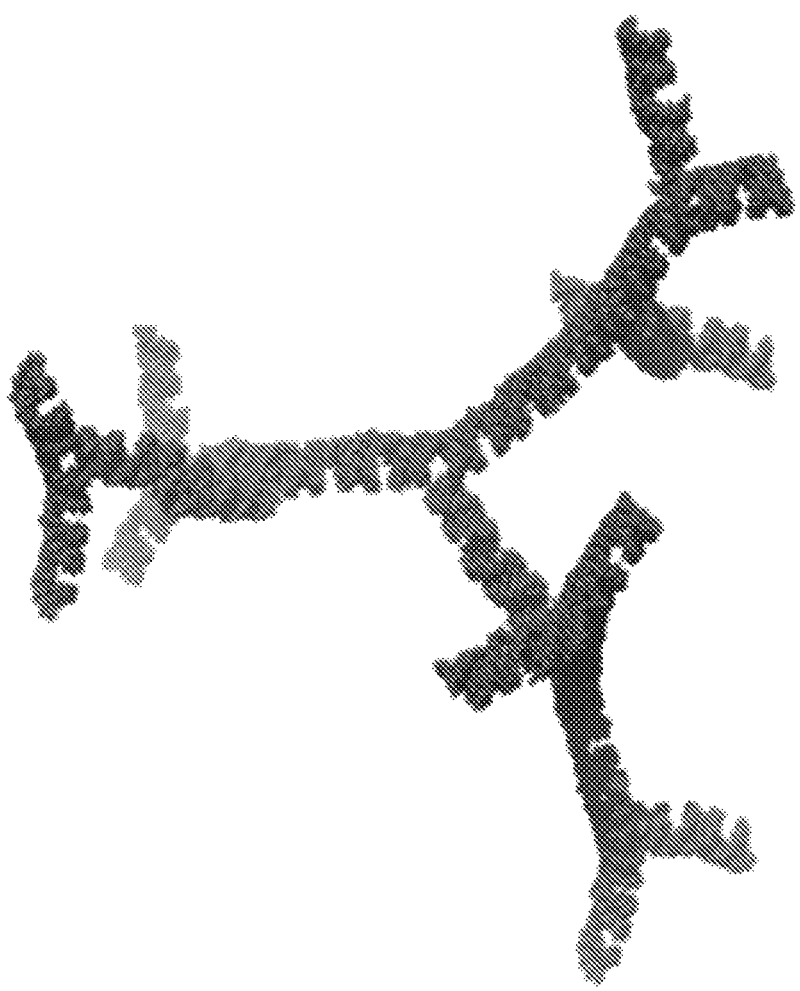
Figure 32C:
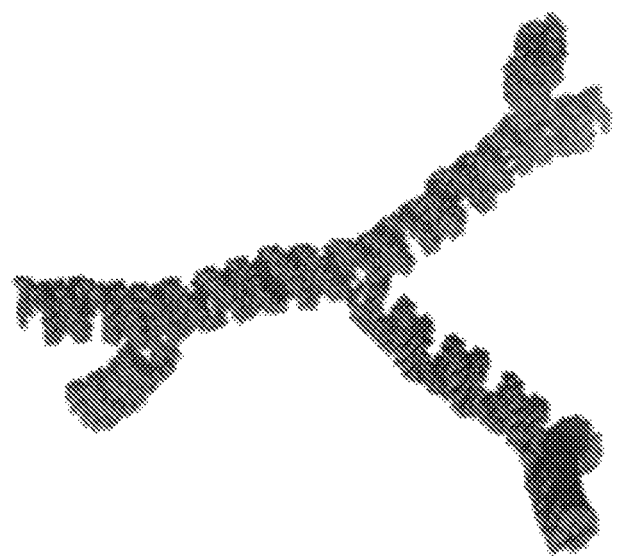
Figure 32D:
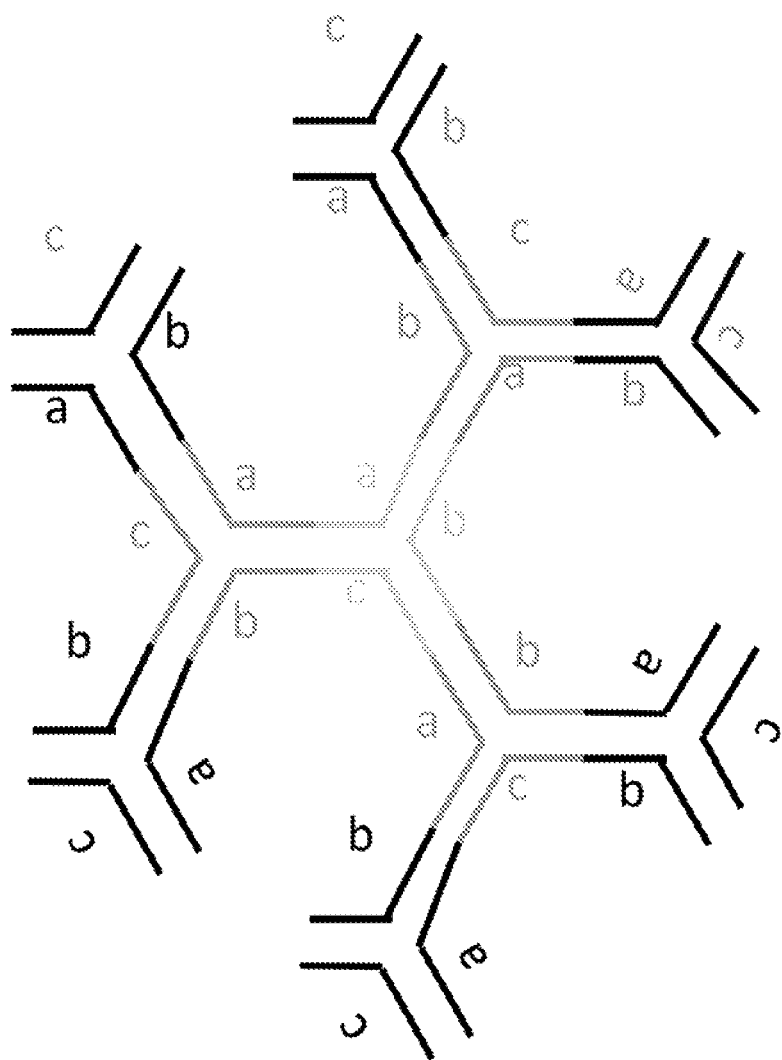

In an RNA nanostructure containing multiple layers, all the layers can be loaded with the same cargo compound and/or functional group type(s). In some aspects in an RNA nanostructure containing multiple layers, two or more layers can be loaded with a different cargo compound and/or functional group type(s). In one non-limiting example, a triple-layered RNA nanostructure can be loaded with one or more type of cargo compound (e.g. 20 to 100 molecules of one or more types of cargo compounds) in the core layer, screened by a second layer (or intermediate layer) which can be loaded with endosome escape and/or radio-MRI-fluorescence imaging modalities, and finally protected by a terminal layer or outermost layer, which can be loaded with targeting and/or biodistribution enhancing functional groups at the solvent exposed extremities of the terminal layer (FIG. 46B) Two layers are connected by coupling the synthetic oligonucleotides of the inner layer with one of the synthetic oligonucleotides of the outer layer as shown in FIG. 32D. Association of the layers is thus governed by the Tm of the layers the particle is composed of which can then be used to determine the release profile of a specific layer of functional group. Alternatively, layers can be coupled through pH, light, or enzyme labile chemical groups to induce release once desired environmental conditions are met, such as cell uptake into low pH endosomes or lysosomes.

FIGS. 44A-44B shows aspects of RNA nanostructures loaded with a single type of cargo compound or functional group. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

FIGS. 45A-45B shows aspects of RNA nanostructures loaded with multiple types of cargo compounds and/or functional groups, including but not limited to active agents. The modular RNA motif in black designates the core or primary modular RNA motif contained in the RNA nanostructure. The modular RNA motif in dark gray designates the secondary or intermediate level(s) of modular RNA motifs contained in the RNA nanostructure. The modular RNA motif in light gray designates the terminal or outer most level of modular RNA motifs contained in the RNA nanostructure.

FIGS. 46A-46B show aspects of RNA nanostructures loaded with multiple types of cargo compounds and/or functional groups, including but not limited to Paclitaxel. FIG. 46A. A nanostructure with a modular RNA motif containing an elongated core with internal modifications that allow specific attachment of active agents to the core of the nanostructure. FIG. 46B. A nanostructure with different functional groups attached to the 5' or 3' termini of oligonucleotides in each layer.

Cargo Compounds and Functional Groups

As previously described, the RNA nanostructures can contain one or more cargo compounds and/or one or more functional groups. In some aspects a single compound or molecule that can be attached or otherwise coupled to the RNA nanostructure can be a cargo compound and functional group. As used in this context herein, the term "cargo compound" refers to any molecule, compound, or composition that can be loaded onto the RNA nanostructure as described herein and can be delivered to a subject (e.g. by release from the RNA nanostructure or elicit a physiological reaction in the subject when in contact with a subject even when attached or otherwise coupled to the RNA nanostructure). The term "functional group" as used in this context herein, refers to compounds that add a functionality to the RNA nanostructure. The cargo compound(s) or functional group(s) can be any biological molecule, chemical molecule, synthetic molecule, or any other molecule that can be encapsulated by, attached to, and/or linked to, as described herein, the RNA nanostructures described herein. The cargo compound and/or functional group can be an active agent. In some aspects, the cargo compound(s) can be encapsulated by, attached to, and/or linked to the RNA nanostructure or component thereof.

In some aspects, the cargo compound and/or functional group can be DNA, RNA, modified ribonucleotides, amino acids, peptides, polypeptides, antibodies, aptamers, aptazymes, riboswitches, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable cargo compounds include sensitizers, (e.g. radio-sensitizers) that can make a cell or subject more responsive (or sensitive) to a treatment or prevention and imaging or other diagnostic agents. The RNA nanostructures can be used as a monotherapy or in combination with other active agents for treatment or prevention of a disease or disorder.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylate, and sodium salicylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papaverine, cyclobenzaprine, carisoprodol, orphenadrine, tizanidine, metaxalone, methocarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, albendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proguanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivir, zidovudine, stavudine, emtricitabine, xalcitabine, telbivudine, simeprevir, boceprevir, telaprevir, lopinavir/ritonavir, fosamprenavir, darunavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzathine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, camptothecin, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *erwinia* chrysanthemic, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, arsenic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein Suitable sensitizing agents can include, but are not limited to, radiosensitizers, insulin sensitizers (e.g. metformin, thiazolidinediones,) and photosensitizers for photodynamic therapy (e.g. aminolevulinic acid (ALA), Silicon Phthalocyanine Pc 4, m-tetrahydroxyphenylchlorin (mTHPC) and mono-L-aspartyl chlorin e6 (NPe6)).

Suitable imaging agents include but are not limited to, fluorescent molecules (e.g. Cy3, Cy5, ICG, and other commercially available fluorflores), paramagnetic ions, nanoparticles that can contain a paramagnetic ion, super-paramagnetic iron oxide molecules and nanoparticles thereof, 18F-fluorodeoxyglucose and other PET imaging agents, gadolinium containing contrast agents, radionuclides and compositions thereof.

In some aspects, the functional group can be a targeting moiety. As used in this context, the phrase "targeting moiety" refers to a compound, molecule, or any other composition that can result in the RNA nanostructure being specifically directed to a location, cell type, organ, or structure within a subject after delivery to a subject. Targeting moieties can include compounds and molecules, such as antibodies, aptamers, and receptor ligands.

Suitable targeting moieties include but are not limited to, aptamers and ligands that bind to Epidermal growth factor receptors (EGFR), prostate specific membrane antigen receptors (PSMA), epithelial cell adhesion molecule (Ep-Cam), vascular endothelial growth factors (VEGF), Galactose Receptors, Folate receptors, G-protein coupled receptors (GPCR), CD receptors, Integrins, Transferrin receptors, Fibroblast growth factors (FGFRs), Sigma receptors (SRs), and/or Epidermal growth factor receptors (EGFR), or chemical ligands such as folate, galactose and GalNac.

In some aspects, the functional group/cargo compound can be a chelating agent. Suitable chelating agents include but are not limited to, NOTA, DOTA, EDTA, Exjade, Chemet, Desferal, Ferriprox, Jadenu, and Syprine.

In some aspects the functional group/cargo compound can be hydrophobic. In some aspects the functional group and/or cargo compound can be hydrophilic. In some aspects, the functional group and/or cargo compound can hold a positive charge. In some aspects, the functional group and/or cargo compound can hold a negative charge. In some aspects, the functional group and/or cargo compound can be neutrally charged. In some aspects, the functional group and/or cargo compound can be uncharged.

In some aspects, the targeting moiety specifically targets a cancer cell. In some aspects the targeting moiety is an EGFR, HER2, and/or EP-CAM aptamer or PSM antigen, or folate. In some aspects, the targeting moiety is a ligand for EGFR. In other aspects, the targeting moiety targets blood, lungs, kidneys, brain tissue, neurons, muscle, heart, tendons, ligaments, liver, pancreas, or other specific tissue.

In some aspects, the functional group can facilitate attachment of a cargo molecule. As described elsewhere herein, nucleotides that make up the synthetic RNA oligonucleotide can be modified. In addition to an alkyne, the synthetic RNA oligonucleotide can be modified with a functional group such as a linker. The individual functional groups can be attached or otherwise coupled to the synthetic RNA oligonucleotide and/or cargo compound or additional functional group using thermodynamic, acid-labile, light-sensitive, or enzyme-labile chemical groups for timed and triggered release. In some aspects, the functional group can be a stimulus responsive linker, such as a photocleavable linker, pH responsive linker, or a linker that is enzyme cleavable. Photocleavable linkers are molecules that contain a photolabile group that is cleavable by a specific wavelength of light. The photocleavable linker can cleavably attach a cargo molecule or other functional moiety (e.g. a targeting moiety) to the RNA nanoparticle. This is another mechanism in which the release of a cargo molecule from the RNA nanoparticle can be tuned and controlled. The photocleavable linker can be activated (e.g. cleaved) via a source of electromagnetic radiation, including but not limited to, visible light, infrared radiation, ultra-violet radiation. Use of a photocleavable linker can allow for time-controlled and spatial control of release of the cargo molecule from the RNA nanoparticle. Exemplary photocleavable linkers can include, but are not limited to phosphoramidites (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6888), photocleavable biotin (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6691); Photocleavable Amino C6 (see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6890), photocleavable spacer (see e.g. see e.g. Olejnik et al., Nucleic Acids Res. (1998); 26:3572-3576; Olejnik et al. Nucleic Acid Res. (1999), 27:4626-4631; and Tang et al., Nucleic Acid Res (2002), 38:3848-3855, Gene Link cat. No. 26-6889); 2-nitrobenzyl linkers (see e.g. Bai et al., (2003) PNAS, 100: 409-413). Other suitable photocleavable linkers will be appreciated by those of ordinary skill in the art.

In some aspects, the linker can be a pH responsive linker. pH responsive linkers can be any compound that can degrade (e.g. hydrolyze) at a certain pH. Thus the pH responsive linkers can be acidic responsive or basic responsive. Th pH responsive linkers can be polymers. Suitable pH responsive linkers are generally known in the art and include, but are not limited to those described in Choy et al. (Bioconjugate. Chem. (2016) 27:824-830; Schmaljohann (2008) Adv. Drug Deliv. Rev. (2006) 58:1655-1670, Balamuralidhara et al. (2011) Am. J. Drug Disc. Devel. 1:24-48; Biomedical Nanomaterials, ed. Zhao and Shen (2016), Chapter 6; Masson et al. (2004) J. Control Release. 99:423-434; Karimi et al., Nanomed. and Nanobiotech. (2016) 8:696-716; International Patent Application Publication No.: WO2016/028700; and Patil et al., 2012. Int. J. Mol. Sci. 13:11681-11693.

In some aspects, the linker can be an enzyme cleavable linker. Enzyme cleavable linkers are those that contain a cleavage site for an enzyme. In some aspects the linkers can be a nucleic acid that contains a sequences for an endonuclease. Endonuclease cleavage sites and how to produce nucleic acid molecules containing them will be appreciated by those of ordinary skill in the art. Other cleavage sites that can be contained can be RNAse or DNAse cleavage sites. In some aspects, the enzyme cleavage site can be a cleavage site for an enzyme that is specific to a target cell. Thus in this way, release can be controlled such that it occurs only at the target cell via interaction with the target-cell specific enzyme. In some aspects the linkers can be a chemical group that can be cleaved or hydrolyzed by an enzyme such as an esterase. Other cleavage sites that can be incorporated into the enzyme cleavable linkers will be instantly appreciated by those of skill in the art.

Rational Design of Modular RNA Motifs and RNA Nanostructures

A principle for designing self-assembled nucleic acid nanostructures is that sequence complementarity in nucleic acid strands is encoded such that, by pairing up complementary segments, the nucleic acid strands self-organize into a predefined nanostructure under appropriate physical conditions. From this basic principle (see, e.g., Seeman N. C. J. Theor. Biol. 99: 237, 1982, incorporated by reference herein), researchers have created diverse synthetic nucleic acid nanostructures (see, e.g., Seeman N. C. Nature 421: 427, 2003; Shih W. M. et al. Curr. Opin. Struct. Biol. 20: 276, 2010, each of which is incorporated by reference herein). Examples of nucleic acid (e.g., DNA) nanostructures, and methods of producing such structures, that may be used in accordance with the present disclosure are known and include, without limitation, lattices (see, e.g., Winfree E. et al. Nature 394: 539, 1998; Yan H. et al. Science 301: 1882, 2003; Yan H. et al. Proc. Natl. Acad. of Sci. USA 100; 8103, 2003; Liu D. et al. J. Am. Chem. Soc. 126: 2324, 2004; Rothemund P. W. K. et al. PLoS Biology 2: 2041, 2004, each of which is incorporated by reference herein), ribbons (see, e.g., Park S. H. et al. Nano Lett. 5: 729, 2005; Yin P. et al. Science 321: 824, 2008, each of which is incorporated by reference herein), tubes (see, e.g., Yan H. Science, 2003; P. Yin, 2008, each of which is incorporated by reference herein), finite two-dimensional and three dimensional objects with defined shapes (see, e.g., Chen J. et al. Nature 350: 631, 1991; Rothemund P. W. K., Nature, 2006; He Y. et al. Nature 452: 198, 2008; Ke Y. et al. Nano. Lett. 9: 2445, 2009; Douglas S. M. et al. Nature 459: 414, 2009; Dietz H. et al. Science 325: 725, 2009; Andersen E. S. et al. Nature 459: 73, 2009; Liedl T. et al. Nature Nanotech. 5: 520, 2010; Han D. et al. Science 332: 342, 2011, each of which is incorporated by reference herein), and macroscopic crystals (see, e.g., Meng J. P. et al. Nature 461: 74, 2009, incorporated by reference herein). The synthetic RNA oligonucleotides can be single-stranded nucleic acids, double-stranded nucleic acids, or a combination of single-stranded and double-stranded nucleic acids.

The RNA nanostructure components (synthetic RNA oligonucleotides and modular RNA motifs can be designed using a computer aided design methodology described herein. Although the computer design is demonstrated using specific RNA nanostructures, it will be appreciated that the principles taught therein will be able to be extrapolated to any desired RNA nanostructure by the skilled artisan.

Each synthetic RNA oligonucleotide can be designed such that when it is combined with 2 or more additional synthetic RNA oligonucleotides that base pairing occurs to produce a highly ordered 2-D and 3-D structure having 3 or more DAs surrounding a core domain that may or may not contain base-pairing between strands and can include 0-4 nucleotides that form symmetric or asymmetric bulges between the DAs. Each synthetic RNA oligonucleotide can be designed to include 16-120 nucleotides. Each synthetic RNA oligonucleotide can be designed to include 1 or more modified nucleotides. Nucleotide modifications are described elsewhere herein. Synthetic RNA oligonucleotides designed to include more than one modification can be designed such that the modified nucleotides are separated by one or more unmodified nucleotides. In some aspects, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more unmodified nucleotides can separate two modified nucleotides.

The rational design of the synthetic RNA oligonucleotides and/or RNA nanostructures described herein can be carried out in a computing environment. The computing environment can include one or more computing devices that can include at least one processor circuit, for example, that can have a processor and a memory. Various applications and/or other functionality may be executed in the computing environment according to various aspects of the disclosure. Also, various data can be stored in one or more data stores that can be accessible to the computing environment.

The components executed on the computing environment, for example, can include a rational RNA design system and other applications, services, processes, systems, engines, or functionalities not discussed in detail herein. The rational RNA design system can be executed to facilitate the design of synthetic RNA oligonucleotides and/or RNA nanostructures as described herein. The rational RNA design system can also perform various back end functions that can be associated with the design of RNA oligonucleotides, such as those synthetic RNA oligonucleotides and/or RNA nanostructures described herein.

As shown in FIG. 48, the rational RNA design system can be executed to dynamically create synthetic RNA oligonucleotide sequences that can be used to generate RNA nanostructures as described herein. The rational RNA design system can generate, identify, and/or select synthetic RNA oligonucleotide sequences that can be compatible with one or more other synthetic RNA oligonucleotide sequences (that can also be generated by the rational RNA design system) and self-assemble to form an RNA nanostructure as described herein. The rational RNA design system can also identify synthetic RNA oligonucleotide sequences that would not be compatible with one or more other synthetic RNA oligonucleotide sequences to form an RNA nanostructure as described herein.

The rational RNA design system can apply one or more optimization algorithms to determine appropriate or optimal synthetic RNA oligonucleotide sequences that can be compatible and form an RNA nanostructure as described herein based at least in part on the GC content of the RNA oligonucleotide(s) and/or RNA nanostructure, the Tm of two or more RNA oligonucleotide(s) and/or RNA nanostructure, the probability and/or ability of self-dimerization of an RNA oligonucleotide, the cross-complementarity of synthetic RNA oligonucleotides, convert between RNA and modified nucleic acid containing oligonucleotides, and/or other data or attributes of the synthetic RNA oligonucleotides.

As shown in FIG. 48, the rational RNA design system can generate various theoretical double stranded arms (DAs) as described elsewhere herein (Generate DA sequences in FIG. 48). The rational RNA design system when executed can then determine if the GC content of the formed theoretical DA is within a desired GC range. The desired GC range can be set by the user. In some aspects the GC range can be from about 50% to 51, 52, 53, 54, 55, 56, 57, 58, 59, or about 60%. In some aspects, the GC range can be about 50, 51, 52, 53, 54, 55, 56, 57, 58, 59 or about 60%. If the formed theoretical DA is not within the desired GC range, the desired Tm range, and/or can self-dimerize, then the theoretical DA(s) are discarded. If the theoretical DA(s) are within the desired GC range, within the desired Tm, and do not self-dimerize then the theoretical DA(s) can be saved. The accepted DA's can then be used by the rational RNA design system to select for a set of oligomers that can form the accepted DA's.

As shown in FIG. 48, the rational RNA design system can select DAs for a set of oligomers. The rational RNA design system can compute the cross complementarity of a saved set (two or more) of DA(s). DAs with the highest cross complementarity can be discarded and DAs with the lowest overall cross complementarity can be saved.

As shown in FIG. 48, the rational RNA design system can use the DAs with the lowest overall cross complementarity to compute oligomer sequences. The rational RNA design system can compute the reverse complement of DA sequences, compute extension RNA oligomer sequences, and can compute termination oligomer sequences. The rational RNA design system can determine suitable oligomer sequences from various computed RNA oligomer sequences by determining if the computed RNA oligomer sequences self-dimerize and/or can form dimers. The rational RNA design system can save those computed RNA oligomer sequences that do not self-dimerize and do not form dimers and can discard those computed RNA oligomer sequences that do self-dimerize or form dimers. If the saved computed RNA oligomer sequences are generated using DNA sequences (e.g. cDNA) the rational RNA design system can convert to RNA sequences. The converted sequences can be saved.

Next, a discussion of the technical devices of the computing environment is provided. Stored in memory are both data and several components that are executable by processor. Also stored in the memory can be a data store and other data. A number of software components are stored in the memory and executable by a processor. In this respect, the term "executable" means a program file that is in a form that can ultimately be run by the processor. Examples of executable programs can be, for example, a compiled program that can be translated into machine code in a format that can be loaded into a random access portion of one or more of the memory devices and run by the processor, code that can be expressed in a format such as object code that is capable of being loaded into a random access portion of the one or more memory devices and executed by the processor, or code that can be interpreted by another executable program to generate instructions in a random access portion of the memory devices to be executed by the processor. An executable program can be stored in any portion or component of the memory devices including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

Memory can include both volatile and nonvolatile memory and data storage components. In addition, a processor can represent multiple processors and/or multiple processor cores, and the one or more memory devices can represent multiple memories that operate in parallel processing circuits, respectively. Memory devices can also represent a combination of various types of storage devices, such as RAM, mass storage devices, flash memory, or hard disk storage. In such a case, a local interface can be an appropriate network that facilitates communication between any two of the multiple processors or between any processor and any of the memory devices. The local interface can include additional systems designed to coordinate this communication, including, for example, performing load balancing. The processor can be of electrical or of some other available construction Although the rational RNA design system and other various systems described herein can be embodied in software or code executed by general-purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include discrete logic circuits having logic gates for implementing various logic functions upon an application of one or more data signals, application specific integrated circuits (ASICs) having appropriate logic gates, field-programmable gate arrays (FPGAs), or other components.

The flowcharts show an example of the functionality and operation of an implementation of portions of components described herein. If embodied in software, each block can represent a module, segment, or portion of code that can include program instructions to implement the specified logical function(s). The program instructions can be embodied in the form of source code that can include human-readable statements written in a programming language or machine code that can include numerical instructions recognizable by a suitable execution system such as a processor in a computer system or other system. The machine code can be converted from the source code. If embodied in hardware, each block can represent a circuit or a number of interconnected circuits to implement the specified logical function(s).

Although the flowcharts show a specific order of execution, it is understood that the order of execution can differ from that which is depicted. For example, the order of execution of two or more blocks can be scrambled relative to the order shown. In addition, two or more blocks shown in succession can be executed concurrently or with partial concurrence. Further, in some examples, one or more of the blocks shown in the drawings can be skipped or omitted.

Also, any logic or application described herein that includes software or code can be embodied in any non-transitory computer-readable medium for use by or in connection with an instruction execution system such as, for example, a processor in a computer system or other system. In this sense, the logic can include, for example, statements including program code, instructions, and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

RNA Nanostructure Formulations

Also provided herein are pharmaceutical formulations that can include an amount of an RNA nanostructure described herein and a pharmaceutical carrier appropriate for administration to an individual in need thereof. The individual in need thereof can have or can be suspected of a cancer, a genetic disease or disorder, a viral, bacterial, fungal, and/or parasitic infection, or other disease or disorder in need of treatment or prevention. In some aspects, the subject in need thereof is in need of a diagnostic procedure, such as an imaging procedure. The pharmaceutical formulations can include an amount of an RNA nanostructure described herein that can be effective to treat or prevent a cancer, a genetic disease or disorder, a viral, bacterial, fungal, and/or parasitic infection, or other disease or disorder or be effective to image the subject or a portion thereof.

Formulations can be administered via any suitable administration route. For example, the formulations (and/or compositions) can be administered to the subject in need thereof orally, intravenously, occularly, intraoccularly, intramuscularly, intravaginally, intraperitoneally, rectally, parenterally, topically, intranasally, or subcutaneously. Other suitable routes are described herein. In some aspects, the RNA nanostructure contains an effective amount of a cargo molecule.

Parenteral Formulations

The RNA nanostructure can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the RNA nanostructures as described herein can be prepared in water or another solvent or dispersing medium suitably mixed with one or more pharmaceutically acceptable excipients including, but not limited to, surfactants, dispersants, emulsifiers, pH modifying agents, and combinations thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium bis-(2-ethylthiol)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the RNA nanostructures.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the RNA nanostructures in the required amount in the appropriate solvent or dispersion medium with one or more of the excipients listed above, as required, followed by filtered sterilization. Dispersions can be prepared by incorporating the various sterilized RNA nanostructures into a sterile vehicle which contains the basic dispersion medium and the required other ingredients from those listed above. Sterile powders for the preparation of sterile injectable solutions can be prepared by vacuum-drying and freeze-drying techniques, which yields a powder of the RNA nanostructures plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more RNA nanostructures. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other aspects, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for use of nanotechnology including nanoformulations for parenteral administration can also contain one or more excipients, such as dispersing agents, wetting agents, and suspending agents.

Topical Formulations

The RNA nanostructures as described herein can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some aspects, the RNA nanostructures can be administered as a liquid formulation, such as a solution or suspension, a semi-solid formulation, such as a lotion or ointment, or a solid formulation. In some aspects, the RNA nanostructures can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some aspects, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some aspects, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some aspects, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macroyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some aspects, the surfactant can be a non-ionic surfactant. In other aspects, the emulsifying agent is an emulsifying wax. In further aspects, the liquid non-volatile non-aqueous material is a glycol. In some aspects, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing RNA nanostructures as described herein are also provided. In some aspects, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing an RNA nanostructure as described herein are also provided. The cream can contain emulsifying agents and/or other stabilizing agents. In some aspects, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some aspects of a cream formulation, the water-base percentage can be about 60% to about 75% and the oil-base can be about 20% to about 30% of the total, with the other percentages being the emulsifier agent, preservatives and additives for a total of 100%.

Ointments containing an RNA nanostructure as described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing an RNA nanostructure as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited to, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include an RNA nanostructure as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some aspects, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain aspects, the formulations can be provided via continuous delivery of one or more formulations to a patient in need thereof. For topical applications, repeated application can be done or a patch can be used to provide continuous administration of the noscapine analogs over an extended period of time.

Enteral Formulations

The RNA nanostructures as described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations containing RNA nanostructures as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing an RNA nanostructure as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing an RNA nanostructure as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing an RNA nanostructure as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some aspects, an amount of one or more additional active agents are included in the pharmaceutical formulation containing an RNA nanostructure. Suitable additional active agents include, but are not limited to, DNA, RNA, modified ribonucleotides, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable additional active agents include, sensitizers (such as radiosensitizers). The RNA nanostructure can be used as a monotherapy or in combination with other active agents for treatment or prevention of a disease or disorder.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-w, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylate, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicaylate).

Suitable antispasmodics include, but are not limited to, mebeverine, papaverine, cyclobenzaprine, carisoprodol, orphenadrine, tizanidine, metaxalone, methocarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirizine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, albendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proguanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, abacavir, zidovudine, stavudine, emtricitabine, xalcitabine, telbivudine, simeprevir, boceprevir, telaprevir, lopinavir/ritonavir, fosamprenavir, darunavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzathine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase *erwinia* chrysanthemic, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine (thioguanine), dabrafenib, erlotinib, bexarotene, temozolomide, thiotepa, thalidomide, BCG, temsirolimus, bendamustine hydrochloride, triptorelin, arsenic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein.

Methods of Using the RNA Nanostructures and Formulations Thereof

The RNA nanostructures and formulations thereof can be used to deliver one or more cargo compounds to a subject in need thereof or a cell. In some aspects, the RNA nanostructures can be used to deliver an RNA or DNA molecule for replacement gene/transcript therapy, deliver RNAi or similar RNA (e.g. microRNA) to a subject to specifically inhibit RNA transcripts to reduce gene expression of a specific gene or genes, deliver an imaging agent, delivering a small molecule drug, and/or deliver any other cargo compound that can be encapsulated in the RNA nanostructures provided herein. Thus, the RNA nanostructures can be used to deliver a treatment, prevention, and/or a diagnostic compound to a subject in need thereof.

In some aspects, the RNA nanostructures described herein can be contacted with a cell or population thereof. In some aspects, the cell or population thereof is sensitized to the treatment or prevention being delivered by the RNA nanostructure. In some aspects, the RNA nanostructure is delivering the sensitizing agent. In some aspects the cargo compound being delivered is not a sensitizing agent. In an aspect, following the administration of a RNA nanostructure, a subject can be sensitized to treatment. In an aspect, an increased sensitivity or a reduced sensitivity to a treatment, such as a therapeutic treatment (such as that provided by a cargo compound being delivered by the RNA nanostructure, can be measured according to one or more methods as known in the art for the particular treatment. In an aspect, methods of measuring sensitivity to a treatment include, but are not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a sensitizing agent and/or the RNA nanostructure (such as a RNA nanostructure carrying a sensitizing agent) the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a sensitizing agent. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a sensitizing agent, such as one being delivered by an RNA nanostructure described herein. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can be modified by changing the dose of a disclosed composition, the route of administration of a disclosed composition, the frequency of administration of a disclosed composition, etc.

In some aspects, where the RNA nanostructure includes a photocleavable linker that is linking the targeting moiety and/or cargo compound the RNA nanostructure can be administered to the subject or population of cells. After administration, light can be applied to the region and/or population of cells in the subject in need thereof where treatment or prevention is needed to cause the release of the RNA nanostructure and/or cargo molecule.

The RNA nanostructure as provided herein can be administered to a subject in need thereof, cell, or population thereof. The subject in need thereof can have a cancer, genetic disease or disorder, a viral, bacterial, parasitic, and/or fungal infection, or any other disease or disorder that would benefit from an effective agent (such as a cargo compound described herein) being delivered. The amount delivered can be an effective amount of an RNA nanostructure provided herein. The subject in need thereof can be symptomatic or asymptomatic. In some aspects, the RNA nanostructures provided herein can be co-administered with another active agent. It will be appreciated that co-administered can refer to an additional compound that is included in the formulation or provided in a dosage form separate from the RNA nanostructure or formulation thereof. The effective amount of the RNA nanostructure or formulation thereof, such as those described herein, can range from about 0.1 mg/kg to about 500 mg/kg. In some aspects, the effective amount ranges from about 0.1 mg/kg to 10 mg/kg. In additional aspects, the effective amount ranges from about 0.1 mg/kg to 100 mg/kg. If further aspects, the effective amount ranges from about 0.1 mg to about 1000 mg. In some aspects, the effective amount can be about 500 mg to about 1000 mg.

Administration of the RNA nanostructures and formulations thereof can be systemic or localized. The compounds and formulations described herein can be administered to the subject in need thereof one or more times per day. In an aspect, the compound(s) and/or formulation(s) thereof can be administered once daily. In some aspects, the compound(s) and/or formulation(s) thereof can be administered given once daily. In another aspect, the compound(s) and/or formulation(s) thereof can be administered twice daily. In some aspects, when administered, an effective amount of the compounds and/or formulations are administered to the subject in need thereof. The compound(s) and/or formulation(s) thereof can be administered one or more times per week. In some aspects the compound(s) and/or formulation(s) thereof can be administered 1 day per week. In other aspects, the compound(s) and/or formulation(s) thereof can be administered 2 to 7 days per week.

In some aspects, the RNA nanostructure(s) and/or formulation(s) thereof, can be administered in a dosage form. The amount or effective amount of the compound(s) and/or formulation(s) thereof can be divided into multiple dosage forms. For example, the effective amount can be split into two dosage forms and the first dosage form can be administered, for example, in the morning, and the second dosage form can be administered in the evening. Although the effective amount is given over two doses, in one day, the subject receives the effective amount. In some aspects the effective amount is about 0.1 to about 1000 mg per day. The effective amount in a dosage form can range from about 0.1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

The modular RNA motifs described herein and the RNA nanostructures described herein can be used in the preparation of a medicament for treatment of a disease or a cancer.

A number of aspects of the invention have been described. Nevertheless, it will be understood that various modifications may be made without departing from the spirit and scope of the invention. Accordingly, other aspects are within the scope of the following claims.

Examples

Example 1: RNA-Based Micelles: A Platform for Chemotherapeutic Drug Loading and Delivery RNA can serve as powerful building blocks for bottom-up fabrication of nanostructures for biotechnological and biomedical applications. In addition to current self-assembly strategies utilizing base pairing, motif piling and tertiary interactions, we reported for the first time to build RNA based micellar nanoconstructs with a cholesterol molecule conjugated onto one helical end of a branched pRNA three-way junction (3WJ) motif. The resulting amphiphilic RNA micelles consist of a hydrophilic RNA head and a covalently linked hydrophobic lipid tail that can spontaneously assemble in aqueous solution via hydrophobic interaction. Taking advantage of the feature of pRNA 3WJ branched structure, the assembled RNA micelles are capable of escorting multiple functional modules. As a proof of concept for delivery of therapeutics, Paclitaxel was loaded into the RNA micelles with significantly improved water solubility. The successful construction of the drug loaded RNA micelles was confirmed and characterized by agarose gel electrophoresis, atomic force microscopy (AFM), dynamic light scattering (DLS), and Nile Red fluorescence encapsulation assay. The critical micelle formation concentration was as low as approximately 100 nM. The Paclitaxel loaded RNA micelles can internalize into cancer cells and inhibit their proliferation. Further studies showed that the Paclitaxel loaded RNA micelles induced cancer cell apoptosis in a Caspase-3 dependent manner but RNA micelles alone exhibited low cytotoxicity. Finally, the Paclitaxel loaded RNA micelles targeted tumor in vivo without accumulation in healthy tissues and organs. There is also no or very low induction of pro-inflammatory response. Therefore, multivalency, cancer cell permeability, combined with controllable assembly, low or no toxicity, and tumor targeting are all promising features that make our pRNA micelles a suitable platform for potential drug delivery.

Introduction

Functional nanoparticles fabricated via molecular self-assembly hold great promise for applications in biotechnology and biomedicine [1-4]. Among these, RNAs have been utilized as unique biomaterials to construct a wide variety of nanoparticles via self-assembly [Li, H. et al. Adv.Mater. 28 (2016) 7501-7507; Guo, P. Nature Nanotechnology 5 (2010) 833-842; Shu, D. et al. Nature Nanotechnology 6 (2011) 658-667; Shu, Y. et al. Methods 54 (2011) 204-214; Haque, F. et al. Nano Today 7 (2012) 245-257; Afonin, K. A. et al. Nano.Lett. 12 (2012) 5192-5195; Shu, Y. et al. Nat.Protoc. 8 (2013) 1635-1659; Khisamutdinov, E. et al. Nucleic Acids Res. 42 (2014) 9996-10004; Jasinski, D. et al. ACS Nano 8 (2014) 7620-7629; Khisamutdinov, E. F. et al. Advanced Materials 28 (2016) 100079-100087; Afonin, K. A. et al. Nano Lett. 14 (2014) 5662-5671; Dibrov, S. M. et al. Proc.Natl.Acad.Sci.U.S.A. 108 (2011) 6405-6408; Afonin, K. A. et al. Nat.Nanotechnol. 5 (2010) 676-682]. These RNA nanoparticles have been demonstrated to be further functionalized for biomedical applications [Lee, J. B. et al. Nat.Mater. 11 (2012) 316-322; Lee, T. J. et al. Oncotarget 6 (2015) 14766-14776; Cui, D. et al. Scientific reports 5 (2015) 10726; Shu, D. et al. ACS Nano 9 (2015) 9731-9740; Rychahou, P. et al. ACS Nano 9 (2015) 1108-1116; Binzel, D. et al. Molecular Therapy 24 (2016) 1267-1277; Afonin, K. A. et al. Nat.Protoc. 6 (2011) 2022-2034]. The strategies for RNA nanoparticle self-assembly were previously reported. Exploiting RNA base pairing and tertiary interactions provides versatile RNA assemblies with accurate control over their composition, structure, and function at the nanometer scale [Shu, Y. et al. Nat.Protoc. 8 (2013) 1635-1659; Khisamutdinov, E. F. et al. Methods Mol Biol 1316 (2015) 181-193]. In this present study, a strategy to fabricate RNA self-assemblies with micellar properties through intermolecular hydrophobic interactions is examined.

Described herein is the desing and manufacture of a stable phi29 pRNA three-way junction (3WJ) motif that can be used as a scaffold to construct multivalent RNA nanoparticles with high chemical and thermodynamic stability [Guo, P. Nature Nanotechnology 5 (2010) 833-842; Haque, F. et al. Nano Today 7 (2012) 245-257]. The resulting branched RNA nanoparticles are uniform in size and shape. They can harbor different functionalities while retaining their tertiary fold and independent functionalities both in vitro and in vivo [Haque, F. et al. Nano Today 7 (2012) 245-257; Jasinski, D. et al. ACS Nano 8 (2014) 7620-7629; Shu, D. et al. ACS Nano 9 (2015) 9731-9740; Binzel, D. et al. Molecular Therapy 24 (2016) 1267-1277; Shu, Y. et al. RNA 19 (2013) 766-777; Khisamutdinov, E. F. et al. ACS Nano. 8 (2014) 4771-4781; Li, H. et al. Nucleic Acid Ther. (2015) 25(4): 188-97; Lee, T. J. et al. Mol Ther. (2017) 25(7):1544-1555; Shu, D. et al. Nucleic Acids Res. (2014) 42(2):e10]. It is also shown that fluorescent dye molecules [Shu, D. et al. EMBO J. 26 (2007) 527-537] and specific cell targeting ligands [Shu, D. et al. ACS Nano 9 (2015) 9731-9740; Rychahou, P. et al. ACS Nano 9 (2015) 1108-1116; Binzel, D. et al. Molecular Therapy 24 (2016) 1267-1277; Lee, T. J. et al.

Mol Ther. (2017) 25(7):1544-1555; Pi, F. et al. Nat Nanotechnol. (2018) 13(1):82-89] can be covalently attached onto RNA strands either through RNA solid phase synthesis or by post-transcriptional chemical conjugation [Shu, Y. et al. Methods 54 (2011) 204-214; Shu, Y. et al. Nat.Protoc. 8 (2013) 1635-1659; Raouane, M. et al. Bioconjug. Chem 23 (2012) 1091-1104]. The feasibility of modifying RNA molecules with different chemical and functional moieties proved the potential of RNA nanoparticles as a multifunctional drug delivery platform.

DNA micelle construction has been described [Gosse, C. et al. J Phys Chem B 108 (2004) 6485-6497; Wu, Y. et al. Proc Natl Acad Sci U.S A 107 (2010) 5-10; Liu, H. et al. Chemistry 16 (2010) 3791-3797; Chen, T. et al. Angew. Chem Int.Ed Engl. 52 (2013) 2012-2016; Jeong, J. H. et al. Bioconjug. Chem 12 (2001) 917-923; Dentinger, P. M. et al. Langmuir 22 (2006) 2935-2937; Alemdaroglu, F. E. et al. Angew. Chem Int.Ed Engl. 45 (2006) 4206-4210; Trinh, T. et al. Chem Commun.(Camb.) 52 (2016) 10914-10917; Li, Z. et al. Nano Letters 4 (2004) 1055-1058; Alemdaroglu, F. E. et al. Adv.Mater. 20 (2008) 899-902]. A hydrophilic RNA molecule can be converted into an amphiphilic construct by fusing a lipophilic moiety onto one of pRNA-3WJ branched helical ends. This amphiphilic construct behaves similarly as a phospholipid while it spontaneously self-assembles into monodispersed, three-dimensional micellar nanostructures with a lipid inner core and a branched exterior RNA corona as the results of intermolecular hydrophobic interactions in aqueous solution. Unlike current DNA micellar systems, which are limited in application by their mono-functionality [Wu, Y. et al. Proc Natl Acad Sci U.S A 107 (2010) 5-10; Jeong, J. H. et al. Bioconjug. Chem 12 (2001) 917-923], the pRNA micelles are capable of covalently attaching diverse types of functional moieties to a single particle, including chemo-drugs for cancer therapeutics, imaging moieties for nanoparticle tracking, and co-delivered RNAi components for combination treatment.

Paclitaxel (PTX), isolated from the bark of Pacific Yew (*Taxus brevifolia*) [Wani, M. C. et al. J Am. Chem Soc 93 (1971) 2325-2327], is one of the most effective chemotherapeutic drugs for a number of cancer types [Spencer, C. M. et al. Drugs 48 (1994) 794-847; Rowinsky, E. K. et al. N.Engl.J Med. 332 (1995) 1004-1014; Jordan, M. A. et al. Nat Rev.Cancer 4 (2004) 253-265]. The mechanism of paclitaxel for cancer treatment is to promote and stabilize microtubules and further inhibit G2 or M phases of the cell cycle followed by cell death [Horwitz, S. B. et al. Trends Pharmacol.Sci 13 (1992) 134-136]. However, Paclitaxel has been classified as IV chemical drugs according to the Biopharmaceutical classification system (BCS), because it has both low water solubility (~0.4 µg/mL) and low permeability. The first formulation of paclitaxel to be used was in a 1:1 (v:v) blend of Cremophor EL (polyethoxylated castor oil) and dehydrated ethanol diluted 5-20 fold with 0.9% sodium chloride or 5% dextrose solution for i.v. administration [Singla, A. K. et al. Int.J Pharm 235 (2002) 179-192]. However, formulation with Cremophor oil has been observed to cause severe side effects [Gelderblom, H. et al. Eur.J Cancer 37 (2001) 1590-1598] as well as unpredictable non-linear plasma pharmacokinetics [Sparreboom, A. et al. Cancer Res 56 (1996) 2112-2115]. Therefore, alternative Paclitaxel formulations have been explored extensively, particularly with nanoparticle-based delivery systems [Kim, S. C. et al. J Control Release 72 (2001) 191-202]. Taking advantage of nano-scale size, tumor targeted delivery, and biocompatibility, the encapsulation of Paclitaxel in a nano-delivery system can increase drug circulation half-life, lower its systemic toxicity, reduce side effects, improve pharmacokinetic and pharmacodynamic profiles, and demonstrate better patient compliance. Paclitaxel albumin-bound nanoparticles (Abraxane®) have been approved by the FDA in 2005. Paclitaxel liposomes (Lipusu®), polymeric micelles (Genexol PM®) and polymeric conjugate with polyglutamate (Xyotax®) are currently commercial available paclitaxel formulations. In addition, there are various types of Paclitaxel nanoparticle formulations either under development or in clinical trials, such as polymer-based nanoparticles [Hamaguchi, T. et al. Br.J Cancer 97 (2007) 170-176; Dong, Y. et al. Biomaterials 25 (2004) 2843-2849; Kim, K. et al. J Control Release 146 (2010) 219-227], lipid-based nanoparticles [Yoshizawa, Y. et al. Int.J Pharm 412 (2011) 132-141; Yuan, H. et al. Int.J Pharm 348 (2008) 137-145], polymer-drug conjugates [Khandare, J. J. et al. Bioconjug. Chem 17 (2006) 1464-1472; Bedikian, A. Y. et al. Melanoma Res 14 (2004) 63-66], inorganic nanoparticles [Hwu, J. R. et al. J Am. Chem Soc 131 (2009) 66-68], carbon nanotubes [Lay, C. L. et al. nanotechnology 21 (2010) 065101], nanocrystals [Deng, J. et al. Int.J Pharm 390 (2010) 242-249], etc. However, formulating Paclitaxel in an RNA based nano-delivery platform has never been reported.

This example describes, inter alia, the design and construction of a well-defined RNA-micelle system to encapsulate Paclitaxel through conjugation to pRNA-3WJ-lipid. It is also the first time to report RNA-Paclitaxel micelles with significantly enhanced Paclitaxel water solubility and tumor permeability. The resulting RNA micelles show a low critical micelle formation concentration (CMC), excellent cell binding and permeability, and efficient inhibition of cancer cell proliferation by induction of Caspase-3 dependent cell apoptosis in vitro. Finally, it was demonstrated that these drug-loaded RNA micelles can be systemically delivered to tumor with advantageous tumor targeting, thus minimizing retention of drug in healthy tissues and crucial organs. There was also no or very low induction of pro-inflammatory response. All of these findings indicate the strong potential of the RNA-micelle system as a suitable drug delivery platform for cancer treatment. These RNA micelles can be used for tumor specific targeting, reducing the drug effective dose and further diminishing adverse effects from chemotherapy. The RNA micelles described herein can be a robust and safe nano-delivery system to carry anti-cancer drugs for specific tumor targeting and treatment with minimum adverse effects to combat cancer and improve the life quality of patients.

Materials and Methods

Synthesis of Paclitaxel Conjugated RNA Strand Via "Click Chemistry"

To synthesize PTX-Azide, 1:2:2:1 eq. of Paclitaxel (Alfa Aesar), 6-Azidohexanoic acid (Azido-HA) (Chem-IMPEX INT'L Inc), N, N'-Dicyclohexyl-carbodiimide (DCC) (Acros Organics), and 4-(Dimethylamino) pyridine (DMAP) (Sigma Aldrich) were weighed into a two neck round bottom flask. The reaction mixture was dissolved in about 20 mL dried Dichloromethane (DCM) and reacted at room temperature while stirring under nitrogen atmosphere for 24 hr. The reaction solution was filtered and concentrated on a rotary evaporator. The concentrated reaction was further purified by silica gel chromatography under serial solvent wash with n-Hexane:ethyl acetate. Fractions containing pure product were combined and dried. The purified final product PTX-Azide was characterized by Nuclear Magnetic Resonance (NMR) Spectroscopy.

5'-alkyne-RNA was synthesized via standard RNA solid phase chemical synthesis using 5'-Hexynyl phosphoramidite (Glen Research Corp.). The theoretical yield of labeled RNA strand is about 68% (0.9819=0.68) with an average coupling efficiency of 98%.

To 5 μL of a 2 mM RNA-Alkyne solution in water, 2 μL of PTX-Azide (50 mM, 5 eq. in 3:1 (v/v) DMSO (Dimethyl sulfoxide, extra dried, Acros Organics)/tBuOH (tert-Butanol, anhydrous, Sigma Aldrich)), 3 μL of freshly prepared "Click Solution" containing 0.1 M CuBr (Copper(I) bromide, Sigma Aldrich) and 0.1 M TBTA (Tris[(1-benzyl-1H-1,2,3-triazol-4-yl)methyl]amine, Sigma Aldrich) in a 1:2 molar ratio in 3:1 DMSO/tBuOH were added. The reaction mixture was thoroughly mixed and reacted at room temperature for 3 hr. The success of the reaction was determined by 20% 8 M Urea PAGE in TBE (89 mM Tris base-borate, 2 mM EDTA) buffer. The reaction was subsequently diluted with 100 μL 0.3 M NaOAc (Sodium Acetate) and 1 mL 100% Ethanol for RNA precipitation. The precipitates were dissolved in water for purification using Ion-Pair Reverse Phase HPLC on an Agilent PLRP-S 4.6×250 mm 300 Å column. PTX-labeled RNA was separated from unreacted RNA-Alkyne in an Acetonitrile ramp. The column was equilibrated in 95% solvent A (0.1 M TEAA, HPLC grade $H_2O$) and 5% solvent B (0.1 M TEAA, 75% Acetonitrile, 25% HPLC grade $H_2O$) at a flow rate of 1.5 mL/min. The samples were filtered through a 0.2 μm spinfilter, loaded onto the column and then eluted by ramping from 5% to 100% B over the course of 30 min. Fractions were collected, combined and buffer exchanged. The final RNA-PTX conjugate was characterized by Mass Spectrometry.

Design and Construction of 2'-F Modified pRNA-3WJ-PTX Micelles

The RNA micelles were constructed using a bottom-up approach [Shu, D. et al. Nature Nanotechnology 6 (2011) 658-667]. The pRNA-3WJ-PTX micelles consisting of three fragments, a3WJ, b3WJ and c3WJ, were functionalized with Paclitaxel (Alfa Aesar) on a3WJ 5'-end (a3WJ-5'PTX), as a therapeutic module; Cholesterol on b3WJ 3'-end (b3WJ-3'chol), as lipophilic module; and Alexa647 (Alexa Fluor® 647, Invitrogen) on c3WJ 3'-end (c3WJ-3'Alexa647), as a near-infra-red (NIR) imaging module. The control RNA nanoparticles are particles without therapeutic module named as pRNA-3WJ micelles, without lipophilic module named as pRNA-3WJ-PTX, and without both lipophilic module and therapeutic module named as pRNA-3WJ.

The following pRNA-3WJ scaffold [Shu, D. et al. Nature Nanotechnology 6 (2011) 658-667] sequences were used: a3WJ 5'-UUgCCaUgUgUaUgUggg-3' (SEQ ID NO:16); b3WJ 5'-CCCaCaUaCUUUgUUgaUCC-3' (SEQ ID NO:17); c3WJ 5'-ggaUCaaUCaUggCaa-3' (SEQ ID NO:18) (upper case indicates 2' Fluoro (2'-F) modified nucleotide). The RNA fragments were synthesized by standard solid phase chemical synthesis [Lay, C. L. et al. nanotechnology 21 (2010) 065101] with commercially available phosphoramidite monomers of 2'-TBDMS Adenosine (n-bz) CED, 2'-TBDMS Guanosine (n-ibu) CED, 2'-Fluoro Cytidine (n-ac) CED, and 2'-Fluoro Uridine CED, followed by deprotection according to manufacturer (Azco Biotech) provided protocols. Paclitaxel (PTX) was conjugated onto a3WJ 5'-end by chemoselective Cu(I)-catalyzed Huisgen 1,3-dipolar cycloaddition reaction ("Click chemistry") and purified through reverse phase HPLC as mentioned above. Cholesterol was attached to the 3'-end of b3WJ strand by using 3'-Cholesteryl-TEG CPG support (Glen Research Corp.), following manufacturer instructions. The theoretical yield of b3WJ-3'chol is ~68% (0.9819=0.68) with an average coupling efficiency of 98%. Synthesized RNA is purified from terminated strands using an ion-pair reverse phase column which typically yields complete labeling with cholesterol during solid phase synthesis. Alexa647 labeled RNA strand was purchased from TriLink Bio Technologies, LLC.

pRNA-3WJ-PTX micelles were assembled by mixing 3WJ strands (a3WJ, b3WJ and c3WJ) at equimolar concentrations in TMS buffer (50 mM Tris pH 8.0, 100 mM NaCl, 10 mM $MgCl_2$) or PBS buffer (137 mM NaCl, 2.7 mM KCl, 10 mM $Na_2HPO_4$ and 2 mM $KH_2PO_4$, pH 7.4) followed by heating to 80° C. for 5 minutes and slow cooling to 37° C. over the course of 40 min with a subsequent 1 hr incubation at 37° C.

Characterization of the Assembled pRNA-3WJ Micelles

The assembly of the functionalized 3WJ nanoparticles was characterized by 1% (w/v) agarose gel shift assays in TAE (40 mM Tris-acetate, 1 mM EDTA) buffer. After electrophoresis, the gel was stained by ethidium bromide and visualized by Typhoon FLA 7000 (GE healthcare).

The apparent hydrodynamic diameters of preassembled pRNA-3WJ-PTX (20 μM in PBS buffer) and pRNA-3WJ-PTX micelles (10 μM in PBS buffer) were measured by Zetasizer nano-ZS (Malvern Instrument, LTD) at 25° C., respectively. The data was obtained from three independent measurements. The Zeta potential of pRNA-3WJ-PTX micelles (1 μM in PBS buffer) was also measured by Zetasizer nano-ZS (Malvern Instrument, LTD) at 25° C.

Size and shape of the RNA micelles were also determined by Atomic Force Microscopy (AFM). For AFM, 10 μM solutions of pRNA-3WJ-PTX micelles in TMS buffer were deposited onto freshly cut mica and dried overnight. After two consecutive rinsing steps with HPLC grade water, the mica was mounted onto a Bruker Multimode IV AFM and imaged in tapping mode.

Successful formation of the RNA micelles was also determined by a Nile Red encapsulation assay as reported previously [Edwardson, T. G. W. et al. Nature Chemistry 5 (2013) 868-875; Zhang, A. et al. Soft Matter 9 (2013) 2224-2233]. A 5 mM stock solution of Nile Red in acetone was used for all experiments. Briefly, 0 μM, 1 μM, 5 μM, and 10 μM of assembled pRNA-3WJ micelles were incubated with 100 μM of Nile Red in TMS buffer, respectively. The mixture was heated to 80° C. for 5 min and slowly cooled to 37° C. over 40 min followed by 1 hr incubation at 37° C. The fluorescence intensity of Nile Red versus RNA micelle concentration was measured on a Fluorolog spectrofluorometer (Horiba Jobin Yvon) with an excitation wavelength of 535 nm and emission spectra taken from 560 nm to 760 nm. The pRNA-3WJ was used as a control.

Determination of Critical Micelle Formation Concentration (CMC)

CMC of pRNA-3WJ micelles was determined by both fluorescent Nile Red encapsulation assay as previously reported [Zhang, A. et al. Soft Matter 9 (2013) 2224-2233] and agarose gel electrophoresis. Briefly, 2-fold serially diluted RNA micelle samples (in the range of 5 μM to 0.005 μM) were incubated with 100 μM Nile Red in a final volume of 50 μL. The samples were heated to 80° C. for 5 min and slowly cooled to 37° C. over 40 min followed by 1 hr incubation at 37° C. The fluorescence intensity of Nile Red versus RNA micelle concentration was measured by Fluorolog spectrofluorometer (Horiba Jobin Yvon) with an excitation wavelength of 535 nm and emission spectra taken from 560 nm to 760 nm. 2-fold serially diluted RNA micelle samples (in the range of 2.5 μM to 0.0390625 μM) were directly loaded onto a 1% (w/v) agarose gel for electrophoresis under 120 V in TAE buffer. The gel was stained by ethidium bromide and visualized by Typhoon FLA 7000.

Formulation Stability Assay

2 µM solutions of pRNA-3WJ micelles were incubated in acidic (pH=4), neutral (pH=7.4), and basic (pH=12) buffers @ 37° C. for 1 hr. Final 2 µM of pRNA-3WJ micelles were also incubated at different temperature (4° C., 37° C., and 65° C.) for 1 hr. All samples after incubation were loaded onto a 1% (w/v) agarose gel for electrophoresis under 120 V in TAE buffer. The gel was stained by ethidium bromide and visualized by Typhoon FLA 7000.

Cell Culture

Human KB cells (American Type Culture Collection, ATCC) were grown and cultured in RPMI-1640 (Thermo Scientific) containing 10% FBS in a 37° C. incubator under 5% $CO_2$ and a humidified atmosphere. Mouse macrophage-like RAW264.7 cells were grown in Dulbecco's Modified Eagle's Medium (DMEM) supplemented with 10% fetal bovine serum, 100 units/ml penicillin and 100 mg/ml streptomycin at 37° C. in humidified air containing 5% $CO_2$.

In Vitro Binding Assay Using Flow Cytometry 250 nM, 500 nM, and 1 µM Alexa647 labeled pRNA-3WJ-PTX micelles and control pRNA-3WJ-PTX nanoparticles without lipophilic module were each incubated with $2\times10^5$ KB cells at 37° C. for 1 hr. After washing twice with PBS, the cells were resuspended in PBS. Flow Cytometry was performed by the UK Flow Cytometry & Cell Sorting core facility to observe the cell binding efficacy of the Alexa647 labeled pRNA-3WJ-PTX micelles. The data was analyzed by FlowJo 7.6.1 software.

In Vitro Binding and Internalization Assay Using Confocal Microscopy

KB cells were grown on glass slides overnight. 1 µM Alexa647 labeled pRNA-3WJ-PTX micelles and control pRNA-3WJ-PTX nanoparticles without lipophilic module were each incubated with cells at 37° C. for 1 hr. After washing with PBS, the cells were fixed by 4% paraformaldehyde (PFA) and washed 3 times with PBS. The cytoskeleton of the fixed cells was treated with 0.1% Triton-X100 in PBS for 5 min to improve cell membrane permeability and then stained by Alexa Fluor 488 Phalloidin (Life Technologies) for 30 min at room temperature and then rinsed with PBS for 3×10 min. The cells were mounted with Prolong® Gold antifade reagent with DAPI (Life Technologies) and DAPI was used for staining the nucleus. The cells were then assayed for binding and cell entry by FluoView FV1000-Filter Confocal Microscope System (Olympus Corp.).

In Vitro Drug Releasing Assay for pRNA-3WJ-PTX

10 µM of The pRNA-3WJ-PTX conjugate was incubated with 50% FBS at 37° C. and samples were collected at different time point (1 hr, 4 hr, 8 hr, 12 hr, 15 hr, 22 hr, 24 hr, 28 hr, and 36 hr) and frozen immediately at −80° C. After completing sample collection through the entire time course, all samples were run on 15% native PAGE in TBM buffer (89 mM Tris base-borate, 5 mM $MgCl_2$). The gel bands were quantified by ImageJ and the percentage of intact particle was calculated as intact particle %=[(intensity of upper band)/(intensity of upper band+lower band)]×100%. Upper band indicates intact RNA-drug conjugate while lower band indicates RNA oligo after drug release.

MTT Assay

In order to assay cytotoxic effects from pRNA-3WJ-PTX micelle treatment, CellTiter 96 Non-Radioactive Cell Proliferation Assay (Promega) was used to assay cell viability changes following manufacturer instructions. Briefly, $1\times10^4$ KB cells were seeded into 96-well plates a day prior to the assay. On the second day, 1 µM, 800 nM, 600 nM, 400 nM, and 200 nM of pRNA-3WJ-PTX micelles were added to the wells in triplets. Paclitaxel alone, pRNA-3WJ micelles, pRNA-3WJ-PTX, and pRNA-3WJ were used as controls in the same testing concentrations. The plate was incubated at 37° C. for 48 hr in a humidified, 5% $CO_2$ atmosphere. After incubation, 15 µl of Dye Solution was added to each well and the plate was incubated at 37° C. for up to 4 hr in a humidified, 5% $CO_2$ atmosphere. Next, 100 µL of the Solubilization Solution/Stop Mix was added to each well and incubated for 1 hr. Finally, the contents of the wells were mixed to get a uniformly colored solution and their absorbance at 570 nm was recorded on a Synergy 4 microplate reader (Bio-Tek).

Apoptosis Study in In Vitro Cell Model

FITC Annexin V Apoptosis Detection Kit (BD Pharmingen) and Caspase-3 Assay Kit (BD Pharmingen) were used as previously reported to study cell apoptosis induced by pRNA-3WJ-PTX micelle treatment. For FITC Annexin V staining assay, KB cells were seeded in 12-well plates overnight. Cells (~30% confluence) were then treated with 1 µM pRNA-3WJ-PTX micelles. The controls include Paclitaxel, pRNA-3WJ micelles, and pRNA-3WJ. According to manufacturer instructions, 48 hr after incubation with the RNA micelles, KB cells were trypsinized to single cell suspension. After two PBS washes, the cells were resuspended in 100 µL 1× Annexin V-FITC binding buffer. Then 5 µL AnnexinV-FITC and 5 µL propidium iodide (PI) were added into each sample and incubated at room temperature for 25 min. The samples were finally added to a flow tube which contained 200 µL 1× binding buffer for FACS analysis within 1 hr.

For Caspase-3 assay, KB cells were seeded on 24-well plates overnight. Cells (about 30% confluence) were then treated with 1 µM pRNA-3WJ-PTX micelles. The controls include Paclitaxel, pRNA-3WJ micelles, and pRNA-3WJ. The cellular Caspase-3 activity was measured and compared by Caspase-3 Assay Kit (BD Pharmingen) according to manufacturer instructions. Briefly, Cell lysates ($1\text{-}10\times10^6$ cells/mL) at different time points (4 hr, 8 hr, 12 hr, and 24 hr) after induction of apoptosis were prepared using cold Cell Lysis Buffer provided by the kit, and incubated for 30 min on ice. For each sample, 25 µL of cell lysate was added with 2 µL reconstituted Ac-DEVD-AMC in 80 µL of 1×HEPES buffer and incubated at 37° C. for 1 hr. The amount of AMC liberated from Ac-DEVD-AMC was measured at an excitation wavelength of 380 nm over an emission wavelength range of 400-500 nm on a Fluorolog spectrofluorometer (Horiba Jobin Yvon).

Animal Models

All protocols involving animals are performed under the supervision of the University of Kentucky Institutional Animal Care and Use Committee (IACUC). To generate xenograft model, female athymic nu/nu mice, 4-8 weeks old, were purchased from Taconic. Subcutaneous tumor xenografts were established by injecting $2\times10^6$ cells/site KB cells resuspended in sterile PBS into the left shoulder of nude mice. When the tumor nodules had reached a volume of 50 $mm^3$, approximately 5 days post-injection, the mice were used for tumor targeting studies.

NIR Fluorescence Imaging to Detect the Targeting of RNA Micelles to Cancer Xenografts In Vivo To investigate the delivery of pRNA-3WJ-PTX micelles in vivo, a fluorescence imaging study was performed after tail vein injection of 100 µL 20 µM Alexa 647 labeled pRNA-3WJ-PTX micelles and pRNA-3WJ-PTX (estimated final concentration in blood is about 1 µM) into mice bearing KB tumor, respectively. PBS injected mice were used as fluorescence negative controls. The whole body images were taken at 30 min, 1 hr, 2 hr, 4 hr, 8 hr, 24 hr. Mice were sacrificed at 24 hr post injection by inhalation of $CO_2$ followed by cervical dislocation, and major internal organs including heart, lungs, liver, spleen, kidneys together with tumor from the sacrificed mice were collected and subjected to fluorescence imaging for assessment of biodistribution profiles using IVIS Spectrum station (Caliper Life Sciences) with excitation at 640 nm and emission at 680 nm.

Evaluation of Pro-Inflammatory Induction of pRNA-3WJ Micelles

For in vitro evaluation of pro-inflammatory cytokine induction, $2.5 \times 10^5$ RAW 264.7 cells per well were seeded in 24-well plates and cultured overnight. pRNA-3WJ micelles (1 μM or 200 nM) as well as Lipopolysaccharide (LPS, 3.6 μg/mL, equal amount as 200 nM pRNA-3WJ micelles) were diluted in DMEM (Life Technologies Corporation) and added to cells for incubation in triplet. After 16 hr incubation, cell culture supernatants were collected and stored at −80° C. immediately for further assay. TNF-α and IL6 in collected supernatants were examined using Mouse ELISA MAX Deluxe sets (BioLegend, San Diego, Calif., USA) while IFN-α was examined using Mouse IFN Alpha ELISA Kit (PBL Assay Science, Piscataway, N.J., USA), following the manufacturer instructions, respectively.

For in vivo evaluation of pro-inflammatory cytokine and chemokine induction, pRNA-3WJ micelles (1 μM), LPS (10 μg per mouse), and DPBS control were injected into 4 to 6 weeks male C57BL/6 mice via tail vein. 3 hr after injection, blood samples were harvested from mice by cardiac puncture and centrifuged at 12,800×g for 10 min to collect serum. Concentrations of TNF-α, IL6 and IFN-α in serum were examined by ELISA as described above following manufacturer instructions. Chemokine induction was assayed using Mouse Chemokine Array Kit (R&D Systems, Minneapolis, Minn., USA) following manufacturer instructions. LiCor was used for blotting spot quantification.

Statistical Analysis

Each experiment was repeated 3 times in duplicates for each sample tested. The results are presented as mean±SD unless otherwise indicated. Statistical differences were evaluated using Student's t-test, and $p<0.05$ was considered significant.

Results and Discussion

Construction and Characterization of pRNA-3WJ Micelles

Figure 1C:
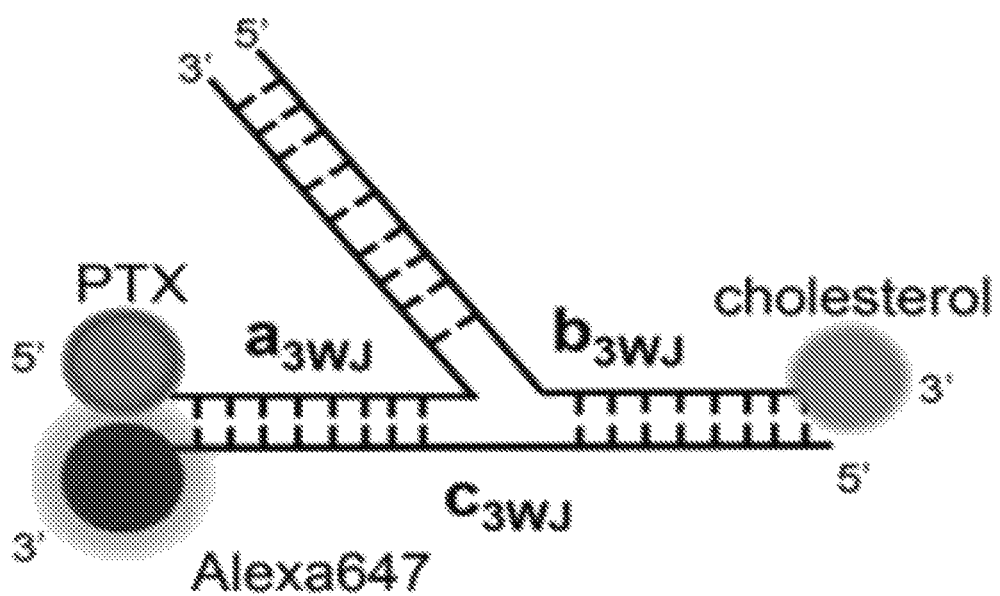
Figure 1D:
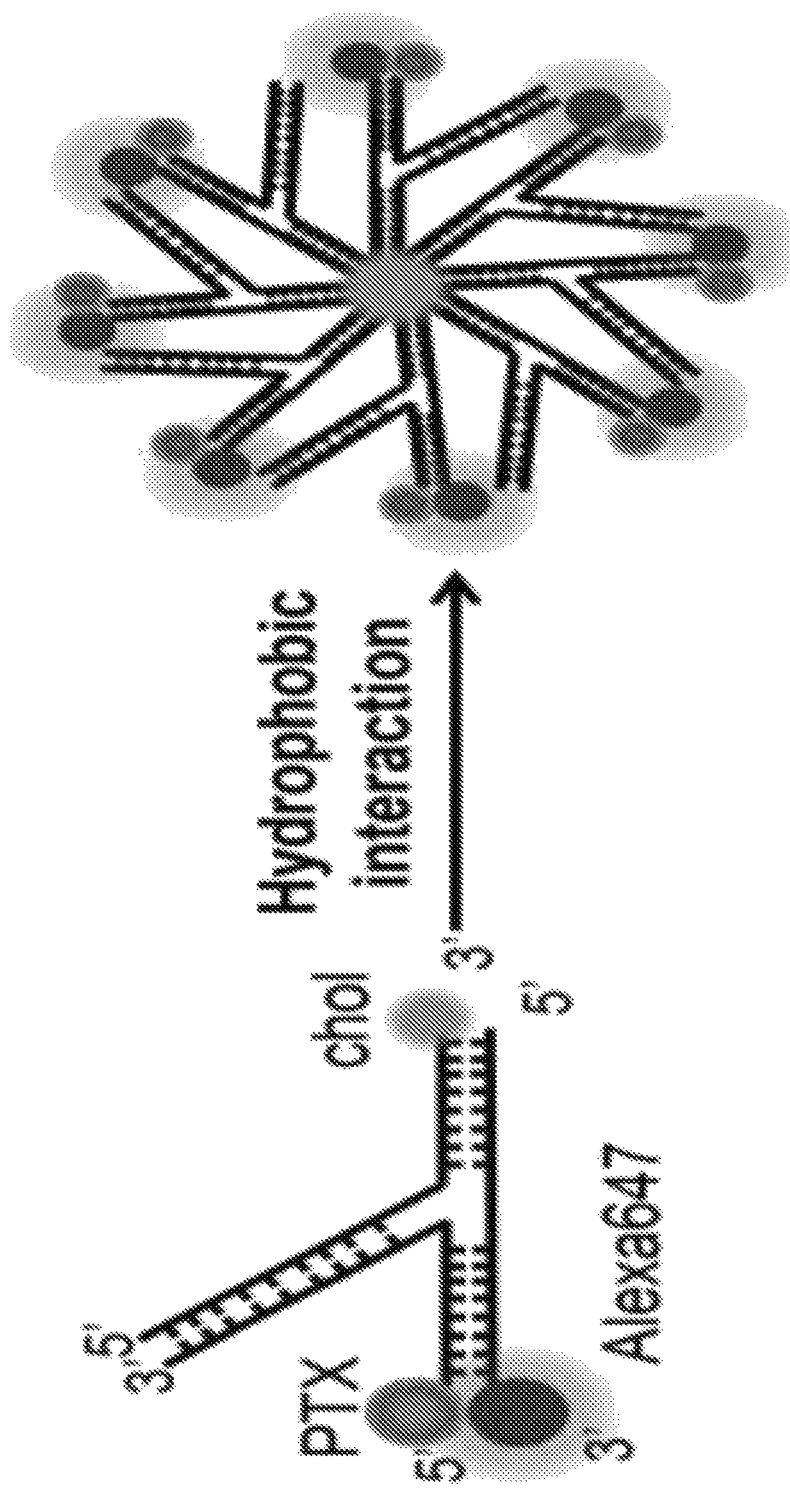

The pRNA-3WJ-PTX micelles utilize a modular design composed of three short RNA fragments from pRNA 3WJ motif [Shu, D. et al. Nature Nanotechnology 6 (2011) 658-667] (FIG. 1A). The lipophilic module, cholesterol, was conjugated to the 3′-end of b3WJ by considering the global folding structure of the pRNA 3WJ motif. The crystal structure of the pRNA 3WJ motif reveals that the angles across the three helices (H1, H2, and H3) of the pRNA 3WJ are about 60° (H1-H2), about 120° (H2-H3), and about 180° (H1-H3) [Zhang, H. et al. RNA 19 (2013) 1226-1237] (FIG. 1B). In order to avoid interference of micelle formation by steric hindrance due to the branched 3WJ structure, the cholesterol molecule was placed onto H3 where it is furthest from the other two helices, H1 and H2. Our current design involved functionalization of H1 with a therapeutic module (Paclitaxel) and an imaging module (Alexa 647 dye) without interfering in micelle formation (FIG. 1C, FIG. 1D). The function of conjugated chemotherapeutic drug and detection dye was also well retained as shown in the following study. The unoccupied helix H2 can be further activated with RNAi modules, such as siRNA or microRNA, for combined treatment to generate enhanced or synergetic therapeutic effects.

Figure 1E:
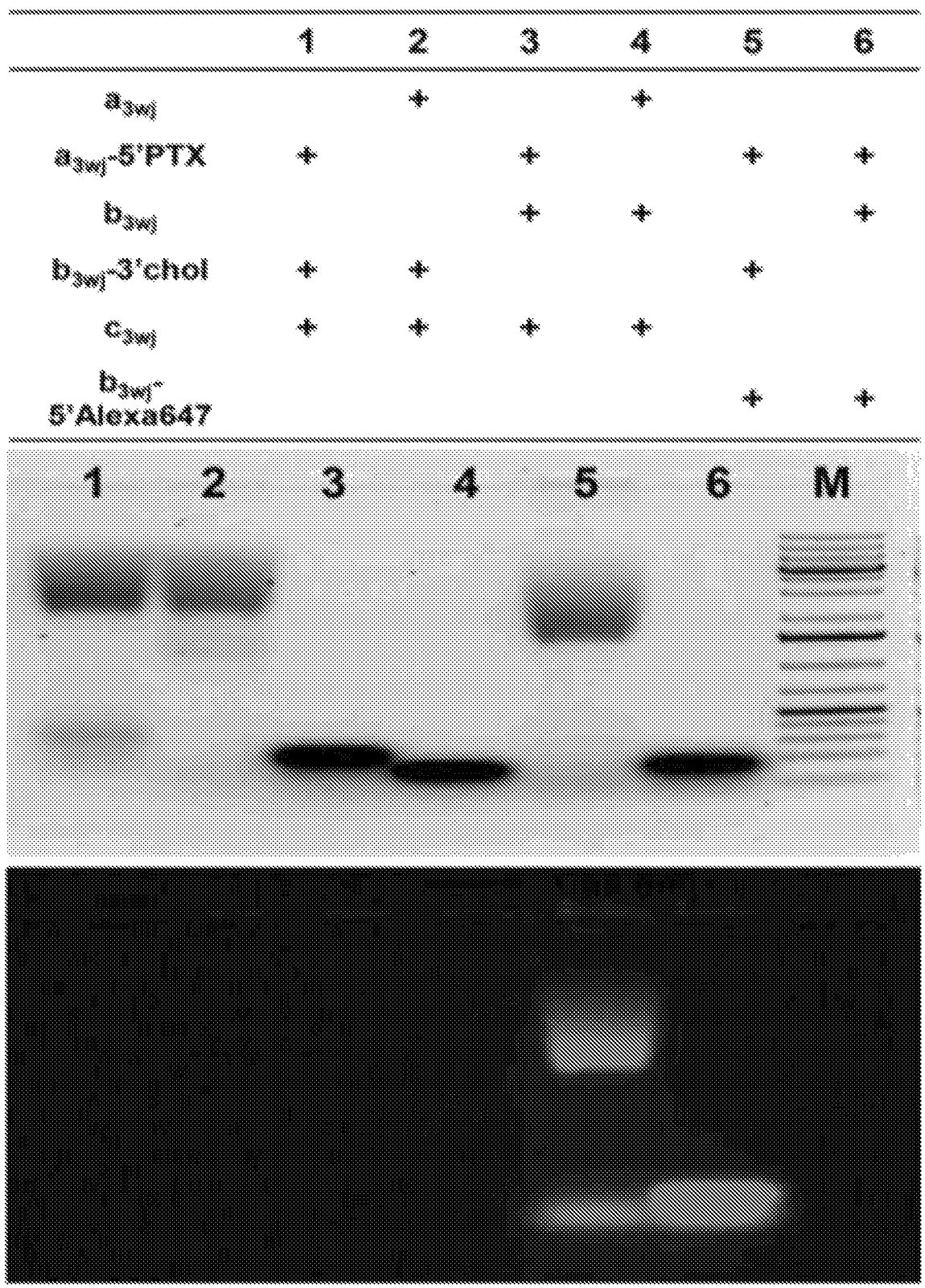
Figure 2A:
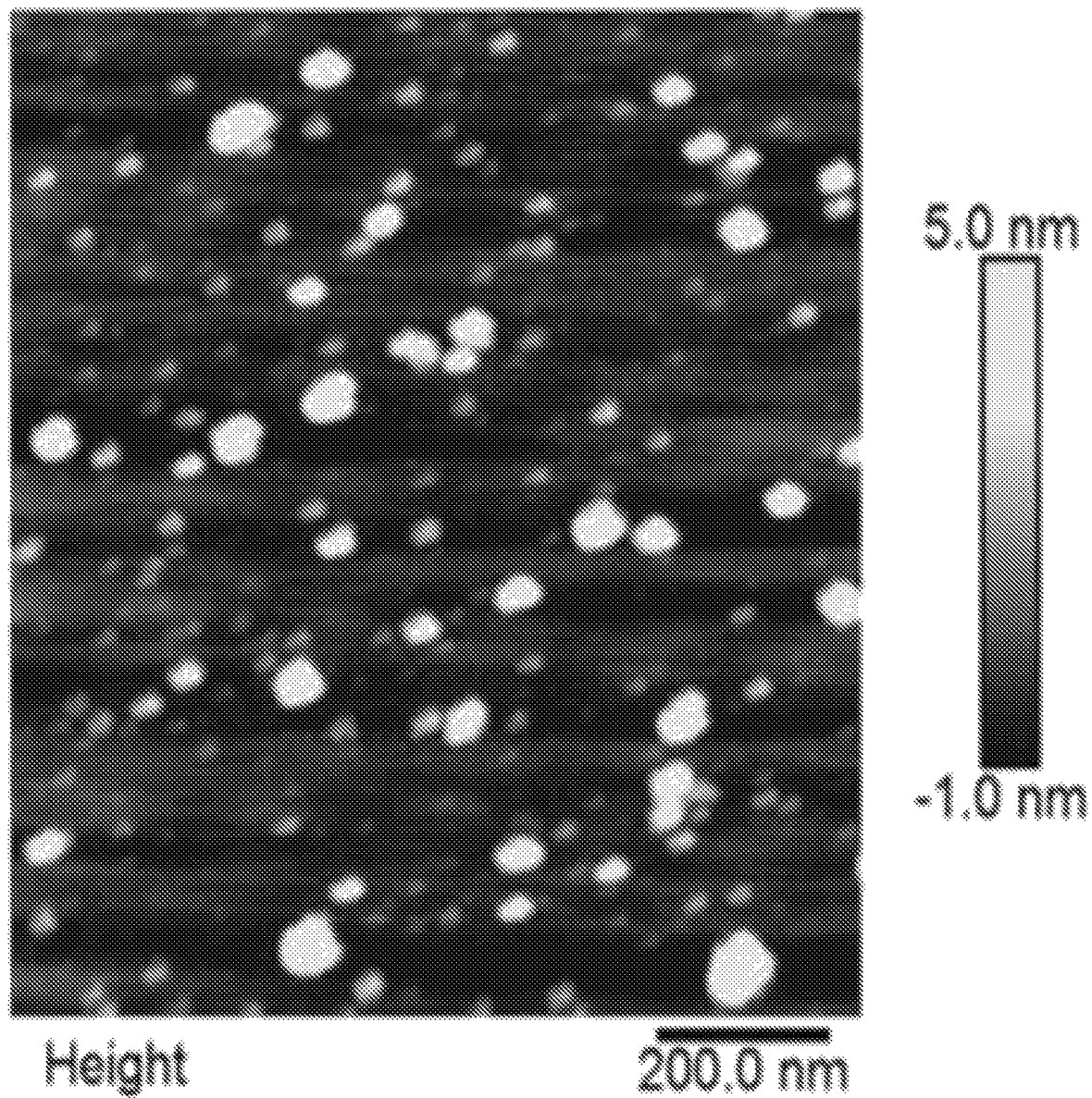
FIGS. 2A to 2D show characterization of pRNA-3WJ micelles.
Figure 2B:
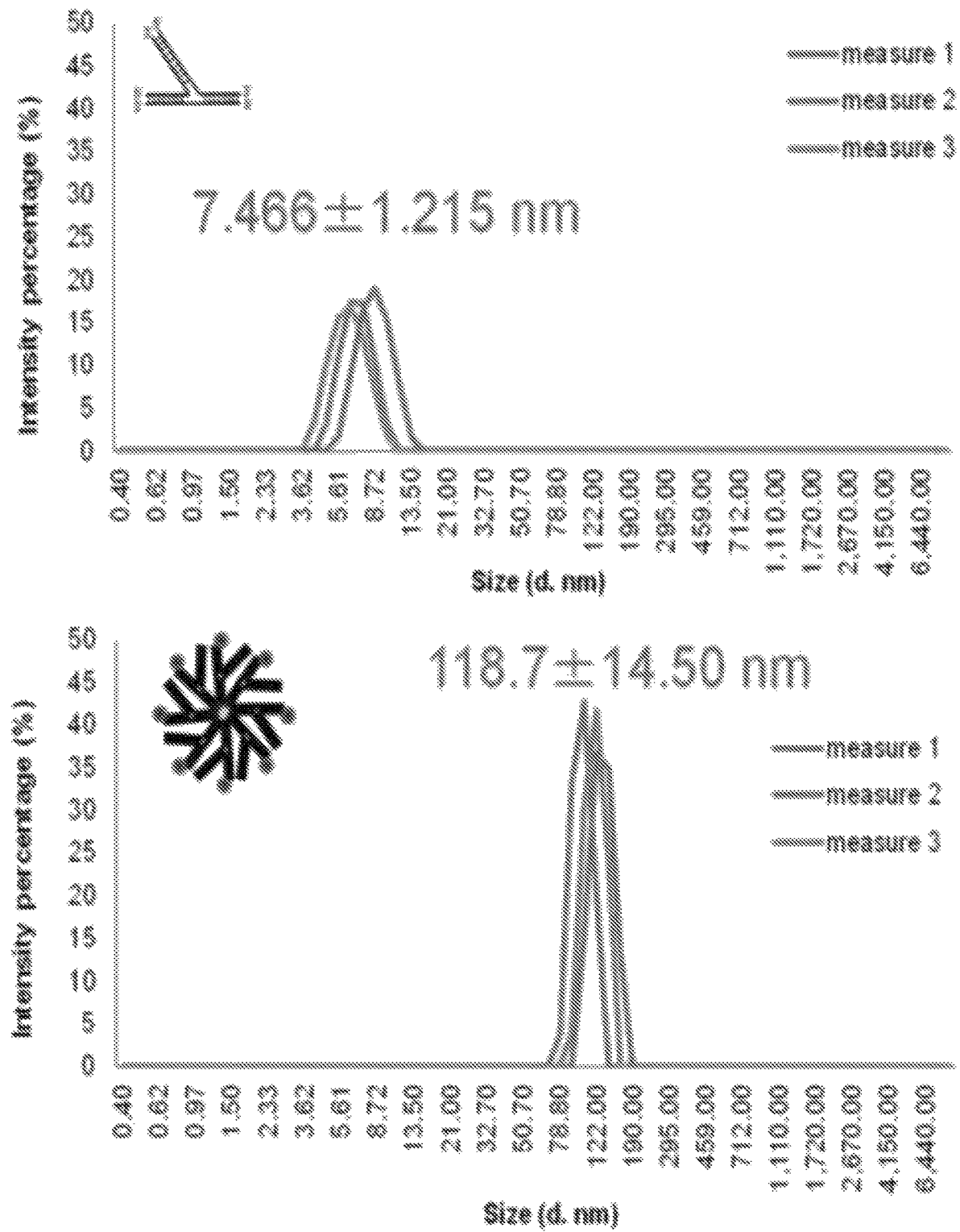
Figure 2C:
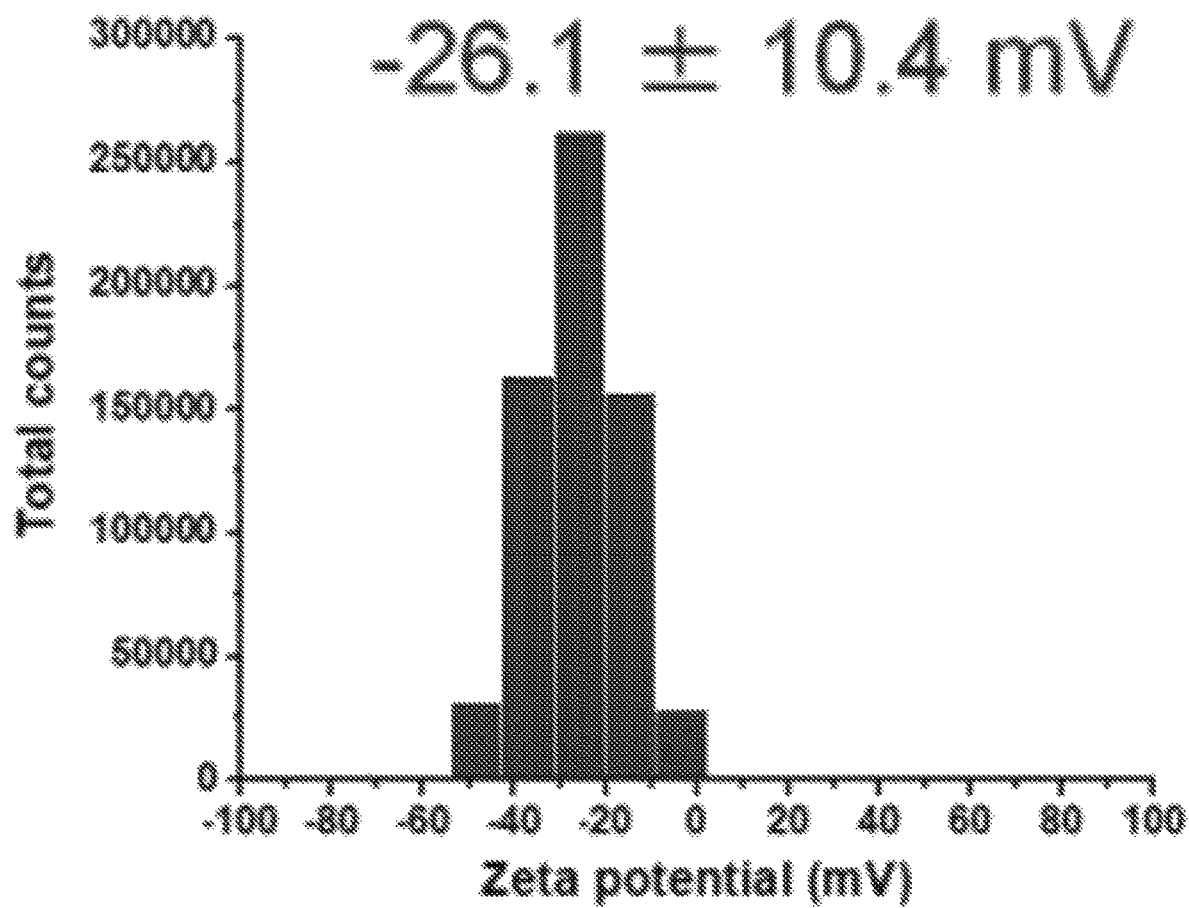
Figure 2D:
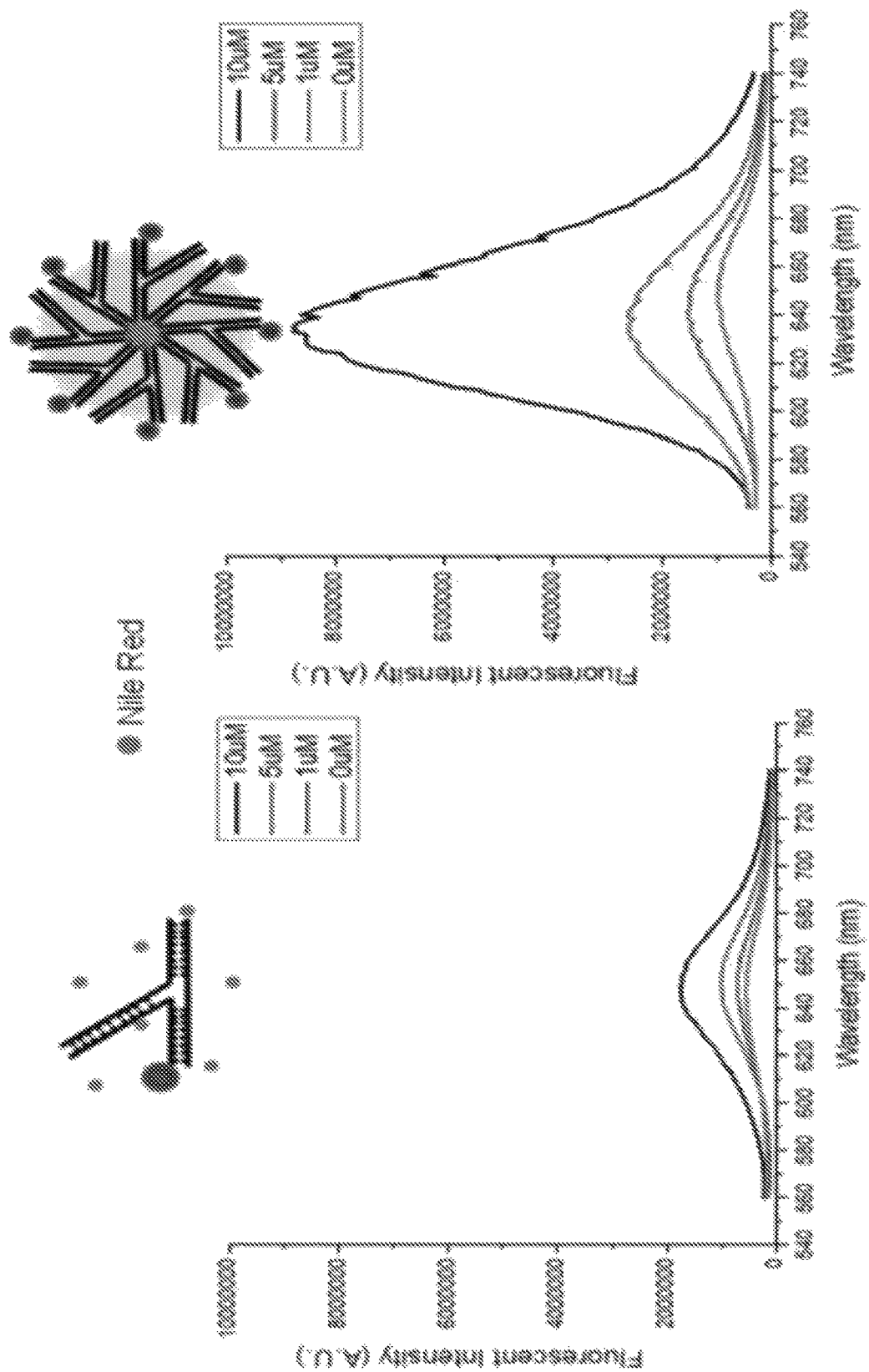

Upon mixing the individual strands in equimolar ratio in PBS or TMS buffer, the complex assembled with high efficiency, as shown in the 1% Agarose gel shift assay (FIG. 1E). Alexa 647 labeled RNA micelles also showed fluorescent bands corresponding to the band indicating successful micelle formation (FIG. 1E). The assembly of the RNA micelles was further demonstrated by AFM which shows homogeneous sphere-shaped architectures (FIG. 2A). DLS assays showed that the average hydrodynamic diameter of pRNA-3WJ-PTX micelles was 118.7±14.50 nm compared to 7.466±1.215 nm for the pRNA-3WJ core scaffold (FIG. 2B). The constructed pRNA-3WJ-PTX micelles are also negatively charged. The Zeta potential is −26.1±10.4 mV as shown in FIG. 2C. Finally, the RNA micelle formation was assayed by a Nile Red encapsulation assay. Nile Red is a hydrophobic dye and nearly non-emissive in bulk aqueous solution, but its inclusion in a nonpolar microenvironment such as the lipid core of the micellar structure results in an intense fluorescence enhancement [Greenspan, P. et al. J Cell Biol 100 (1985) 965-973]. Therefore, an increase in fluorescence intensity associated with the incubation of RNA micelles at varying concentrations with fixed amounts of Nile Red dye indicates formation of RNA micelles in the buffer solution (FIG. 2D). In contrast, no significant increase of fluorescent intensity was observed in the control pRNA-3WJ without a lipid core (FIG. 2D).

To make pRNA-3WJ micelles chemically stable in vivo, 2′-F modified U and C nucleotides were used [Behlke, M. A. Oligonucleotides. 18 (2008) 305-319; Vestweber, H. et al. Synthetic Metals 68 (1995) 263-268] during RNA strand synthesis. The 2′-F modified RNA nanoparticles were proved to be chemically stable and exhibit longer half-life in circulation compared to its unmodified RNA counterparts [Shu, D. et al. Nature Nanotechnology 6 (2011) 658-667; Behlke, M. A. Oligonucleotides. 18 (2008) 305-319]. The presence of 2′-F nucleotides not only makes the RNA nanoparticles resistant to RNase degradation, but also enhances the melting temperature of pRNA-3WJ [Binzel, D. W. et al. Biochemistry 53 (2014) 2221-2231], without compromising the authentic folding and functionalities of the core and incorporated modules [Shu, D. et al. Nature Nanotechnology 6 (2011) 658-667; Liu, J. et al. ACS Nano 5 (2011) 237-246].

Figure 8:
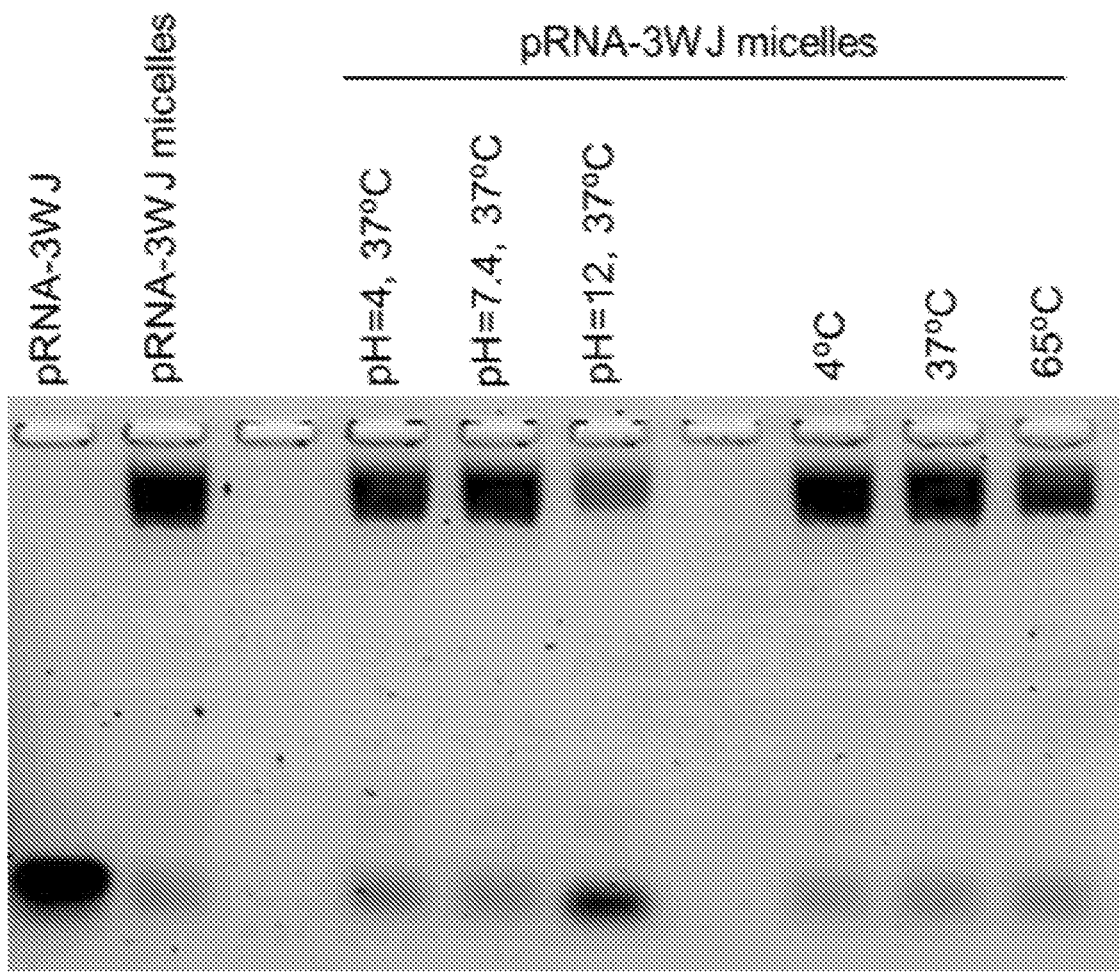
FIG. 8 shows pRNA-3WJ micelle formulation stability versus different pH and temperatures.

The pRNA-3WJ formulation stability was further assayed versus pH (acidic pH 4, neutral pH 7.4, and basic pH 12) and temperature (4° C., 37° C., and 65° C.). The results indicated that pRNA-3WJ micelles are stable across a wide range of temperatures and in acidic and neutral conditions. Although pRNA-micelles showed dissociation at basic condition as reported in FIG. 8, pRNA-3WJ micelle formulation is clearly chemically and thermodynamically stable in physiological condition (pH 7.4, 37° C.).

Synthesis of Paclitaxel Conjugated RNA Strand Via "Click Chemistry"

Figure 9A:
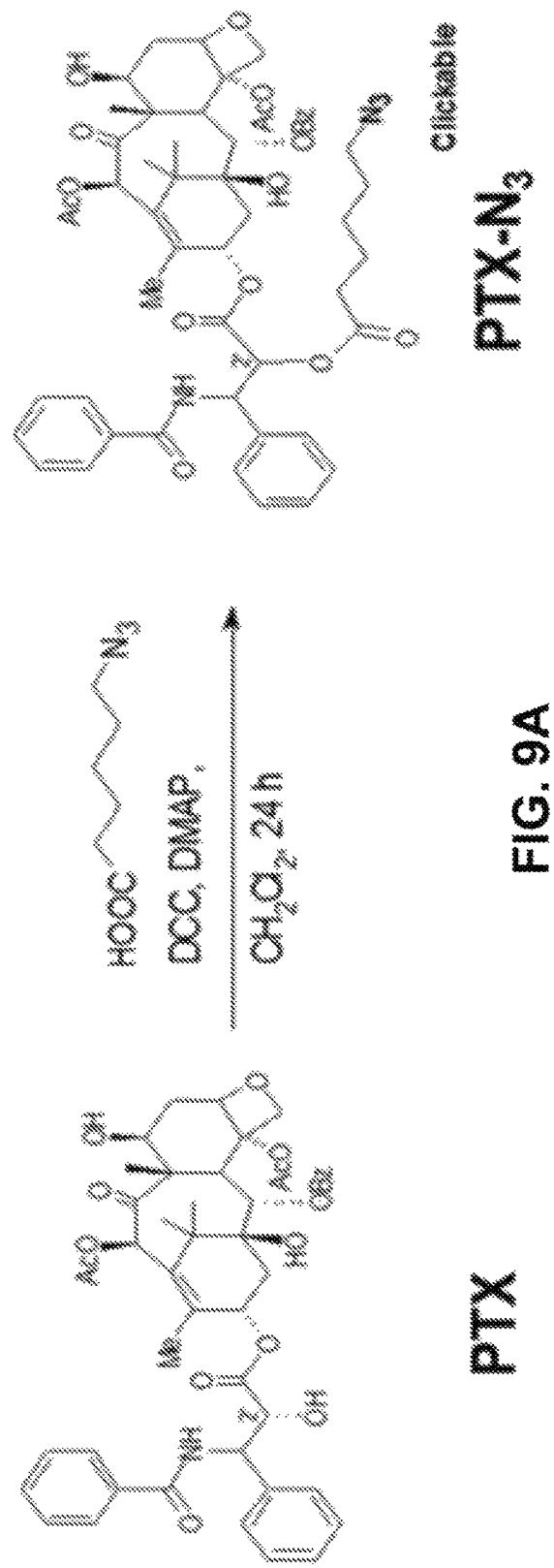
FIGS. 9A to 9C shows synthesis of PTX-N3 (FIG. 9A), 1H NMR (400 MHz) spectrum of PTX (FIG. 9B), and PTX-N3 (FIG. 9C).

In order to load pRNA micelles with therapeutic module, PTX was firstly functionalized with -Azide ($-N_3$) in order to further react with alkyne modified RNA. Azide group on 2′-OH was introduced to PTX using 6-azidohexanoic acid linker via esterification, in the presence of N,N′-dicyclohexylcarbodiimide (DCC) and 4-(dimethylamino)pyridine (DMAP) in dry dichloromethane to afford azide-functionalized PTX (PTX-N3) as the predominant product (FIG. 9A). Although both hydroxyl groups at the 7′ and 2′ positions of PTX are chemically reactive, the 2′-OH typically showed higher reactivity than the 7′-OH, because acetylation of 7′-OH is very unstable in aqueous media, losing the C-7 substituent rapidly [Skwarczynski, M. et al. J Med. Chem 49

Figure 9B:
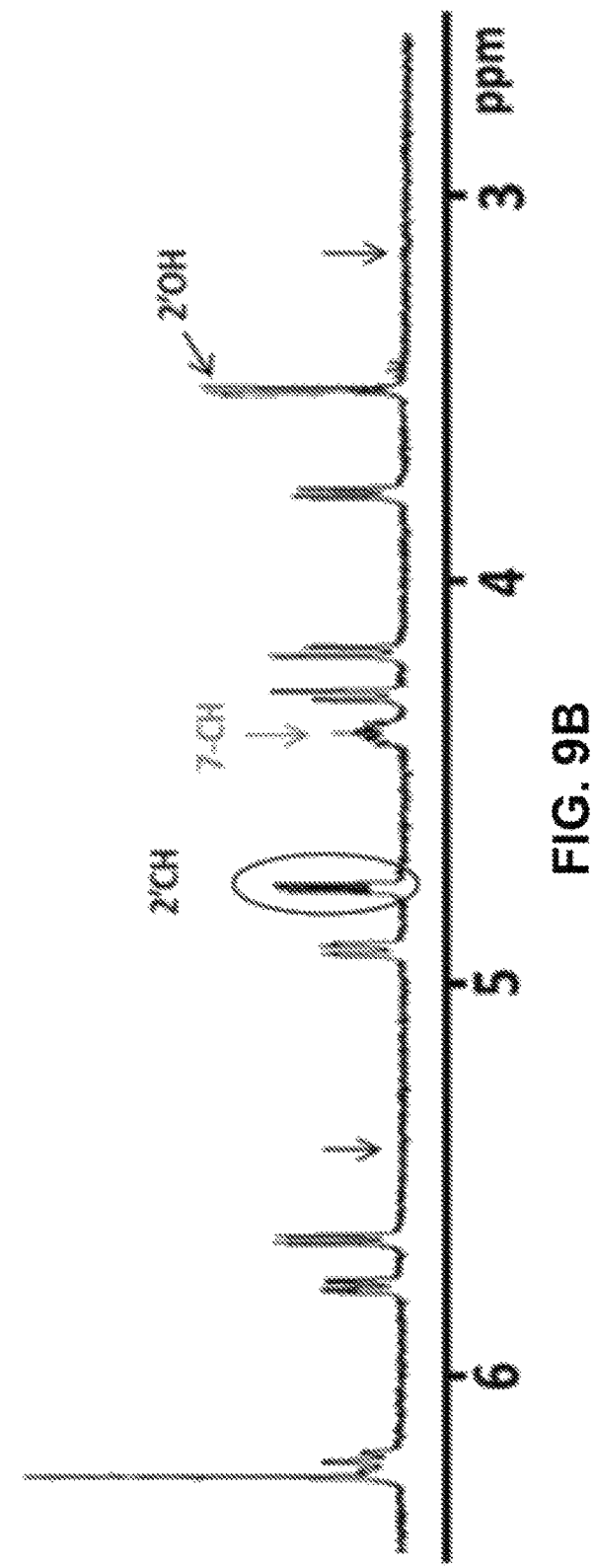
Figure 9C:
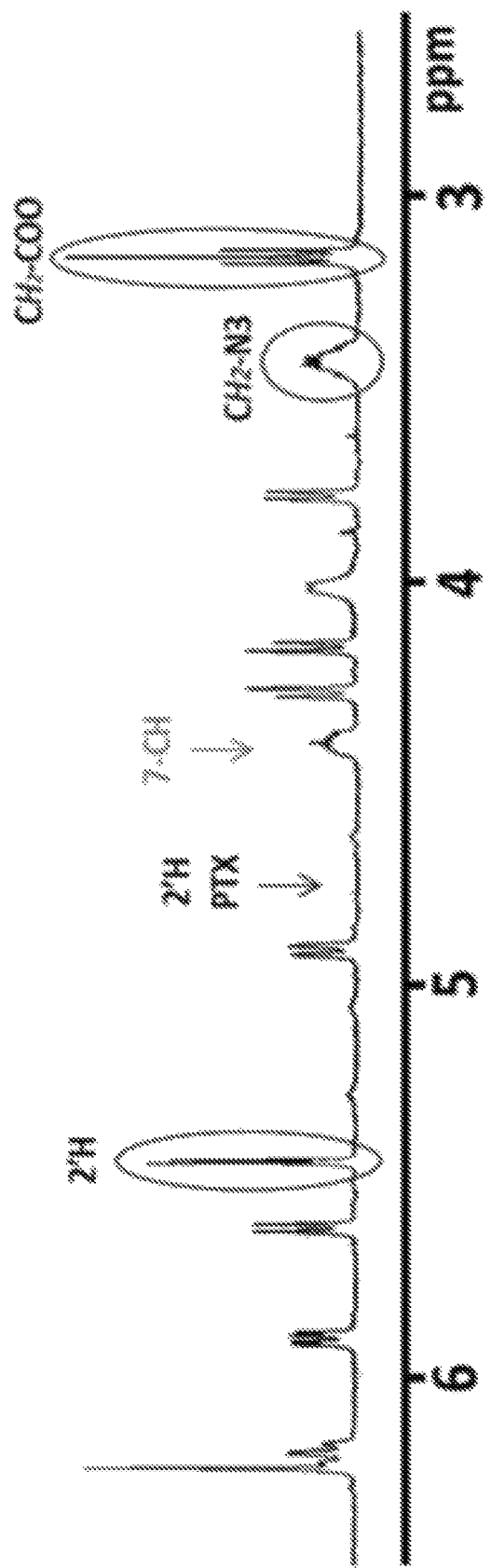

(2006) 7253-7269]. PTX-N3 with functionality at the 2' position was obtained in 73% yield after purification. The $^1$H NMR spectroscopy is employed to confirm the chemical structure of the PTX-N3 in CDCl$_3$. In the $^1$H NMR spectrum of PTX-N3, the 7'-CH resonates at 4.4 ppm and no significant chemical shift change was observed for the 7-CH—OH signal (at 4.40 ppm) before and after esterification (FIG. 9B) while the resonance of 2'-CH proton shifted from 4.78 ppm (before esterification) to 5.46 ppm (after esterification) (FIG. 9C).

Figure 3A:
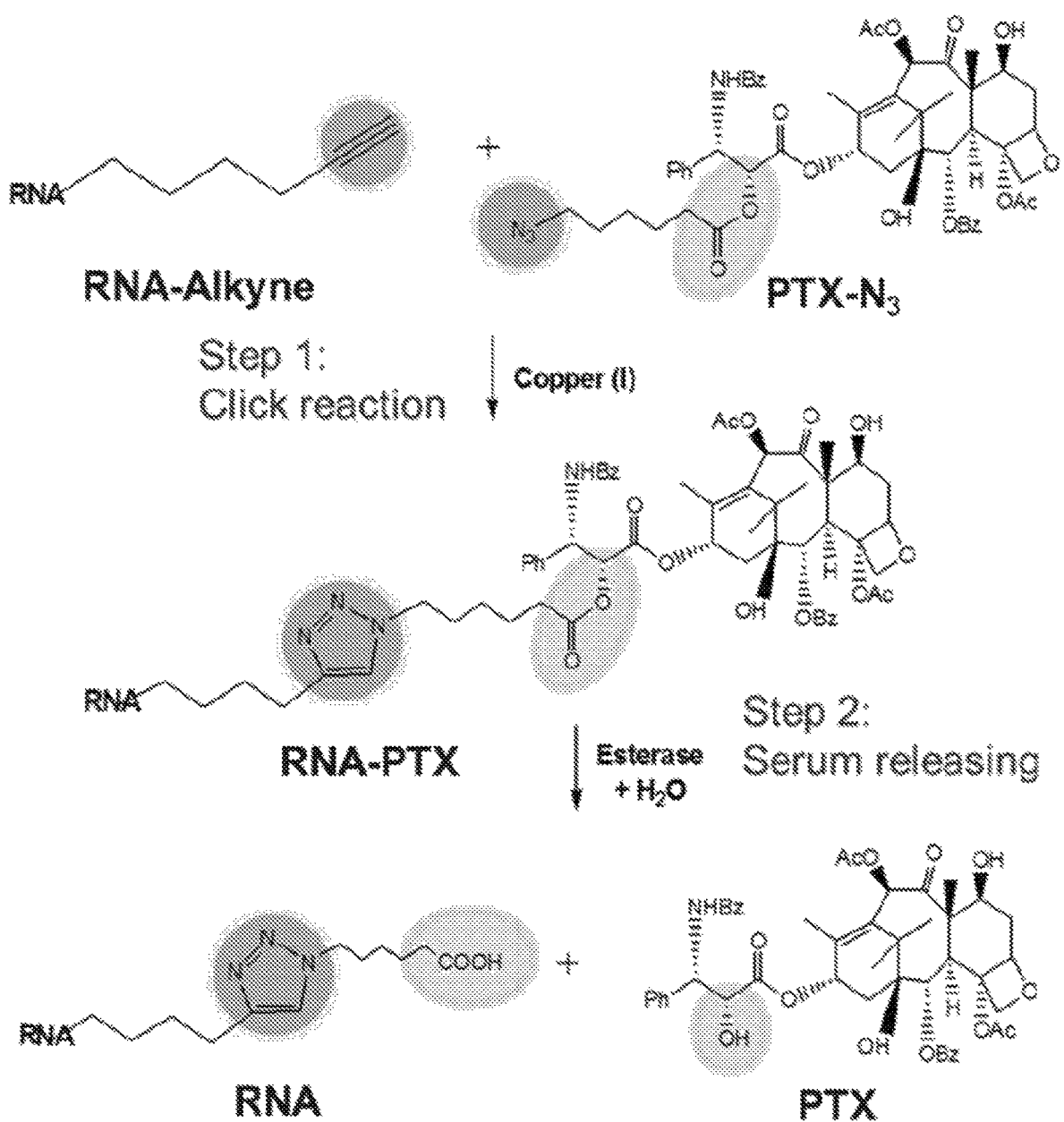
FIGS. 3A to 3D show RNA-PTX conjugates.
Figure 3B:
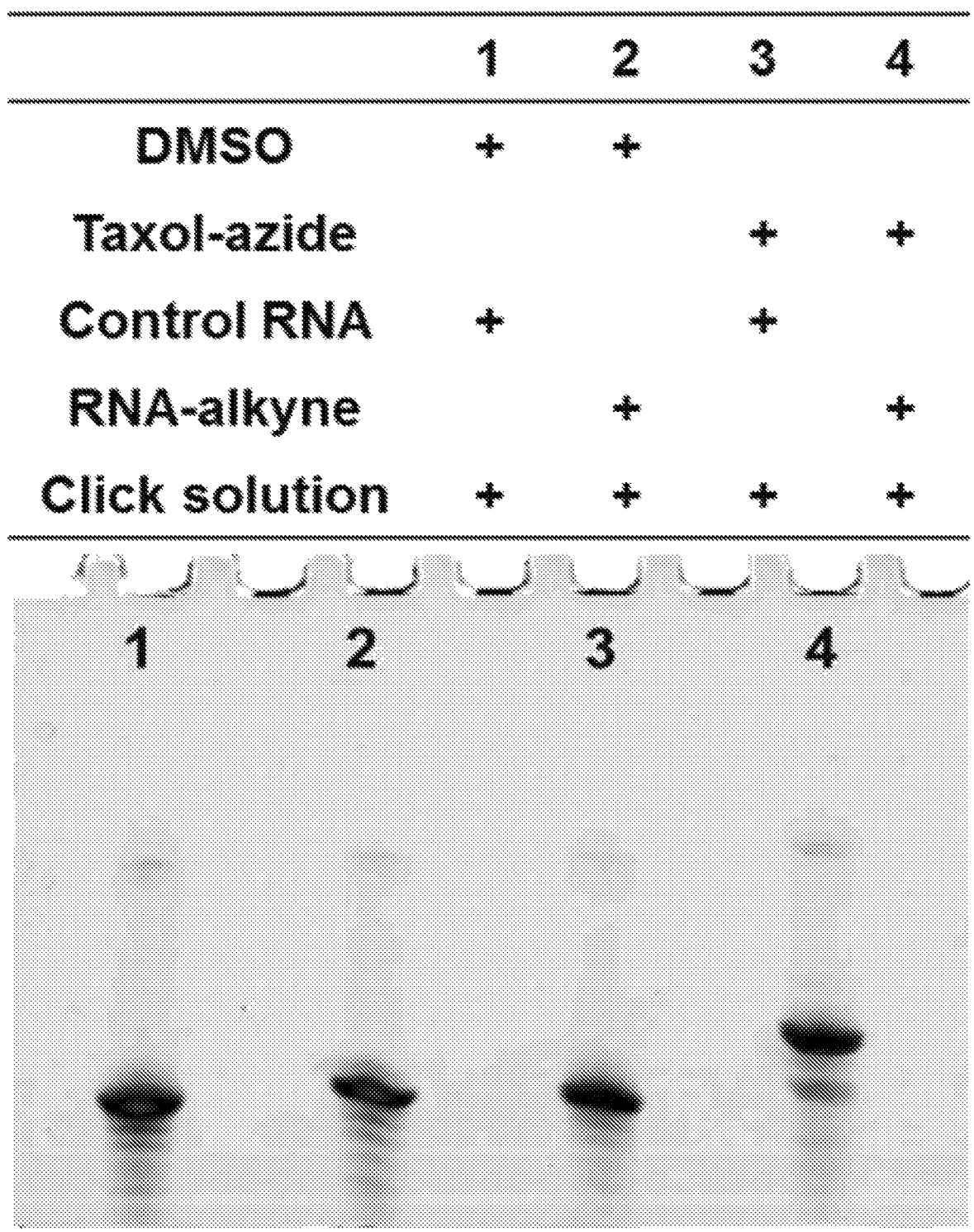
Figures 3C, 3D:
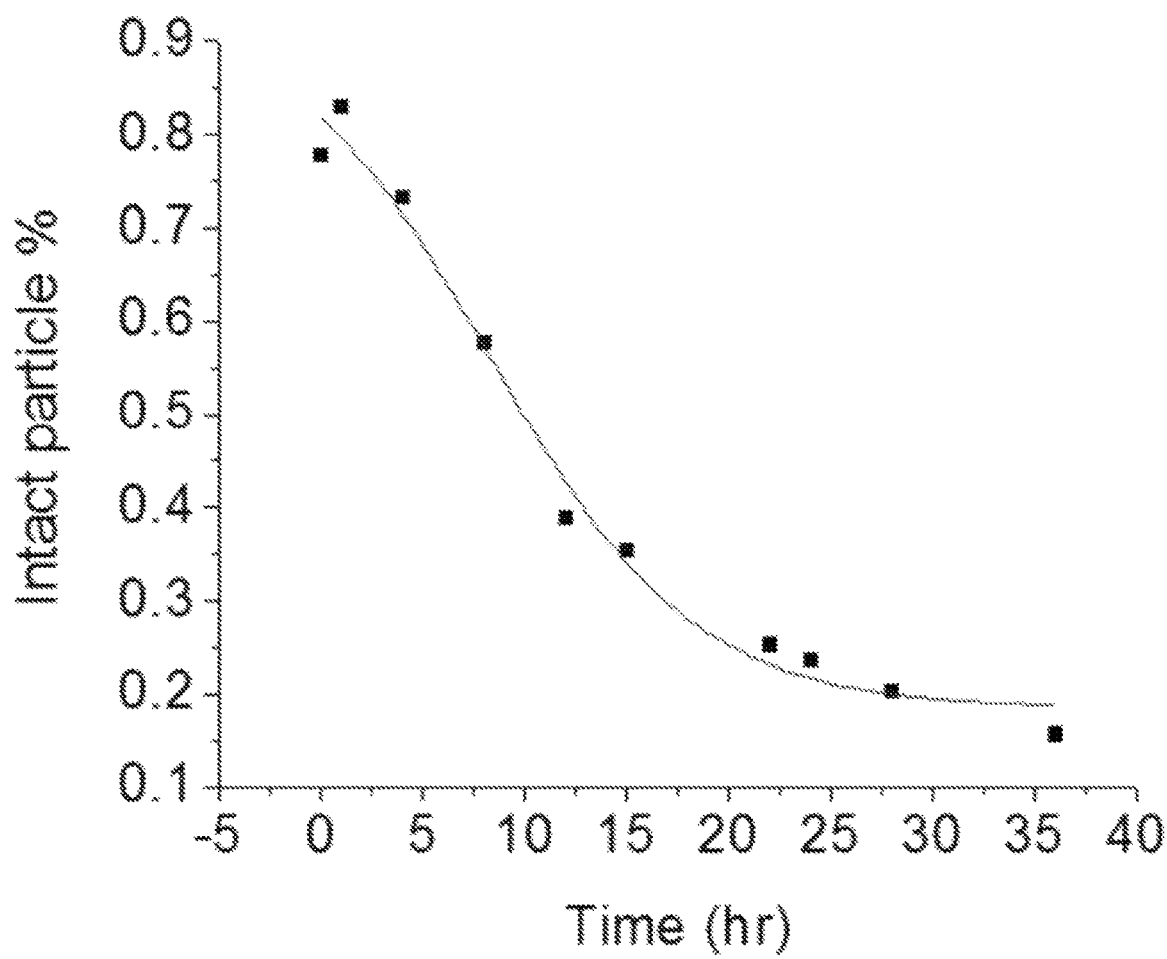
Figure 10A:
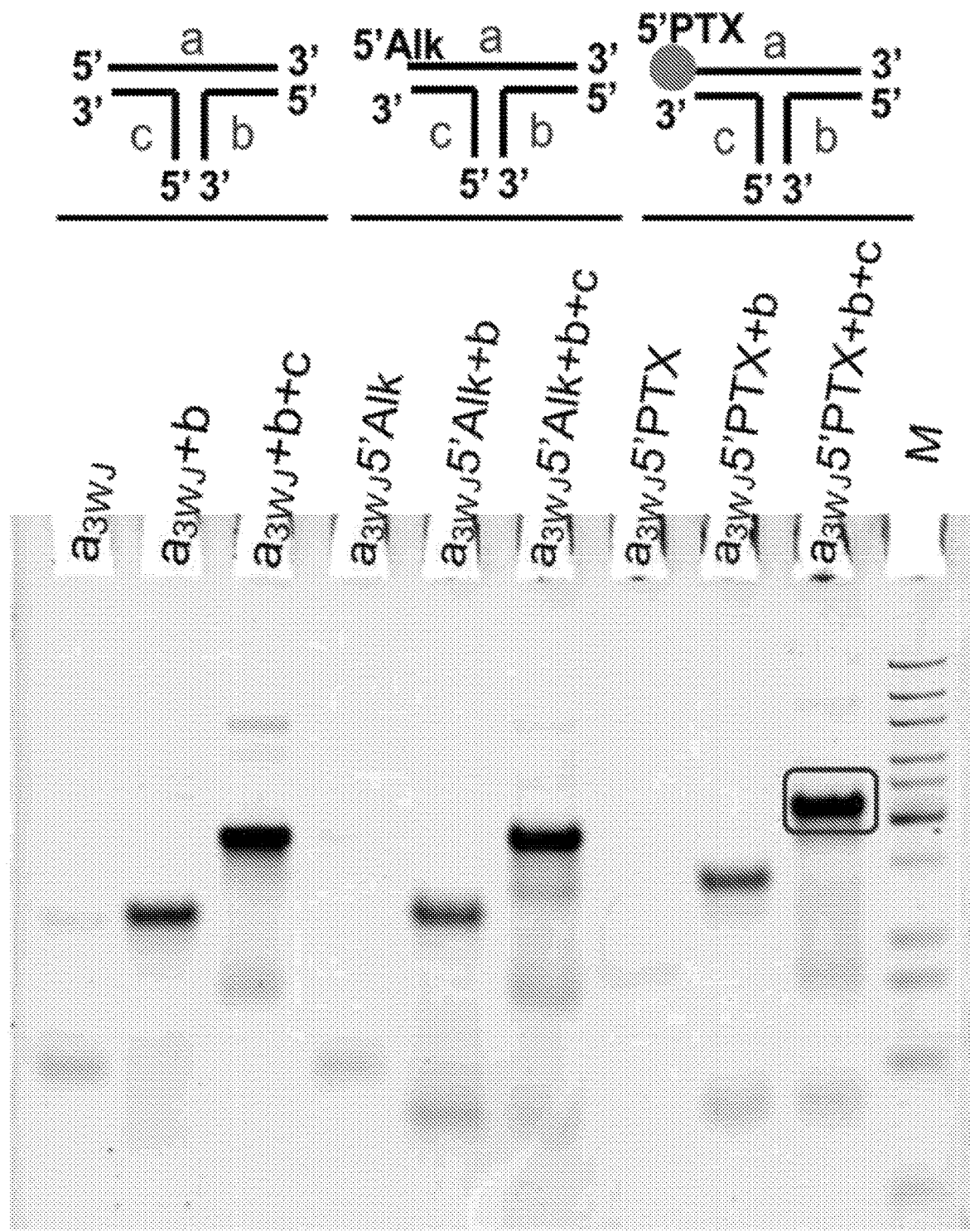
FIGS. 10A and 10B show RNA-PTX conjugates.
Figure 10B:
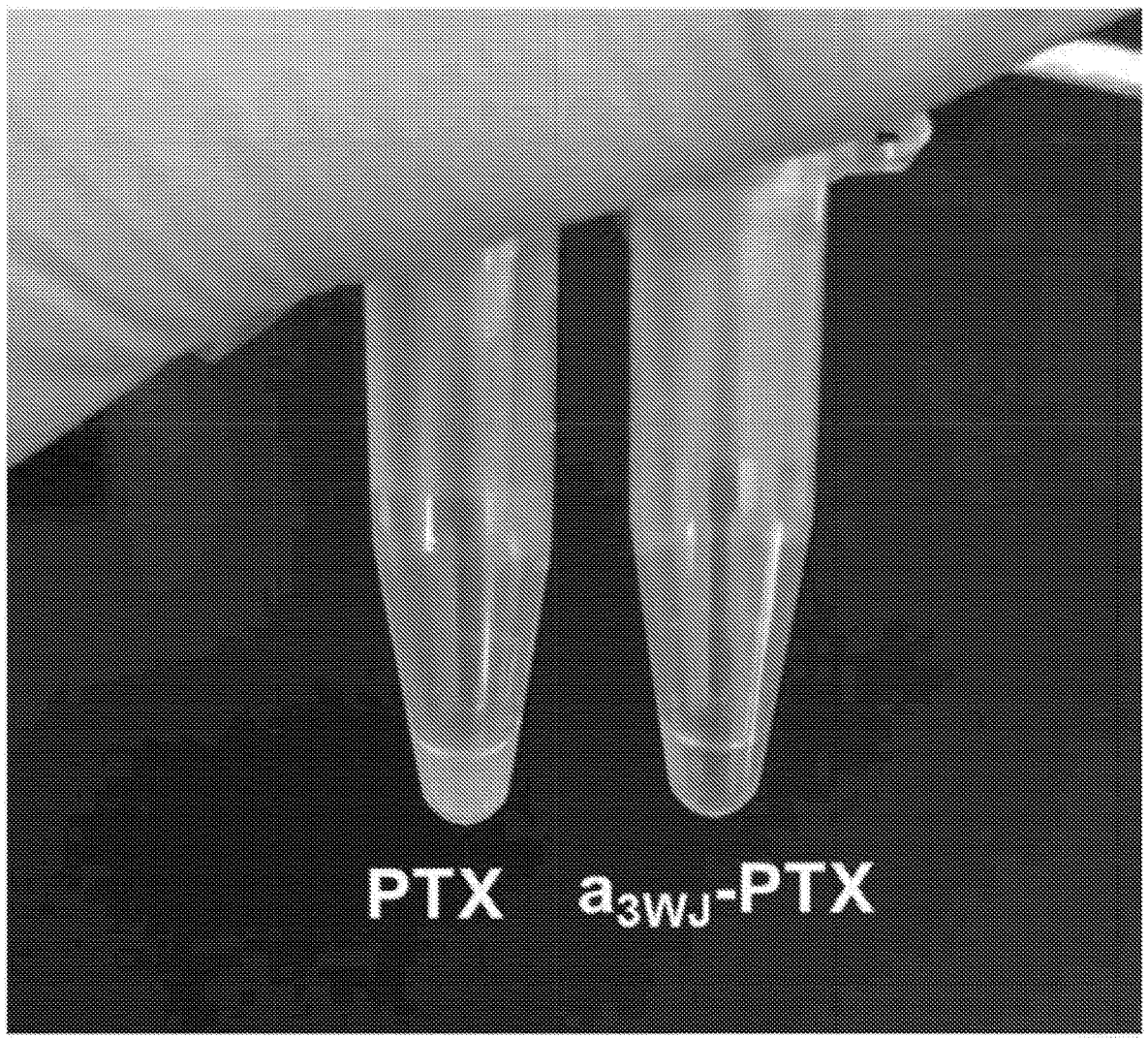

PTX-N3 reacted with -Alkyne modified RNA (a3WJ) at above 90% efficiency via Copper I mediated Click reaction as shown in FIG. 3A. The successful conjugation was confirmed by 20% 8 M Urea PAGE (FIG. 3B) and Mass Spectrometry. The experimental mass of a3WJ-PTX determined by Mass Spectrometry is 6939.2 (m/z) which is close to the theoretical mass (6936.82 (m/z)) calculated based on the chemical structure (FIG. 3C). The ester bond formed between Paclitaxel and RNA can then be hydrolyzed in presence of either esterase or in aqueous solution, which allows slow release of the loaded drug in a controllable manner as indicated by in vitro drug release assay (FIGS. 3A, 3D). This is the first report to "click" an RNA molecule with the chemotherapeutic drug, Paclitaxel. PTX conjugation did not interfere with the stepwise assembly of pRNA-3WJ (FIG. 10A). It is also the first demonstration of improving the water insolubility of Paclitaxel by fusion to an RNA oligo. 1 mM RNA-Paclitaxel conjugates dissolved in DEPC H$_2$O showed clear solution compared to cloudy solution prepared using equal concentration of Paclitaxel in DEPC H$_2$O (FIG. 10B). The significantly improved water solubility of Paclitaxel after conjugation to RNA and assembly into micellar nanostructures allows the use of normal saline solution for in vivo administration instead of Cremophor EL formulation. In addition to Click chemistry, functionalizing RNA oligos and candidate drugs with other chemical coupling reactive groups, such as —NH$_2$/—NHS —NH$_2$/-COOH, or —SH/-maleimide, are also feasible RNA-drug conjugation approaches which can be applied for drug candidates that are not suitable for Click chemistry.

Determination of the Critical Micelle Formation Concentration

Figure 11A:
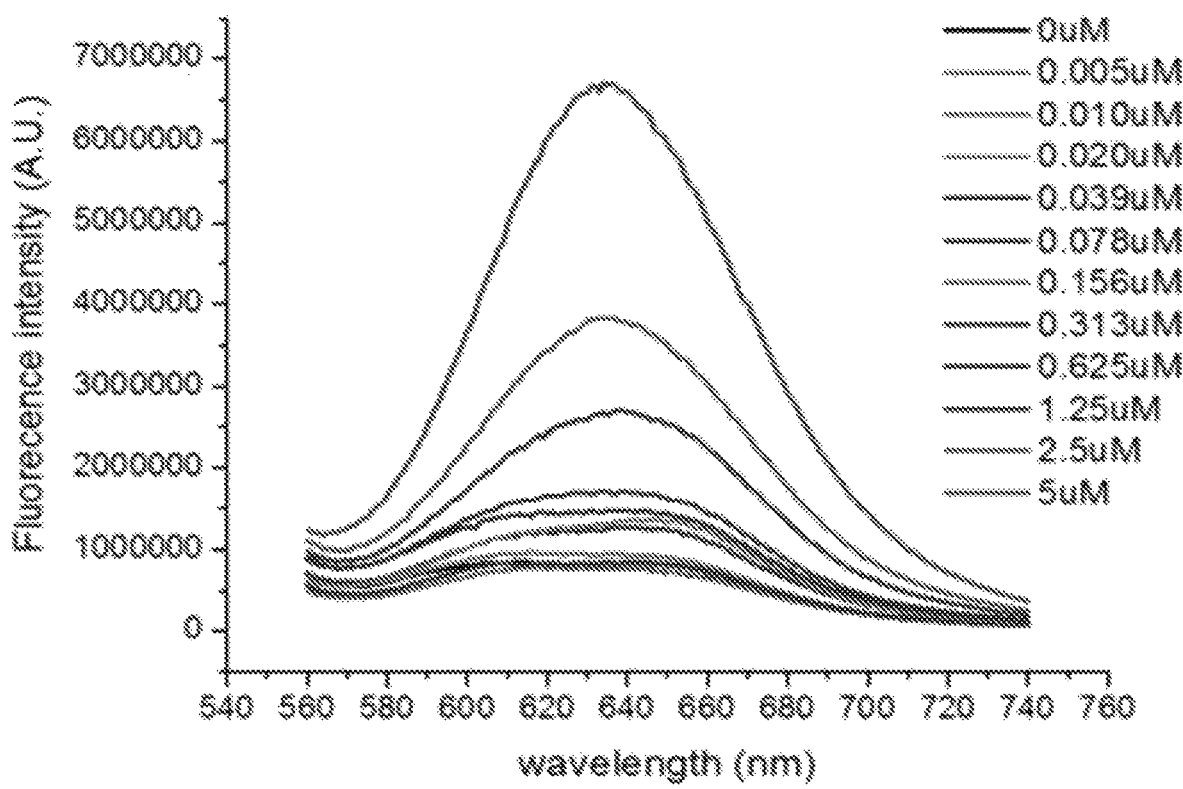
FIGS. 11A-11C show graphs and a gel image that can demonstrate micelle formation.
Figure 11B:
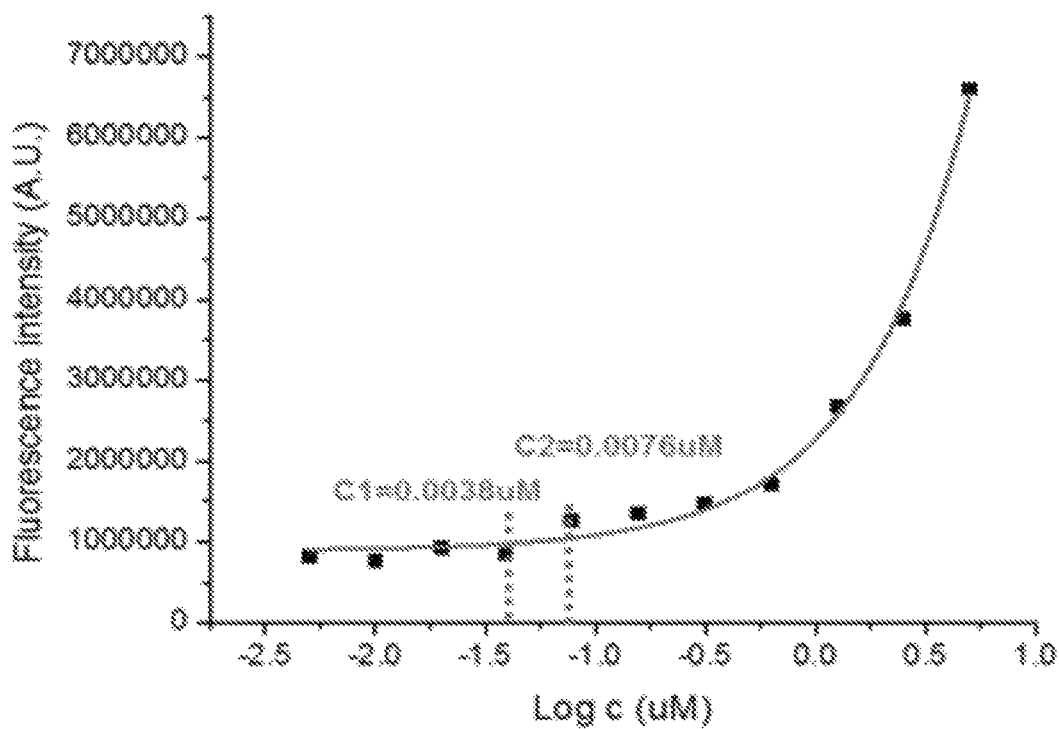
Figure 11C:
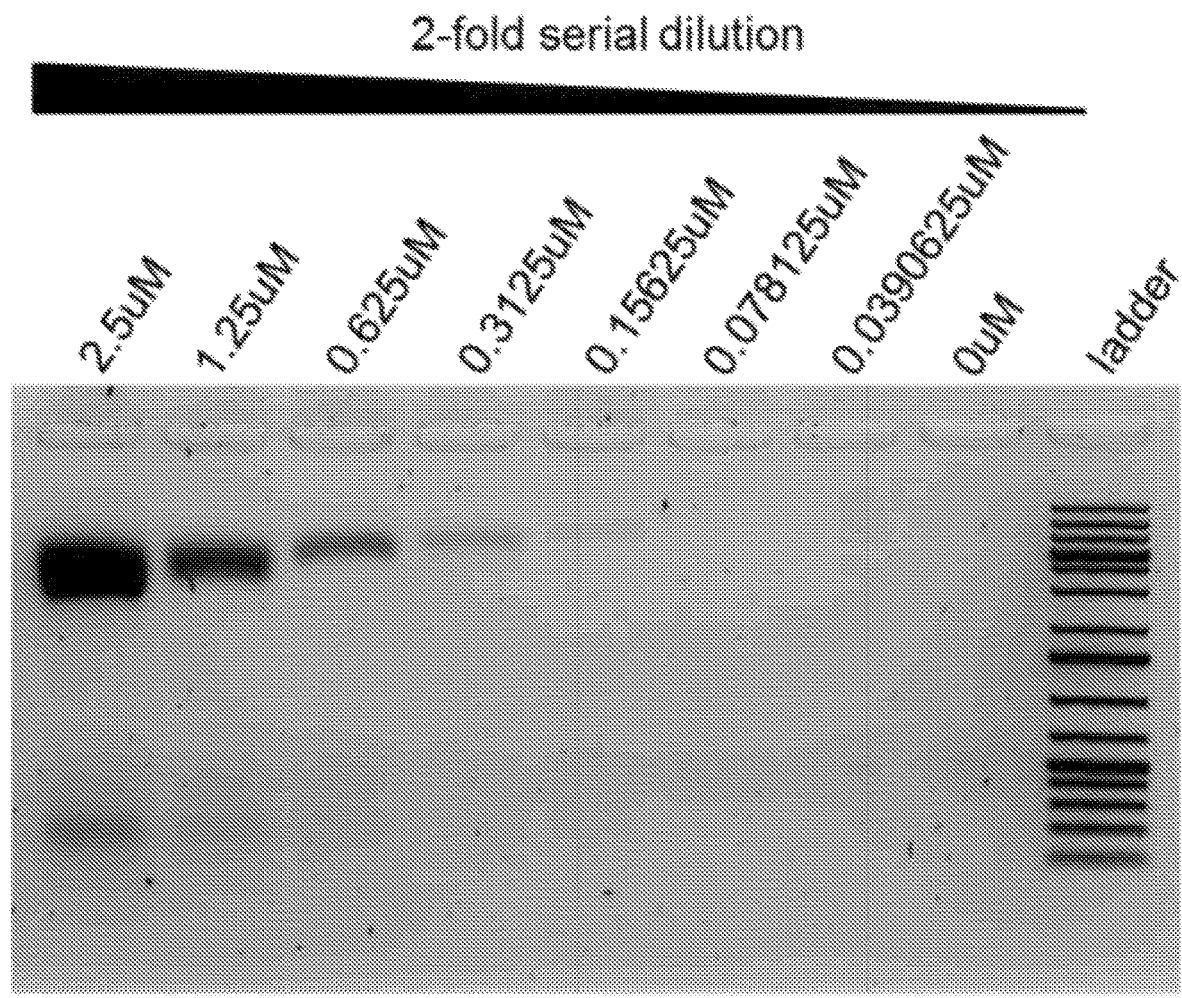
Figure 12A:
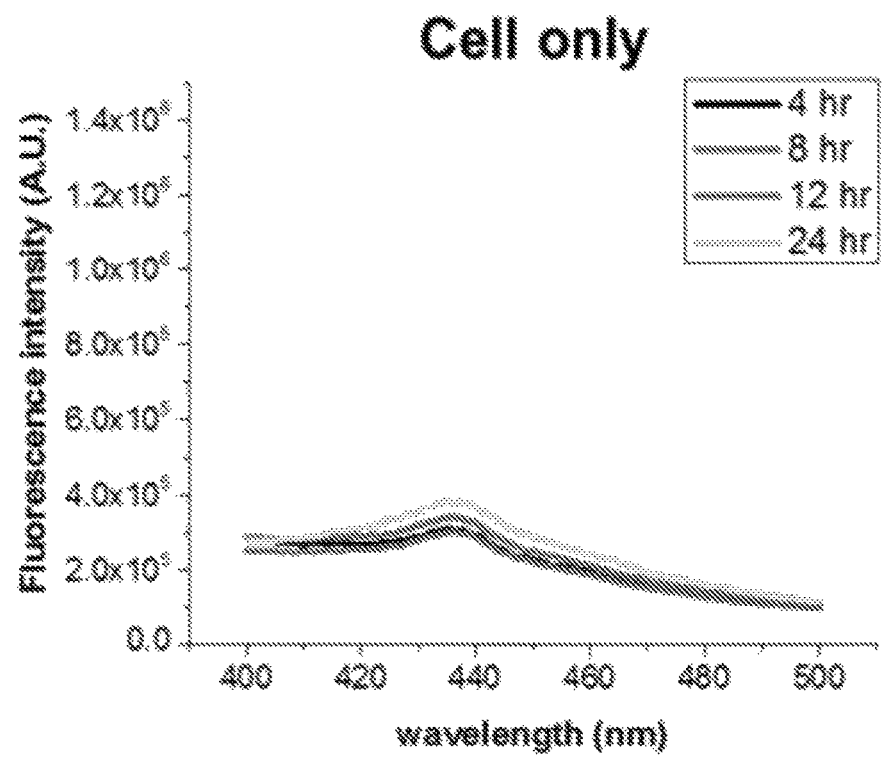
FIGS. 12A to 12F show a time course of pRNA-3WJ-Taxol micelle induced apoptosis in Caspase-3 dependent manner.
Figure 12B:
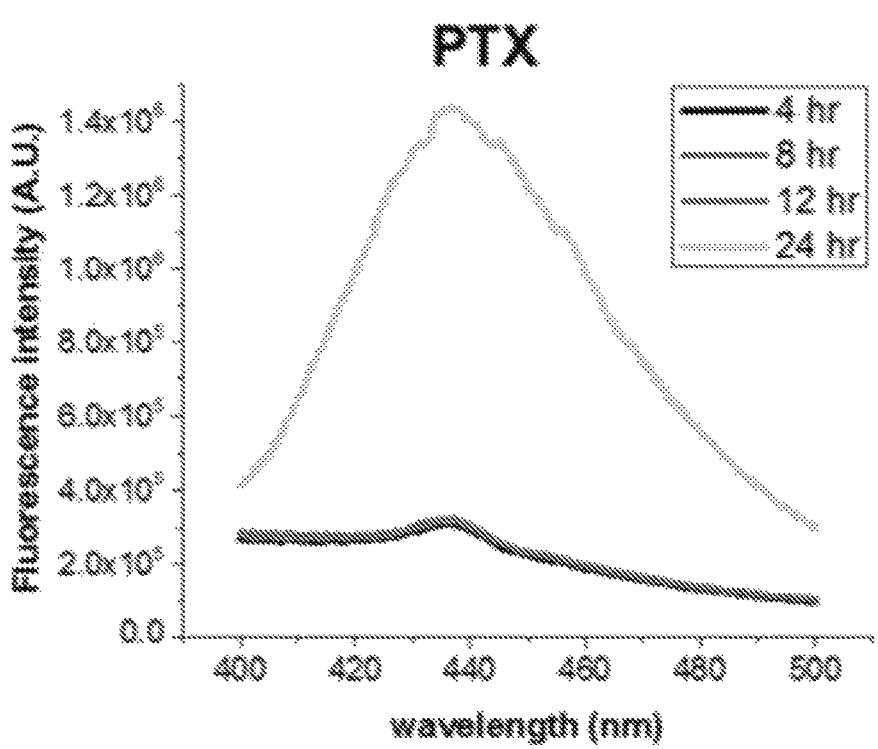
Figure 12C:
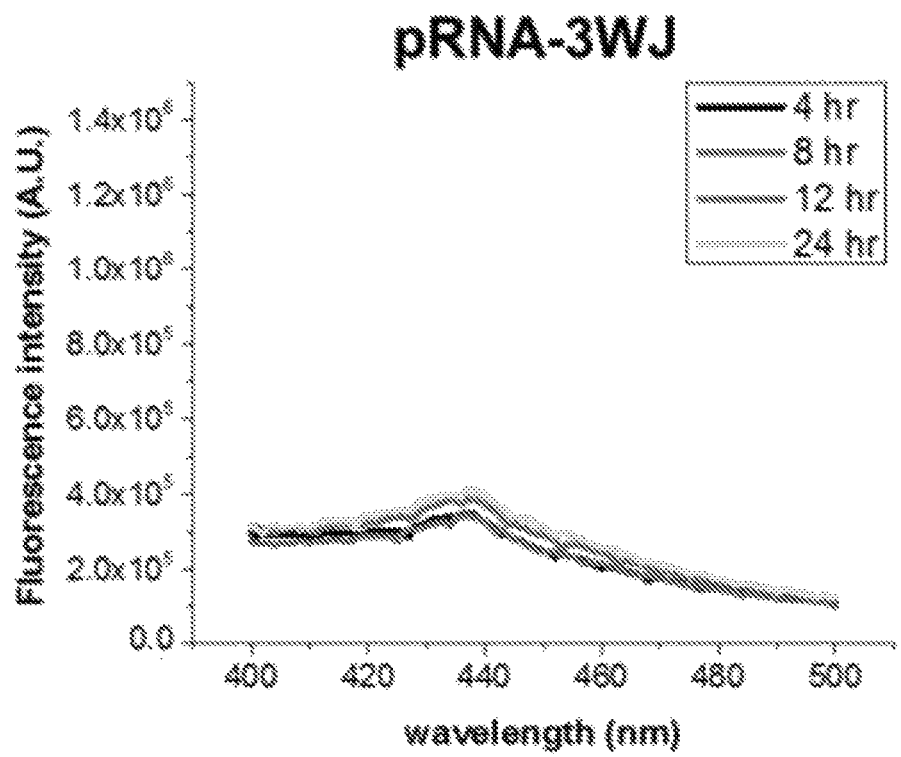
Figure 12D:
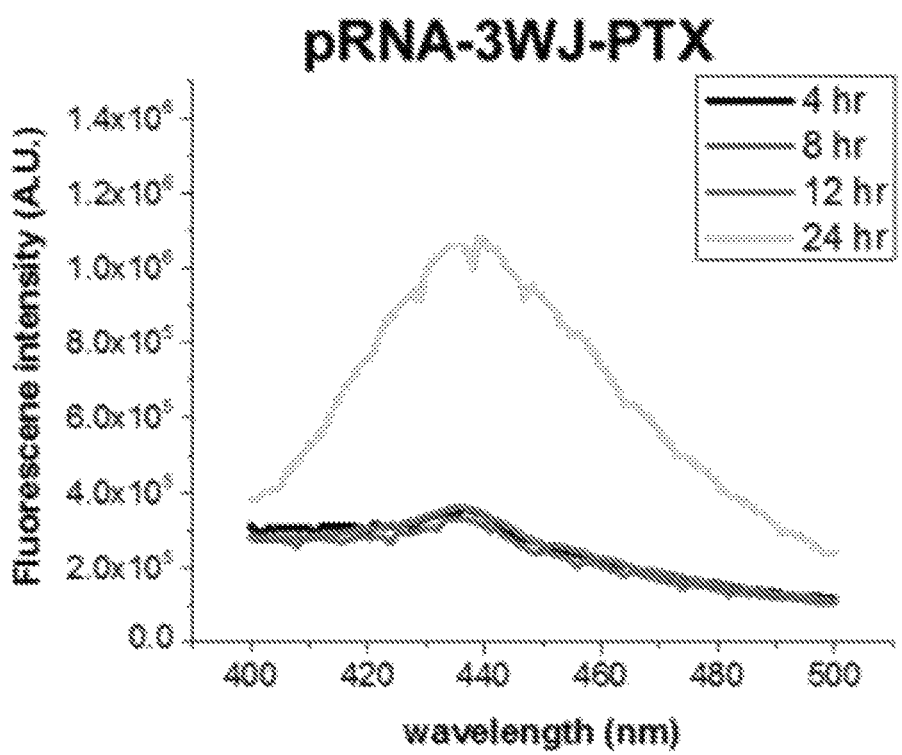
Figure 12E:
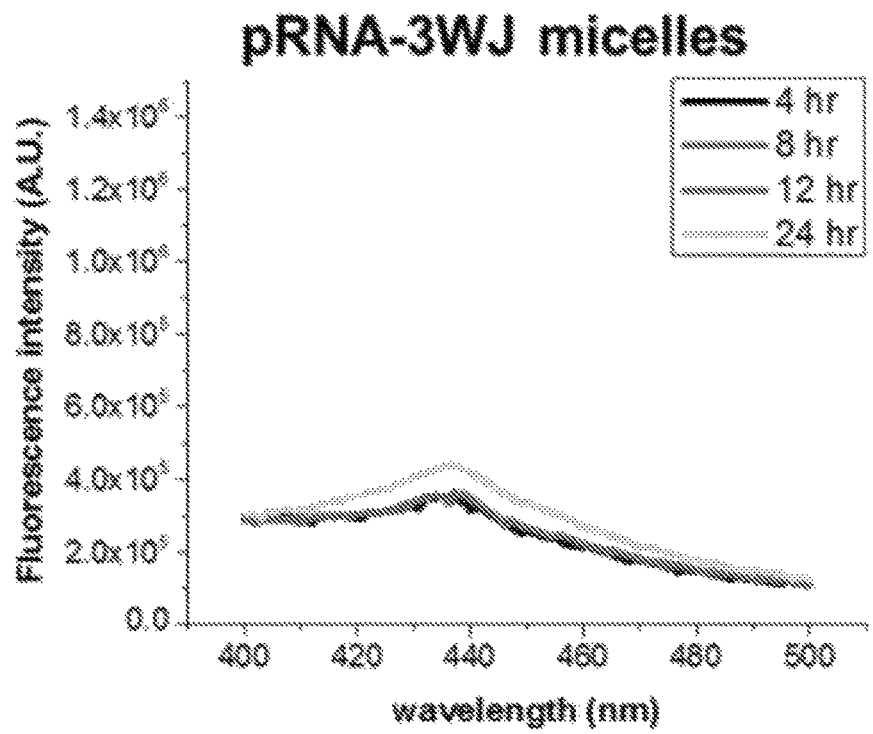
Figure 12F:
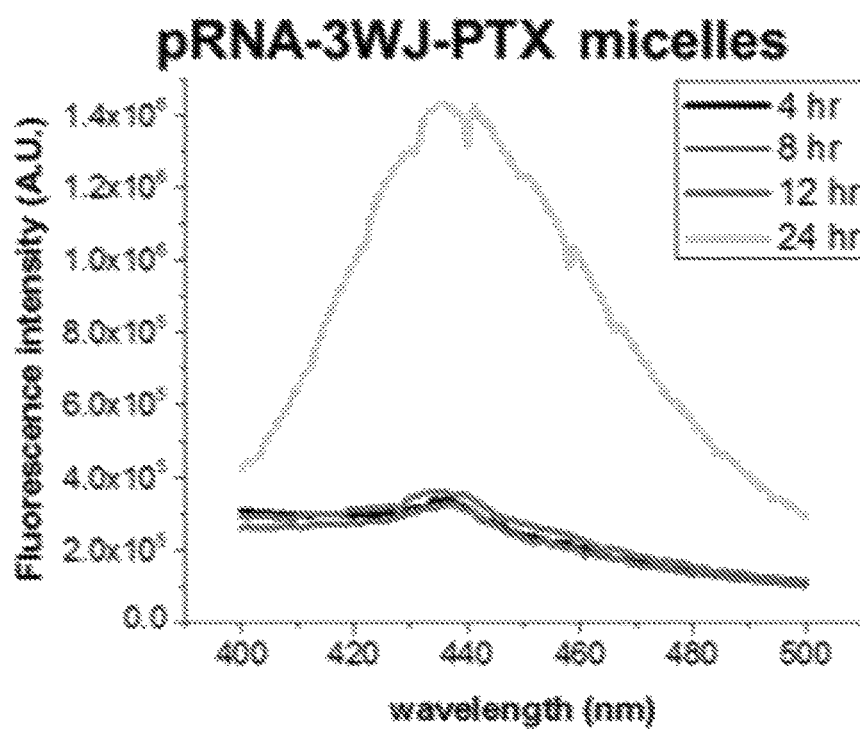

In order to determine the Critical Micelle Formation Concentration (CMC) of pRNA-3WJ-PTX micelles, the Nile Red assay was used as previously reported [Zhang, A. et al. Soft Matter 9 (2013) 2224-2233]. Nile red is a hydrophobic dye which has low fluorescence in water and other polar solvents but emits strong fluorescence in nonpolar environments such as the lipid core of a micelle. Therefore, Nile Red fluorescence emission intensity is utilized as an indicator for micelle formation. To determine CMC, the fluorescence intensity of Nile Red was plotted as a function of the sample concentration. As shown in FIG. 11A, Nile Red exhibits low fluorescence intensity at concentrations below 0.078 μM indicating that the Nile Red was in water and few micelles were present. With increasing concentration, the fluorescence intensity increased dramatically demonstrating that Nile Red was encapsulated in the lipid core of RNA micelles. The CMC can be estimated as the intersection of the tangents to the horizontal line of intensity ratio with relatively constant values and the diagonal line with rapidly increased intensity ratio (FIG. 11B). The CMC is about 100 nM and 1% TAE agarose gel further confirmed the CMC is about 150 nM due to sensitivity limit (FIG. 11C). All the pRNA micelle concentrations used in in vitro and in vivo experiments performed were above the CMC to make sure micelles are formed.

Binding and Internalization of pRNA-3WJ-PTX Micelles into KB Cells

Figure 4A:
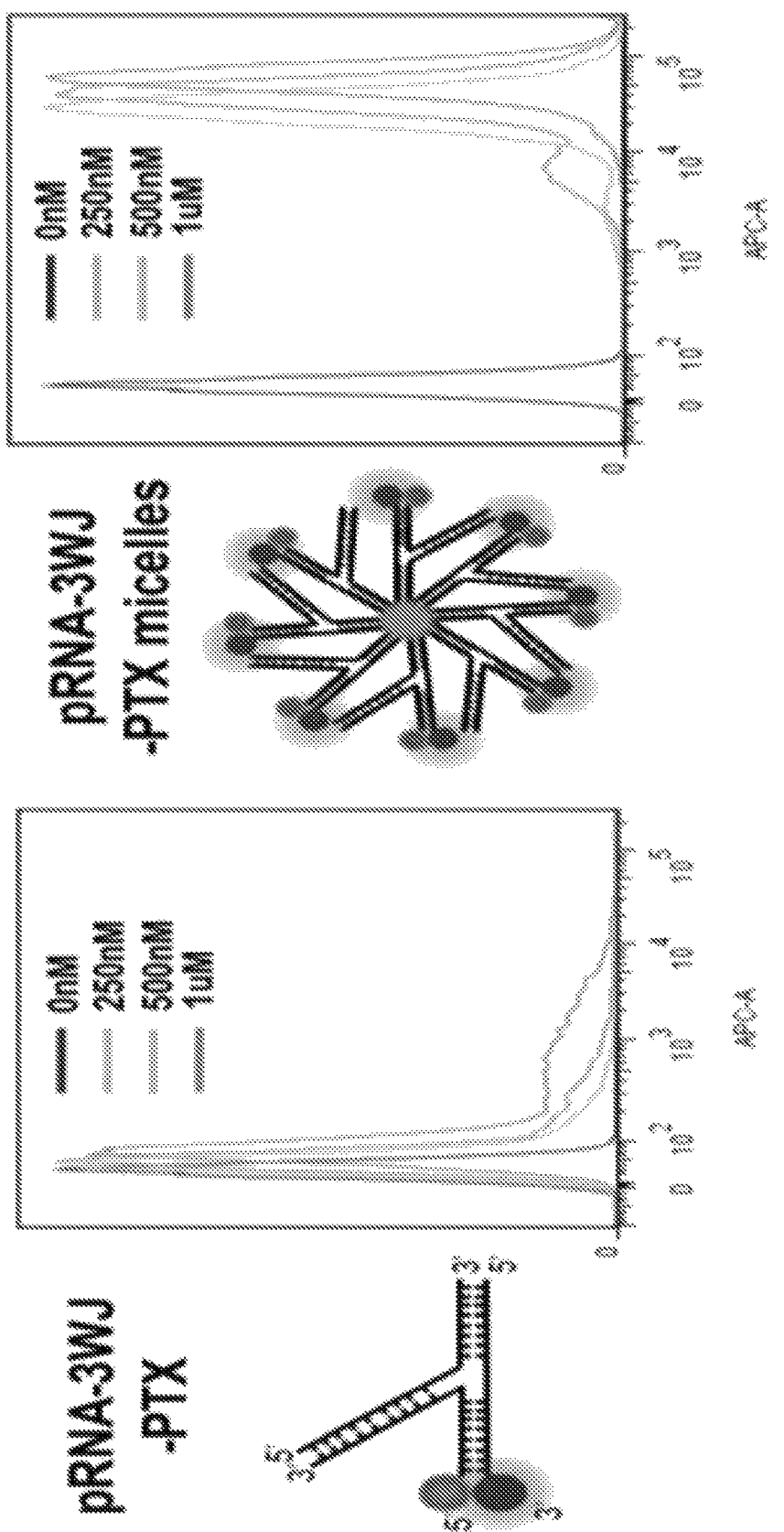
FIGS. 4A and 4B show assay of tumor cell binding and internalization of pRNA-3WJ-PTX micelles in vitro by flow cytometry (FIG. 4A) and confocal microscopy (FIG. 4B). Shown are nuclei staining; cytoskeleton staining; and pRNA-3WJ-PTX micelle binding.
Figure 4B:
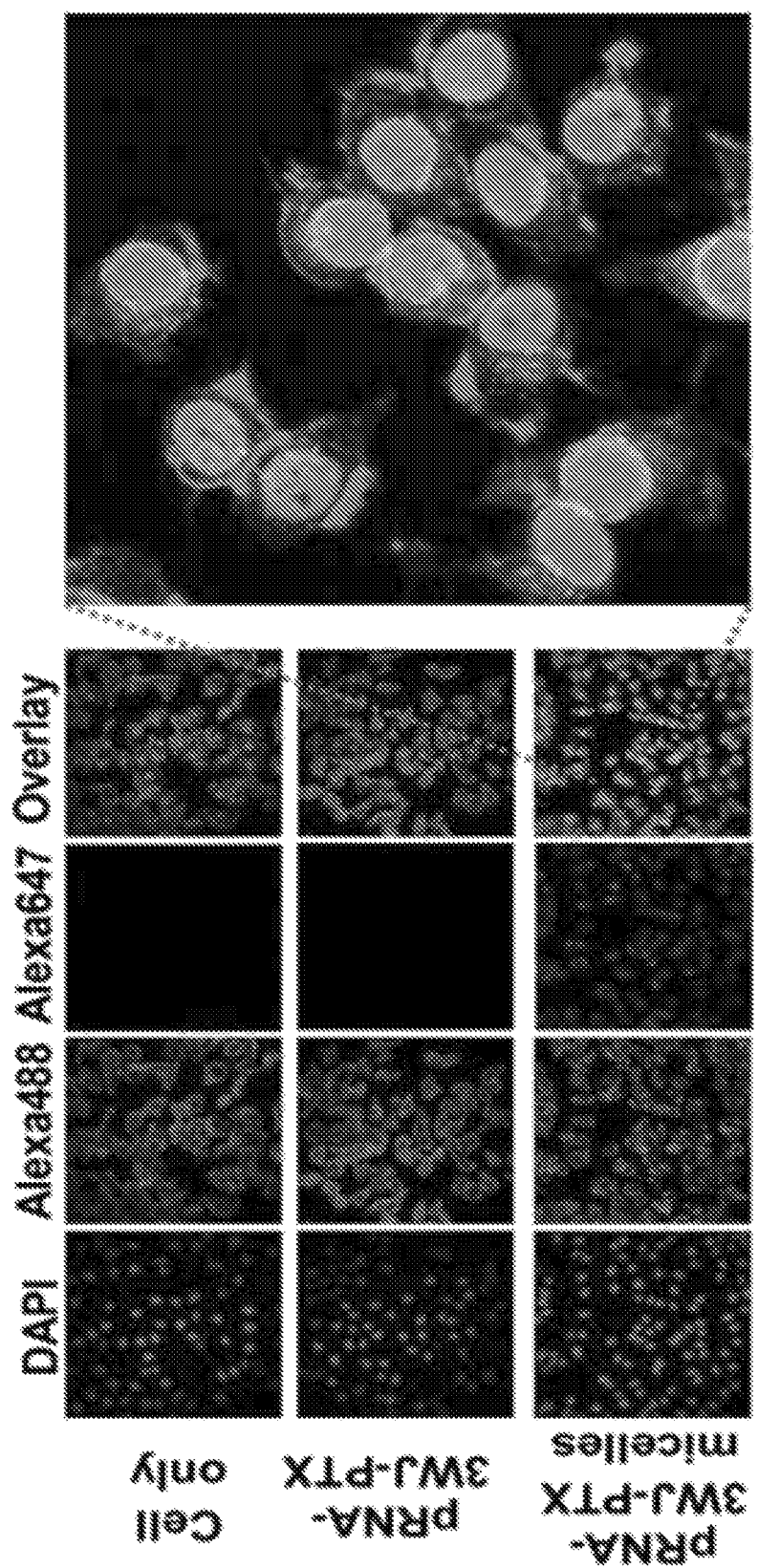

In order to assay the tumor cell targeting in vitro, pRNA-3WJ-PTX micelles and control pRNA-3WJ-PTX without lipophilic module were incubated with KB cells, trypsinized, washed and then analyzed by Fluorescence-Activated Cell Sorting (FACS) assay. Strong binding (almost 100%) was observed for pRNA-3WJ-PTX micelles compared to pRNA-3WJ-PTX scaffold control (0% binding) (FIG. 4A). Confocal microscopy images further confirmed the efficient binding and internalization of pRNA-3WJ-PTX micelles into cancer cells, as demonstrated by excellent overlap of fluorescent RNA nanoparticles (FIG. 4B) and cytoplasm (FIG. 4B). Very low signal was observed for control pRNA-3WJ-PTX without lipophilic modules. These results indicate that the RNA micelles have a high affinity for cancer cell binding. Although the current RNA micelle design did not include a tumor specific targeting module, the highly charged RNA micelles (as RNA is negatively charged, also shown in Zeta potential study) were able to disintegrate themselves and insert into the cell membrane when interacting with the cells similar as DNA micelles as reported previously [Liu, H. et al. Chemistry 16 (2010) 3791-3797]. Without being bound by theory, it is believed that the internalization of the RNA micelles was mediated possibly by subsequent endocytosis after inserting into the cell membrane.

Figure 5A:
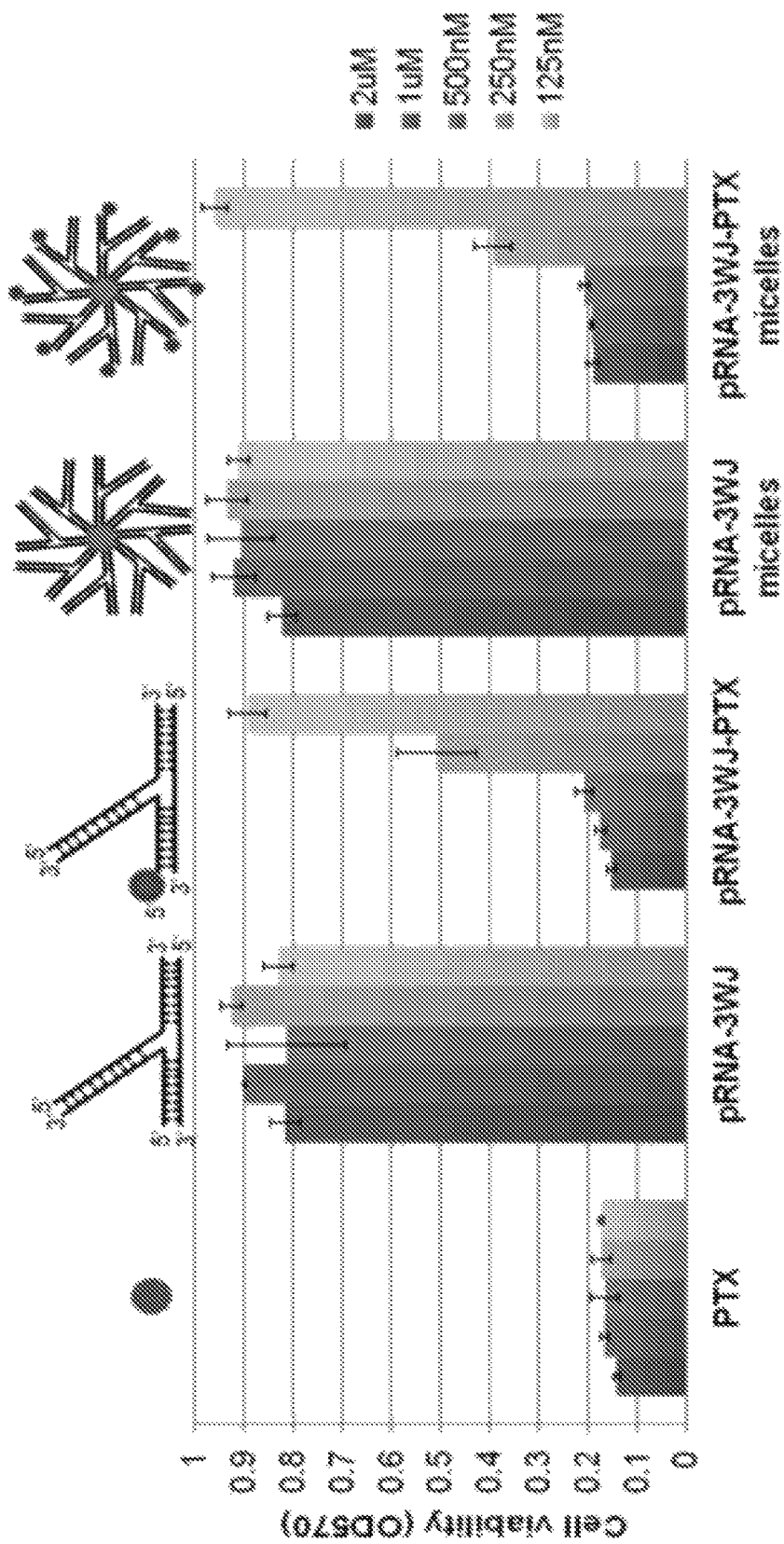
FIGS. 5A to 5D show cytotoxicity and apoptotic effects of PTX loaded pRNA-3WJ micelles in vitro.

Effects of pRNA-3WJ-PTX Micelles on Growth and Apoptosis of Cancer Cells In Vitro In order to determine the cellular effects of RNA micelle treatment, MTT assay was performed to assay the cell viability after treatment. The RNA micelles harboring PTX can successfully inhibit tumor cell growth at or above 250 nM, compared to RNA micelles only and 3WJ controls without Paclitaxel conjugation (FIG. 5A).

Concentrations below 125 nM were not evaluated to stay above the CMC. Cell growth inhibition caused by pRNA-3WJ-PTX micelles indicates release of Paclitaxel from RNA strands due to the linker ester hydrolysis in aqueous solution. There is very little possibility of free Paclitaxel contamination to the testing constructs as all RNA-PTX conjugates underwent HPLC purification. In addition, pRNA-3WJ micelles without Paclitaxel loading showed no effects on cell viability and proliferation which indicates the low cytotoxicity of RNA micelle scaffolds and their potential as a safe drug delivery platform.

Figure 5B:
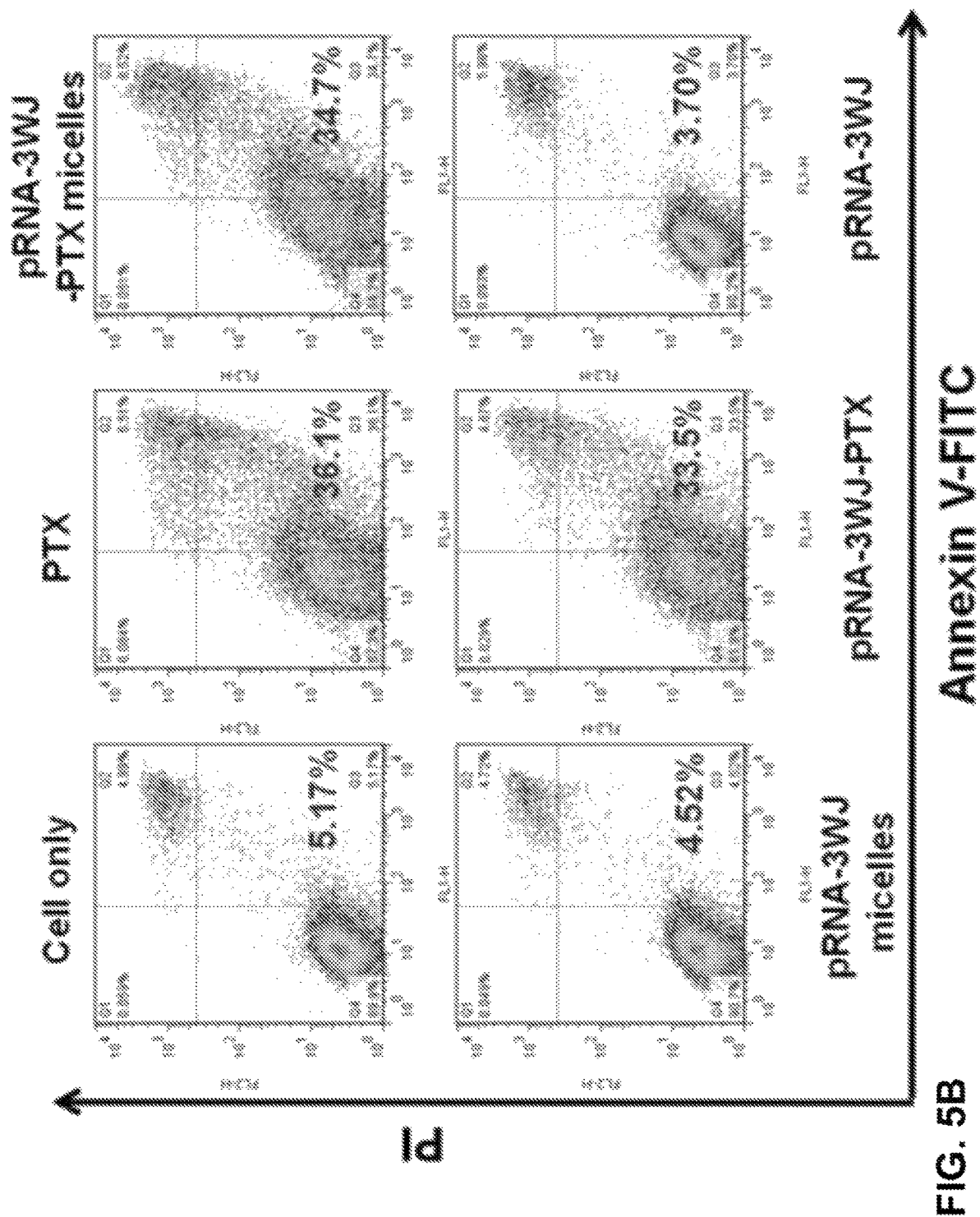

FITC labeled Annexin V staining confirmed that the majority of the cancer cell death is due to cell apoptosis as shown in FIG. 5B. Loss of plasma membrane is one of the earliest features in apoptotic cells. The externalization of membrane phospholipid phosphatidylserine (PS) from the inner to the outer leaflet of the plasma membrane allows FITC labeled Annexin V to bind PS for detecting cells that are undergoing apoptosis. Staining with FITC Annexin V is used in conjunction with PI to identify early apoptotic cells (Q3: PI negative, FITC Annexin V positive) and cells that are in late apoptosis or already dead (Q2: FITC Annexin V and PI positive). In our study, over 30% of the cells were undergoing apoptosis after 48 hr treatment with pRNA-3WJ-PTX micelles compared to the control micelles without PTX (4.52%) or pRNA-3WJ without PTX (3.7%), indicating that the cancer viability change is due to the induction of cell apoptosis.

Figure 5C:
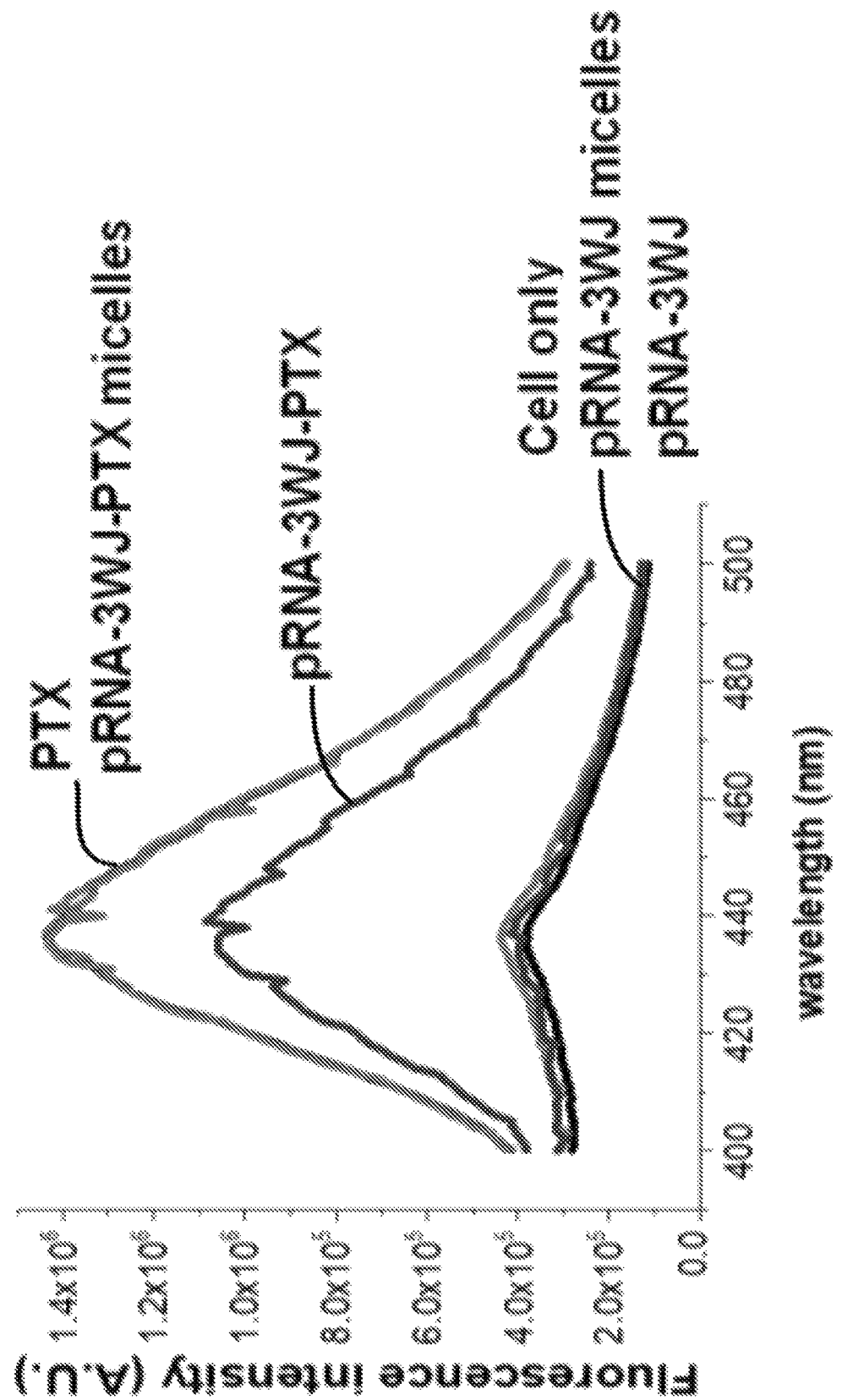
Figure 5D:
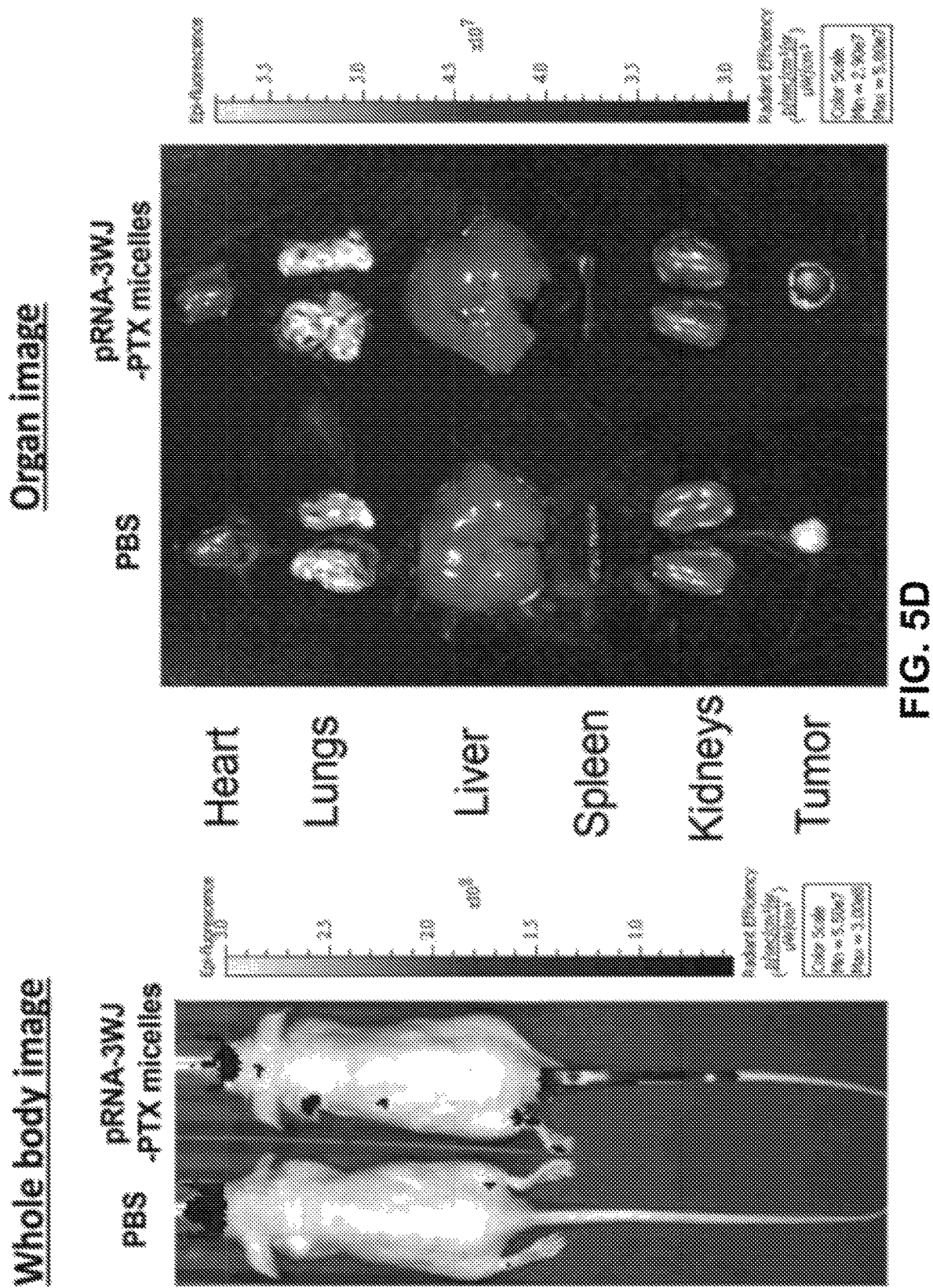

Caspase-3 is an early cellular apoptotic marker. The increase of the Caspase-3 activity is closely related to cell apoptosis. The elevation of Caspase-3 activity, as reflected by increased fluorescence intensity, appeared 12 hr after treatment with pRNA-3WJ-PTX micelles (FIGS. 12A-12F). It was found that pRNA-3WJ-PTX micelles treated cell lysates showed the highest fluorescence emission similar to Paclitaxel alone compared to the control nanoparticles (pRNA-3WJ micelles and pRNA-3WJ), which indicate the induction of cell apoptosis in a Caspase-3 dependent manner (FIG. 5C).

Figure 6C:
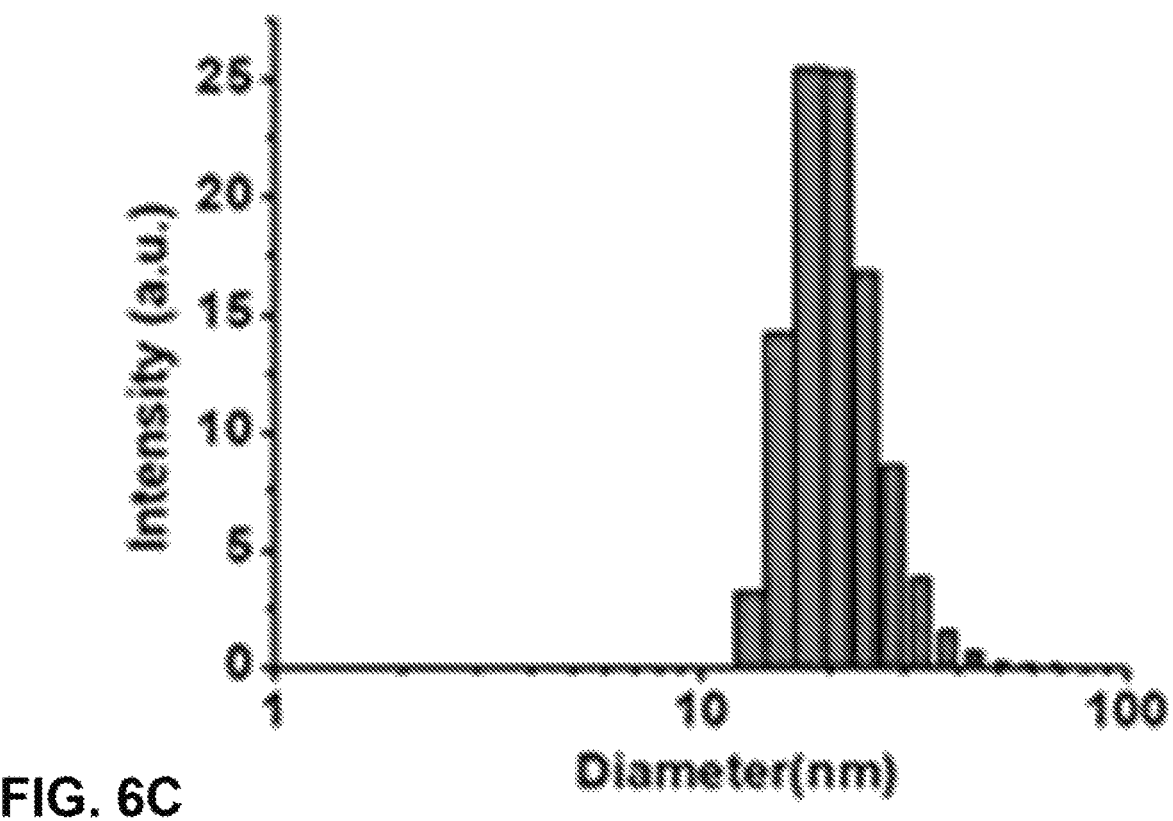
Figure 6D:
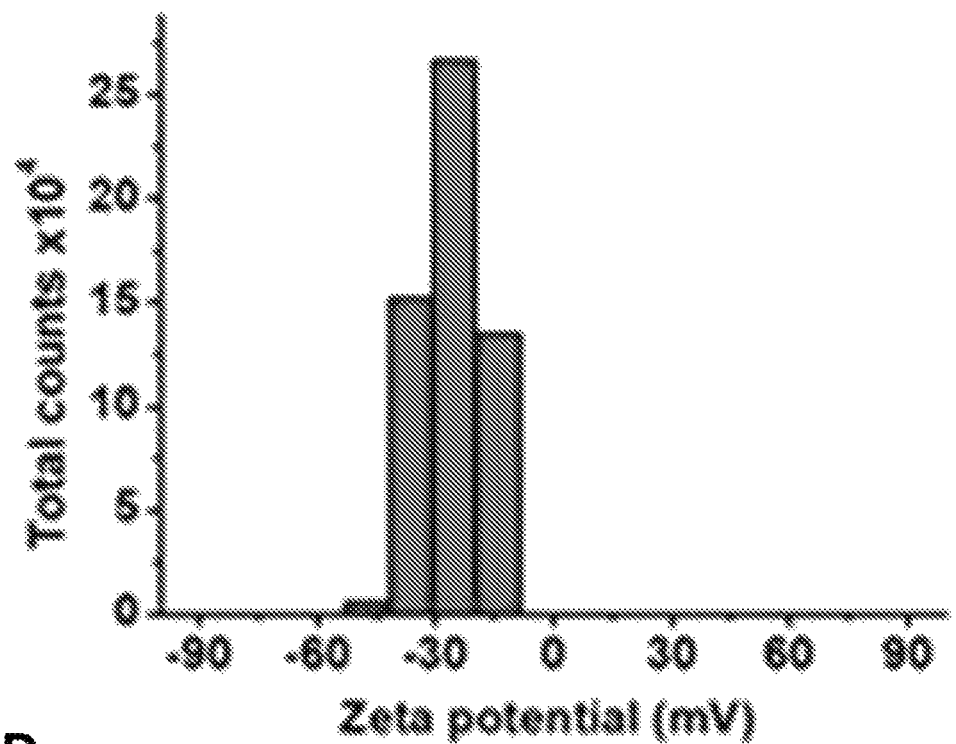
Figure 6E:
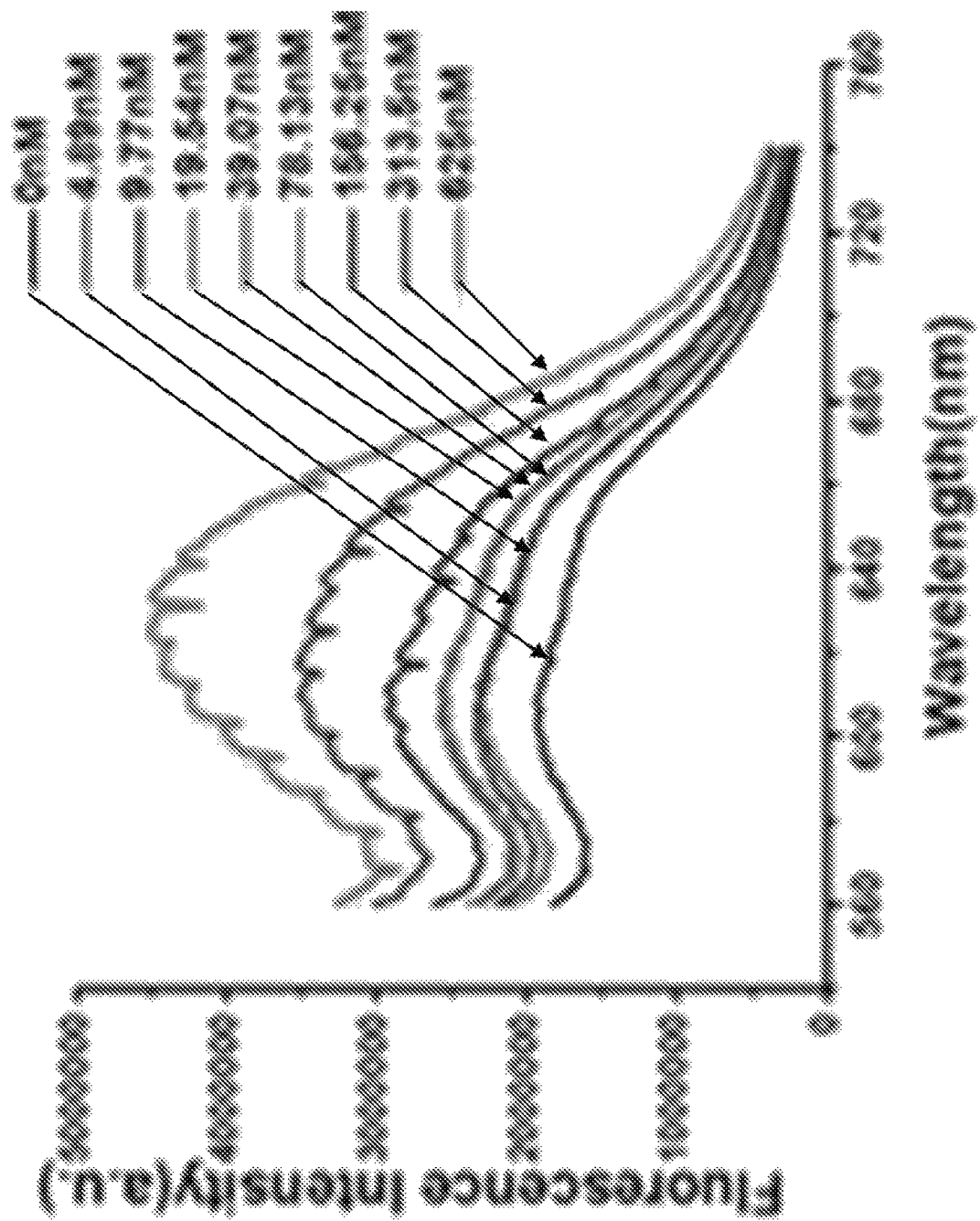
FIGS. 6E-6G. CMC determined by Nile Red encapsulation assay and stability study of RNA micelles in different temperature, pH and RNase condition.
Figure 6F:
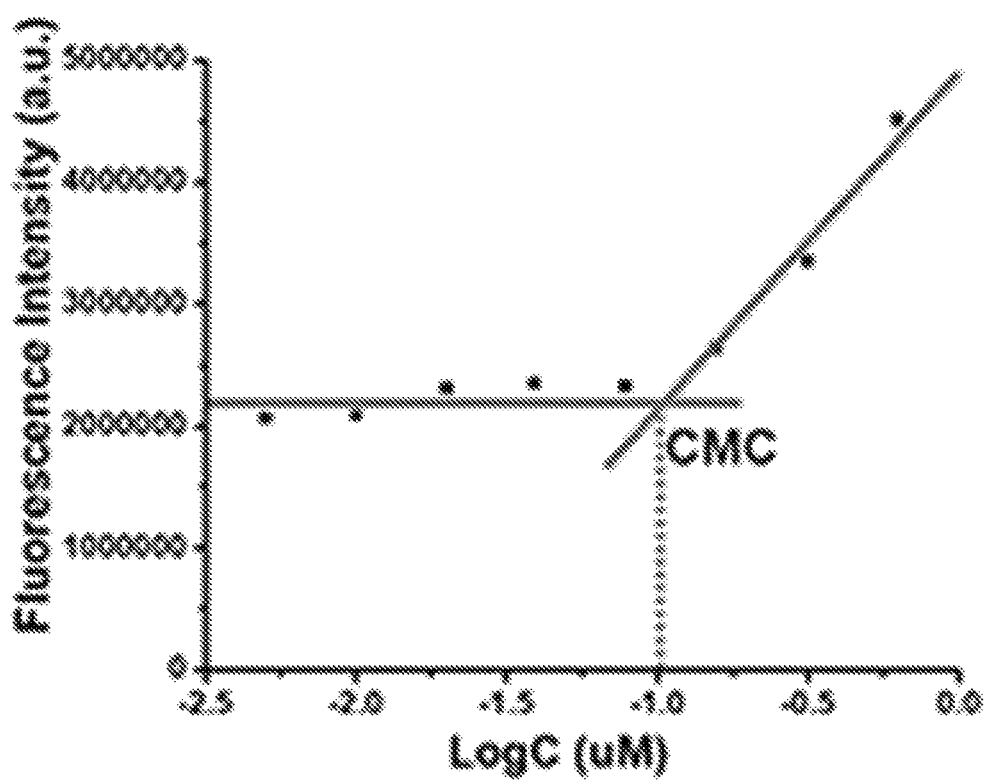
Figure 6G:
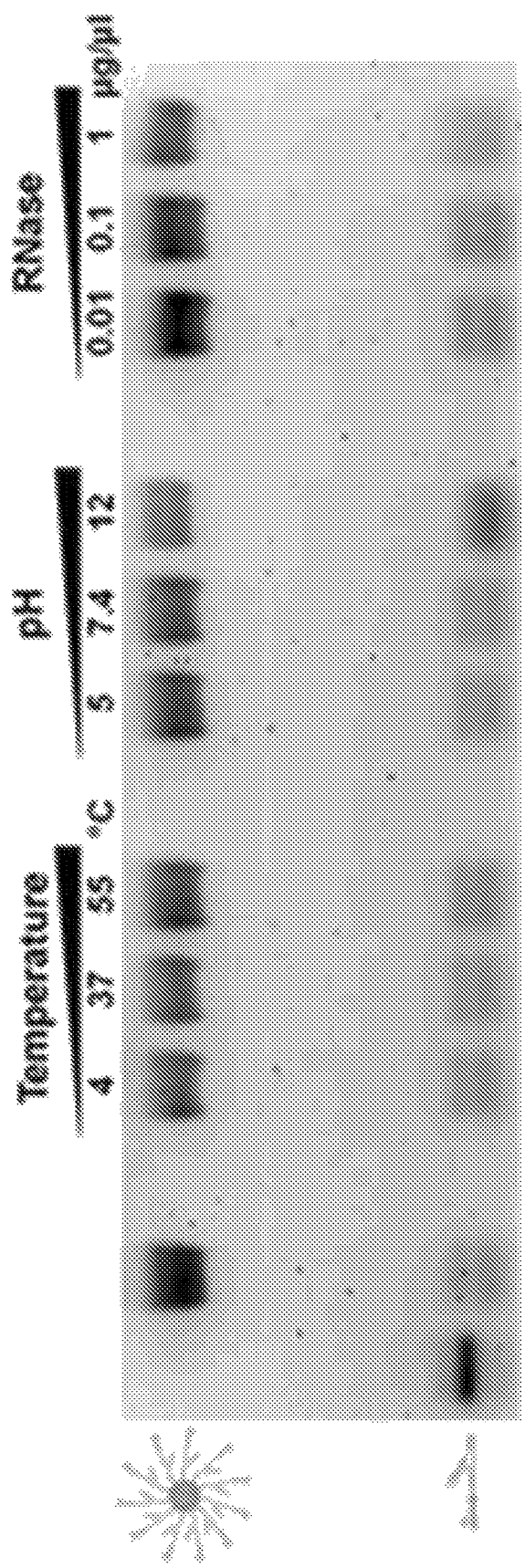
Figure 6H:
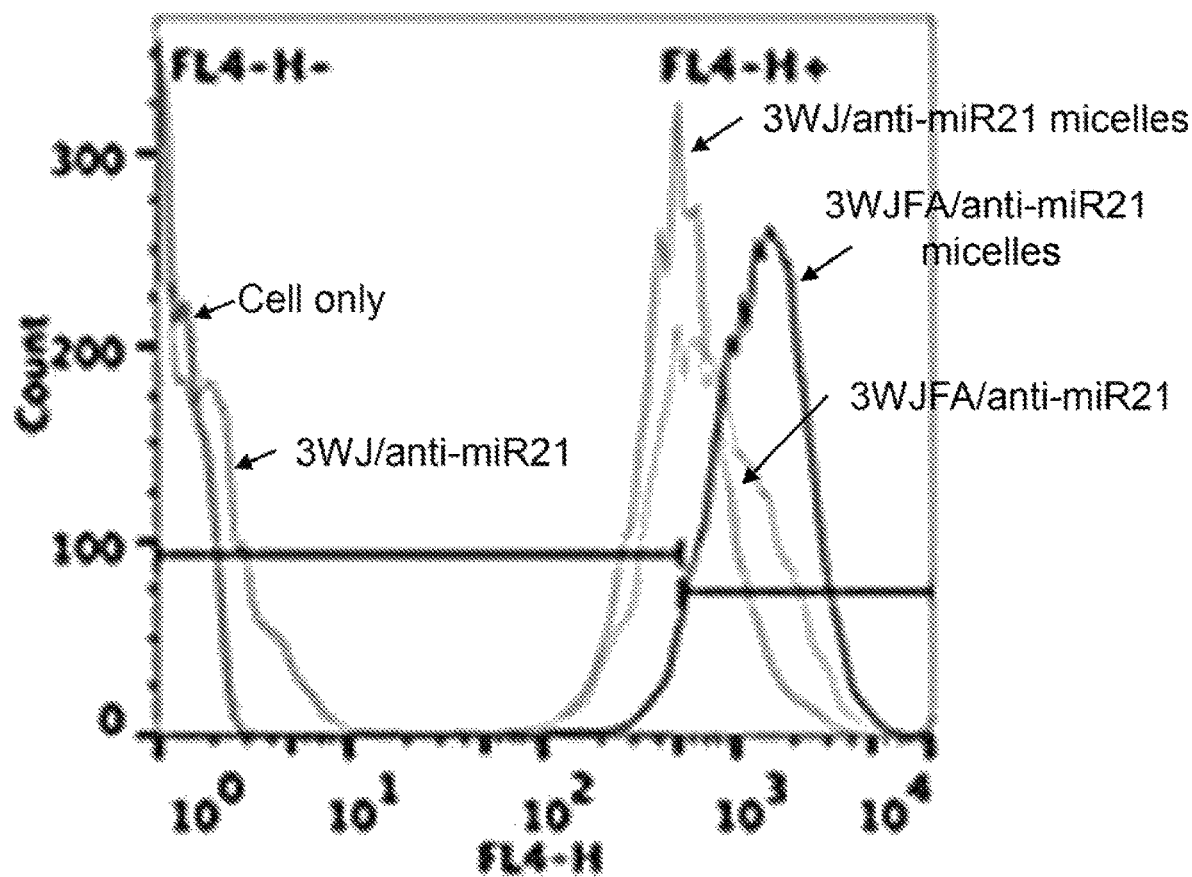
FIGS. 6H-6I shows in vitro binding and internalization of RNA micelles to cancer cell. Flow cytometry comparing binding affinity to KB cells after treatment for 1 hr. Confocal microscope showing internalization profile. nuclei; cytoskeleton; RNA nanoparticles.
Figure 6I:
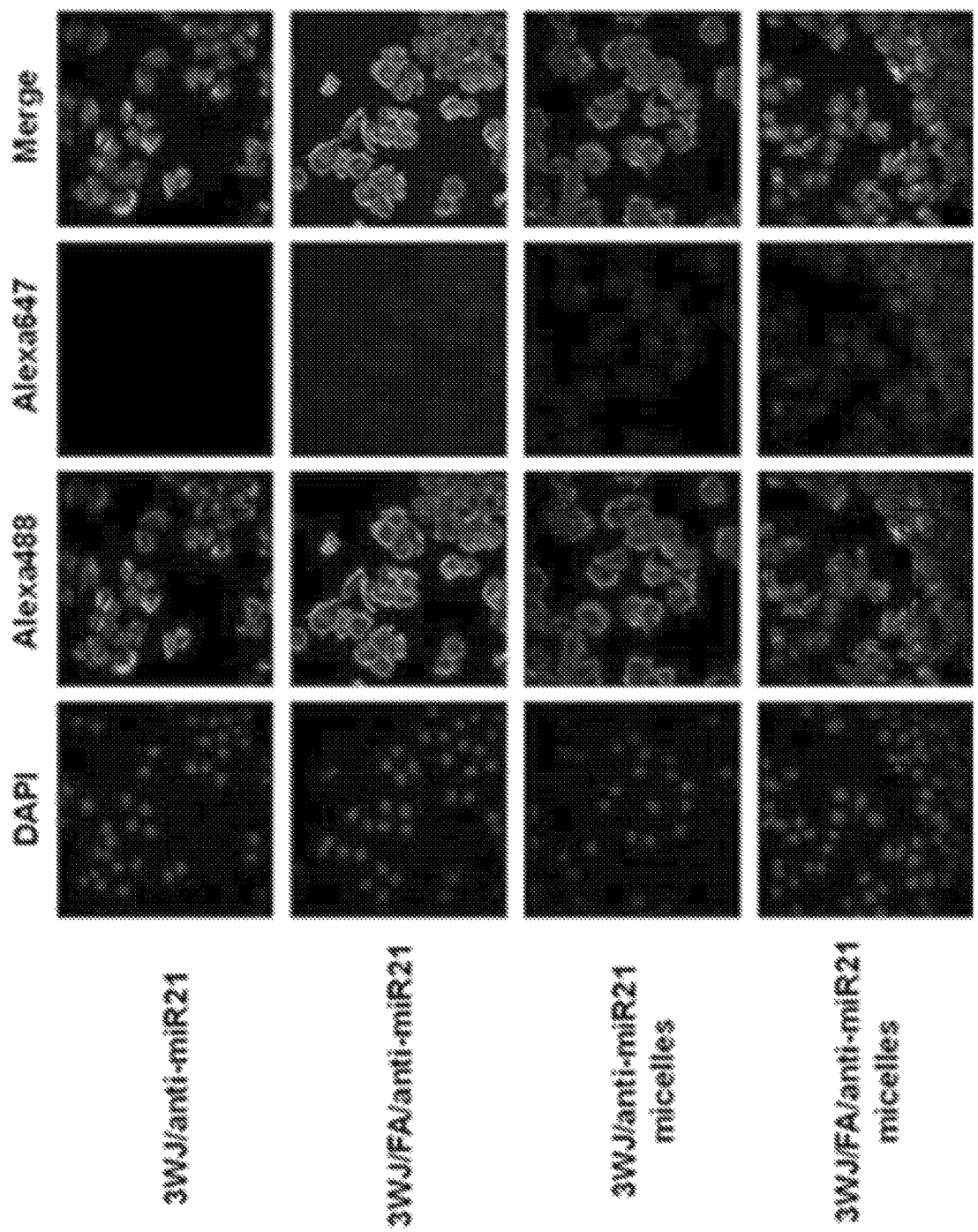
Figure 6J:
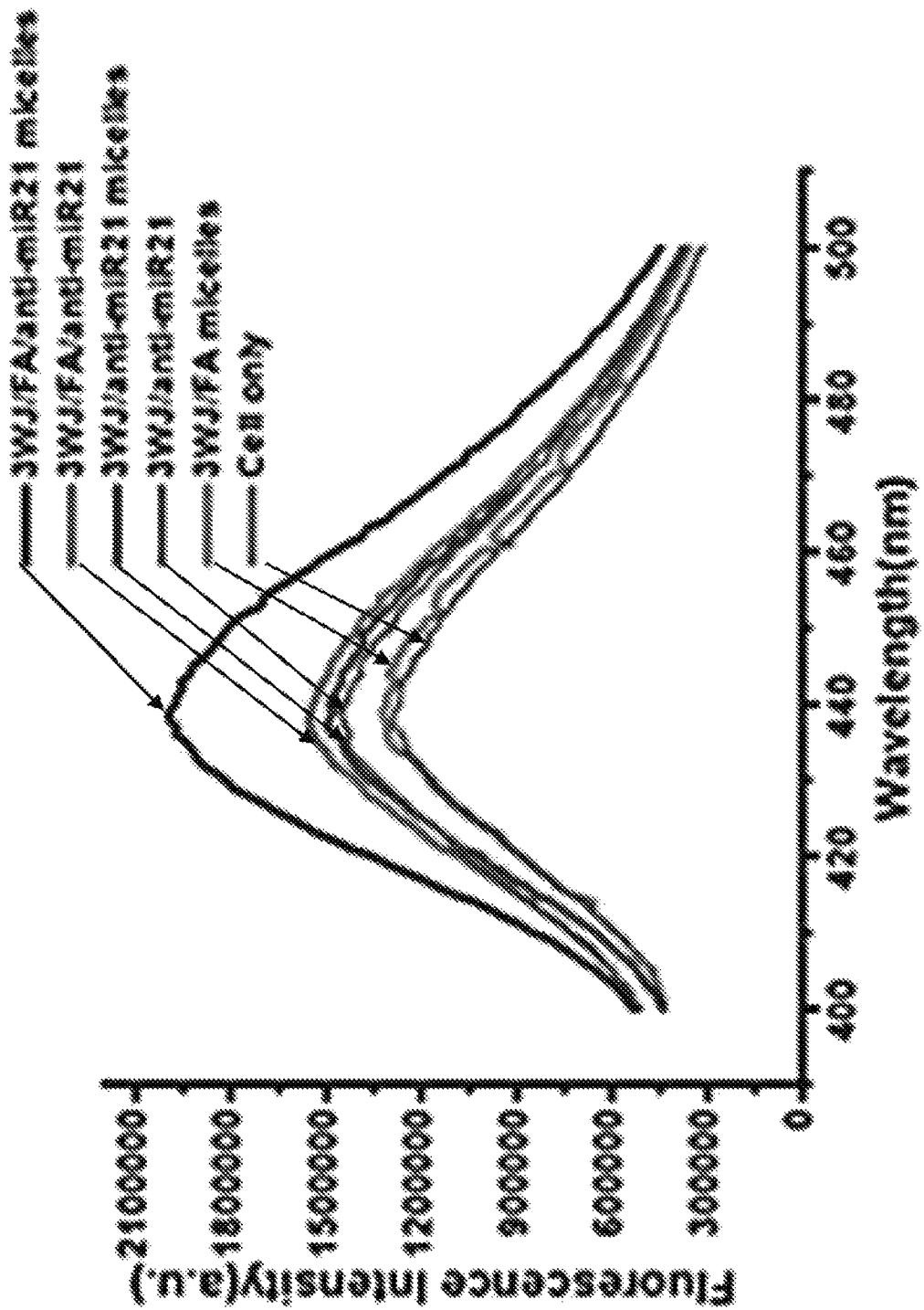
FIGS. 6J-6L shows in vitro studies of RNA micelles carrying anti-miR21. Dual-luciferase assay demonstrating delivery of anti-miR21 to KB cells. qRT-PCR showing effect of miR21 knock down on the target gene PTEN expression. Caspase-3 assay exhibiting cell apoptosis induction after treatment.
Figure 6L:
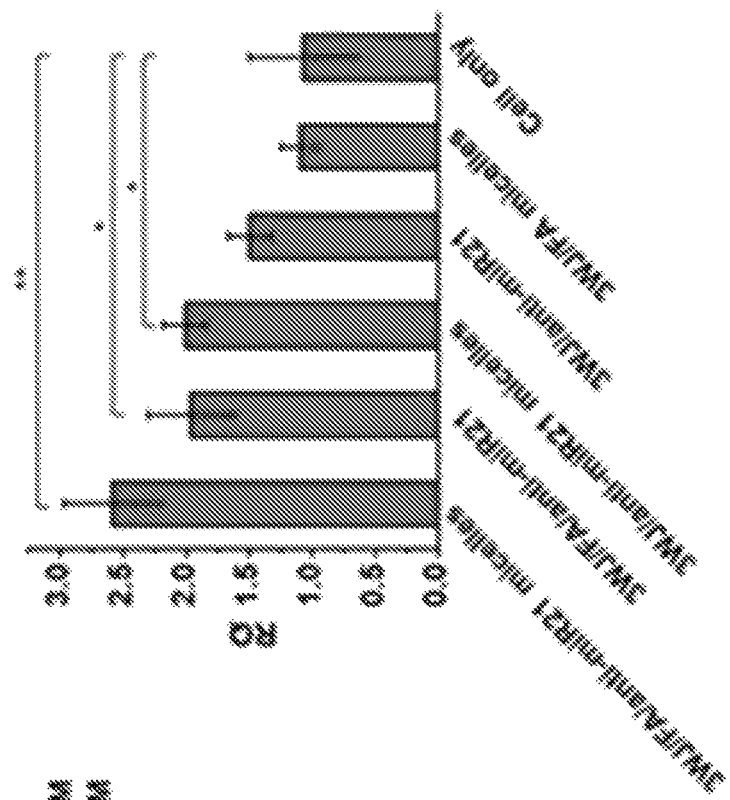
Figure 6K:
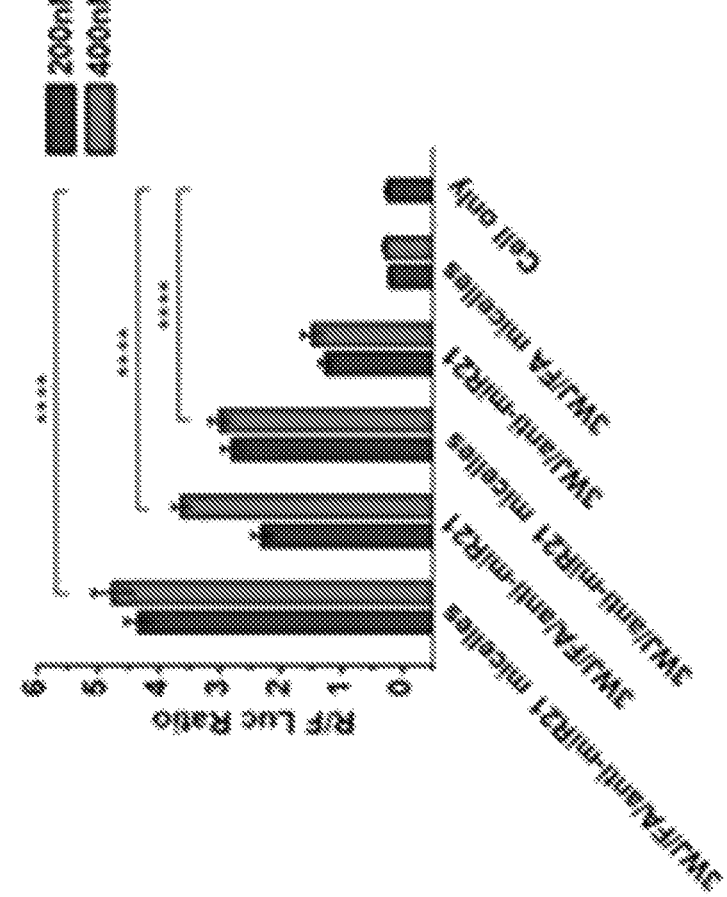
Figure 6M:
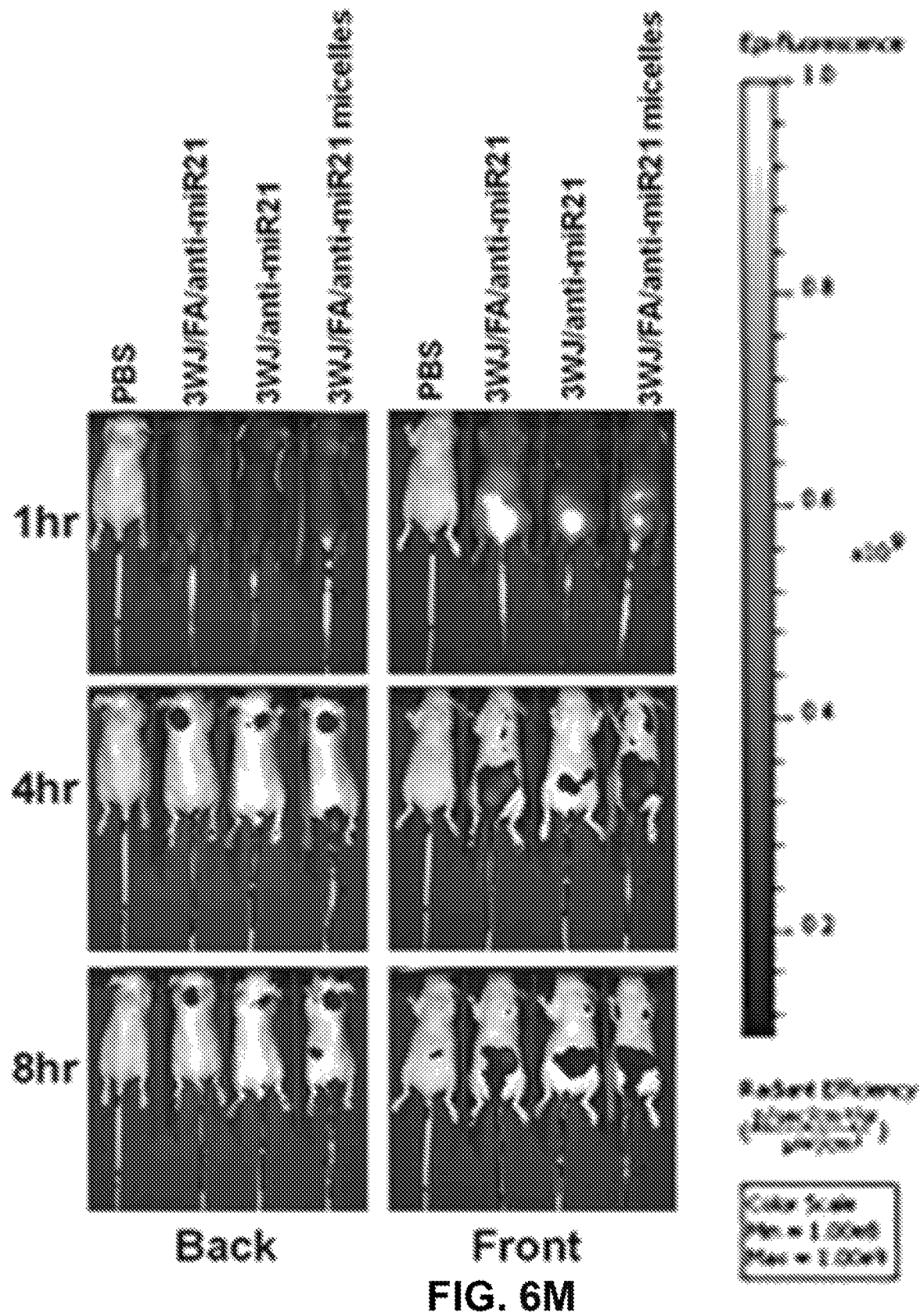
FIGS. 6M-6N shows in vivo biodistribution study in mice with xenograft. Whole body image. Ex vivo organ image 8 hr post injection.
Figure 6N:
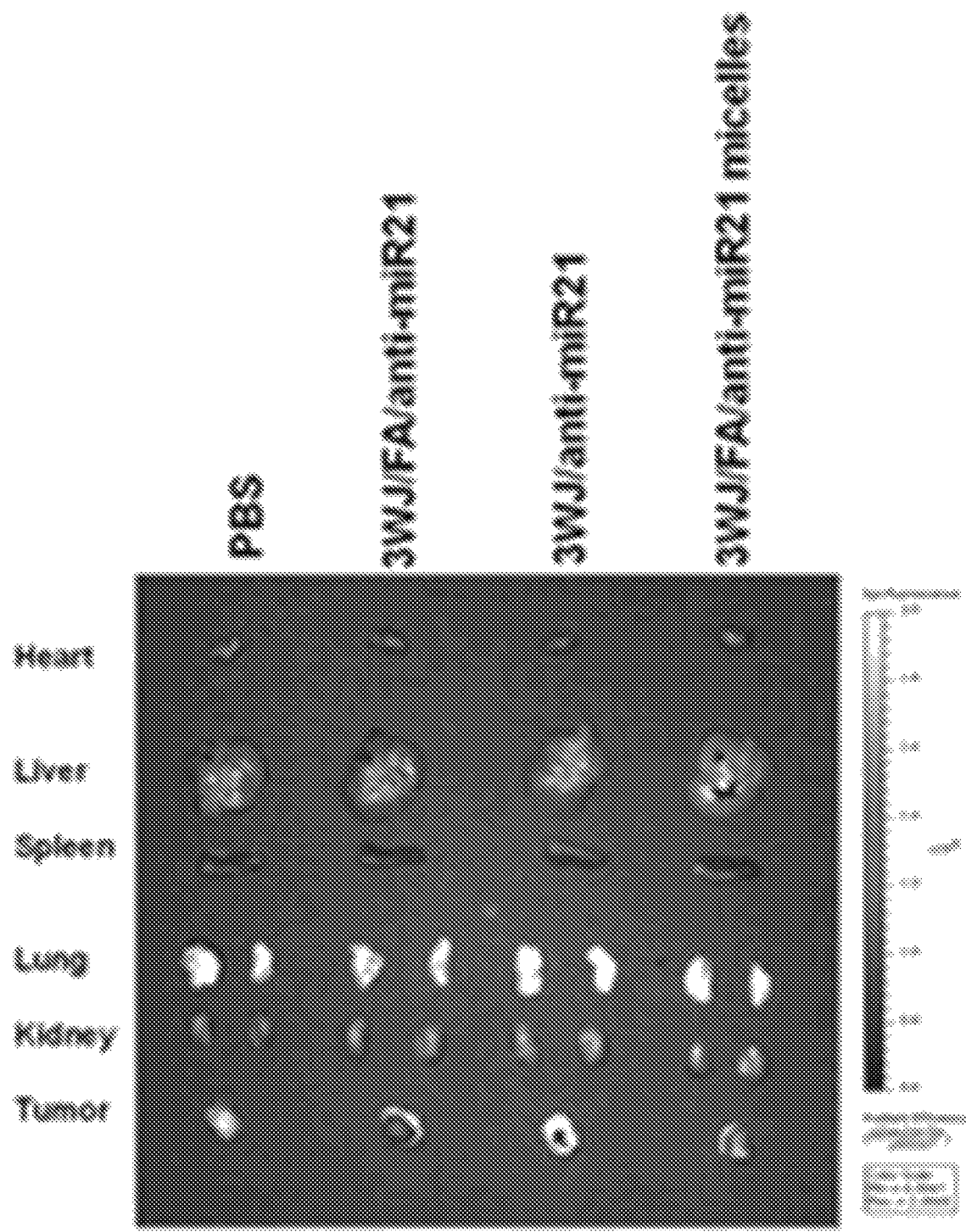
Figure 6O:
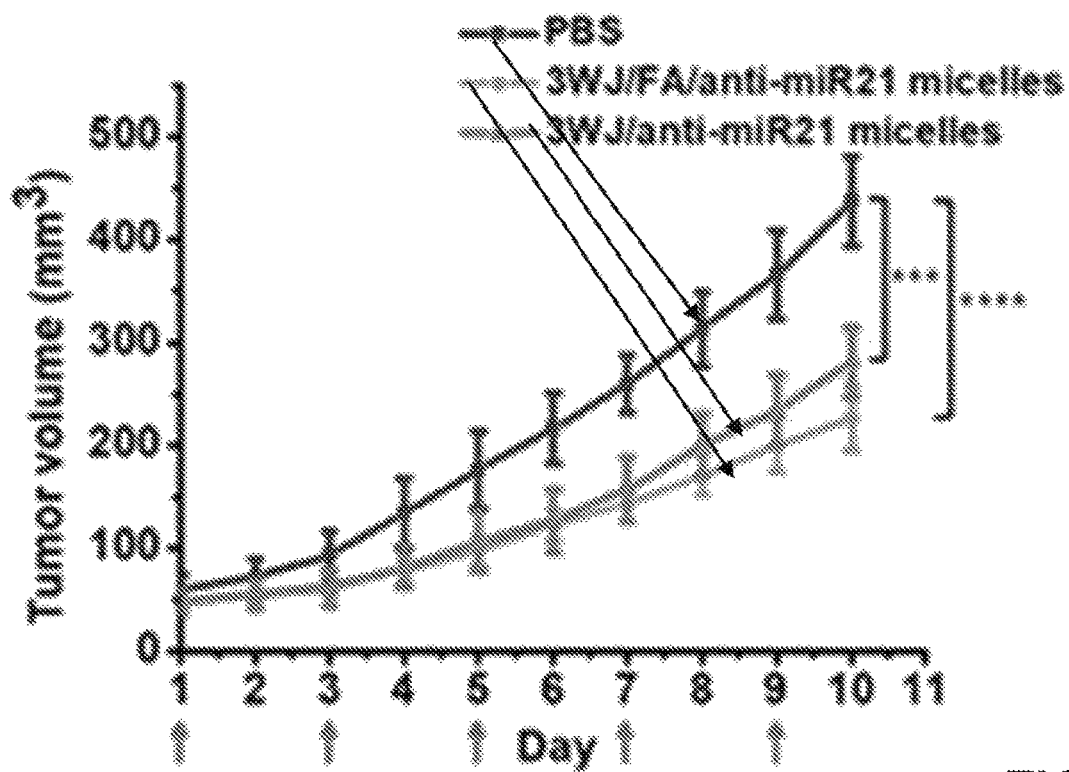
Figure 6P:
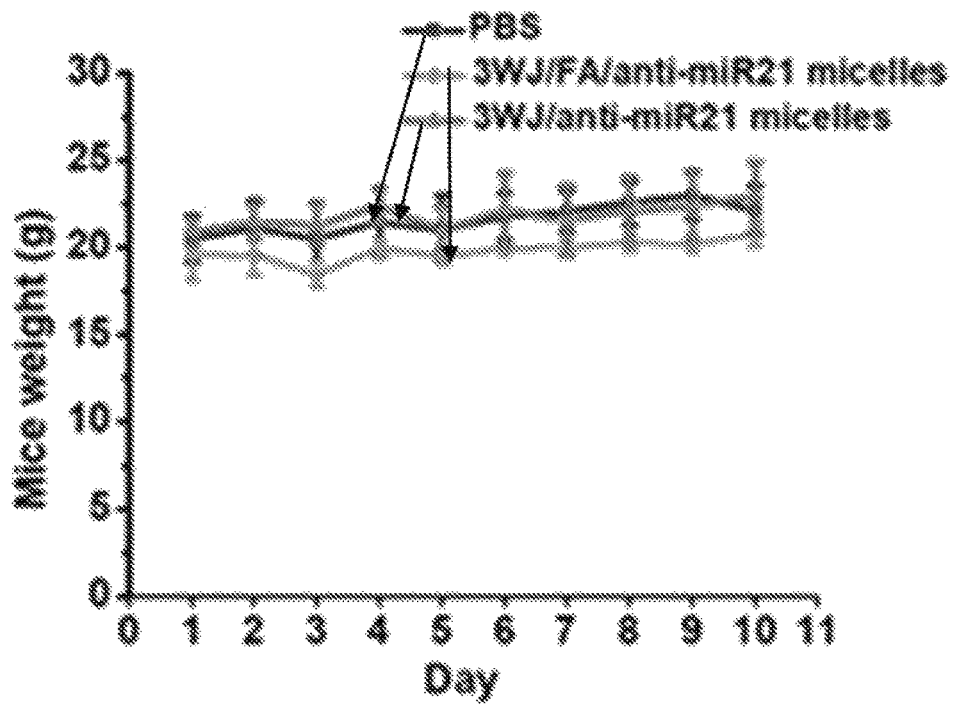
Figure 6Q:
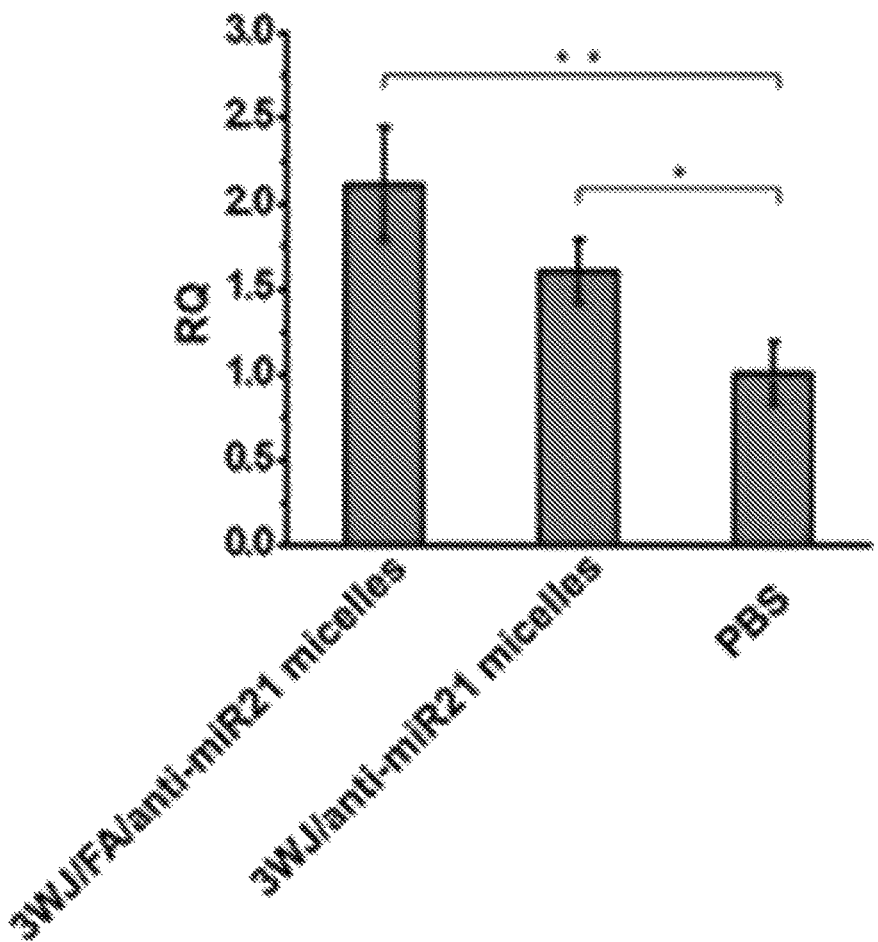
Figure 6R:
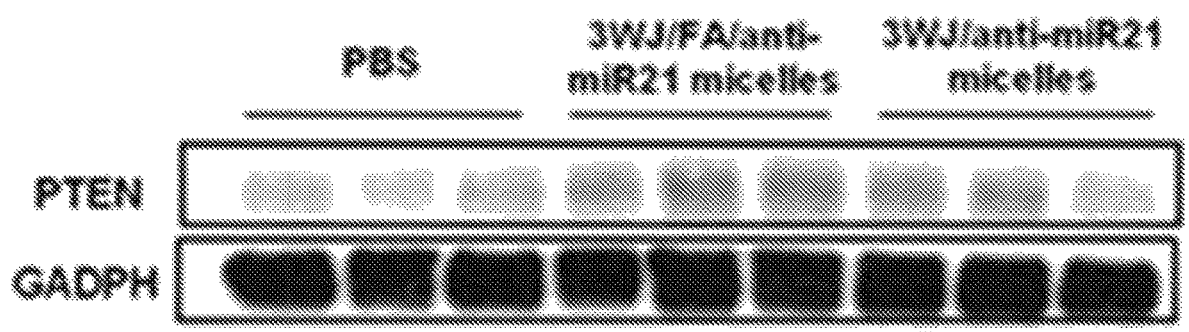

Specific Targeting of Tumors in Xenografted Animal Models Via Imaging Using NIR Fluorescent pRNA-3WJ-PTX Micelles Tumor targeting efficiency by pRNA-3WJ-PTX micelles was investigated by collecting in situ fluorescence images of tumor xenografts in nude mice at different post injection time points. Images of the tumor area became readily defined 4 hr after injection (FIGS. 6A-6D and 13). Ex vivo images of normal tissues, organs, and tumors taken from the RNA micelle-injected mice showed that the tumors taken at 24 hr post injection exhibited the strongest signal (FIG. 6E-6G). FIGS. 6H-6I shows in vitro binding and internalization of RNA micelles to cancer cell. Flow cytometry comparing binding affinity to KB cells after treatment for 1 hr. Confocal microscope showing internalization profile. Blue: nuclei; Green: cytoskeleton; Red: RNA nanoparticles. FIGS. 6J-6L shows in vitro studies of RNA micelles carrying anti-miR21. Dual-luciferase assay demonstrating delivery of anti-miR21 to KB cells. qRT-PCR showing effect of miR21 knock down on the target gene PTEN expression. Caspase-3 assay exhibiting cell apoptosis induction after treatment. FIGS. 6M-6N shows in vivo biodistribution study in mice with xenograft. Whole body image. Ex vivo organ image 8 hr post injection. FIGS. 60-6R shows in vivo therapeutic effect of RNA micelles in mice with xenograft. Tumor regression curve over the course of 5 injections (Red arrow shows day of injection). Mice weight curve during treatment period. qRT-PCR and Western Blot showing the upregulation of PTEN after in vivo delivery of anti-miR21. In terms of tumor accumulation kinetics, RNA nanoparticles reached their highest accumulation 4 hr post injection and remained longer in the tumor compared to healthy organs and tissues, which indicates a high tumor targeting efficiency and tumor retention capability of the constructed RNA micelles. Such distinct tumor retention behavior of RNA micelles suggests this delivery system makes the advantage of the EPR (enhanced permeability and retention) effect due to its nano-scale size and particle shape. In addition, the RNA micelle constructs showed prolonged tumor retention possibly due to its larger particle size. The specificity of in vivo tumor targeting of RNA micelle nanoparticle can be further secured by including a tumor targeting module, such as folate [Shu, D. et al. Nature Nanotechnology 6 (2011) 658-667; Lee, T. J. et al. Mol Ther. (2017) 25(7):1544-1555; Zhang, H. et al. RNA 19 (2013) 1226-1237; Rychahou, P. et al. Methods Mol Biol 1297 (2015) 121-135; Guo, S. et al. Gene Ther 13 (2006) 814-820] and RNA aptamers [Shu, D. et al. ACS Nano 9 (2015) 9731-9740; Binzel, D. et al. Molecular Therapy 24 (2016) 1267-1277; Pi, F. et al. Nanomedicine 13 (2016) 1183-1193], to the empty helical branch on the RNA micelles.

No or Low Induction of Pro-Inflammatory Response by pRNA-3WJ Micelles

Figure 7A:
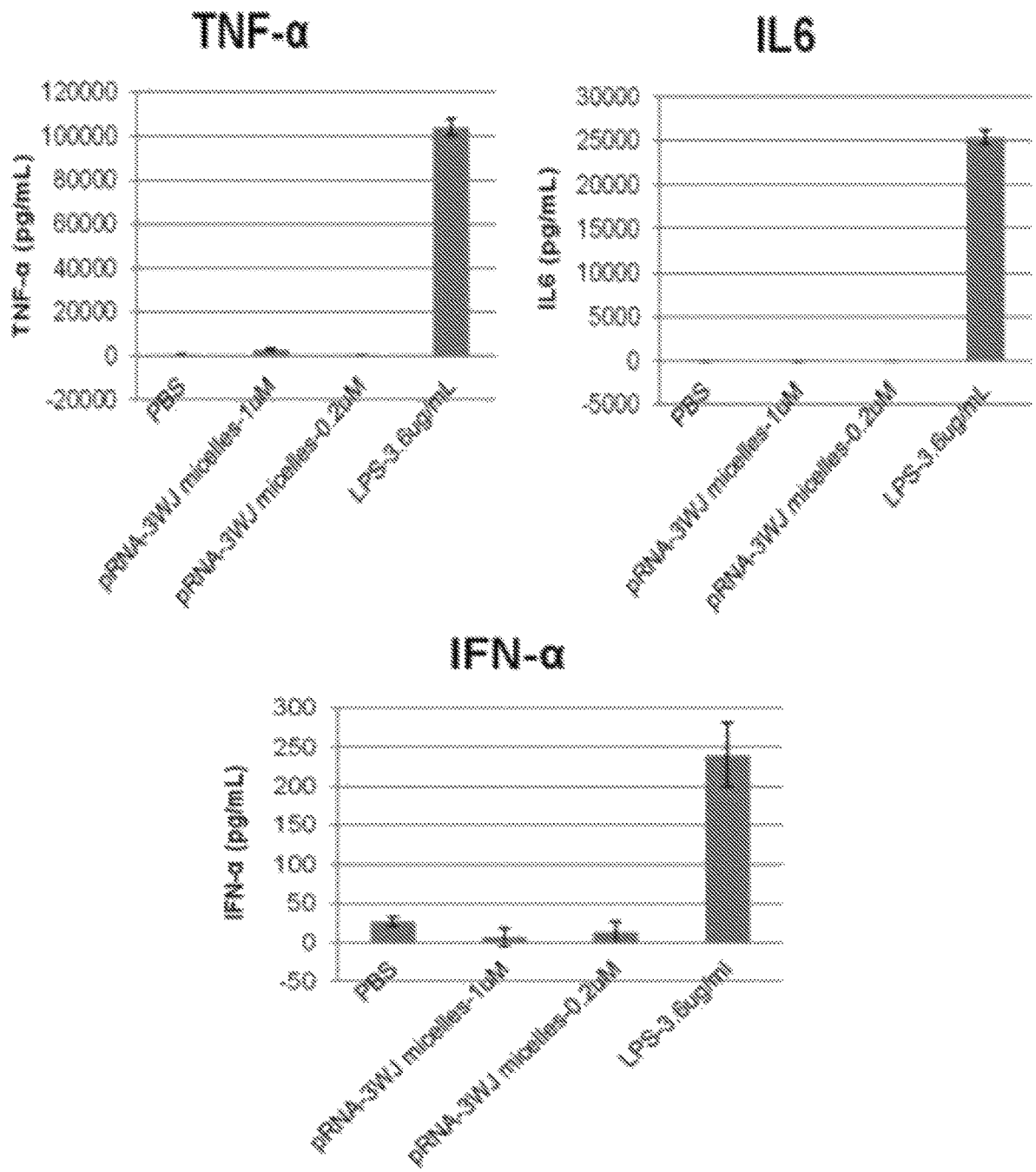
FIGS. 7A and 7C show assay inductions of pro-inflammatory cytokines and chemokines by pRNA-3WJ micelle formulation.
Figure 7B:
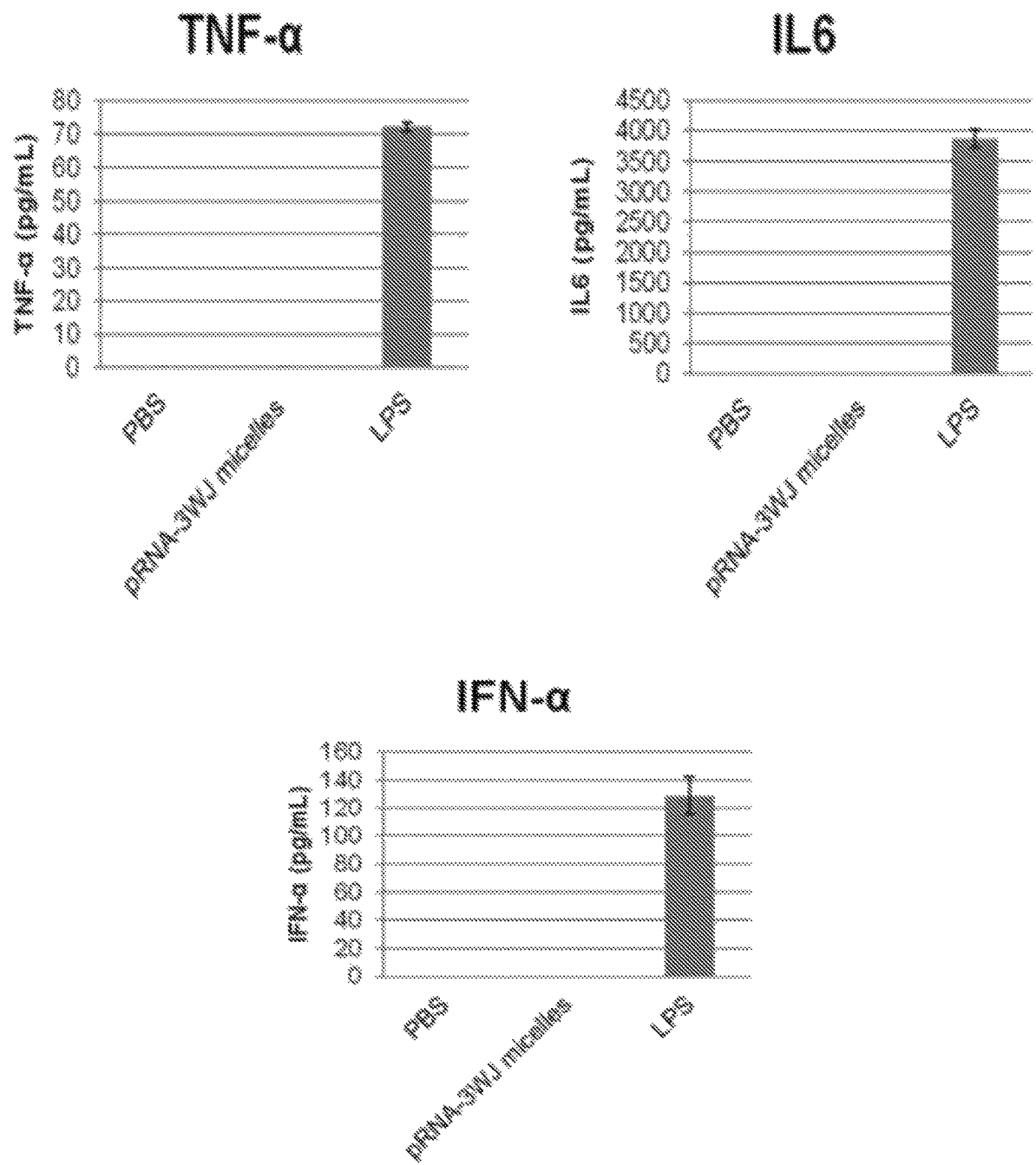
FIG. 7B. In vivo evaluation of the TNF-α, IL6, and IFN-α production after injecting pRNA-3WJ micelles into C57BL/6 mice by ELISA assay.

Pro-inflammatory response could be potentially induced by both RNA component [Guo, S. et al. Mol Ther Nucleic Acids. 2017 9:399-408] and cholesterol component [Tall, A. R. et al. Nat Rev.Immunol. 15 (2015) 104-116] in pRNA-3WJ micelle formulations. In order to address this concern, the production of pro-inflammatory cytokines and chemokines upon pRNA-3WJ micelle treatment were evaluated both in vitro and in vivo. Tumor necrosis factor-α (TNF-α) is a cytokine involved in systemic inflammation and one of the cytokines that make up the acute phase reaction [Jaffer, U. et al. HSR Proc Intensive Care Cardiovasc.Anesth. 2 (2010) 161-175]. Interleukin 6 (IL6) is an interleukin that acts as both a pro-inflammatory cytokine and an anti-inflammatory myokine. IL6 is secreted to stimulate immune response during infection [Scheller, J. et al. Biochim.Biophys Acta 1813 (2011) 878-888]. IFN-α, which belongs to type I interferon, is also a cytokine involved in pro-inflammatory reaction released in response to the presence of viral pathogens. The results in FIG. 7A showed that pRNA-3WJ micelles at high dose (1 μM) and low dose (200 nM) did neither induce IL6 nor IFN-α production compared to LPS positive control while incubating with mouse macrophage-like cells in vitro. TNF-α induction is not detectable at low dose of pRNA-3WJ-micelle treatment but was slightly increased at high dose of RNA micelle treatment. All three cytokines were not induced after in vivo injection of pRNA-3WJ-micelles into immune competent C57BL/6 mice compared to LPS control as shown in FIG. 7B.

Figure 7C:
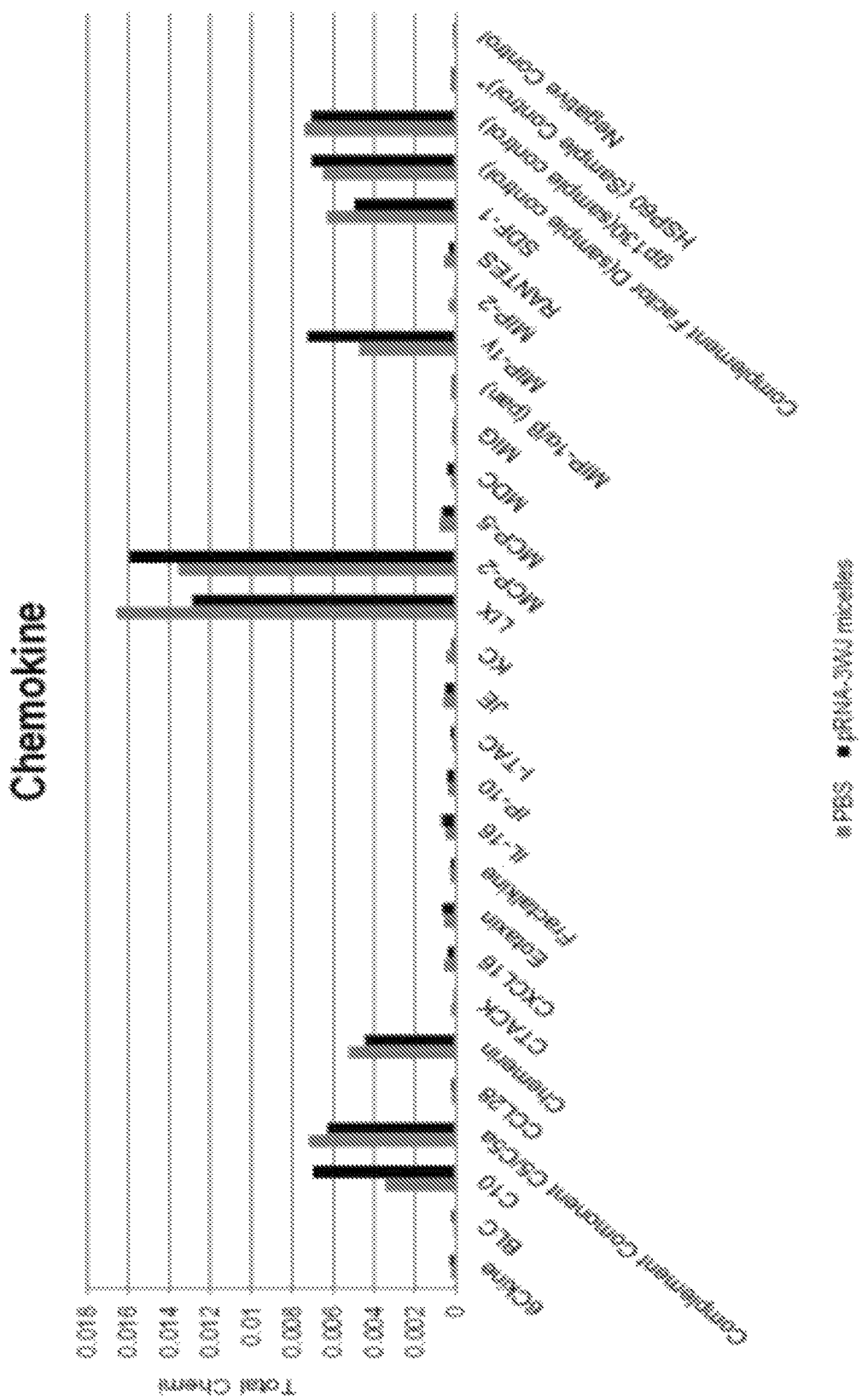
Figure 14:
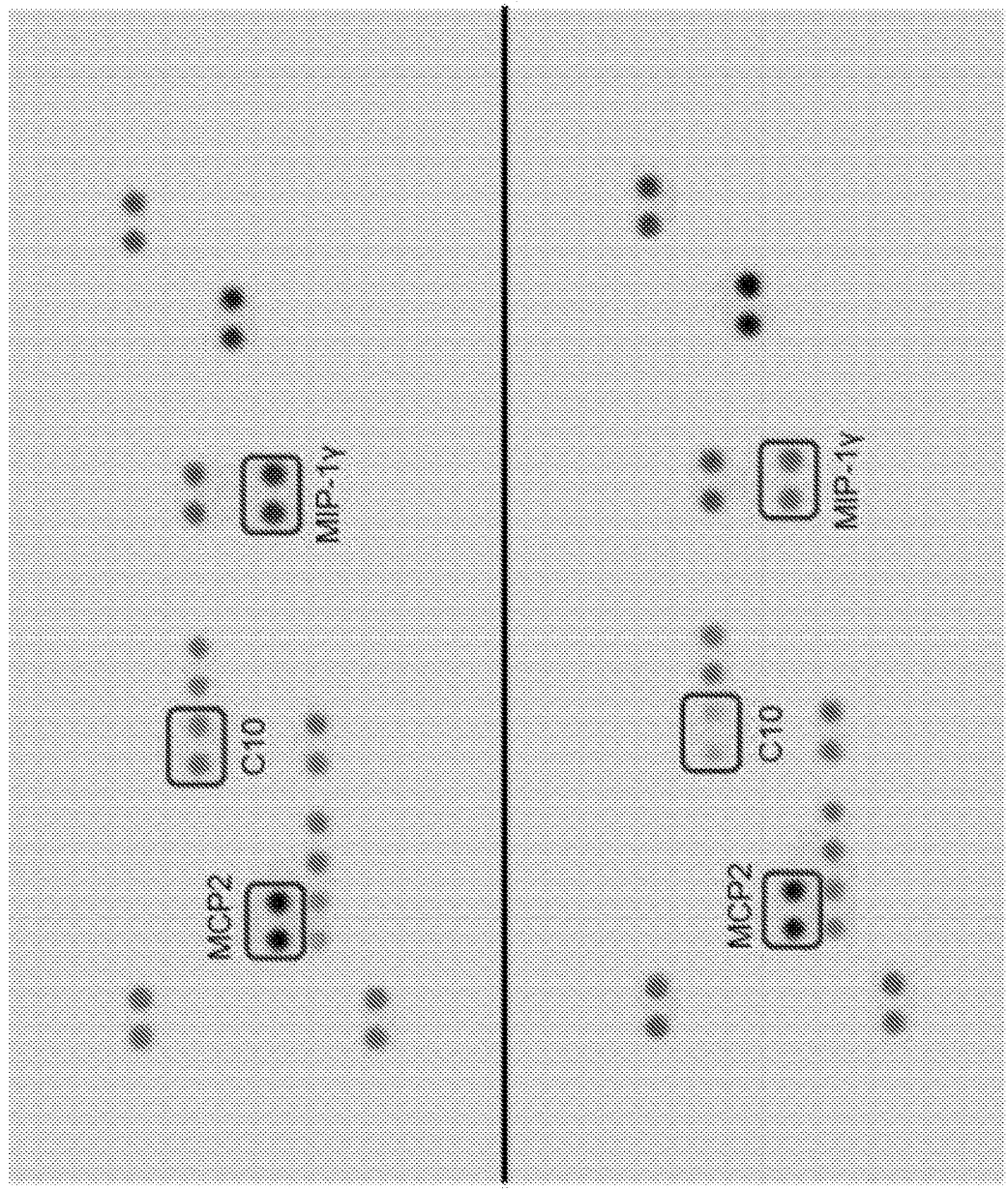
FIG. 14 shows a blot image for pRNA-3WJ micelles treated mouse serum and control PBS treated mouse serum.
Figure 15A:
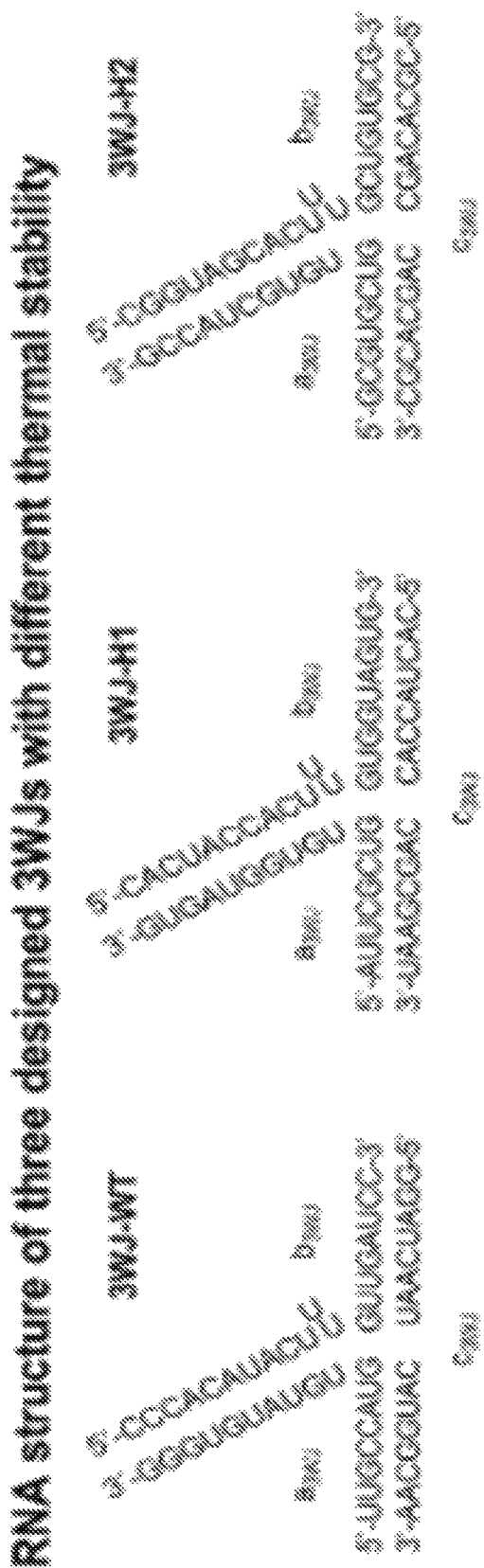
FIGS. 15A to 15D show modular RNA motif shape, size, and orientation for high melting temperature (Tm).
Figure 15B:
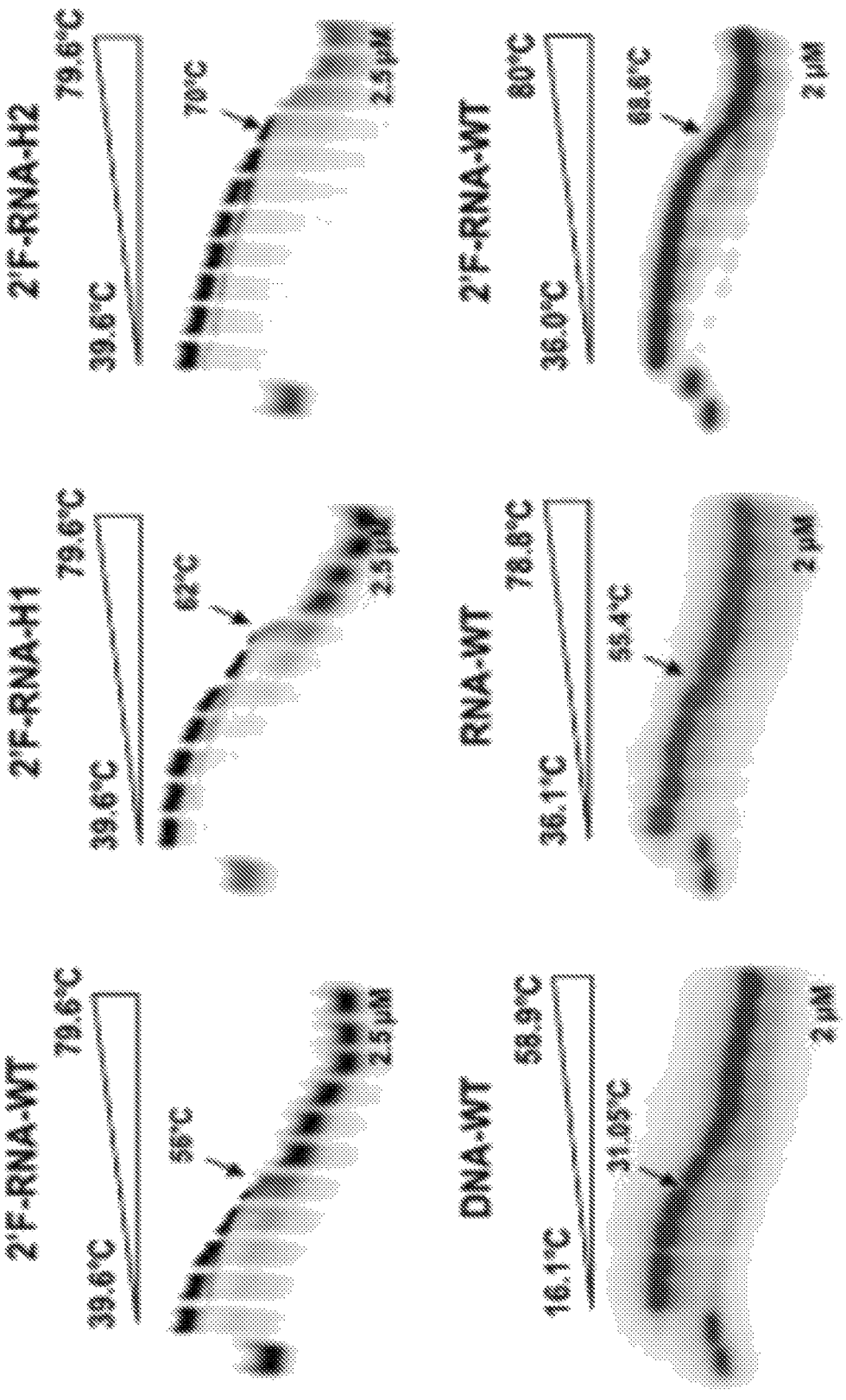
Figure 15C:
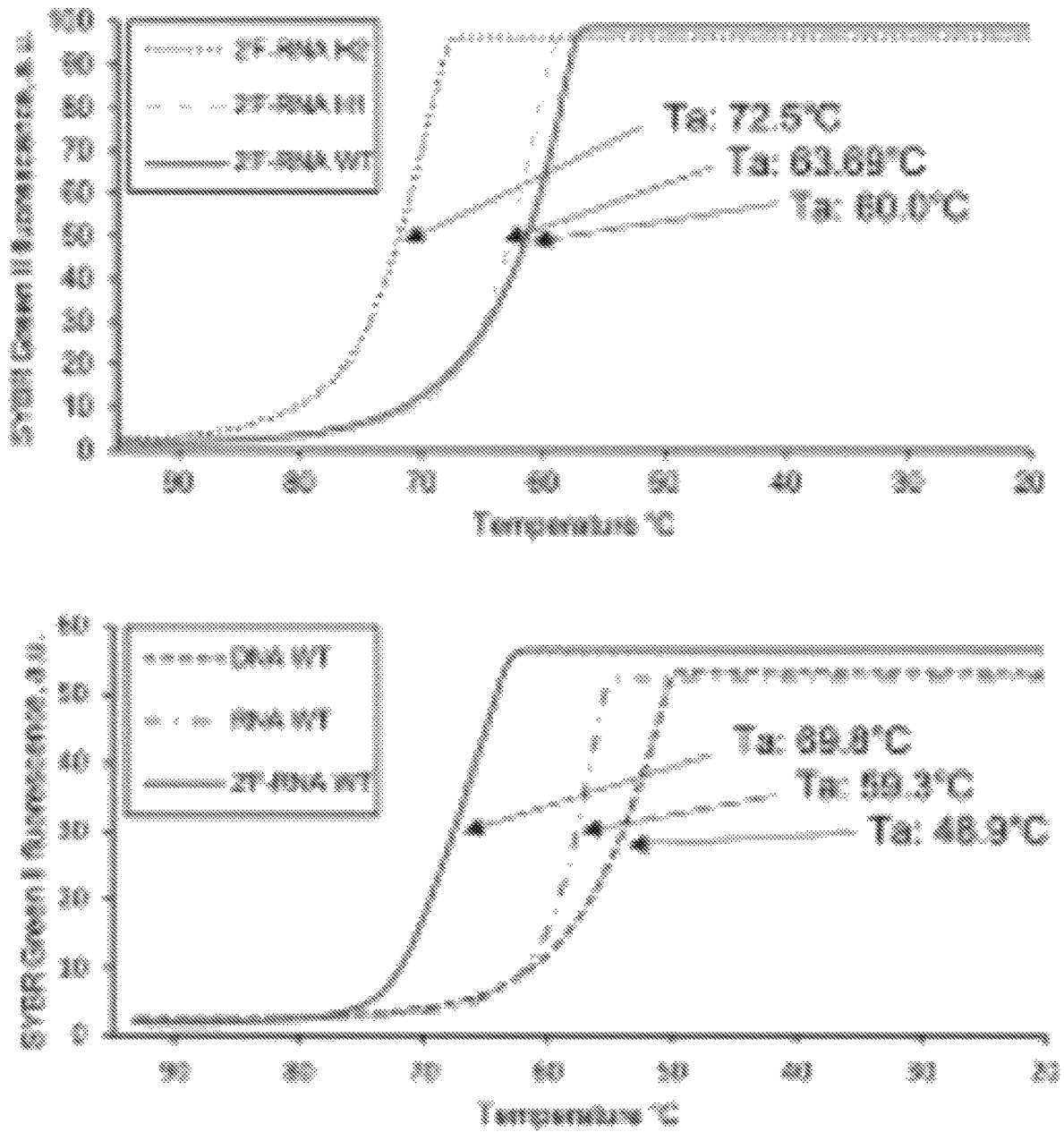
Figure 15D:
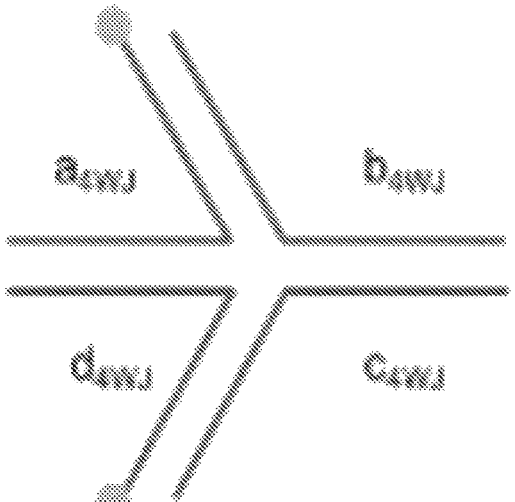
Figure 15D:
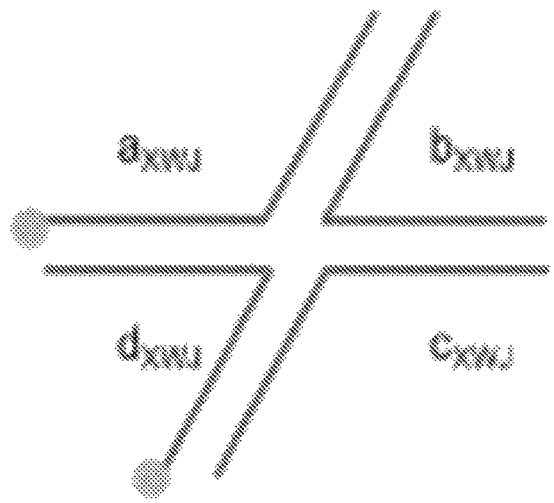
Figure 15D:
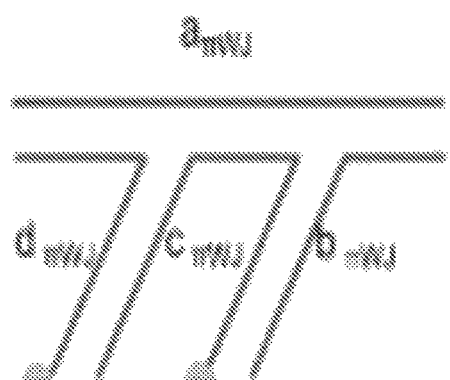

Chemokines are the main proinflammatory mediators [Wang, Z. M. et al. J Biol Chem 275 (2000) 20260-20267; Turner, M. D. et al. Biochim.Biophys Acta 1843 (2014) 2563-2582]. 25 chemokines were profiled for increased production upon pRNA-micelle treatment in vivo. The as shown in FIG. 7C can evidence that pRNA-3WJ micelles did not induce new chemokines compared to PBS group. There were three chemokines, macrophage inflammatory protein-1 gamma (MIP-1γ), Chemokine10 (C10), and Monocyte chemoattractant protein 2 (MCP2) showed elevated induction compared to PBS control as highlighted by red square in the FIG. 14. In summary, pRNA-3WJ micelle formulation induced no or very low pro-inflammatory response.

Figure 13:
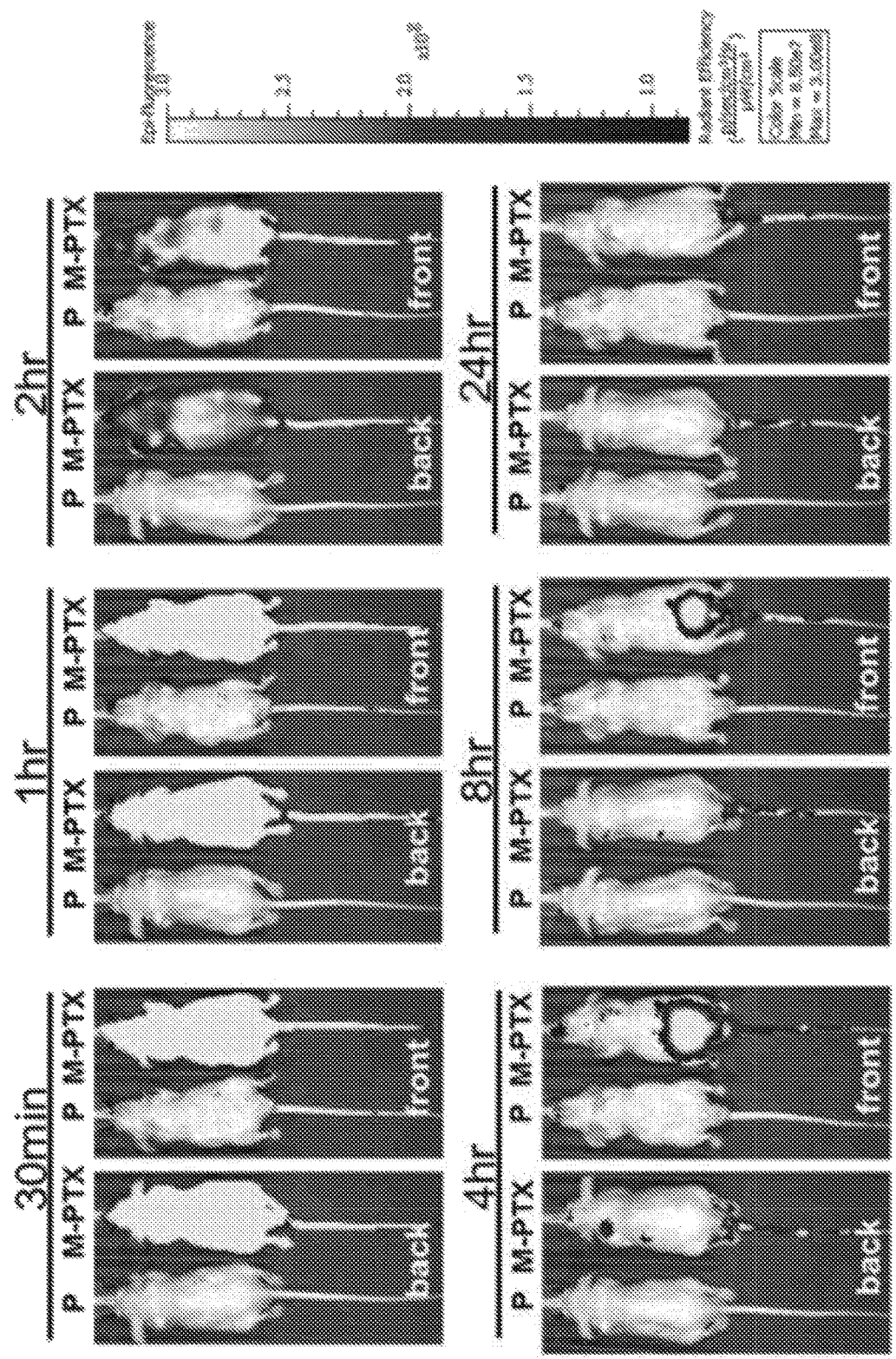
FIG. 13 shows results from a time course of in vivo tumor targeting of pRNA-3WJ-PTX micelle. P: PBS; M-PTX: pRNA-3WJ-PTX micelles.

In conclusion, described in this Example, inter alia, is the design and construction of well-defined pRNA based micelles composed of a hydrophobic lipid core and a hydrophilic pRNA-3WJ corona. Chemotherapy drug Paclitaxel has been loaded into RNA micelles with significantly improved water solubility. It was also demonstrated that the Paclitaxel loaded pRNA micelles exhibit excellent tumor cell binding and internalization as well as effective induction of cytotoxicity effects on tumor cells in vitro. There is also no or very low induction of pro-inflammatory responses upon pRNA-micelle injection. Tumor targeting was achieved upon systemic injection of pRNA micelles into xenografted mouse models without accumulation into normal organs and tissues. FIG. 13 shows a time course of in vivo tumor targeting of pRNA-3WJ-PTX micelle. P: PBS; M-PTX: pRNA-3WJ-PTX micelles.

The branched pRNA-3WJ corona gives incomparable versatility that can be designed and constructed in any desired combination. For example, the multifunctional pRNA-3WJ micelles can be construed by combing targeting, imaging and therapeutic modules all in one nanoparticle. pRNA-3WJ micelles can also simultaneously deliver siRNAs or microRNAs against multiple genes or different location of one gene to generate synergetic effects. In addition, different types of anti-cancer drugs can be loaded onto one pRNA-3WJ micelle to enhance the therapeutic effect or overcome the drug resistance by combination therapy. Therefore, this innovative RNA based micellar nano-delivery platform holds great potential for clinical applications.

Example 2: RNA Nanoparticles, Three-Way Junctions, Multi-Branch or Multi-Arm RNA Nanostructures to Carry Multiple Copies of Paclitaxel and its Derivatives for the Treatment of Cancer and Other Diseases FIGS. 15A to 19 show RNA nanoparticles, three-way junctions, multi-branch or multi-arm RNA nanostructures to carry multiple copies of Paclitaxel and its derivatives for the treatment of cancer and other diseases.

Example 3: RNA-Drug Conjugation

Figure 24A:
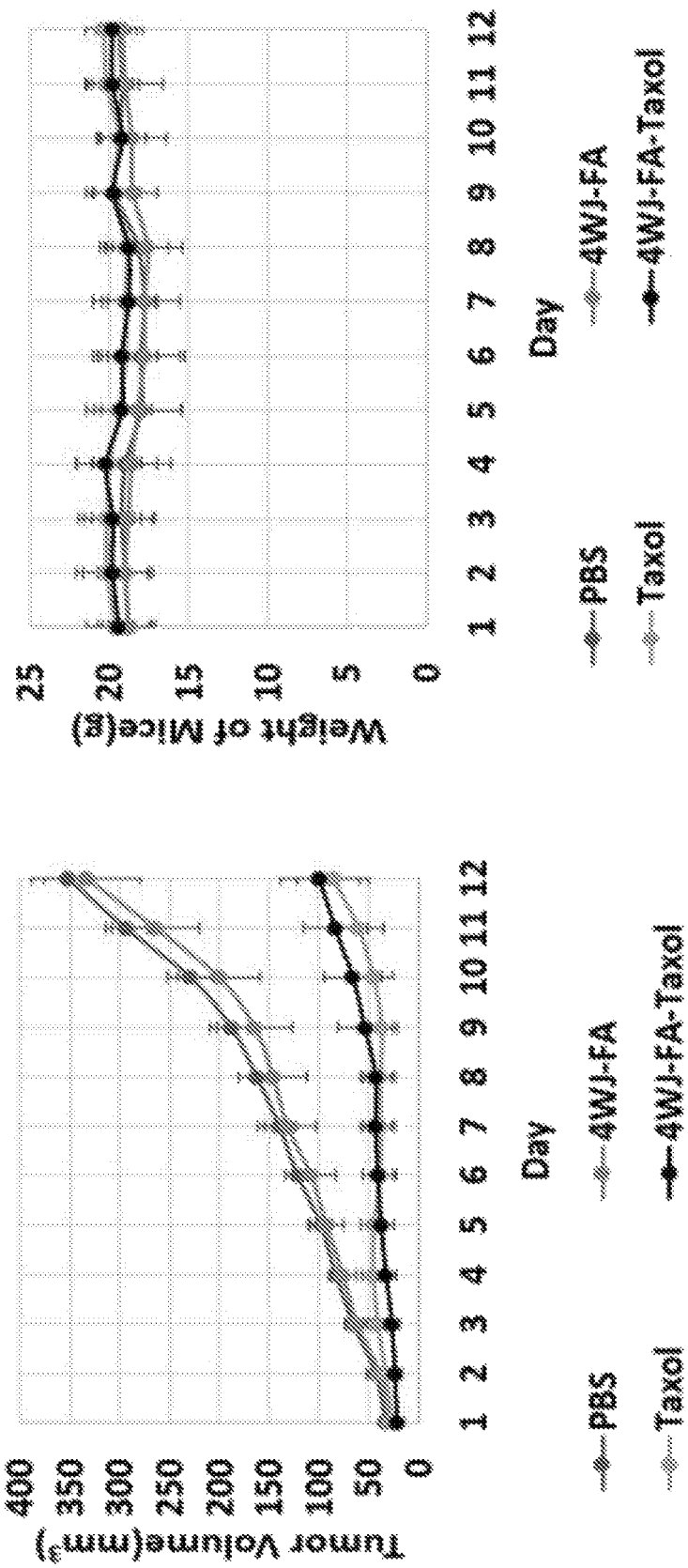
FIGS. 24A and 24B show results of an animal trial to examine therapeutic effects.
Figure 24B:
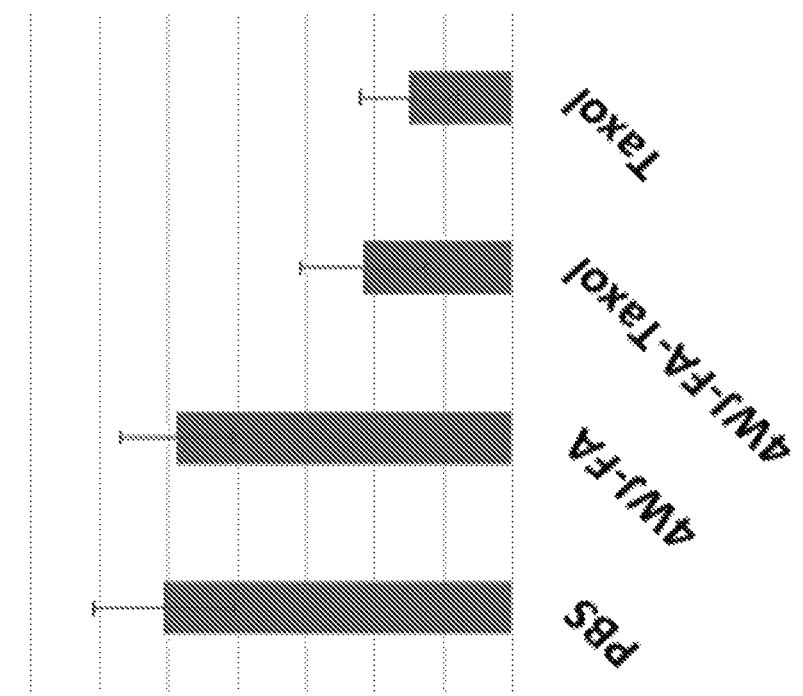
Figure 24B:
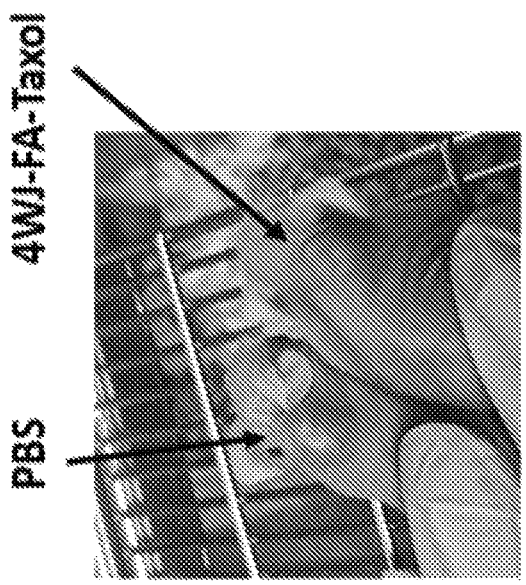
Figure 25A:
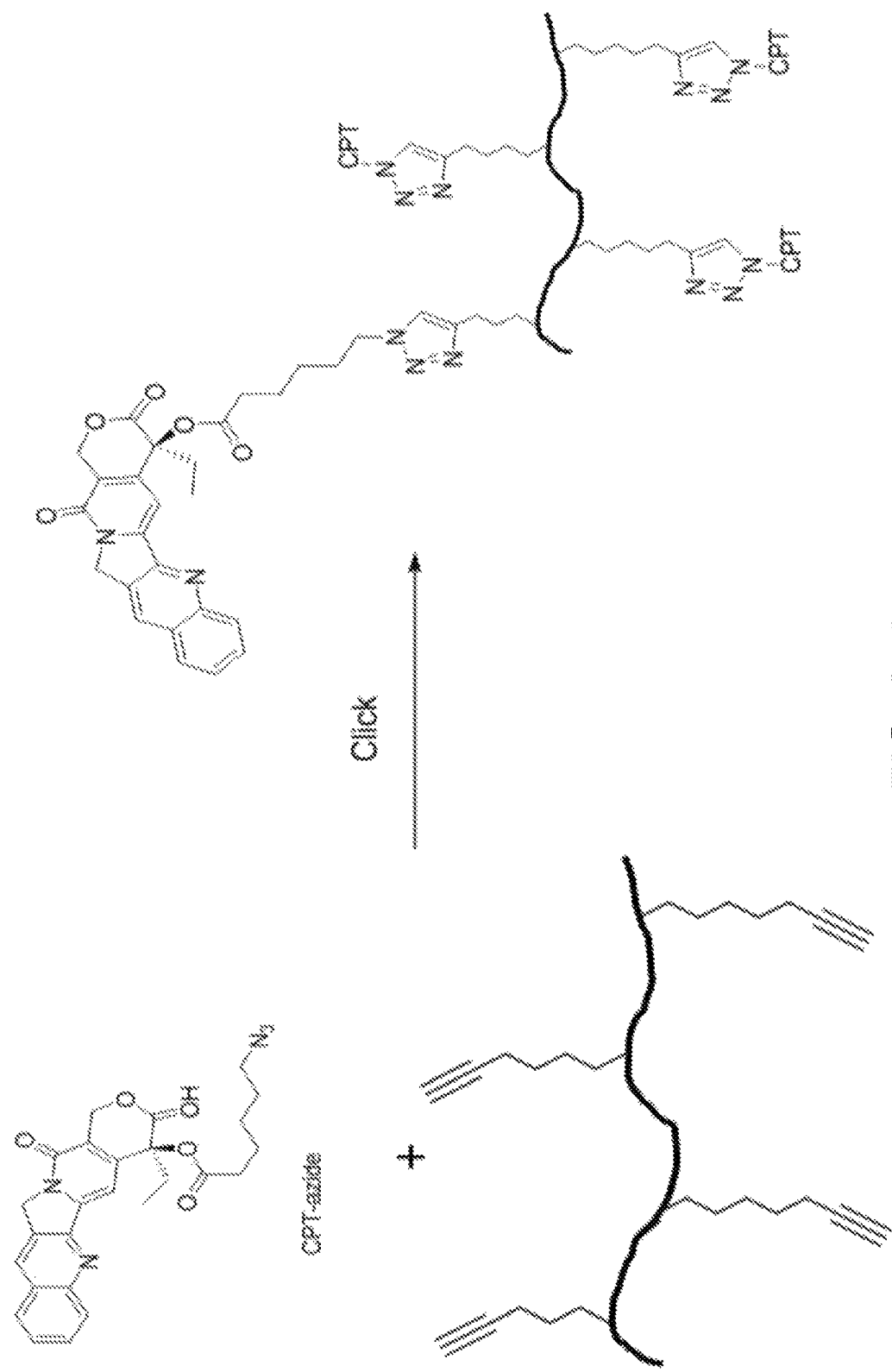
FIGS. 25A to 25C show design and drug conjugation.
Figure 25B:
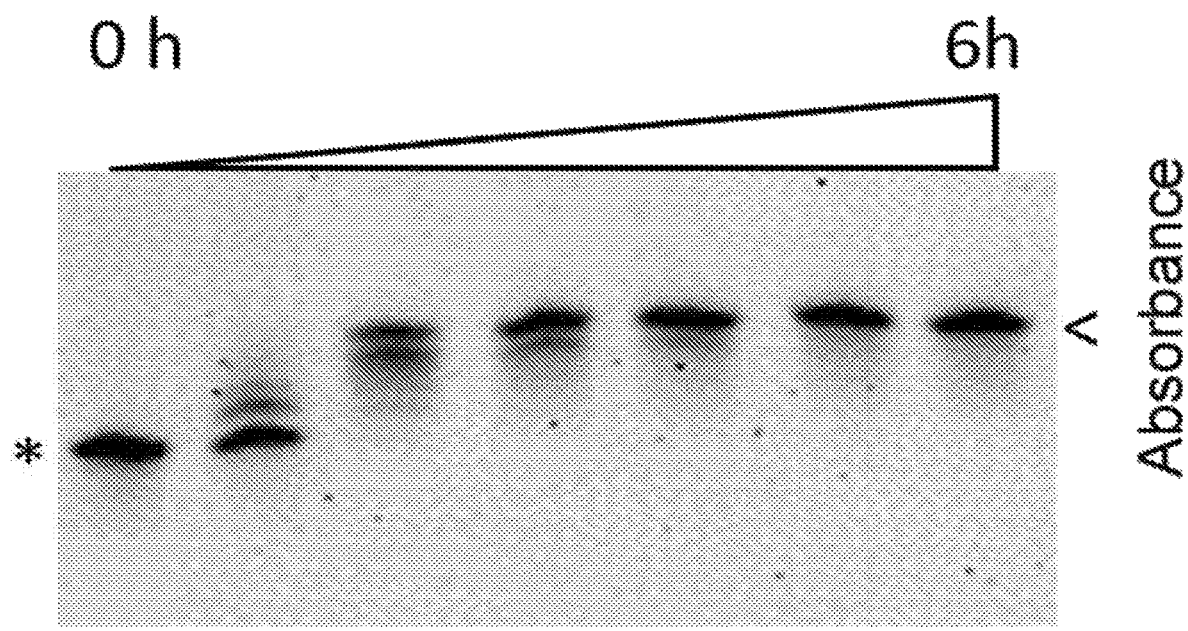
Figure 25C:
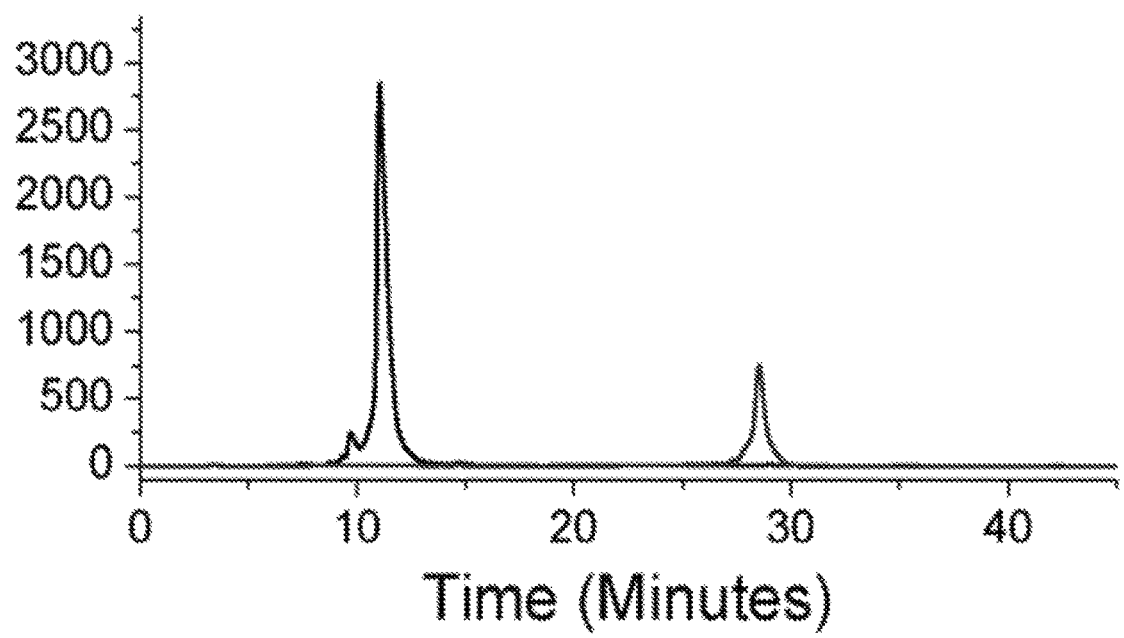
Figure 26A:
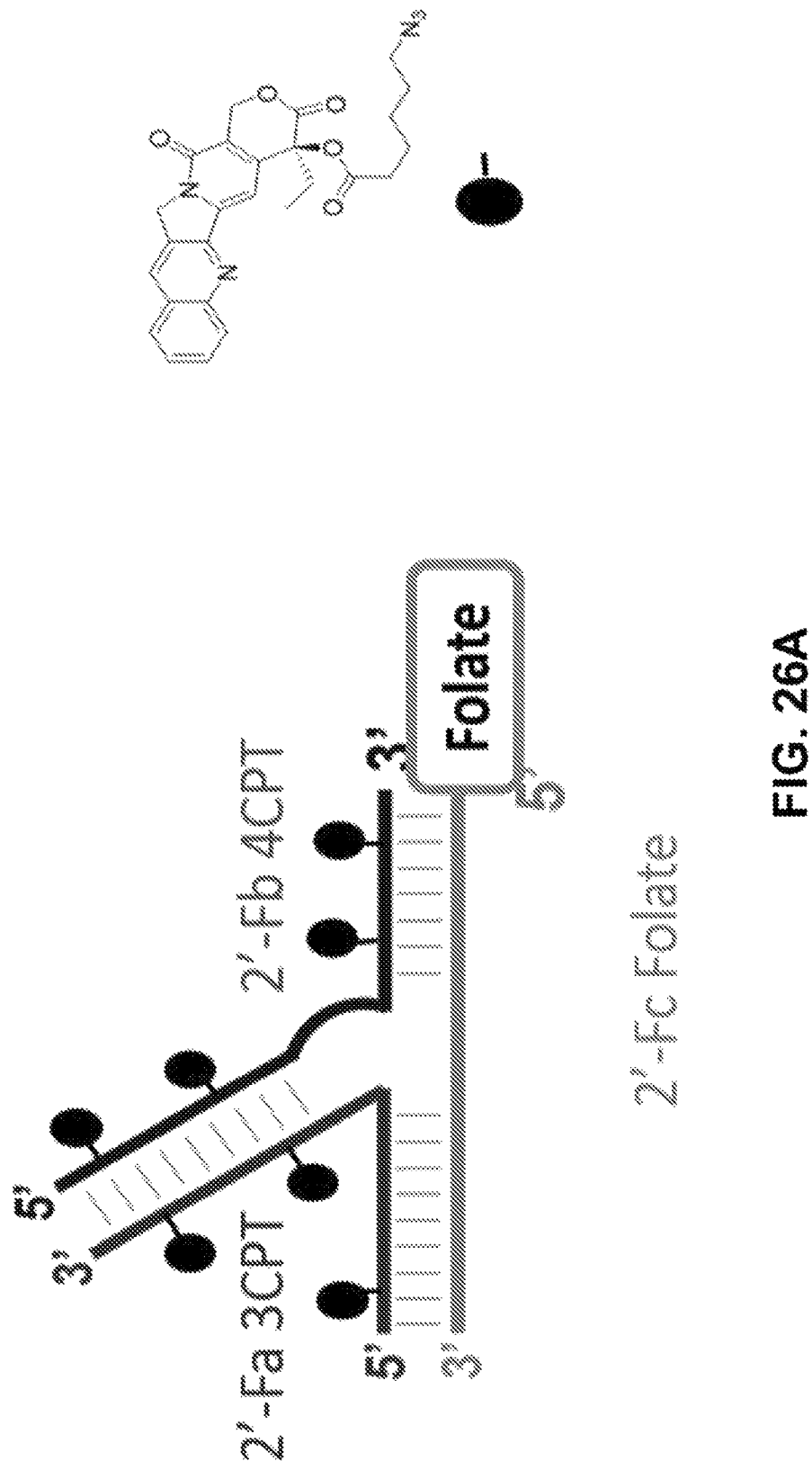
FIGS. 26A to 26C show assembly and in vitro characterization of a 3 arm modular RNA motif loaded with a cargo compound.
Figures 26B, 26C:
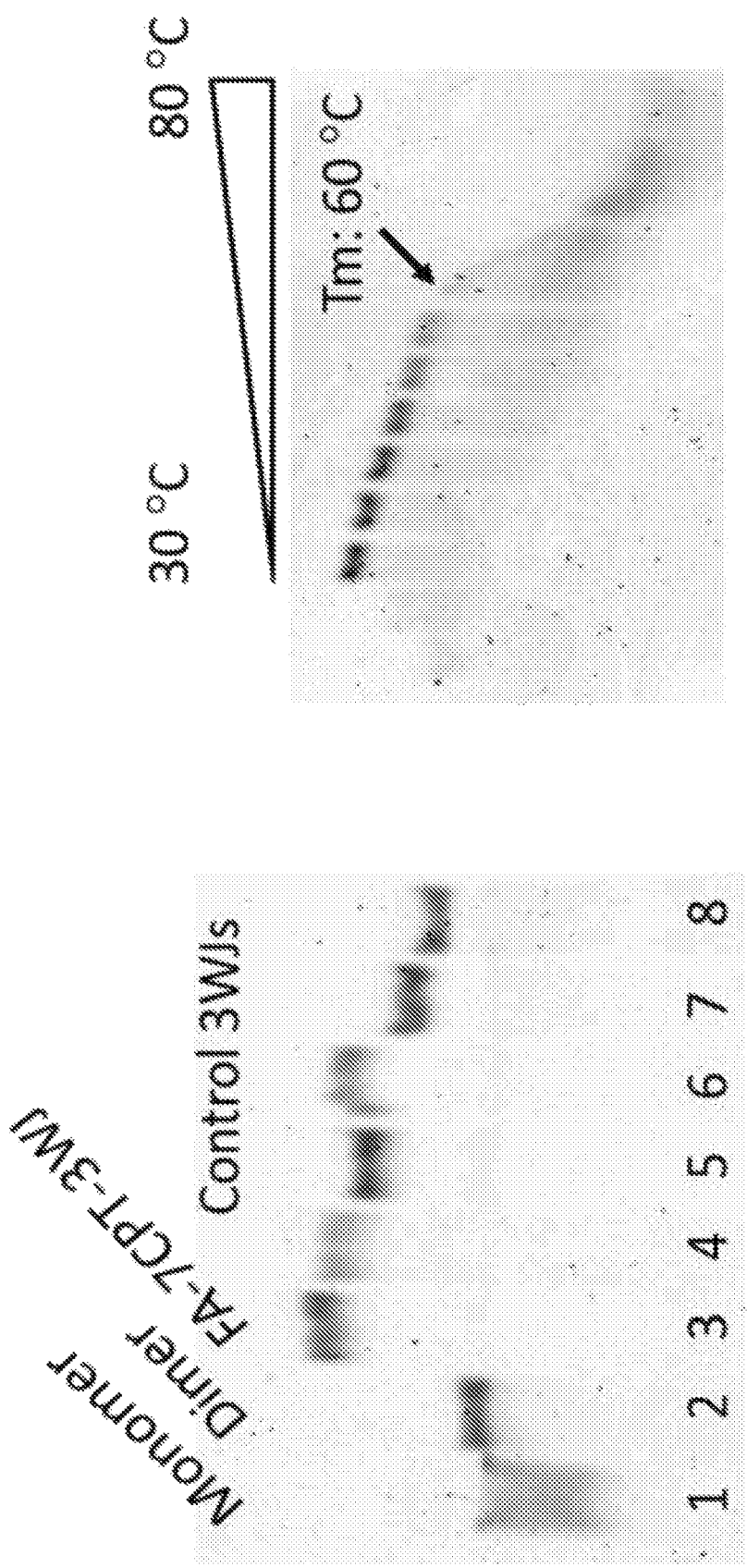
Figure 27:
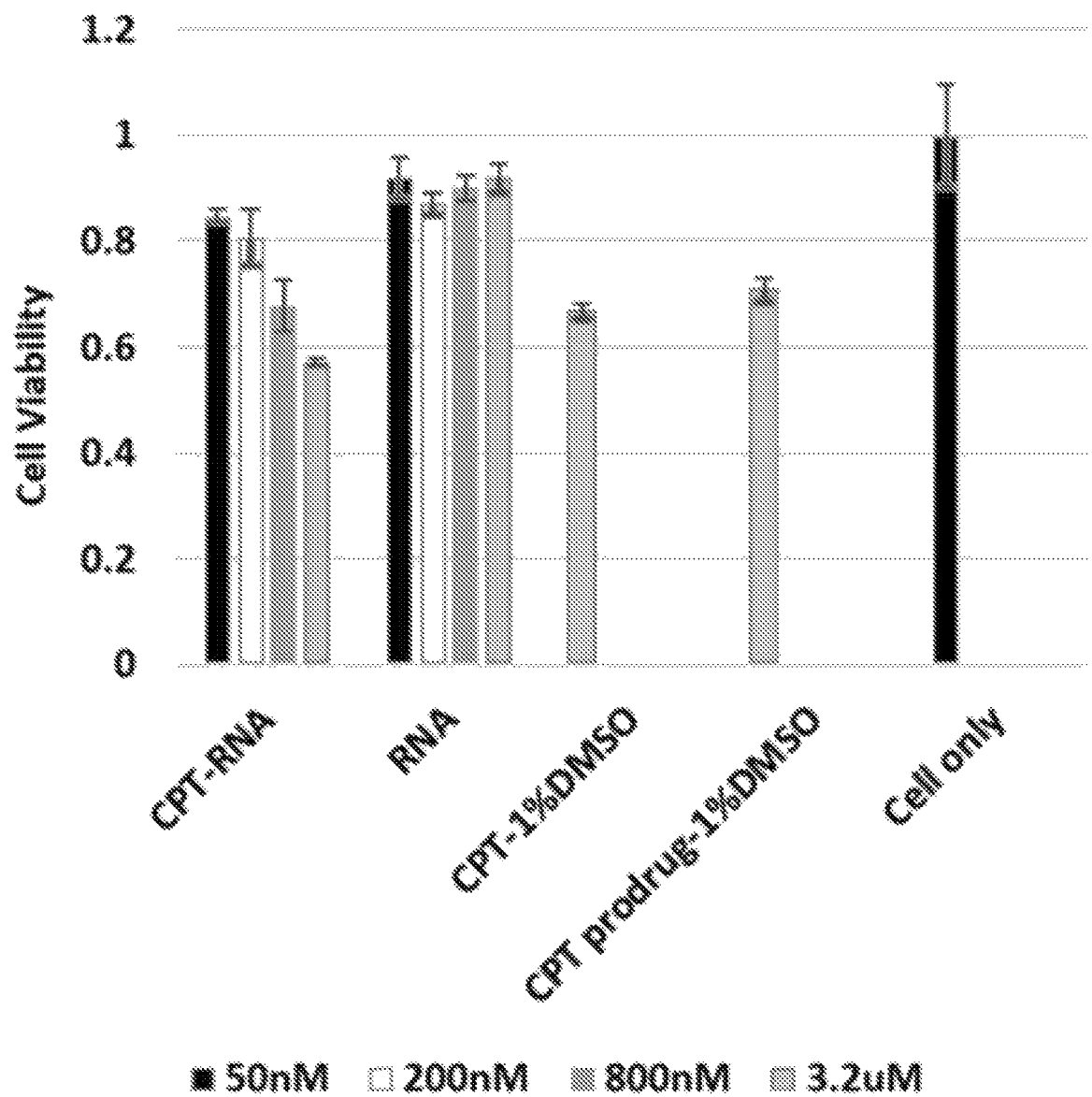
FIG. 27 shows KB cell viability test of RNA with one CPT. 3WJ with one CPT was observed to have slightly greater cytotoxicity compared to CPT only at the same CPT concentration.

FIGS. 20A to 24B show RNA-Taxol sequence design and drug conjugation (FIGS. 20A to 20C), in vitro characterization (FIGS. 21A to 21C), thermal stability (TGGE & qPCR, FIGS. 22A and 22B), in vitro toxicity (FIG. 23), and results of a therapeutic study in an animal trial (FIGS. 24A and 24B).

Figure 28:
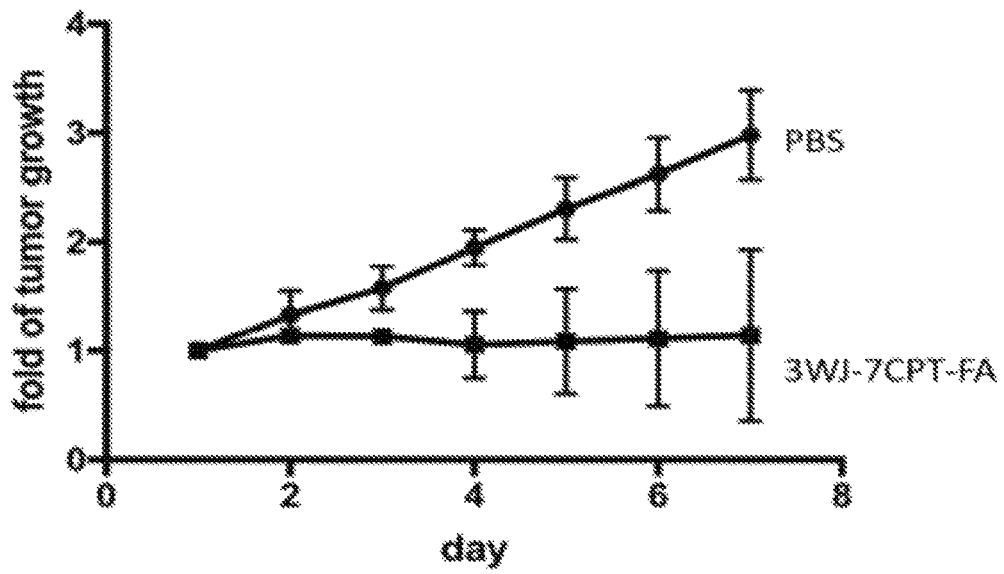
FIG. 28 shows a comparison of tumor growth between 3WJ-FA-7CPT and PBS. 3WJ-FA-CPT was observed to result in much slower tumor growth as compared with negative control groups.

FIGS. 25A to 28 show RNA-CPT design and drug conjugation (FIGS. 25A to 25C), in vitro characterization (assembly gel and TGGE, FIGS. 26A to 26C), in vitro toxicity (FIG. 27), and results of a therapeutic study in an animal trial (FIG. 28).

Example 4: In Silico Design of Thermodynamically Stable Multiply Branched RNA Nanostructures FIGS. 29A to 31B show design (FIGS. 29A and 29B), thermal stability (qPCR & TGGE, FIGS. 30A to 30C), and enzymatic stability (serum stability assay, FIGS. 31A and 31B) of branched 3WJs with different core and helix.

FIGS. 32A to 36B show design (FIGS. 32A to 32C), in vitro characterization (gel electrophoresis and DLS, FIGS. 33A to 33C), thermal stability (qPCR and TGGE, FIGS. 34A and 34B), enzymatic stability (serum stability assay, FIGS. 35A to 35C), and shielding property (cell binding assay, FIGS. 36A and 36B) of branched 3WJs Design:

Native RNA structural elements, such as the phi29 3WJ motif have evolved over centuries to serve a specific purpose which can be a structural scaffold or structurally dynamic element for a biological function. For drug delivery, a nanoscale particle of tunable size and shape with a high structural/thermodynamic stability and the capability to carry a high density of cargo to a specific target in the body without inducing an immune response or toxicity is desirable.

To achieve this goal, a platform was designed that allows the formation of highly stable, 3-dimensional RNA nanostructures that assemble from 3-9 individual synthetic oligonucleotides of 16-120 nt in length. The oligomers can be synthesized using solid phase synthesis which allows site-specific modifications and thus incorporation of modified nucleotides for 1) increase of enzymatic stability, 2) increase of thermodynamic stability, or 3) increase of sites for high density cargo attachment. Each oligomer is synthesized according to its specific functional requirements and assembled into the desired nanostructure using self-assembly at equimolar concentrations of all component strands.

To achieve efficient self-assembly from a large number of individual strands (3-9), design of the oligomer sequences needs to be done with a few concepts in mind: i) the interlocking domains need to have high thermodynamic stability, ii) the sequences need to be specific, iii) the oligomers should not have strong internal structure, and iv) cargo molecules should have sufficient spacing from the core and one other.

The stability of the interlocking domains determines the stability of the final 3D structure. As each strand may contain a different module (therapeutics, targeting, imaging) of the particle it is essential that the nanostructure remains intact in order for all modules to be delivered. While this could be achieved on a linear double stranded oligomer, use of higher order structures provides benefits such as control of particle size and shape which affect biodistribution and EPR effects, protection of cargo from exposure during delivery which allows delivery of hydrophobic molecules, and reduction of enzymatic activity due to of steric hindrance. In order to achieve higher order structure, oligomers are split into at least two interlocking domains that may or may not be spaced by a structural link. In our branched nanostructures, by example, each oligomer is split into three domains, a 5'DA, a core bulge, and a 3'DA (FIG. 47C). The number of strands that make up the nanostructure is equivalent to the number of DA domains in the structure. Furthermore, the number of DA domains is equivalent to the number of independent sequences in the nanostructure. Consequently, the sequence of any 3'DA is the reverse complement sequence of one specific 5'DA and vice versa. An 8-branch nanostructure is then defined by 8 independent DA domains that interlock with their reverse complements via specific design of the synthesized oligomers. Oligomers are then designed in two types: extending oligomers and terminating oligomers. Oligomers can be fully identified by defining the DA number (1, 2, . . . , 9) and whether the sequence is normal or its reverse complement (rev). Extending oligomers generally connect consecutive DA domains, e.g. 12rev, 23rev, 34rev, while terminating oligomers close the cycle by connecting the last DA with the reverse complement of the first DA, e.g. 41rev, in this case making a 4-DA nanostructure in a tetrahedral arrangement (FIGS. 47A-B). Similarly, 12rev, 23rev, 34rev, 45rev, 56rev, plus 61rev can form a 6-DA nanostructure, with at equal spacing of the DA domains can assemble in an octahedral arrangement around the nanoparticle core (FIG. 47A).

Computation-Guided Design of Spherical Sequences:

As per the above examples, the 6-DA structure will use some of the same sequences as the 4-DA structure (12rev, 23rev, 34rev). Thus, in order to make a series of 3-9 DA nanostructures, 8 extending and 7 terminating strands are required. Computationally, this requires identification of thermodynamically stable sequences for 9 DA domains of pre-defined length (number of nucleotides), determination of desired core bulge linking nucleotides, and optimizing sequences to achieve minimal self- and cross complementarity to achieve efficient self-assembly of thermodynamically stable nanostructures.

The flow of the algorithm is outlined in FIG. 48. In the first step, the user defines the following input parameters: 1) number of DA domains, 2) length of DA domains, 3) identity of nucleotides in the linking domains, 4) range of melting temperatures (Tm) for DA domains, 5) range of GC content allowed, 6) percentage of self-complementarity allowed, 7) percentage of cross-complementarity allowed.

The algorithm then generates a DA sequence using random number generation and tests whether the sequence falls within the desired GC content and Tm range. If the sequence falls within range, it is saved, and the process is repeated until 25×# of DA sequences have been determined. Once a sufficient # of sequences have been identified they are tested for self-complementarity. Sequences that show low self-complementarity are then sorted based on their degree of cross-complementarity with other saved DA sequences. The sequences with the lowest overall complementarity are then used to compute sequences of the nanostructure strands according to (seq1+UG$_{link}$+seq2$_{RevComp}$) for extending oligos and (seq2+UG$_{link}$+seq1$_{RevComp}$) for terminating oligos. Full length oligomer strands are retested for self and cross-complementarity to ensure the reverse complements do not negatively affect the overall specificity of the sequences. If nanostructure sequences pass the QC tests they are converted to RNA letter code and saved to file, otherwise the routine repeats until a suitable set of oligomers is found.

Figure 37A:
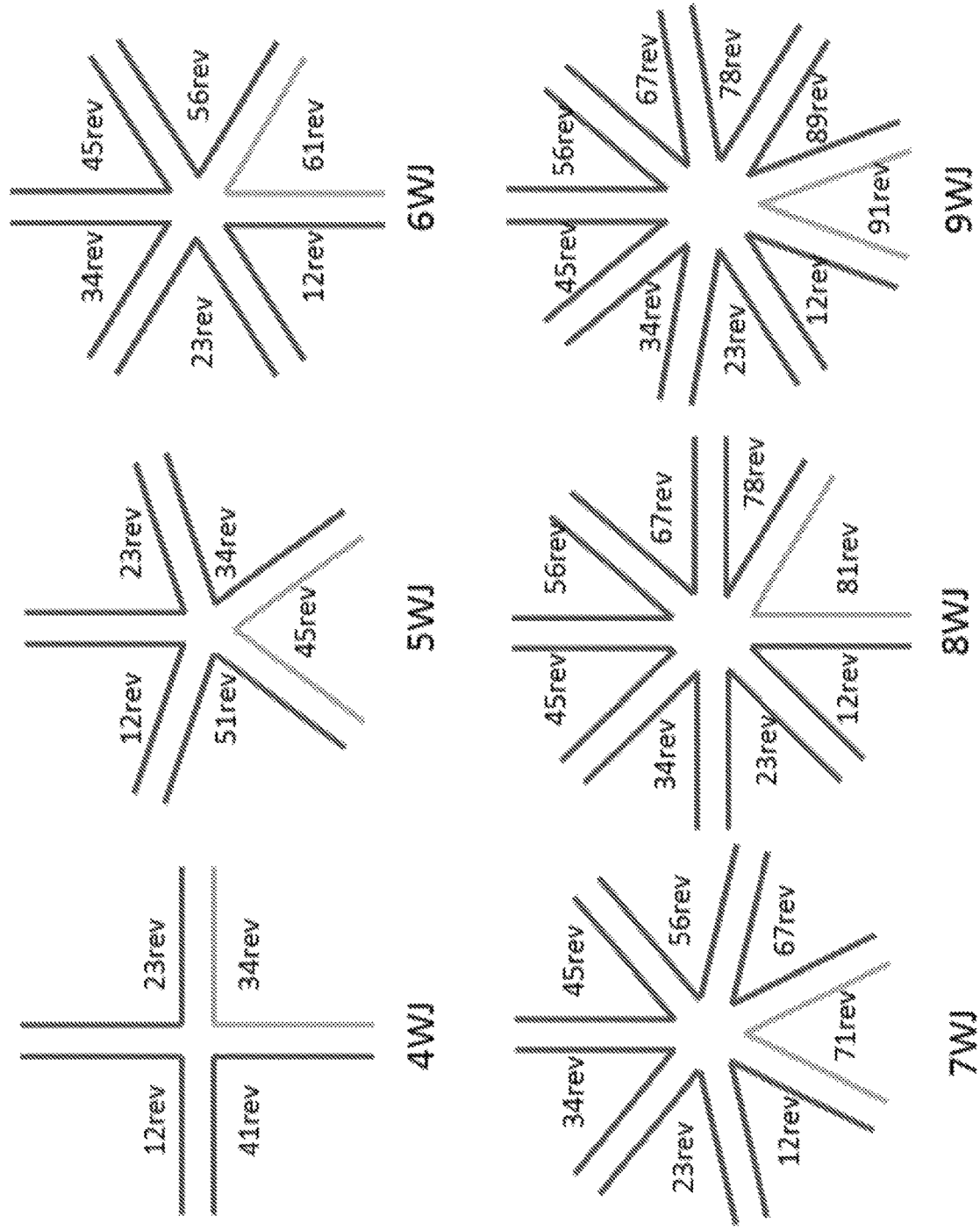
Figure 37C:
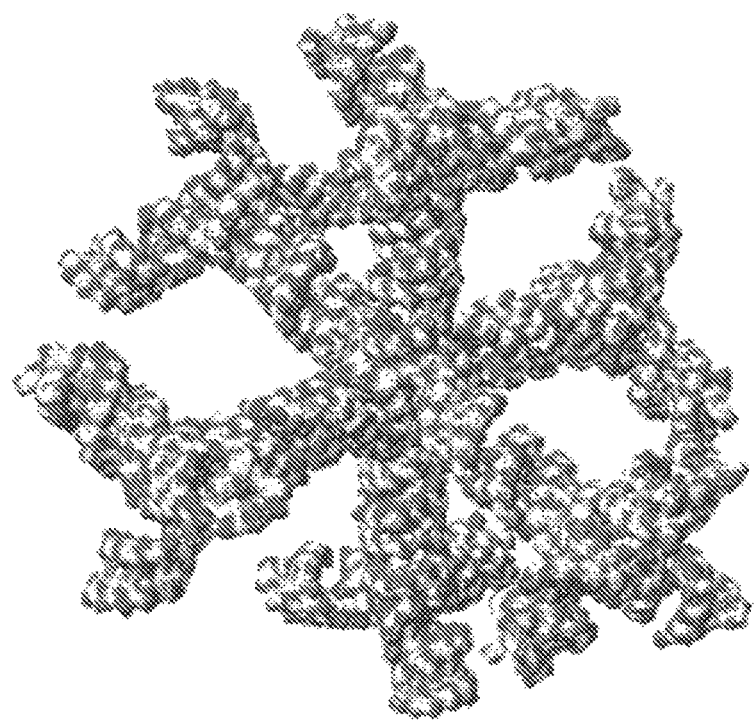
Figure 38A:
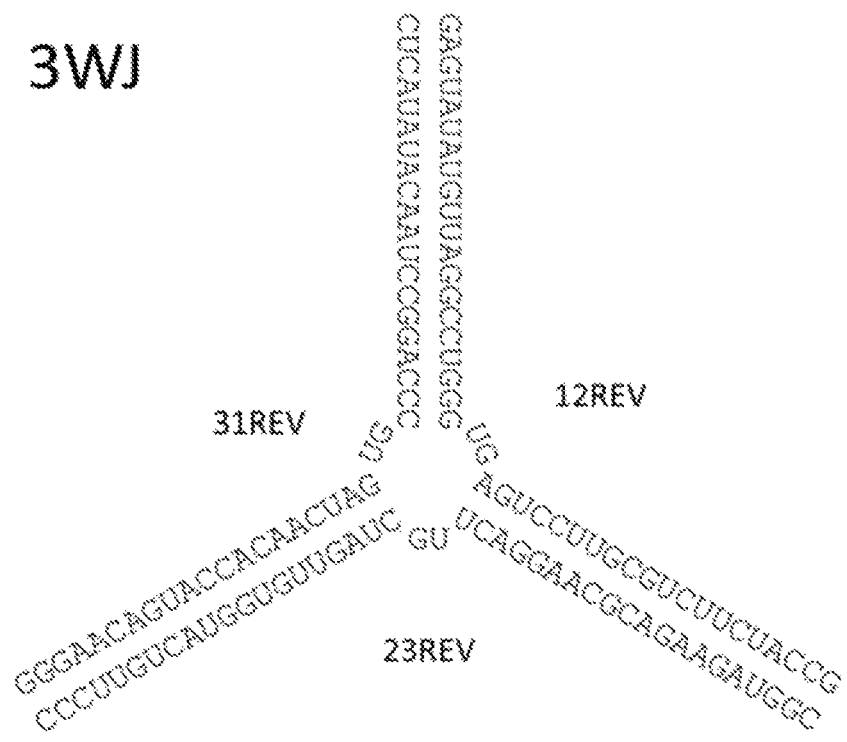
FIGS. 38A to 38G show 2D structures of 3WJ (FIG. 38A), 4WJ (FIG. 38B), 5WJ (FIG. 38C), 6WJ (FIG. 38D), 7WJ (FIG. 38E), 8WJ (FIG. 38F), and 9WJ (FIG. 38G) modular RNA motifs showing example synthetic RNA oligonucleotide sequences.
Figure 38B:
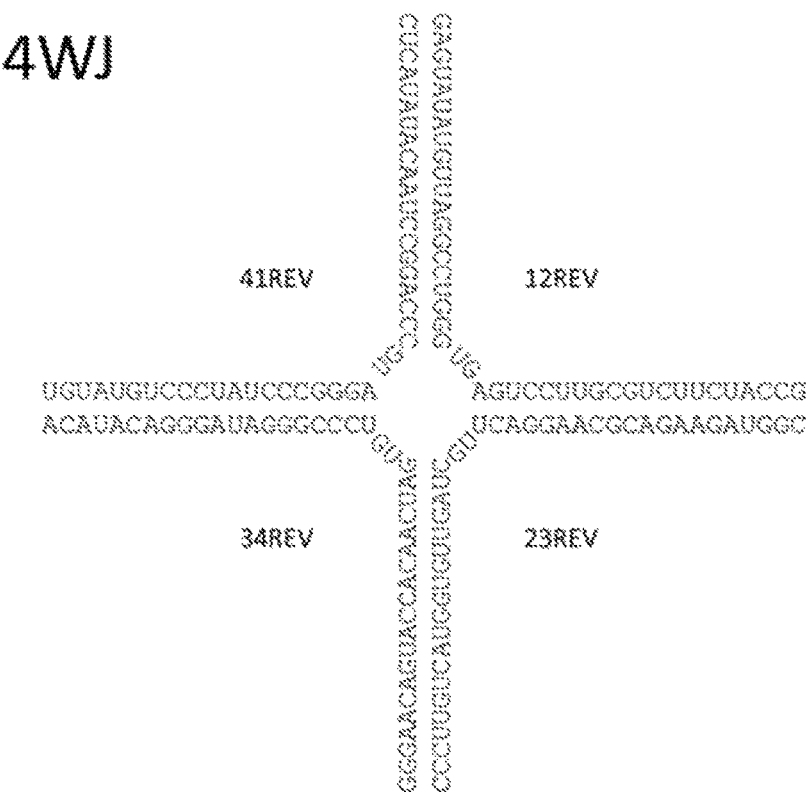
Figure 38C:
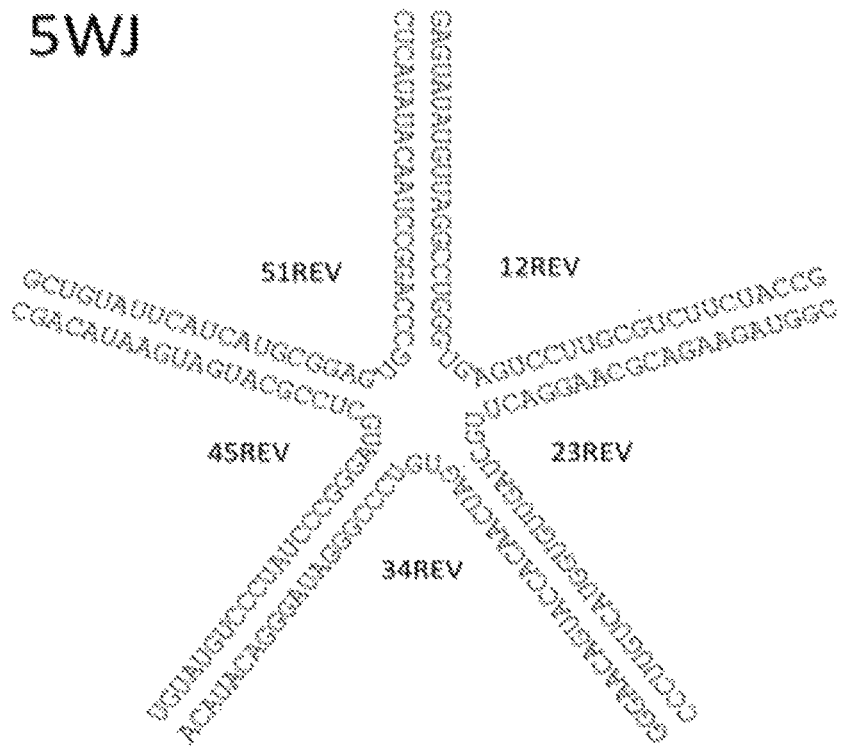
Figure 38D:
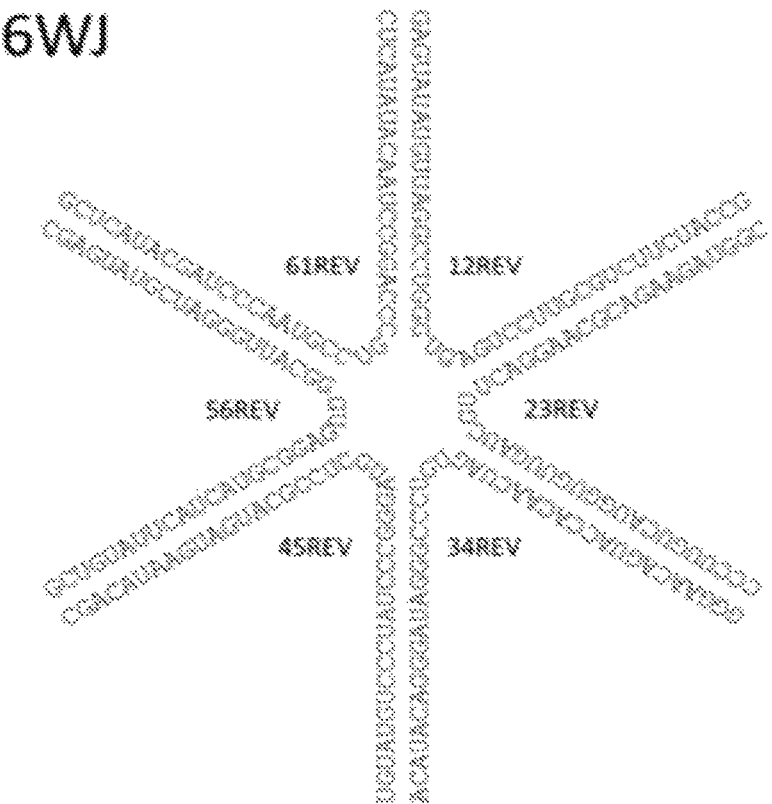
Figure 38E:
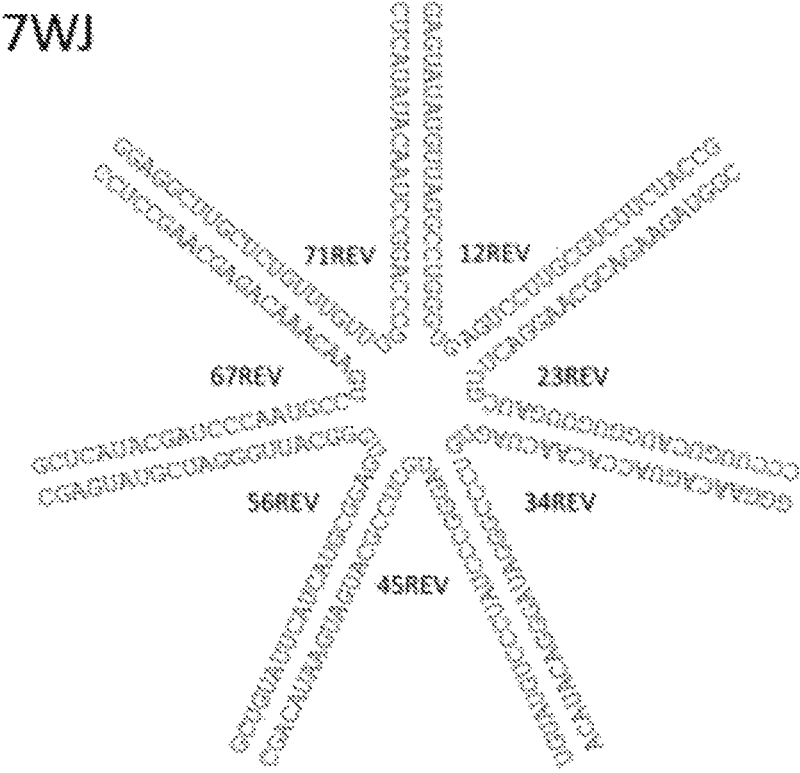
Figure 38F:
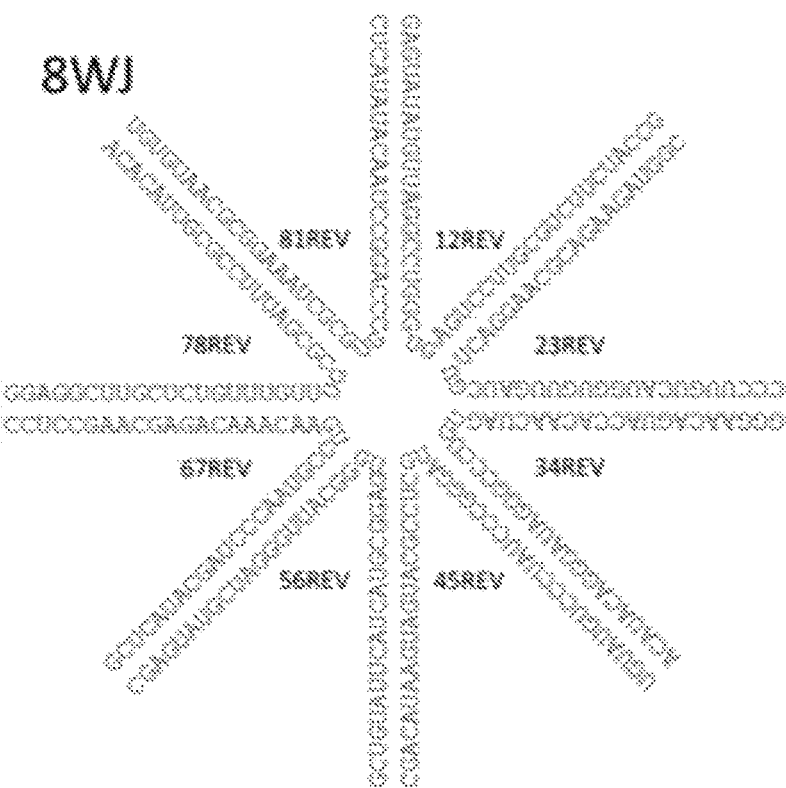
Figure 38G:
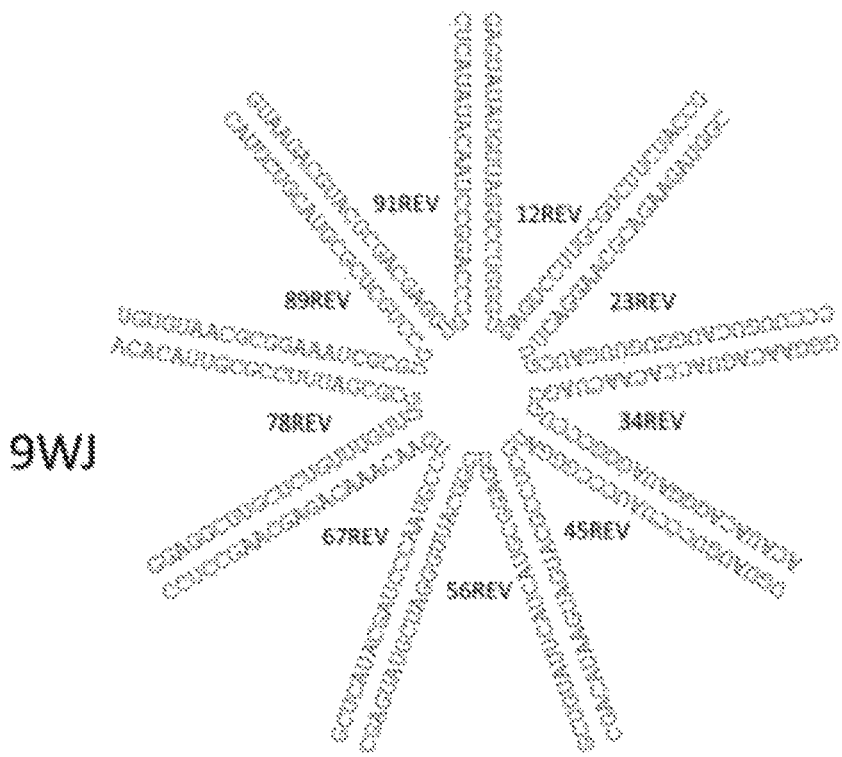

FIGS. 37A-37C show design and construction of branched 3WJ-based modular RNA motifs and variants having different arm numbers. FIG. 37A. Different higher order junctions (cores) used as the building block of modular RNA motifs. FIG. 37B. Nucleotide sequences for synthetic modular RNA motifs. FIG. 37C. 3D structure of one of modular RNA motif using 6WJ as core and 4WJ as an arm (or branch).

FIGS. 38A to 38G show 2D structures of 3WJ (FIG. 38A), 4WJ (FIG. 38B), 5WJ (FIG. 38C), 6WJ (FIG. 38D), 7WJ (FIG. 38E), 8WJ (FIG. 38F), and 9WJ (FIG. 38G) modular RNA motifs showing example synthetic RNA oligonucleotide sequences.

FIGS. 39A to 39C show thermal stability of various modular RNA motifs. FIG. 39A. qPCR showing annealing profile. FIG. 39B. TGGE showing melting profile. FIG. 39C. Comparison of Tm for modular RNA motif annealing and melting.

FIGS. 40A and 40B show in vitro characterization of branched 3WJ based modular RNA motifs. FIG. 40A. Size comparison gel: 2% agarose gel showing the assembly of 4-6WJ (from left to right: ladder, phi29-3WJ, monomer, dimer, trimer, 4WJ, 5WJ, 6WJ). FIG. 40B. Size distribution of 4-6WJ measured by dynamic light scattering (DLS).

Exemplary Sequences produced using the method described in this Example.

12REV
GACUAUAUGUUAGGCCUGGGUGAGUCCUUGCGUCUUCUACCG (SEQ ID NO: 1).

23REV
CGGUAGAAGACGCAAGGACUUGCUAGUUGUGGUACUGUUCCC (SEQ ID NO: 2).

31REV
GGGAACAGUACCACAACUAGUGCCCAGGCCUAACAUAUACUC (SEQ ID NO: 3).

34REV
GGGAACAGUACCACAACUAGUGUCCCGGGAUAGGGACAUACA (SEQ ID NO: 4).

41REV
UGUAUGUCCCUAUCCCGGGAUGCCCAGGCCUAACAUAUACUC (SEQ ID NO: 5).

45REV
UGUAUGUCCCUAUCCCGGGAUGCUCCGCAUGAUGAAUACAGC (SEQ ID NO: 6).

51REV
GCUGUAUUCAUCAUGCGGAGUGCCCAGGCCUAACAUAUACUC (SEQ ID NO: 7).

56REV
GCUGUAUUCAUCAUGCGGAGUGGGCAUUGGGAUCGUAUGAGC (SEQ ID NO: 8).

61REV
GCUCAUACGAUCCCAAUGCCUGCCCAGGCCUAACAUAUACUC (SEQ ID NO: 9).

67REV
GCUCAUACGAUCCCAAUGCCUGAACAAACAGAGCAAGCCUCC (SEQ ID NO: 10).

71REV
GGAGGCUUGCUCUGUUUGUUUGCCCAGGCCUAACAUAUACUC (SEQ ID NO: 11).

78REV
GGAGGCUUGCUCUGUUUGUUUGCGCGAUUUCCGCGUUACACA (SEQ ID NO: 12).

81REV
UGUGUAACGCGGAAAUCGCGUGCCCAGGCCUAACAUAUACUC (SEQ ID NO: 13).

89REV
UGUGUAACGCGGAAAUCGCGUGCCUGCUCGCGUACGUCUUAC (SEQ ID NO: 14).

91REV
GUAAGACGUACGCGACGAGGUGCCCAGGCCUAACAUAUACUC (SEQ ID NO: 15).

a3WJ
UUGCCAUGUGUAUGUGGG (SEQ ID NO: 16).

b3WJ
CCCACAUACUUUGUUGAUCC (SEQ ID NO: 17).

c3WJ
GGAUCAAUCAUGGCAA (SEQ ID NO: 18).

| Exemplary Sequences produced using the method described in this Example. |
|---| aPhi29-Mod
AUUCGCUGUGUGGUAGUG (SEQ ID NO: 19)

bPhi29-Mod
CACUACCACUUUGUCCUACG (SEQ ID NO: 20).

cPhi29-Mod
CGUAGGACCAGCGAAU (SEQ ID NO: 21).

aPhi29-30
GCGUGCUGUGUGCUACCG (SEQ ID NO: 22).

bPhi29-30
CGGUAGCACUUUGCUGUGCG (SEQ ID NO: 23).

cPhi29-30
CGCACAGCCAGCACGC (SEQ ID NO: 24).

aSF5-30
GCGUGCUGGUGCUACCG (SEQ ID NO: 25).

bSF5-30
CGGUAGCACGGGCUGUGCG (SEQ ID NO: 26).

cSF5-30
CGCACAGCCAGCACGC (SEQ ID NO: 27)

aM2-30
GCGUGCUGGUGCUACCG (SEQ ID NO: 28).

bM2-30
CGGUAGCACCGCUGUGCG (SEQ ID NO: 29).

cM2-30
CGCACAGCCUCAGCACGC (SEQ ID NO: 30).

aPhi29-32
ACGCGACGUGUGCAUGCC (SEQ ID NO: 31).

bPhi29-32
GGCAUGCACUUUGCGUUGCG (SEQ ID NO: 32).

cPhi29-32
CGCAACGCCGUCGCGU (SEQ ID NO: 33).

aSF5-32
ACGCGACGGUGCAUGCC (SEQ ID NO: 34)

bSF5-32
GGCAUGCACGGGCGUUGCG (SEQ ID NO: 35)

cSF5-32
CGCAACGCCGUCGCGU (SEQ ID NO: 36).

aM2-32
ACGCGACGGUGCAUGCC (SEQ ID NO: 37)

bM2-32
GGCAUGCACCGCGUUGCG (SEQ ID NO: 38)

cM2-32
CGCAACGCCUCGUCGCGU (SEQ ID NO: 39)

Mod-a/WT-b
AUUCGCUGUGUGGUAGUGCCCACAUACUUUGUUGAUCC (SEQ ID NO: 40)

Mod-b/WT-b
CACUACCACUUUGUCCUACGCCCACAUACUUUGUUGAUCC (SEQ ID NO: 41)

Mod-c/WT-b
CGUAGGACCAGCGAAUCCCACAUACUUUGUUGAUCC (SEQ ID NO: 42)

30a/Mod-b
GCGUGCUGUGUGCUACCGCACUACCACUUUGUCCUACG (SEQ ID NO: 43)

-continued

Exemplary Sequences produced using the method described in this Example.

30b/Mod-b
CGGUAGCACUUUGCUGUGCGCACUACCACUUUGUCCUACG (SEQ ID NO: 44)

30c/Mod-b
CGCACAGCCAGCACGCCACUACCACUUUGUCCUACG (SEQ ID NO: 45)

Ext30-a/Mod-b
CCUAUUCAGGUGCGUGCUGUGUGCUACCGAUGUAAUUCAACACUACCACUUU
GUCCUACG (SEQ ID NO: 46)

Ext30-b/Mod-b
UUGAAUUACAUCGGUAGCACUUUGCUGUGCGAGGCUGAACAGCACUACCACU
UUGUCCUACG (SEQ ID NO: 47)

Ext30-c/Mod-b
CUGUUCAGCCUCGCACAGCCAGCACGCACCUGAAUAGGCACUACCACUUUGU
CCUACG (SEQ ID NO: 48)

WT-b/Mod-a
CCCACAUACUUUGUUGAUCCAUUCGCUGUGUGGUAGUG (SEQ ID NO: 49)

WT-b/Mod-c
CCCACAUACUUUGUUGAUCCCGUAGGACCAGCGAAU (SEQ ID NO: 50)

SF5-4WJ-a
UUAGGUAAAGCCACCUGCAGGUGCUACCGAUGUAAUUCAA (SEQ ID NO: 51)

SF5-4WJ-b
UUGAAUUACAUCGGUAGCACGGGCUGUGCGAGGCUGAACAG (SEQ ID NO: 52)

SF5-4WJ-c
CUGUUCAGCCUCGCACAGCCAGCACGCACCUGAAUAGG (SEQ ID NO: 53)

SF5-4WJ-d
CCUAUUCAGGUGCGUGCUGGGCUGCAGGUGGCUUUACCUAA (SEQ ID NO: 54)

Example 5. Nanostructures for Imaging

FIG. 49A-49C. Conjugation of fluorophores to nucleic acid nanostructures (also referred to herein as nanoparticles) for use in in vivo cancer imaging. FIG. 49A. PAGE analysis demonstrating RNA oligomers and nanoparticles can carry multi-color fluorescent materials. FIG. 49B. Assembly gel demonstrating that oligomers can efficiently assemble after modification with fluorophores. FIG. 49C. Biodistribution of Phi29 3WJ nanoparticles coupled with ICG fluorophores.

FIGS. 50A-50C. High density conjugation of DOTA chelator to RNA oligomers and nanoparticles. FIGS. 50A-50B. Assembly of amine modified and DOTA conjugated oligomers into RNA nanoparticles. FIGS. 50B-50C. Comparison of RNA nanoparticles with varying densities of DOTA conjugates with and without chelated $Gd^{3+}$.

FIGS. 51A-51C. High density conjugation of NOTA chelator to oligomers and nanoparticles. FIG. 51A. Schematic of NOTA chelation of Cu64 to RNA nanoparticle for PET imaging. FIGS. 51B-51C. Assembly gel of NOTA conjugated RNA nanoparticles and reverse phase HPLC purification.

FIGS. 52A-52E shows design and synthesis of pRNA strands with multiple aldehyde groups to conjugate drugs for pH responsive drug release. FIG. 52A. Schematic illustration of conjugation of multiple drugs on 3WJ core. FIG. 52B Example of drugs bearing free amine groups for imine bond linkage. FIG. 52C. Example of drugs bearing hydroxyl groups for acetal linkage. FIG. 52D. Example of pH sensitive linker design using hydrazine bonds. FIG. 52E. Example of acil labile linker to conjugate P1103 prodrug to nucleic acid oligomers.

FIGS. 53A-53H shows design and preparation of RNA-based thermostable micelles for delivery of erlotinib for cancer therapy. FIG. 53A. Amphiphilic RNA strands with tunable hydrophobic modifications for formation of RNA micelles. FIG. 53B. Illustration of RNA-tocopherol micelles conjugated with functional moieties. FIGS. 53C-53H. Critical micelle concentration determination of 5 amphiphilic RNA strands with tunable hydrophobic modifications.

FIGS. 54A-54Q shows design and preparation of CPT-RNA conjugates for suppression of KB tumor xenograft growth. FIGS. 54A-54C. CPT-RNA conjugation. FIGS. 54B-54D. Drug solubilization by conjugation to RNA. FIGS. 54C-54H. Assembly, thermodynamic stability and size distribution of CPT carrying RNA nanoparticles. FIGS. 54D-54I. CPT release profile from RNA nanoparticles. FIGS. 54J-54K. Cell binding and internalization of CPT-RNA nanoparticles. FIGS. 54L-54M. Cytotoxicity and Apoptosis effect of CPT RNA nanoparticles. FIGS. 54N-54P. Tumor suppression of CPT RNA NPs in KB tumor xenograft mouse model.

What is claimed is:

1. An RNA nanostructure comprising: at least three synthetic RNA oligonucleotides,
    wherein the at least three synthetic RNA oligonucleotides are coupled to each other to form a central core domain and at least three double-stranded arms arranged around the core domain and extending away from the central core domain,
    wherein at least 3 cargo compound molecules are conjugated to each of the at least three synthetic RNA oligonucleotides,
    wherein the melting temperature of the RNA nanostructure with the conjugated 3 to 100 cargo compounds is greater than 65 degrees Celcius, and
    wherein the at least three synthetic RNA oligonucleotides are configured to self-assemble to form the RNA nanostructure.

2. The RNA nanostructure of claim 1, wherein the RNA nanostructure comprises three to nine synthetic RNA oligonucleotides and three to nine double stranded arms.

3. The RNA nanostructure of claim 1, wherein one or more of the at least three synthetic RNA oligonucleotides comprises one or more nucleotides modified with an alkyne or a linker.

4. The RNA nanostructure of claim 1, further comprising a functional group attached to a nucleotide of one or more of the at least three synthetic RNA oligonucleotides, wherein the cargo compound is conjugated to the functional group.

5. The RNA nanostructure of claim 1, wherein each of the at least three synthetic RNA oligonucleotides comprises a oligonucleotide sequence having a sequence that is at least 80% identical to any one of SEQ ID NOS: 1-54.

6. The RNA nanostructure of claim 1 comprising:
    a central core, wherein the central core comprises a first modular RNA motif;
    a first layer, wherein the first layer comprises at least three modular RNA motifs, wherein each of modular RNA motifs in the at least three modular RNA motifs of the first layer is attached to the first modular RNA motif; and
    a second layer, wherein the second layer comprises at least three modular RNA motifs, wherein each of the at least three modular RNA motifs of the second layer is attached to a modular RNA motif of the at least three modular motifs of the first layer.

7. The RNA nanostructure of claim 6, wherein the first modular RNA motif has a greater Tm then the modular RNA motifs of the first layer and the modular RNA motifs of the second layer.

8. The RNA nanostructure of claim 7, wherein the modular RNA motifs of the first layer have a greater Tm than the modular RNA motifs of the second layer.

9. The RNA nanostructure of claim 1, wherein the cargo compound is an anti-cancer compound, a chelator, radioactive isotope, a fluorophore, an miRNA, an anti-miRNA, an siRNA, a pH responsive prodrug, an enzyme cleavable prodrug, or any combination thereof.

10. The RNA nanostructure of claim 1, comprising at least two different types of cargo compounds.

11. The RNA nanostructure of claim 1, wherein at least 4 cargo compound molecules are conjugated to each synthetic RNA oligonucleotide.

12. The RNA nanostructure of claim 1, wherein at least 6 cargo compound molecules are conjugated to each synthetic RNA oligonucleotide.

13. The RNA nanostructure of claim 1, wherein the RNA nanostructure comprises four synthetic RNA oligonucleotides coupled to each other to form a central core domain and four double-stranded arms arranged around the core domain and extending away from the central core domain.

14. The RNA nanostructure of claim 13, wherein at least 3 cargo compound molecules are conjugated to each of the four synthetic RNA oligonucleotides.

15. The RNA nanostructure of claim 13, wherein at least 4 cargo compound molecules are conjugated to each of the four synthetic RNA oligonucleotides.

16. The RNA nanostructure of claim 13, wherein at least 6 cargo compound molecules are conjugated to each of the four synthetic RNA oligonucleotides.

17. The RNA nanostructure of claim 1, wherein the cargo compound is a hydrophobic small molecule compound.

18. The RNA nanostructure of claim 17, wherein the cargo compound comprises paclitaxel.

19. The RNA nanostructure of claim 1, wherein the cargo compound is conjugated to the at least three synthetic RNA oligonucleotides by a thermodynamic, acid-labile, light-sensitive, or enzyme-labile chemical group.

\* \* \* \* \*